(12) United States Patent
Park et al.

(10) Patent No.: US 10,593,887 B2
(45) Date of Patent: Mar. 17, 2020

(54) CONDENSED CYCLIC COMPOUND AND AN ORGANIC LIGHT-EMITTING DEVICE INCLUDING THE SAME

(71) Applicant: SAMSUNG DISPLAY CO., LTD., Yongin-si, Gyeonggi-do (KR)

(72) Inventors: Junha Park, Yongin-si (KR); Youngkook Kim, Yongin-si (KR); Munki Sim, Yongin-si (KR); Hyoyoung Lee, Yongin-si (KR); Eunjae Jeong, Yongin-si (KR); Seokhwan Hwang, Yongin-si (KR)

(73) Assignee: SAMSUNG DISPLAY CO., LTD., Yongin-si, Gyeonggi-Do (KR)

( * ) Notice: Subject to any disclaimer, the term of this patent is extended or adjusted under 35 U.S.C. 154(b) by 279 days.

(21) Appl. No.: 15/618,982

(22) Filed: Jun. 9, 2017

(65) Prior Publication Data

US 2017/0365792 A1    Dec. 21, 2017

(30) Foreign Application Priority Data

Jun. 20, 2016    (KR) ........................ 10-2016-0076607

(51) Int. Cl.
*H01L 51/50* (2006.01)
*H01L 51/00* (2006.01)
(Continued)

(52) U.S. Cl.
CPC ........ *H01L 51/0071* (2013.01); *C07D 498/14* (2013.01); *C07D 513/14* (2013.01);
(Continued)

(58) Field of Classification Search
None
See application file for complete search history.

(56) References Cited

U.S. PATENT DOCUMENTS

| 5,645,948 A | 7/1997 | Shi et al. |
| 2004/0053069 A1 | 3/2004 | Sotoyama et al. |

(Continued)

FOREIGN PATENT DOCUMENTS

| JP | 10-017860 | 1/1998 |
| JP | 11-087067 | 3/1999 |

(Continued)

OTHER PUBLICATIONS

Pandey et al., Synthesis of biologically active pyridoimidazole/imidazobenzothiazole annulated polyheterocycles using cyanuric chloride in water, 2014, RSC Advances (2014), 4(51), 26757-26770 (Year: 2014).*

(Continued)

*Primary Examiner* — Gregory D Clark
(74) *Attorney, Agent, or Firm* — F. Chau & Associates, LLC

(57) ABSTRACT

A condensed cyclic compound represented by Formula 1 and an organic light-emitting apparatus including the same.

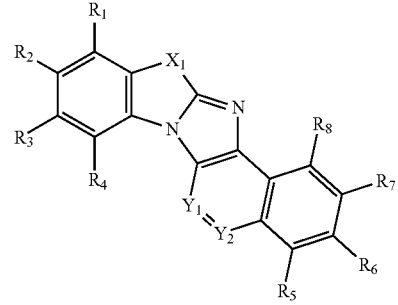

[Formula 1]

20 Claims, 4 Drawing Sheets

(51) Int. Cl.

| | |
|---|---|
| C07D 498/14 | (2006.01) |
| C07D 513/14 | (2006.01) |
| C07D 519/00 | (2006.01) |
| C07F 9/6561 | (2006.01) |
| C09K 11/02 | (2006.01) |
| C09K 11/06 | (2006.01) |
| H01L 51/52 | (2006.01) |

(52) U.S. Cl.
CPC .......... *C07D 519/00* (2013.01); *C07F 9/6561* (2013.01); *C09K 11/025* (2013.01); *C09K 11/06* (2013.01); *H01L 51/0052* (2013.01); *H01L 51/0056* (2013.01); *H01L 51/0058* (2013.01); *H01L 51/0065* (2013.01); *H01L 51/0067* (2013.01); *H01L 51/0072* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01)

(56) References Cited

U.S. PATENT DOCUMENTS

| | | |
|---|---|---|
| 2005/0079387 A1 | 4/2005 | Lee et al. |
| 2012/0181922 A1 | 7/2012 | Kawamura et al. |
| 2017/0125696 A1 | 5/2017 | Park et al. |

FOREIGN PATENT DOCUMENTS

| | | |
|---|---|---|
| JP | 2002-105085 | 4/2002 |
| JP | 4060669 | 12/2007 |
| KR | 10-017860 | 1/1998 |
| KR | 10-2005-0035569 | 4/2005 |
| KR | 10-0525408 | 10/2005 |
| KR | 10-2012-0117622 | 10/2012 |
| KR | 10-2015-0025010 | 3/2015 |
| KR | 10-2015-0034029 | 4/2015 |
| KR | 10-2017-0052819 | 5/2017 |

OTHER PUBLICATIONS

S. Yamaguchi, et al., "Diphenylamino-Substituted 2,5-Diarylsiloles for Single-Layer Organic Electroluminescent Devices", Chemistry Letters 2001, pp. 98-99.

N. Johansson, et al., "Solid-State Amplified Spontaneous Emission in Some Spiro-Type Molecules: A New Concept for the Design of Solid-State Lasing Molecules", Advanced Materials 10, 1998, pp. 1136-1141.

Y.T. Tao, et al., "Sharp green electroluminescence from 1H-pyrazolo[3,4-b]quinolone-based light-emitting diodes", Applied Physics Letters 77, 2000, pp. 1575-1577.

Y. Sakamoto, et al., "Synthesis, Characterization, and Electron-Transport Property of Perfluorinated Phenylene Dendrimers", J. Am. Chem. Soc. 2000, 122, pp. 1832-1833.

C. Adachi, et al., "Confinement of charge carriers and molecular excitons within 5nmthick emitter layer in organic electroluminescent devices with a double heterostructure", Applied Physics Letters 57, 1990, pp. 531-533.

C.W. Tang, et al., "Organic electroluminescent diodes", Applied Physics Letters 51, 1987, pp. 913-915.

* cited by examiner

| 190 |
|-----|
| 150 |
| 110 |

| 190 |
|-----|
| 150 |
| 110 |
| 210 |

| 220 |
|---|
| 190 |
| 150 |
| 110 |

| 220 |
|---|
| 190 |
| 150 |
| 110 |
| 210 |

CONDENSED CYCLIC COMPOUND AND AN ORGANIC LIGHT-EMITTING DEVICE INCLUDING THE SAME

CROSS-REFERENCE TO RELATED APPLICATION

This application claims the benefit of Korean Patent Application No. 10-2016-0076607, filed on Jun. 20, 2016 in the Korean Intellectual Property Office, the disclosure of which is incorporated by reference herein in its entirety.

TECHNICAL FIELD

Exemplary embodiments of the present invention relate to a condensed cyclic compound, and more particularly to an organic light-emitting device including the same.

DISCUSSION OF RELATED ART

Organic light-emitting devices may be self-emission devices. Organic light-emitting devices may have relatively wide viewing angles, relatively high contrast ratios, relatively short response times, and increased brightness, driving voltage, and response speed characteristics. Organic light-emitting devices may produce full-color images.

Organic light-emitting devices may include a first electrode disposed on a substrate. Organic light-emitting devices may include a hole transport region, an emission layer, an electron transport region, and a second electrode sequentially disposed on the first electrode. Holes provided from the first electrode may move toward the emission layer through the hole transport region. Electrons provided from the second electrode may move toward the emission layer through the electron transport region. Carriers, such as holes and electrons, may recombine in the emission layer to produce excitons. The excitons may transition from an excited state to a ground state, thus generating light.

SUMMARY

One or more exemplary embodiments of the present invention include a condensed cyclic compound and an organic light-emitting device including the same.

One or more exemplary embodiments of the present invention provide a condensed cyclic compound. The condensed cyclic compound is represented by Formula 1:

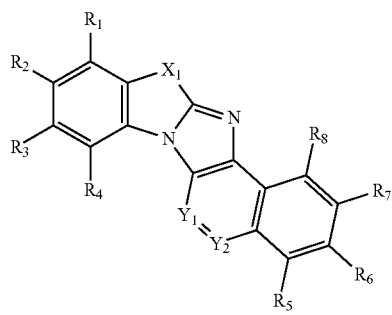

<Formula 1>

$*-(L_1)_{a1}-(Ar_1)_{b1}$,  <Formula 2>

In Formulae 1 and 2,
$X_1$ is O or S.
$Y_1$ is $C(R_9)$ or N.
$Y_2$ is $C(R_{10})$ or N.

$L_1$ is selected from a substituted or unsubstituted $C_3$-$C_{60}$ carbocyclic group, a substituted or unsubstituted $C_1$-$C_{60}$ heterocyclic group, $*-S(=O)(Q_1)-*'$, $*-S(=O)_2-*'$, $*-P(=O)(Q_1)-*'$, $*-P(=O)_2-*'$, $*-P(=S)(Q_1)-*'$, or $*-P(=S)_2-*'$.

a1 is an integer selected from 0 to 4. When a1 is 2 or greater, at least two $L_1(s)$ may be the same or different from each other.

$Ar_1$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-S(=O)(Q_1)(Q_2)$, $-S(=O)_2(Q_1)$, $-P(=O)(Q_1)(Q_2)$, $-P(=O)_2(Q_1)$, $-P(=S)(Q_1)(Q_2)$, or $-P(=S)_2(Q_1)$.

b1 is an integer selected from 1 to 4. When b1 is 2 or greater, at least two $Ar_1(s)$ may be the same or different from each other.

$R_1$ to $R_{10}$ are each independently be selected from a group represented by Formula 2, hydrogen, deuterium, $-F$, $-Cl$, $-Br$, $-I$, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, or $-P(=O)(Q_1)(Q_2)$.

At least one of $R_1$ to $R_{10}$ is the group represented by Formula 2.

At least one substituent selected from a substituent(s) of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group is selected from:
deuterium, $-F$, $-Cl$, $-Br$, $-I$, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), or —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, or a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), or —P(=O)($Q_{21}$)($Q_{22}$); or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

$Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, or a terphenyl group.

* and *' each indicate a binding site to a neighboring atom.

One or more exemplary embodiments of the present invention provide an organic light-emitting device. The organic light-emitting device includes a first electrode; a second electrode facing the first electrode; and an organic layer that is disposed between the first electrode and the second electrode. The organic layer includes an emission layer. The organic layer includes at least one of the condensed cyclic compounds represented by Formula 1.

BRIEF DESCRIPTION OF THE DRAWINGS

The above and other features of the present invention will become more apparent by describing in detail exemplary embodiments thereof, with reference to the accompanying drawings, in which:

FIG. 1 is a schematic cross-sectional diagram illustrating an organic light-emitting device according to an exemplary embodiment of the present invention;

FIG. 2 is a schematic cross-sectional diagram illustrating an organic light-emitting device according to an exemplary embodiment of the present invention;

FIG. 3 is a schematic cross-sectional diagram illustrating an organic light-emitting device according to an exemplary embodiment of the present invention; and FIG. 4 is a schematic cross-sectional diagram illustrating an organic light-emitting device according to an exemplary embodiment of the present invention.

DETAILED DESCRIPTION OF THE EMBODIMENTS

One or more exemplary embodiments of the present invention provide a condensed cyclic compound. The condensed cyclic compound may be represented by Formula 1:

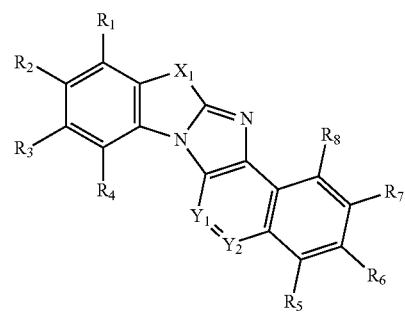

<Formula 1>

\*-(L$_1$)$_{a1}$-(Ar$_1$)$_{b1}$. <Formula 2>

$X_1$ in Formula 1 may be oxygen (O) or sulfur (S).

$Y_1$ in Formula 1 may be C($R_9$) or nitrogen (N).

$Y_2$ in Formula 1 may be C($R_{10}$) or nitrogen (N).

$R_1$ to $R_{10}$ in Formula 1 may each independently be selected from a group represented by Formula 2, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —B(=O)$_2$($Q_1$), or —P(=O)($Q_1$)($Q_2$).

$Q_1$ to $Q_3$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, or a terphenyl group.

At least one of $R_1$ to $R_{10}$ in Formula 1 may be the group represented by Formula 2.

According to an exemplary embodiment of the present invention, in Formula 1, $Y_1$=C($R_9$) and at least one of $R_1$ to $R_3$ and $R_9$ may be the group represented by Formula 2. According to one or more exemplary embodiments of the present invention, in Formula 1, $Y_2$=C($R_{10}$), and at least one of $R_1$ to $R_3$ and $R_{10}$ may be the group represented by Formula 2.

According to an exemplary embodiment of the present invention, when at least one of $R_1$ to $R_3$ is the group represented by Formula 2, $R_9$ or $R_{10}$ may be selected from a phenyl group, a pyridinyl group, or a biphenyl group; however, exemplary embodiments of the present invention are not limited thereto.

$R_4$ to $R_8$ may be hydrogen; however, exemplary embodiments of the present invention are not limited thereto.

$L_1$ in Formula 2 may be selected from a substituted or unsubstituted $C_3$-$C_{60}$ carbocyclic group, a substituted or unsubstituted $C_1$-$C_{60}$ heterocyclic group, *—S(=O)($Q_1$)-*', *—S(=O)$_2$—*', *—P(=O)($Q_1$)-*', *—P(=O)$_2$—*', *—P(=S)($Q_1$)-*', or *—P(=S)$_2$—*'.

$Q_1$ may be selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, or a terphenyl group, in which * and *' each may indicate a binding site to a neighboring atom.

According to an exemplary embodiment of the present invention, $L_1$ in Formula 2 may be selected from: a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzofuran group, a dibenzothiophene group, a dibenzosilole group, a carbazole group, a benzocarbazole group, a dibenzocarbazole group, a benzimidazole group, or an imidazopyridine group; a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzofuran group, a dibenzothiophene group, a dibenzosilole group, a carbazole group, a benzocarbazole group, a dibenzocarbazole group, a benzimidazole group, and an imidazopyridine group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a carbazolyl group, a pyridinyl group, a pyrazinyl group, a pyrimidinyl group, a pyridazinyl group, a benzofuranyl group, a benzothiophenyl group, a dibenzofuranyl group, a dibenzothiophenyl group, a benzocarbazolyl group, a dibenzocarbazolyl group, —Si($Q_{31}$)($Q_{32}$)($Q_{33}$), —N($Q_{31}$)($Q_{32}$), or —B($Q_{31}$)($Q_{32}$); or *—S(=O)($Q_1$)-*', *—S(=O)$_2$—*', *—P(=O)($Q_1$)-*', *—P(=O)$_2$—*' *—P(=S)($Q_1$)-*', or *—P(=S)$_2$—*', in which * and *' may indicate a binding site to a neighboring atom.

$Q_1$ and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, or a pyridinyl group According to an exemplary embodiment of the present invention, $L_1$ in Formula 2 may be selected from: a benzene group, an anthracene group, a dibenzofuran group, a benzimidazole group, an imidazopyridine group, or a triazine group; a benzene group, a fluorene group, or a carbazole group, each substituted with at least one of a cyano group, a $C_1$-$C_{20}$ alkyl group, a phenyl group, a biphenyl group, or a pyridinyl group; and *—S(=O)($Q_1$)-*', *—S(=O)$_2$—*', *—P(=O)($Q_1$)-*', *—P(=O)$_2$—*' *—P(=S)($Q_1$)-*', or *—P(=S)$_2$—*', in which * and *' may each indicate a binding site to a neighboring atom. However, exemplary embodiments of the present invention are not limited thereto.

According to an exemplary embodiment of the present invention, $L_1$ in Formula 2 may be selected from groups represented by Formulae 3-1 to 3-50.

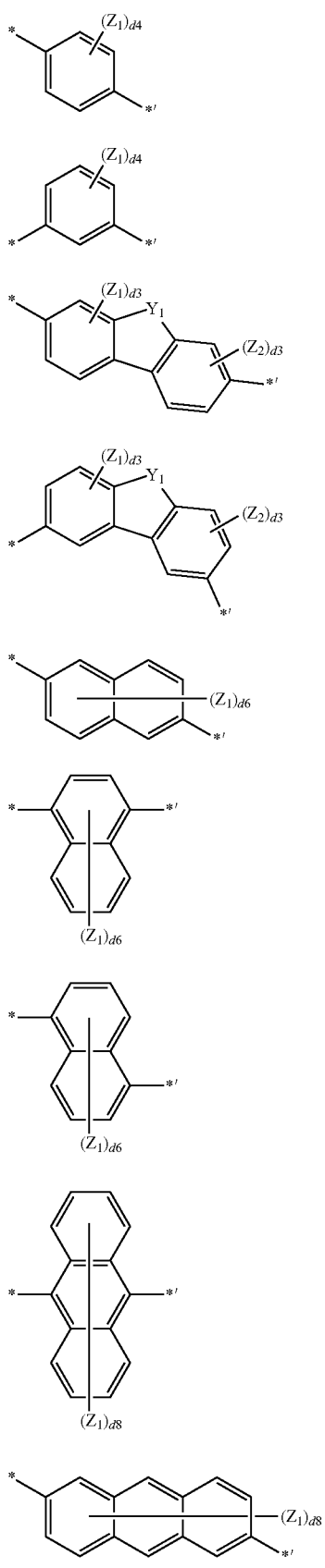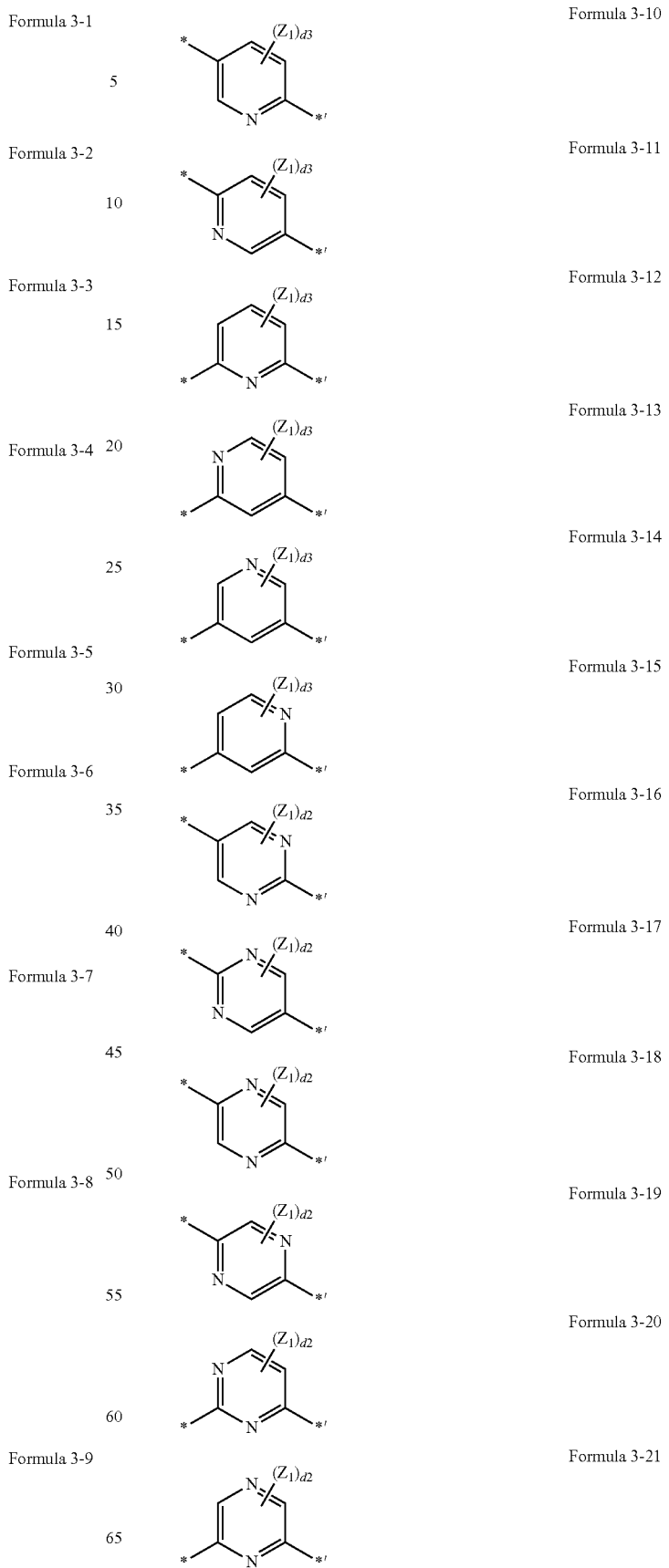

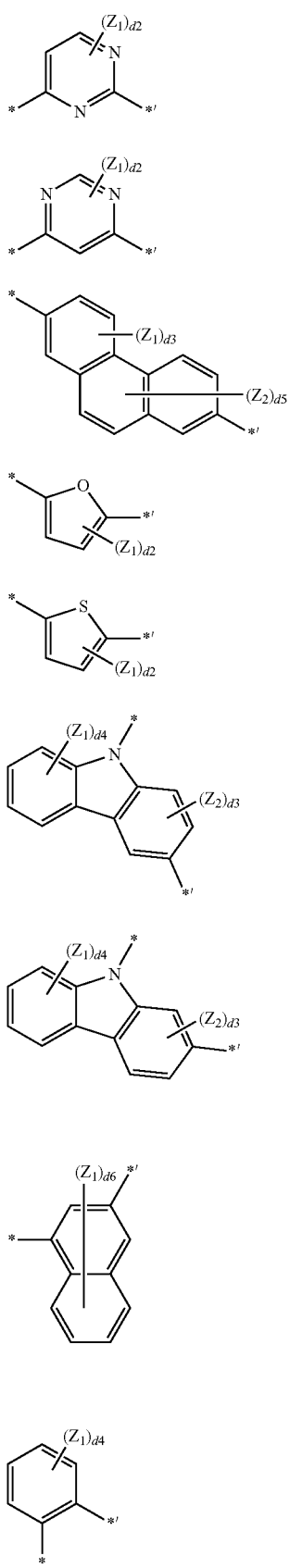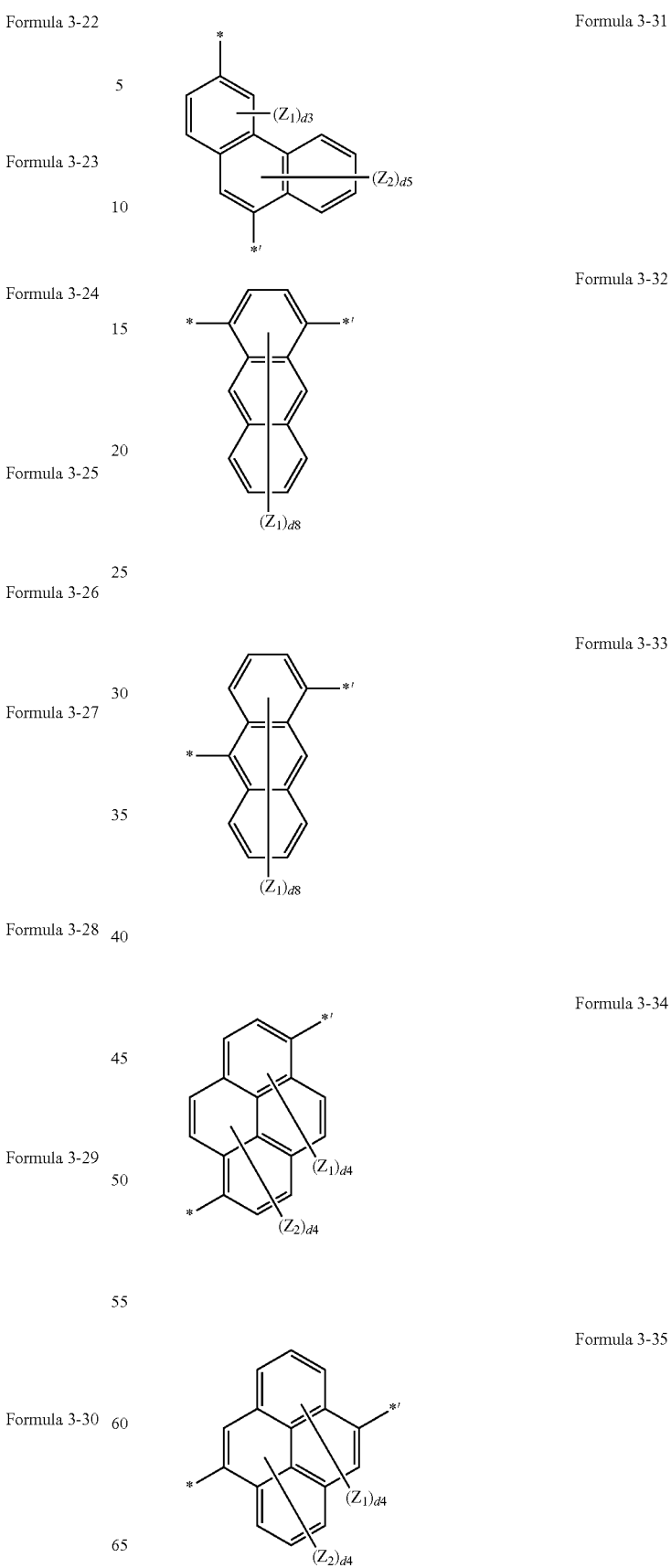

-continued

Formula 3-36
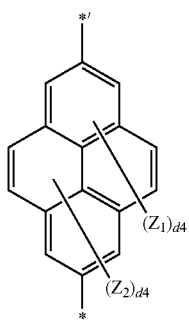

Formula 3-37
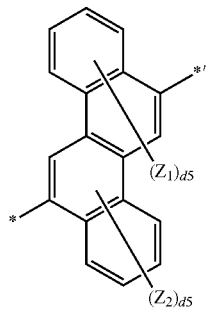

Formula 3-38
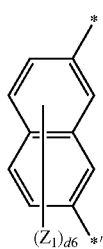

Formula 3-39
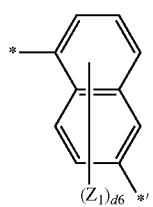

Formula 3-40
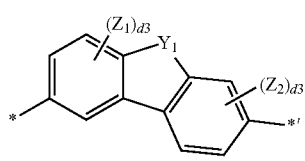

Formula 3-41
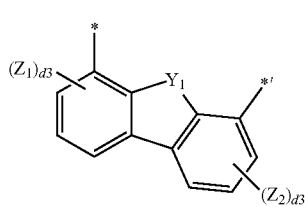

Formula 3-42
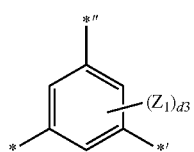

Formula 3-43
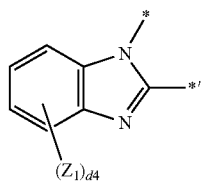

Formula 3-44
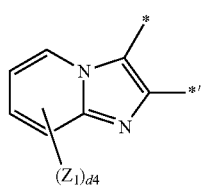

Formula 3-45
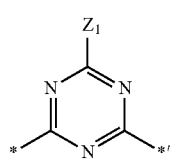

Formula 3-46
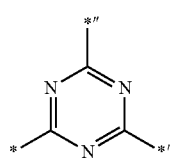

Formula 3-47
*—S(=O)—*'

Formula 3-48
*—S(=O)₂—*'

Formula 3-49
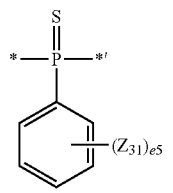

Formula 3-50
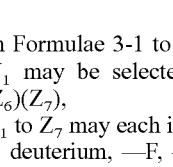

In Formulae 3-1 to 3-50:

$Y_1$ may be selected from O, S, $C(Z_3)(Z_4)$, $N(Z_5)$, or $Si(Z_6)(Z_7)$, $Z_1$ to $Z_7$ may each independently be selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, or —Si$(Q_{31})(Q_{32})(Q_{33})$, $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, or a pyridinyl group, d2 may be an integer selected from 0 to 2,
d3 may be an integer selected from 0 to 3,
d4 may be an integer selected from 0 to 4,
d5 may be an integer selected from 0 to 5,
d6 may be an integer selected from 0 to 6,
d8 may be an integer selected from 0 to 8, and
\*, \*', and \*" may each indicate a binding site to a neighboring atom.

According to an exemplary embodiment of the present invention, $L_1$ in Formula 2 may include a group represented by Formulae 3-1 to 3-3, 3-8, 3-27, or 3-42 to 3-50; however, exemplary embodiments of the present invention are not limited thereto.

According to an exemplary embodiment of the present invention, $Y_{31}$ in Formulae 3-40 and 3-41 may be oxygen (O) or C$(Z_{33})(Z_{34})$; however, exemplary embodiments of the present invention are not limited thereto.

a1 in Formula 2 may indicate the number of $L_1$(s). Thus, a1 may be an integer selected from 0 to 4. When a1 is 2 or greater, at least two $L_1$(s) may be the same or different from each other. When a1 is zero, *-$(L_1)_{a1}$-*' may be a single bond.

a1 in Formula 2 may be an integer selected from 0 to 2; however, exemplary embodiments of the present invention are not limited thereto.

$Ar_1$ in Formula 2 may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —S(=O)$(Q_1)(Q_2)$, —S(=O)$_2(Q_1)$, —P(=O)$(Q_1)(Q_2)$, —P(=O)$_2(Q_1)$, —P(=S)$(Q_1)(Q_2)$, or —P(=S)$_2(Q_1)$. $Q_1$ and $Q_2$ may each independently be selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, or a terphenyl group.

According to an exemplary embodiment of the present invention, $Ar_1$ in Formula 2 may be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a carbazolyl group, a benzofuranyl group, a benzothiophenyl group, a dibenzofuranyl group, a dibenzothiophenyl group, a benzonaphthofuranyl group, a dinaphthofuranyl group, a benzocarbazolyl group, a dibenzocarbazolyl group, a dibenzosilolyl group, a benzonaphthosilolyl group, a dinaphthosilolyl group, a benzimidazolyl group, or an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a carbazolyl group, a benzofuranyl group, a benzothiophenyl group, a dibenzofuranyl group, a dibenzothiophenyl group, a benzonaphthofuranyl group, a dinaphthofuranyl group, a benzocarbazolyl group, a dibenzocarbazolyl group, a dibenzosilolyl group, a benzonaphthosilolyl group, a dinaphthosilolyl group, a benzimidazolyl group, or an imidazopyridinyl group, each substituted with at least one of deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, a dibenzosilolyl group, —N$(Q_{31})(Q_{32})$, or —Si$(Q_{31})(Q_{32})(Q_{33})$; or —S(=O)$(Q_1)(Q_2)$, —S(=O)$_2(Q_1)$, —P(=O)$(Q_1)(Q_2)$, —P(=O)$_2(Q_1)$, —P(=S)$(Q_1)(Q_2)$, or —P(=S)$_2(Q_1)$.

$Q_1$, $Q_2$, and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, or a pyridinyl group; however, exemplary embodiments of the present invention are not limited thereto.

According to an exemplary embodiment of the present invention, $Ar_1$ in Formula 2 may be selected from:

a phenyl group, a biphenyl group, a terphenyl group, a fluorenyl group, a spiro-bifluorenyl group, a pyridinyl group, a triazinyl group, a carbazolyl group, a dibenzofuranyl group, a naphthofuranyl group, a benzimidazolyl group, or an imidazopyridinyl group;

a phenyl group, a terphenyl group, a fluorenyl group, a spiro-bifluorenyl group, a pyridinyl group, a triazinyl group, a carbazolyl group, a dibenzofuranyl group, a dinaphthofuranyl group, a benzimidazolyl group, and an imidazopyridinyl group, each substituted with at least one selected from deuterium, —F, a cyano group, a $C_1$-$C_{20}$ alkyl group, a phenyl group, a biphenyl group, a terphenyl group, a fluorenyl group, a spiro-bifluorenyl group, a pyridinyl group, a carbazolyl group, a dibenzofuranyl group, —N($Q_{31}$)($Q_{32}$), or —Si($Q_{31}$)($Q_{32}$)($Q_{33}$); or —S(=O)($Q_1$)($Q_2$), —S(=O)$_2$($Q_1$), —P(=O)($Q_1$)($Q_2$), —P(=O)$_2$($Q_1$), —P(=S)($Q_1$)($Q_2$), or —P(=S)$_2$($Q_1$). $Q_1$, $Q_2$, and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, or a pyridinyl group; however, exemplary embodiments of the present invention are not limited thereto.

According to an exemplary embodiment of the present invention, $Ar_1$ in Formula 2 may be selected from groups represented by Formulae 5-1 to 5-30, —S(=O)($Q_1$)($Q_2$), —S(=O)$_2$($Q_1$), —P(=O)($Q_1$)($Q_2$), —P(=O)$_2$($Q_1$), —P(=S)($Q_1$)($Q_2$), or —P(=S)$_2$($Q_1$).

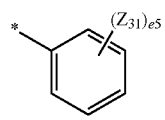

Formula 5-1

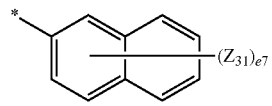

Formula 5-2

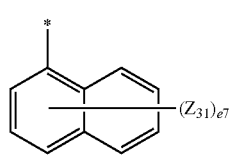

Formula 5-3

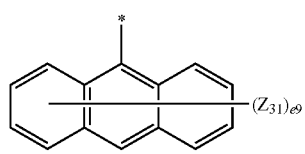

Formula 5-4

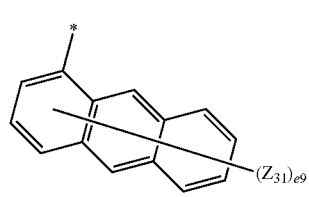

Formula 5-5

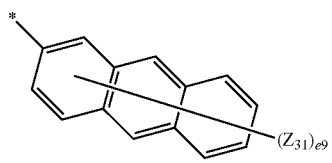

Formula 5-6

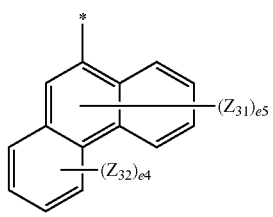

Formula 5-7

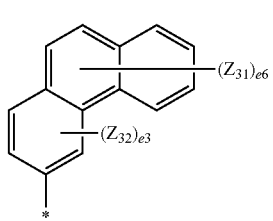

Formula 5-8

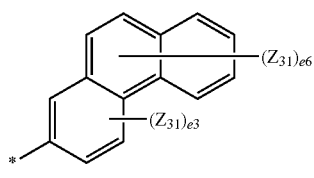

Formula 5-9

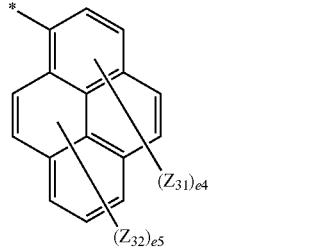

Formula 5-10

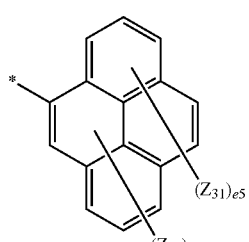

Formula 5-11

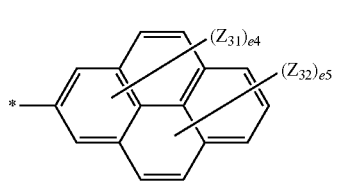

Formula 5-12

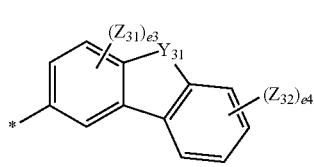

Formula 5-13

In Formulae 5-1 to 5-30:

Y$_{31}$ may be selected from oxygen (O), sulfur (S), C(Z$_{33}$)(Z$_{34}$), N(Z$_{35}$), or Si(Z$_{36}$) (Z$_{37}$), $Z_{31}$ to $Z_{37}$ may each independently be selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, a pyridinyl group, an indolyl group, an isoindolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, or —Si($Q_{31}$)($Q_{32}$)($Q_{33}$), $Q_1$, $Q_2$, and $Q_{31}$ to $Q_{33}$ may each independently be selected from a $C_1$-$C_{20}$ alkyl group, a $C_1$-$C_{20}$ alkoxy group, a phenyl group, a biphenyl group, a terphenyl group, a naphthyl group, or a pyridinyl group, e3 may be an integer selected from 0 to 3,
e4 may be an integer selected from 0 to 4,
e5 may be an integer selected from 0 to 5,
e6 may be an integer selected from 0 to 6,
e7 may be an integer selected from 0 to 7,
e9 may be an integer selected from 0 to 9, and
* may indicates a binding site to a neighboring atom.

According to an exemplary embodiment of the present invention, $Ar_1$ in Formula 2 may be selected from a group represented by Formulae 5-1, 5-3, 5-4, 5-7, 5-13, 5-14, 5-22, or 5-27 to 5-30; however, exemplary embodiments of the present invention are not limited thereto.

$Y_{31}$ in Formulae 5-13 to 5-15 may be oxygen (O), C($Z_{33}$)($Z_{34}$), or N($Z_{35}$); however, exemplary embodiments of the present invention are not limited thereto.

$Y_{31}$ in Formula 5-29 may be N($Z_{35}$); however, exemplary embodiments of the present invention are not limited thereto.

According to an exemplary embodiment of the present invention, $Ar_1$ in Formula 2 may be selected from groups represented by Formulae 6-1 to 6-138 or groups represented by Formulae 10-1 to 10-7; however, exemplary embodiments of the present invention are not limited thereto.

Formula 6-1

Formula 6-2

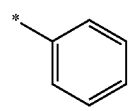

Formula 6-3

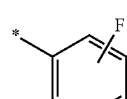

Formula 6-4

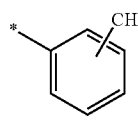

Formula 6-5

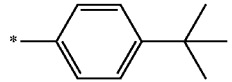

Formula 6-6

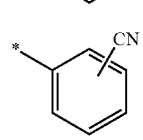

Formula 6-7

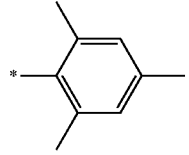

Formula 6-8

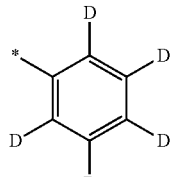

Formula 6-9

Formula 6-10

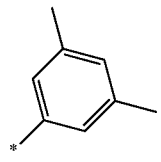

Formula 6-11

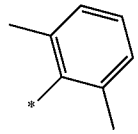

Formula 6-12

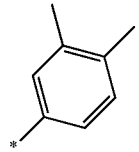

Formula 6-13

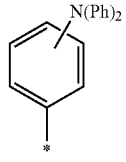
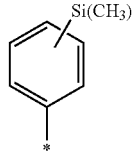
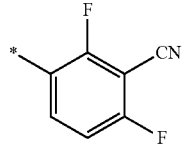

Formula 6-14 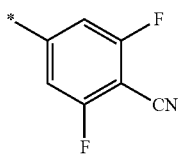
Formula 6-15 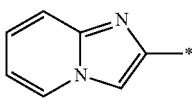
Formula 6-16 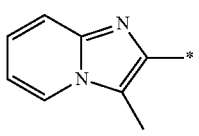
Formula 6-17 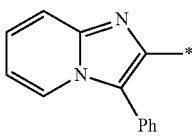
Formula 6-18 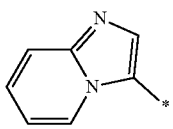
Formula 6-19 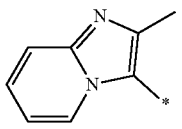
Formula 6-20 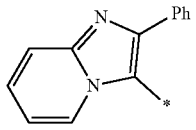
Formula 6-21 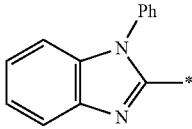
Formula 6-22 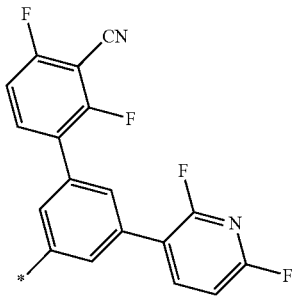
Formula 6-23 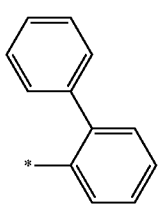
Formula 6-24 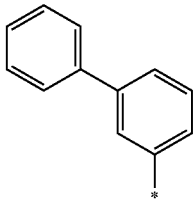
Formula 6-25 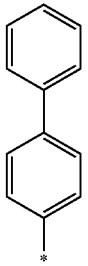
Formula 6-26 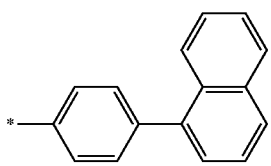
Formula 6-27 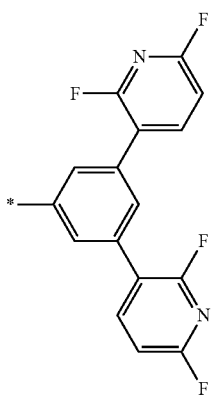
Formula 6-28 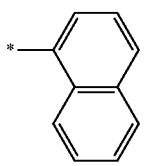
Formula 6-29 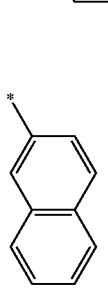

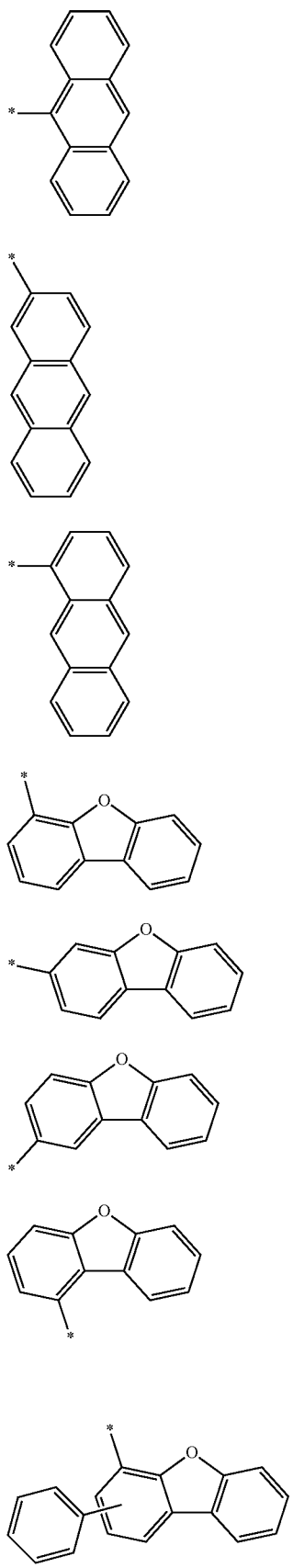
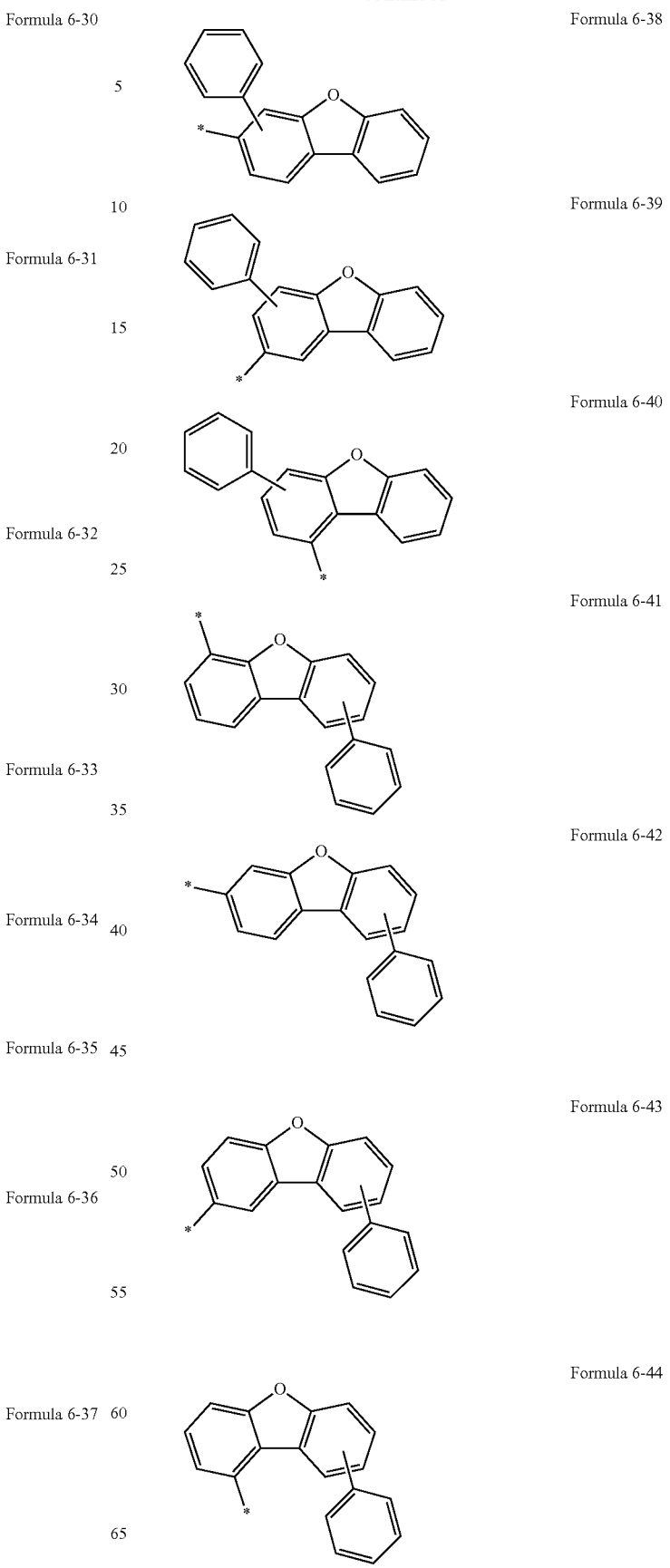

Formula 6-45
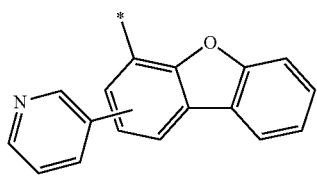
Formula 6-46
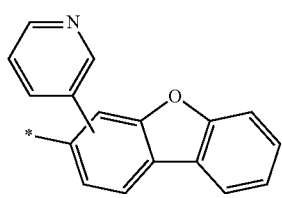
Formula 6-47
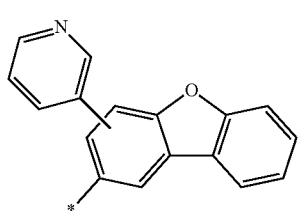
Formula 6-48
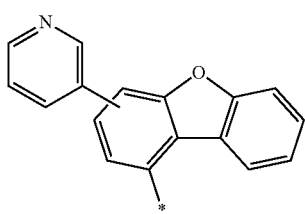
Formula 6-49
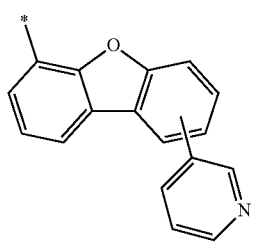
Formula 6-50
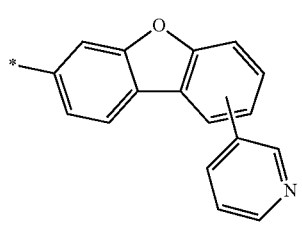
Formula 6-51
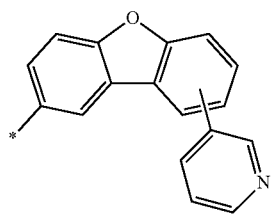
Formula 6-52
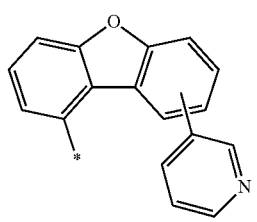
Formula 6-53
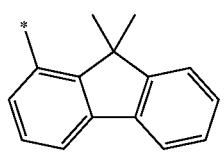
Formula 6-54
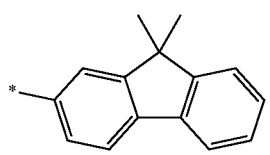
Formula 6-55
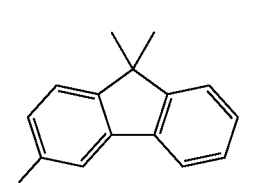
Formula 6-56
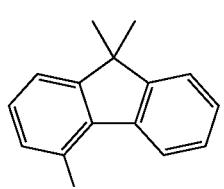
Formula 6-57
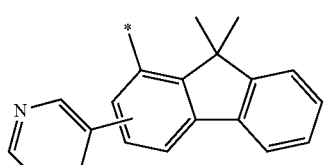
Formula 6-58
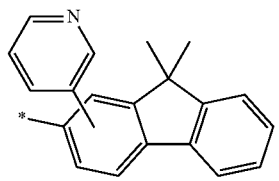
Formula 6-59

-continued
Formula 6-60
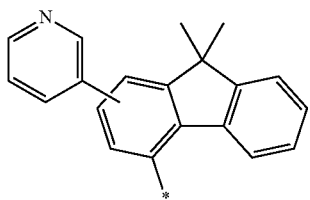
Formula 6-61
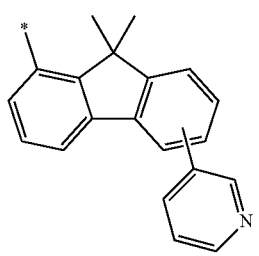
Formula 6-62
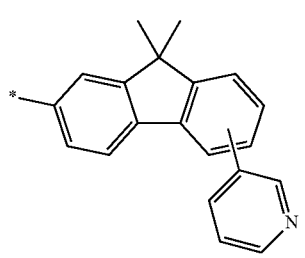
Formula 6-63
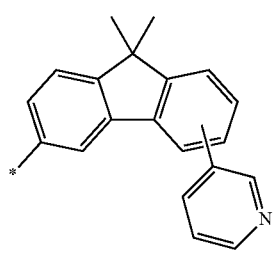
Formula 6-64
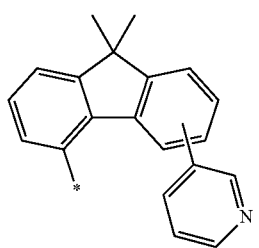
Formula 6-65
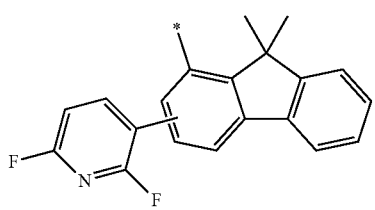
-continued
Formula 6-66
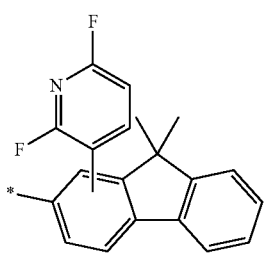
Formula 6-67
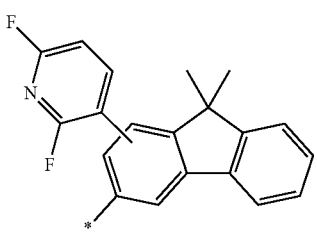
Formula 6-68
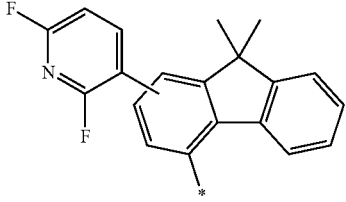
Formula 6-69
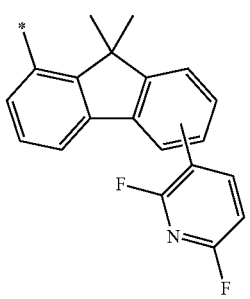
Formula 6-70
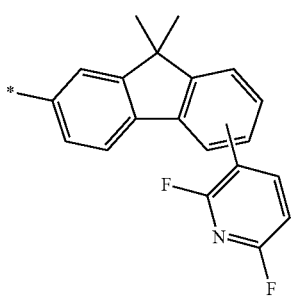
Formula 6-71
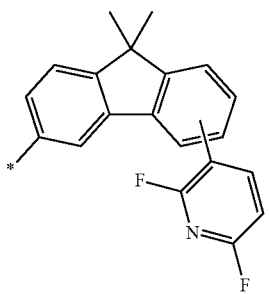

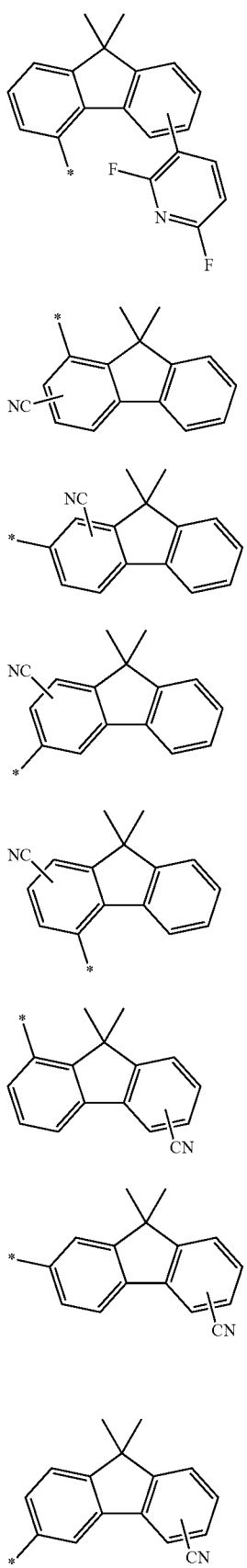
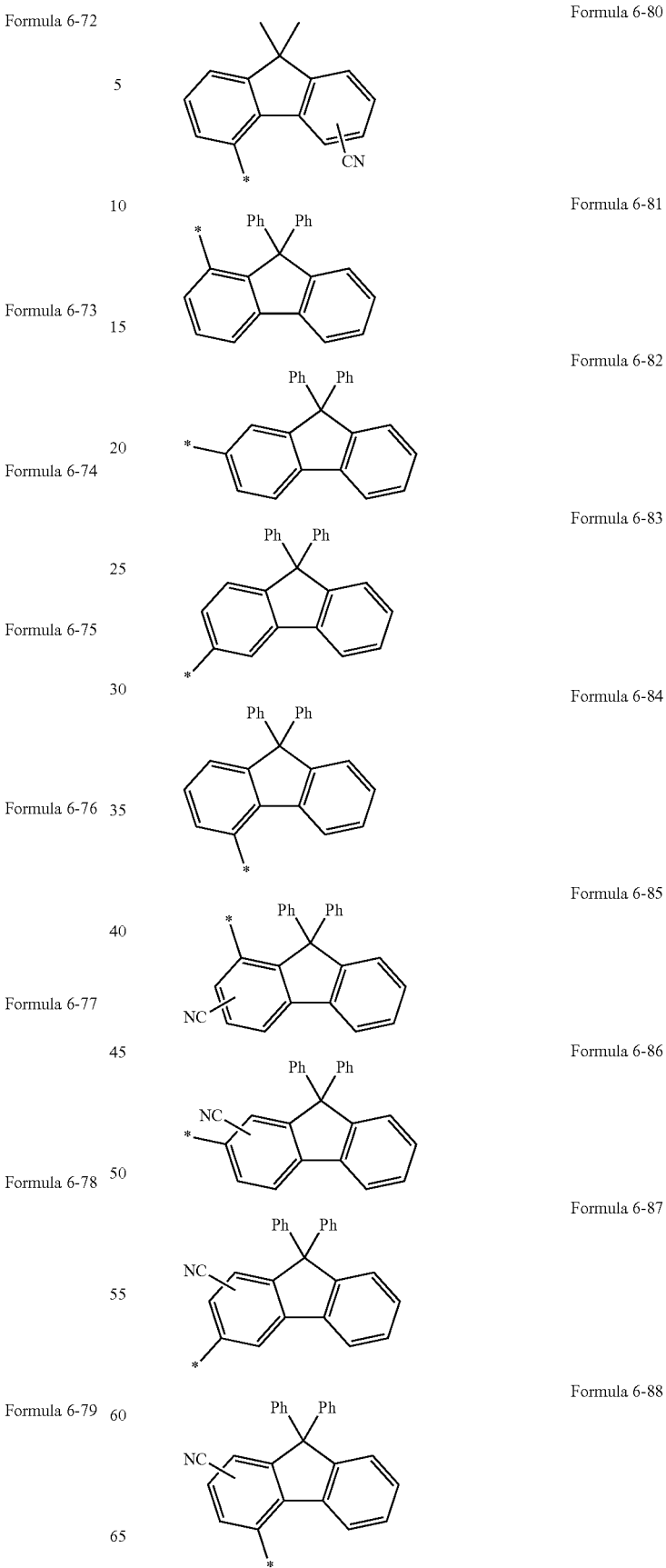
Formula 6-72
Formula 6-73
Formula 6-74
Formula 6-75
Formula 6-76
Formula 6-77
Formula 6-78
Formula 6-79
Formula 6-80
Formula 6-81
Formula 6-82
Formula 6-83
Formula 6-84
Formula 6-85
Formula 6-86
Formula 6-87
Formula 6-88

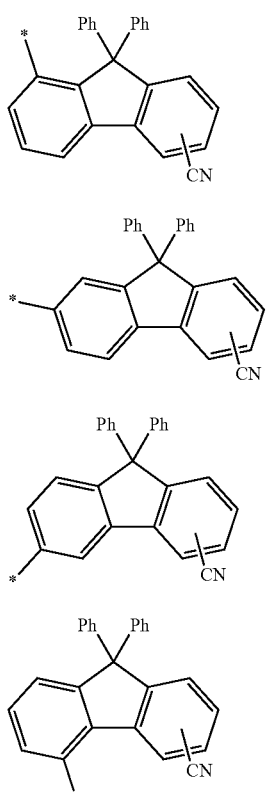
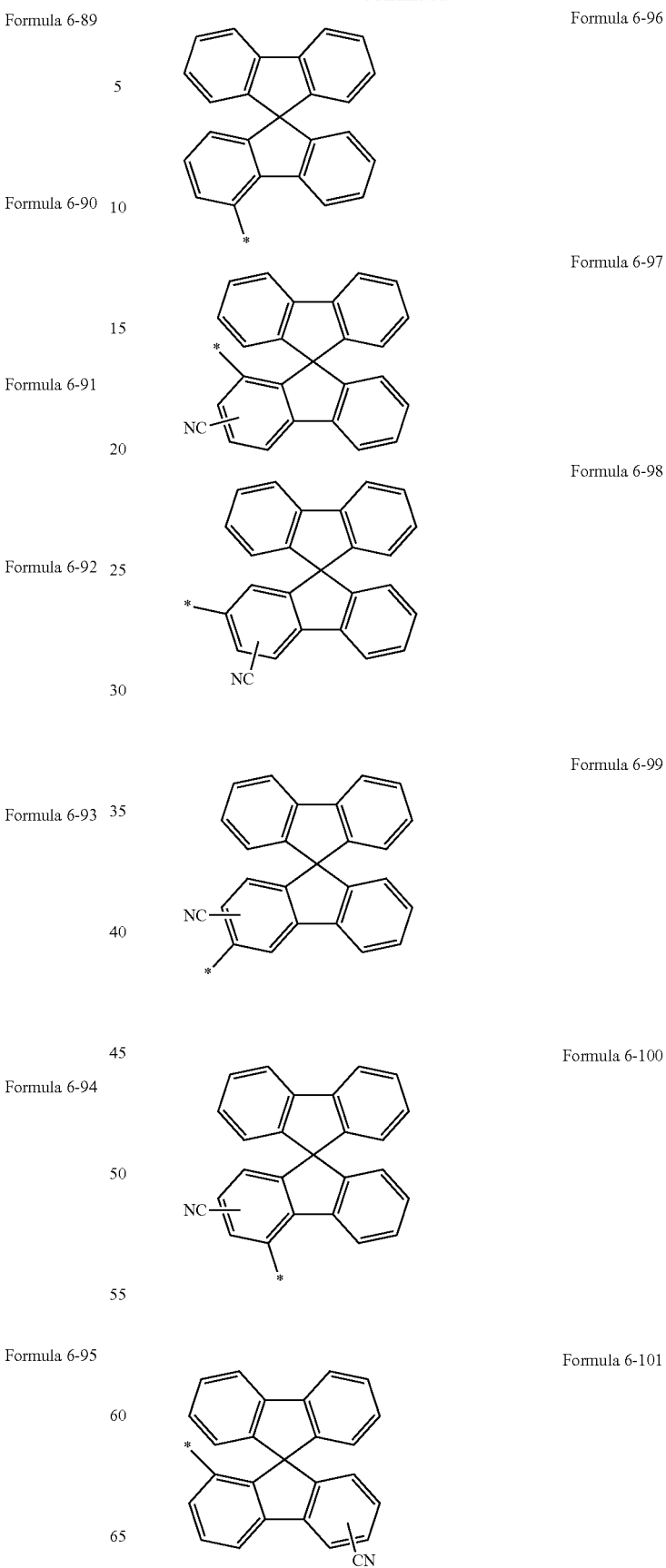
Formula 6-89
Formula 6-90
Formula 6-91
Formula 6-92
Formula 6-93
Formula 6-94
Formula 6-95
Formula 6-96
Formula 6-97
Formula 6-98
Formula 6-99
Formula 6-100
Formula 6-101

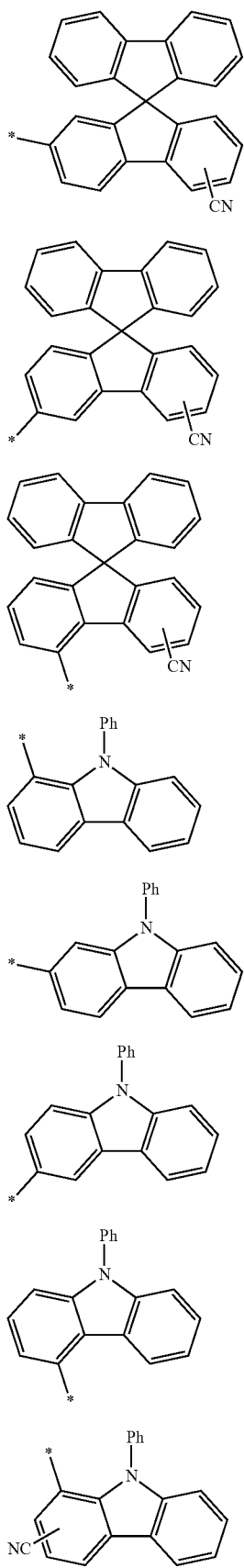
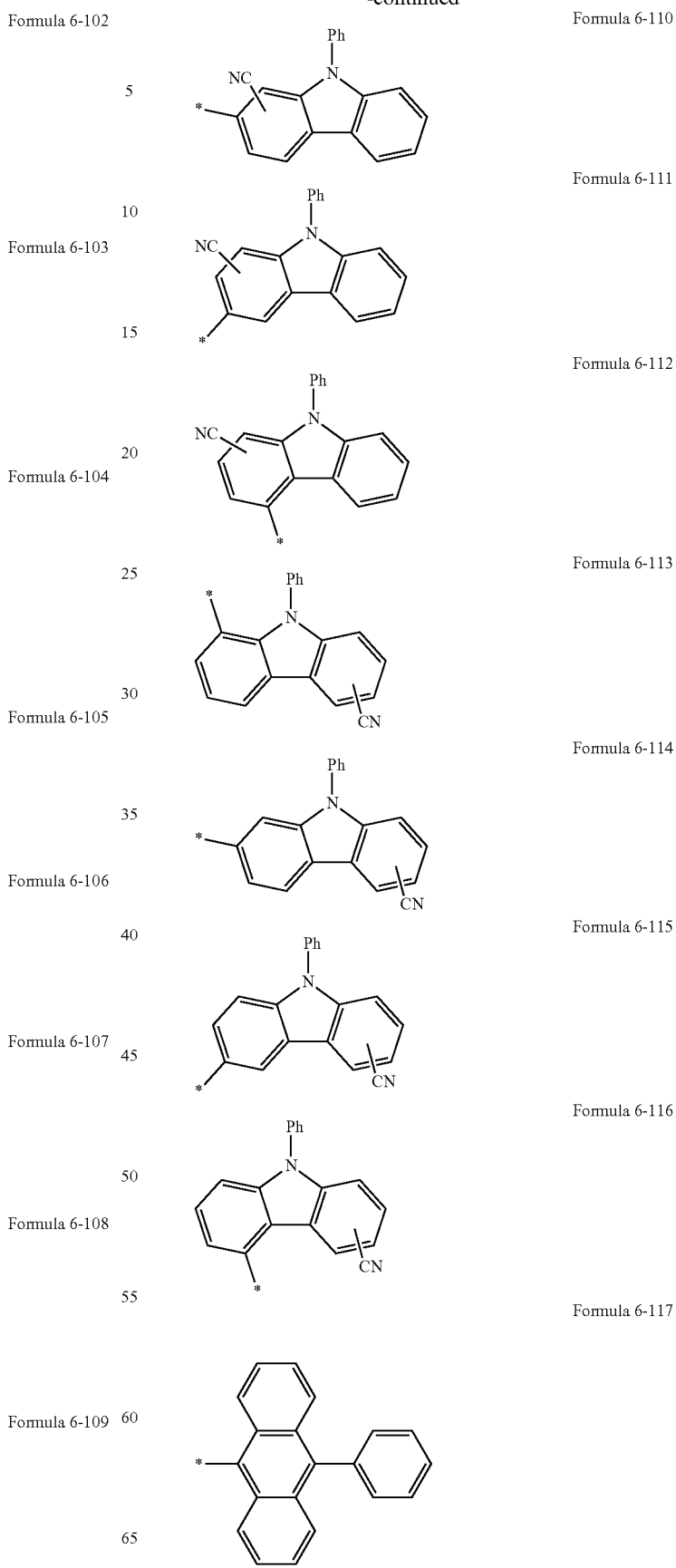

Formula 6-118
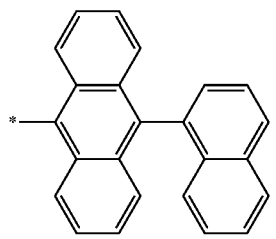
Formula 6-119
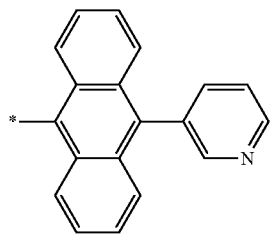
Formula 6-120
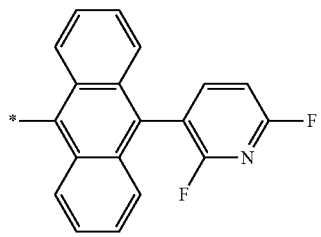
Formula 6-121
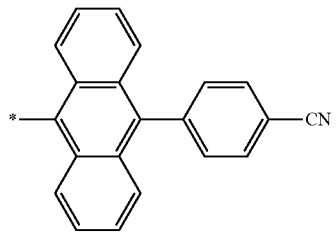
Formula 6-122
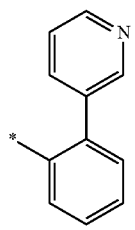
Formula 6-123
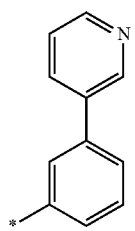
Formula 6-124
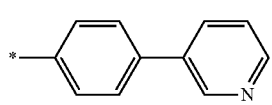
Formula 6-125
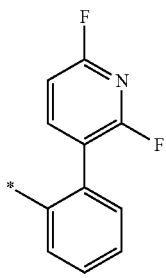
Formula 6-126
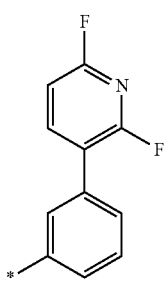
Formula 6-127
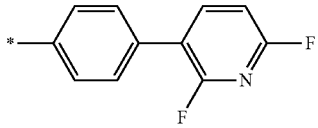
Formula 6-128
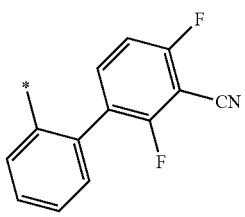
Formula 6-129
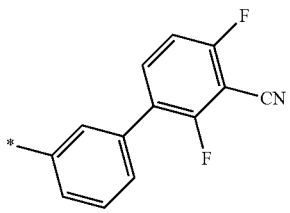
Formula 6-130
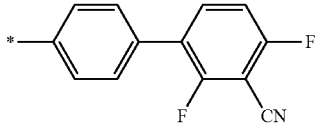
Formula 6-131
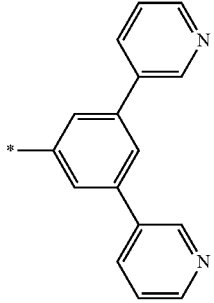

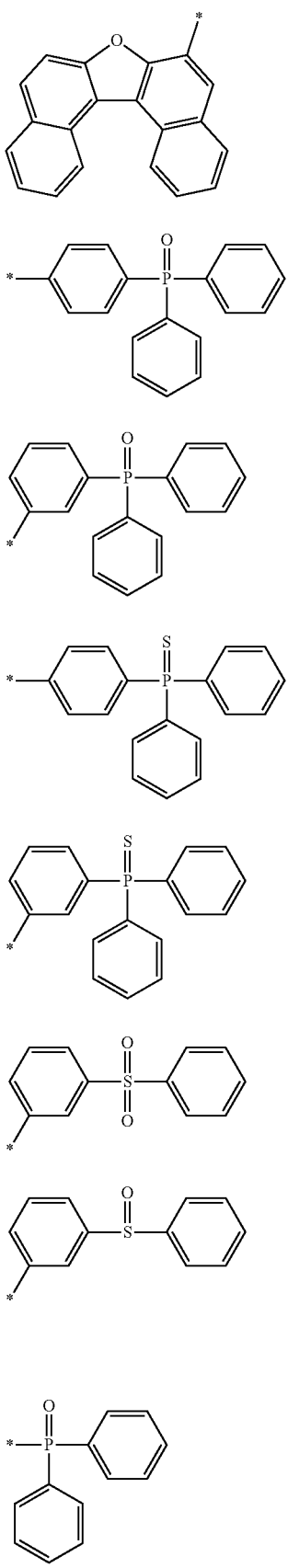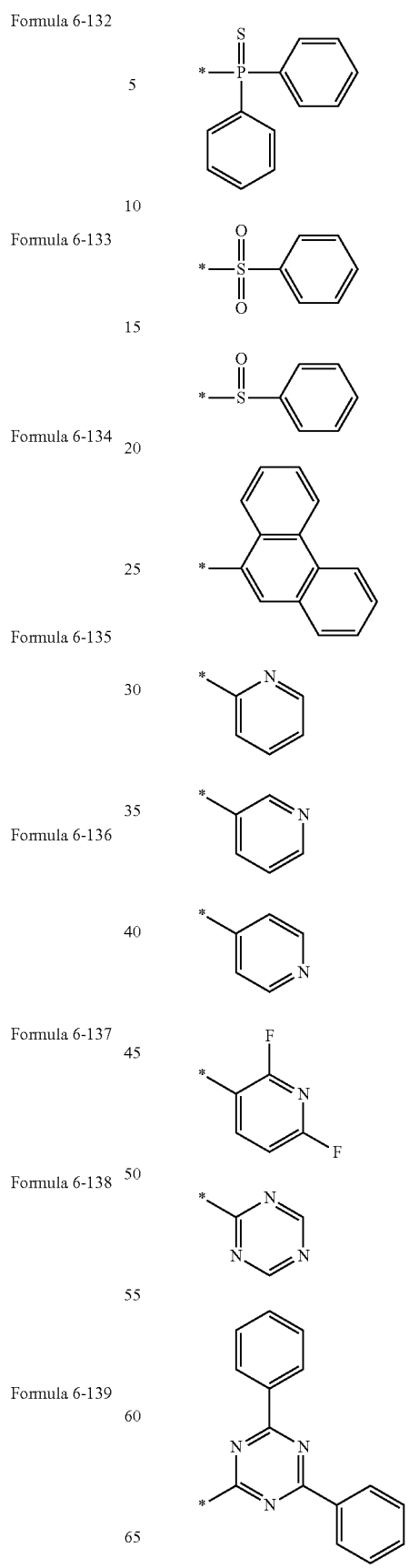

Formula 10-7

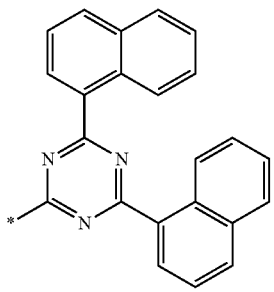

In Formulae 6-1 to 6-143 and 10-1 to 10-7, Ph refers to a phenyl group and * indicates a binding site to a neighboring atom.

According to an exemplary embodiment of the present invention, Ar₁ in Formula 2 may be selected from groups represented by Formulae 6-1, 6-13, 6-15, 6-16, 6-20 to 6-22, 6-25, 6-27, 6-34, 6-41, 6-49, 6-54, 6-62, 6-70, 6-78, 6-90, 6-102, 6-114, 6-115, 6-117 to 6-120, 6-123, 6-124, 6-126, 6-127, 6-129, 6-131, 6-132 to 6-143, 10-2, or 10-4 to 10-7; however, exemplary embodiments of the present invention are not limited thereto.

b1 in Formula 2 may indicate the number of Ar₁(s). b1 in Formula 2 may be an integer selected from 1 to 4. When b1 is 2 or greater, at least two Ar₁(s) may be the same or different from each other.

According to an exemplary embodiment of the present invention, the condensed cyclic compound represented by Formula 1 may be selected from Compounds 1 to 155; however, exemplary embodiments of the present invention are not limited thereto.

1
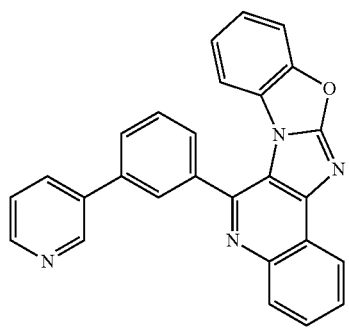

2
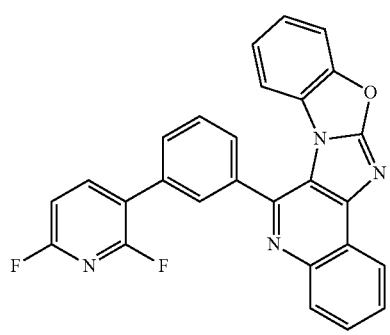

3
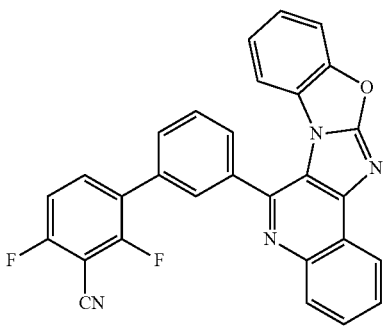

4
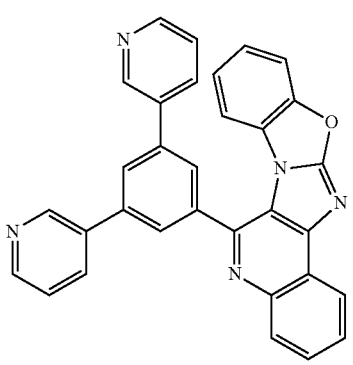

5
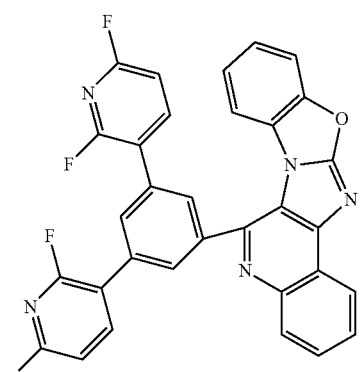

6
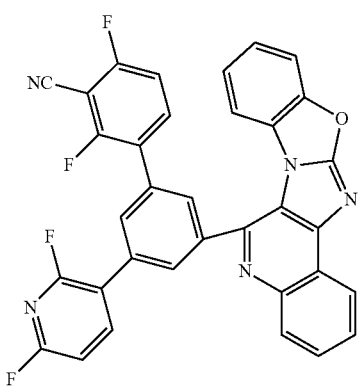

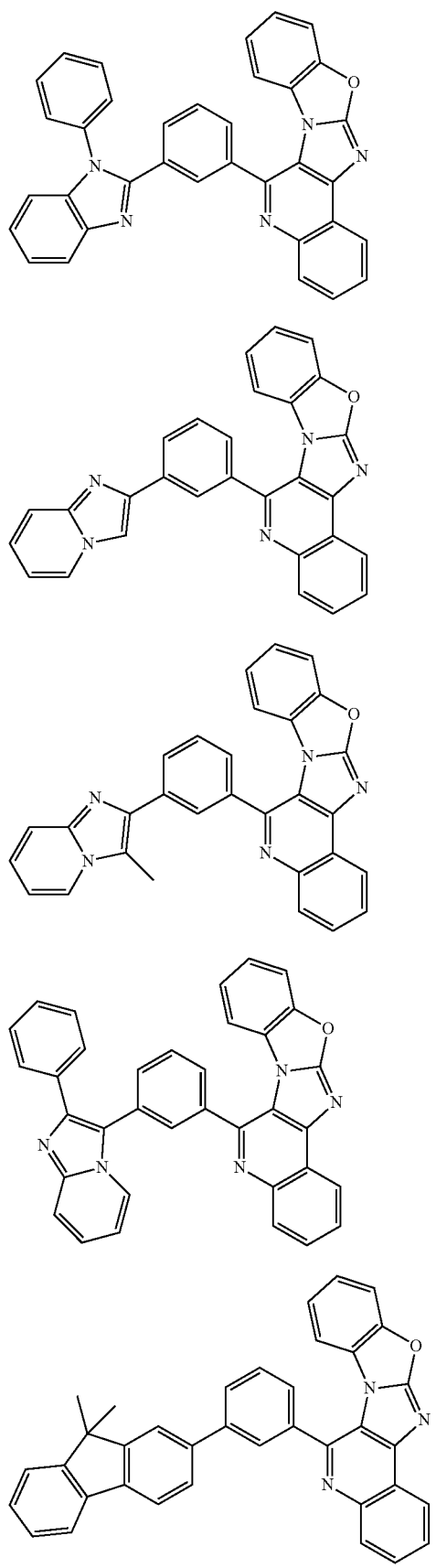
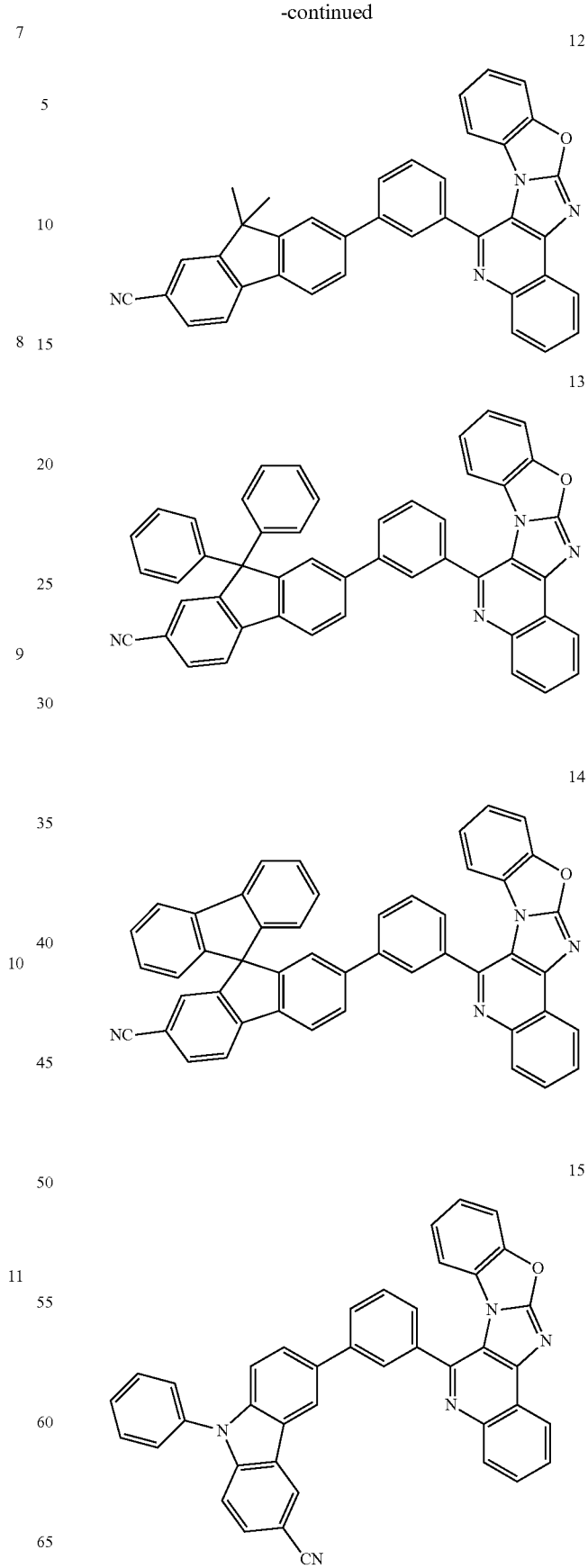

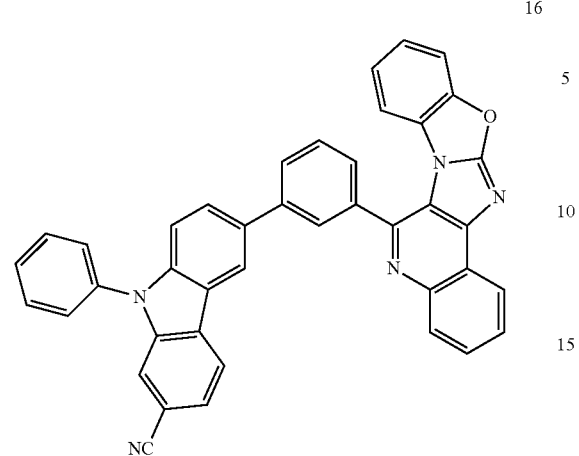
16
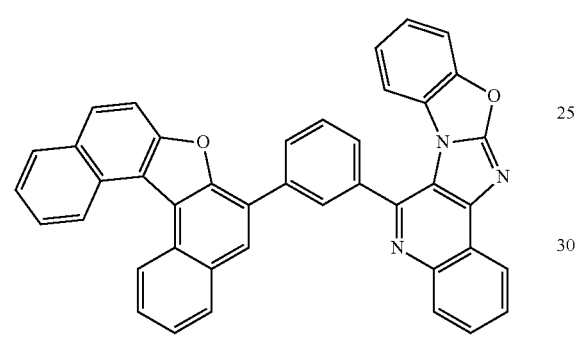
17
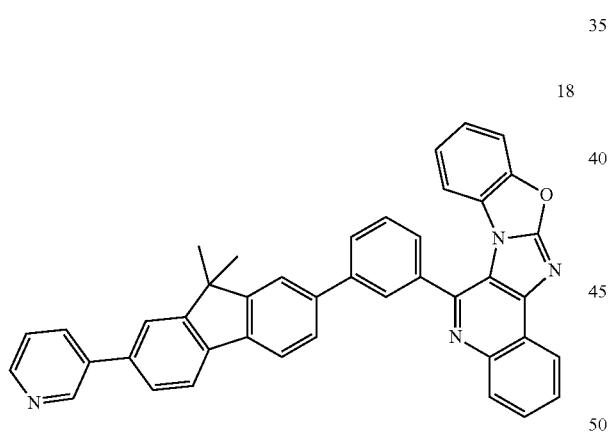
18
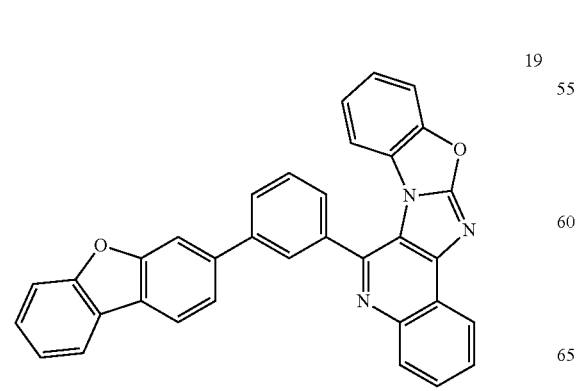
19
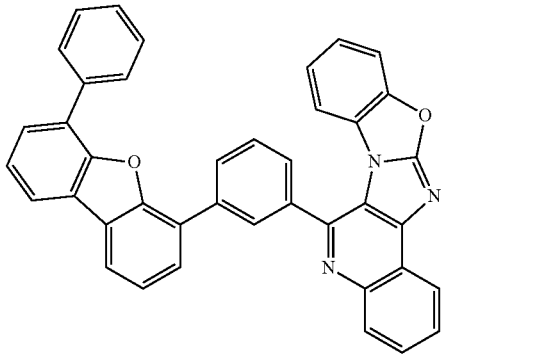
20
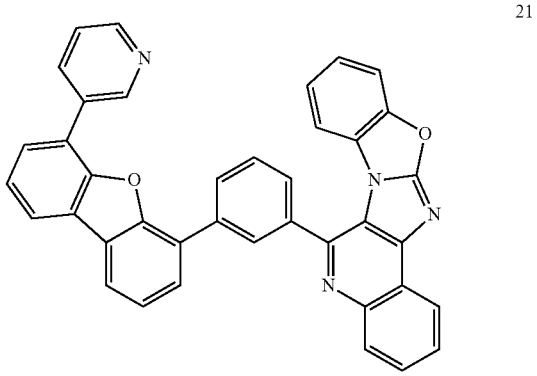
21
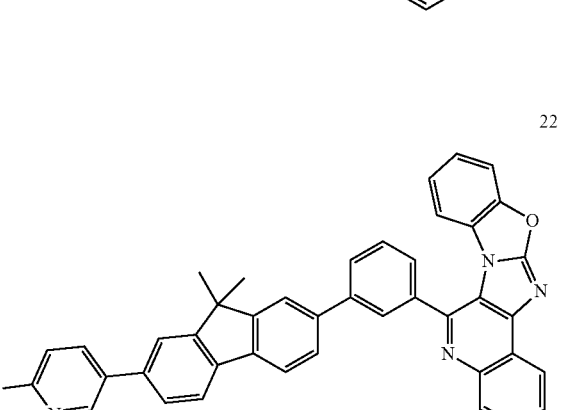
22
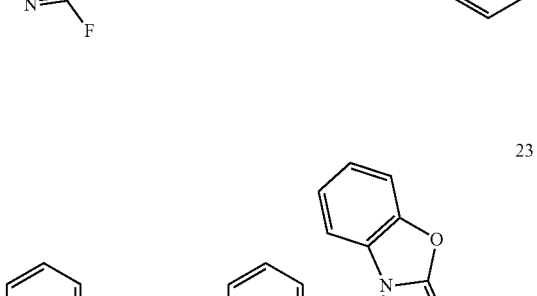
23
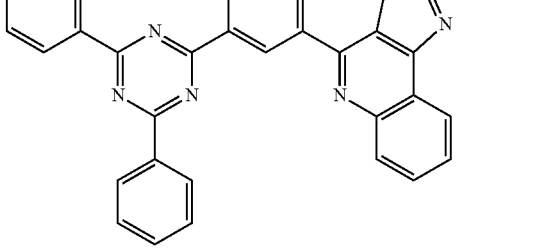

24
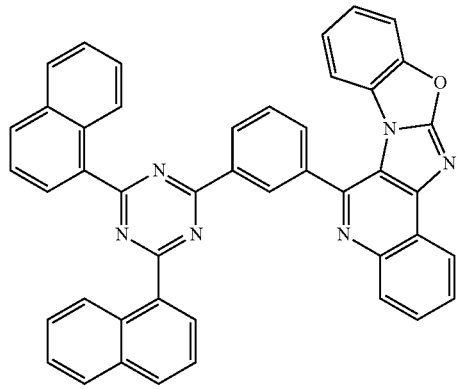
25
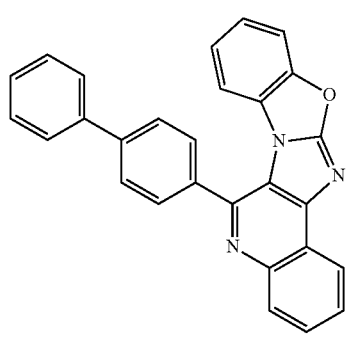
26
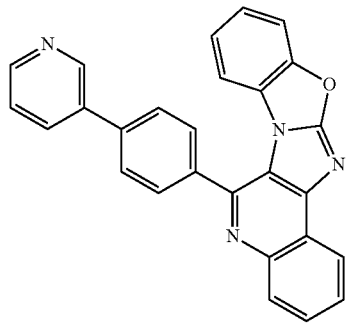
27
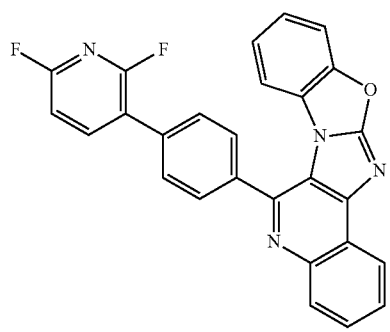
28
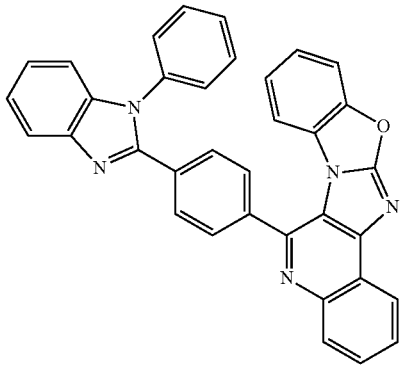
29
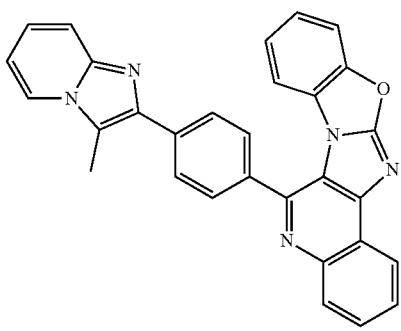
30
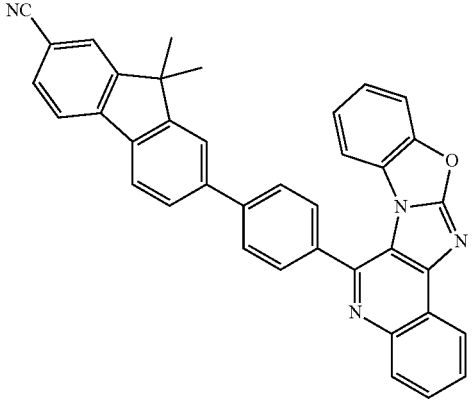
31
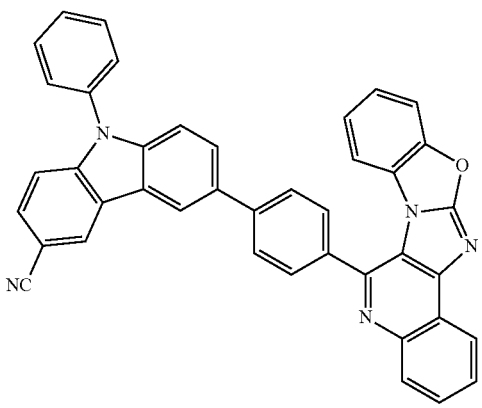

32
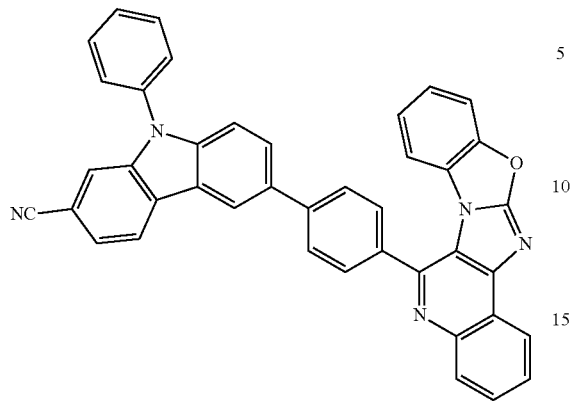
33
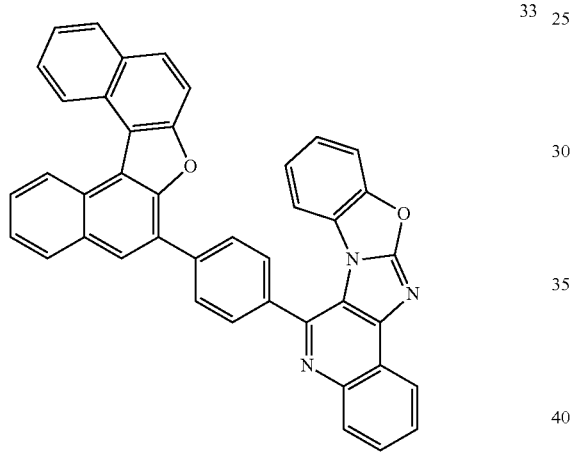
34
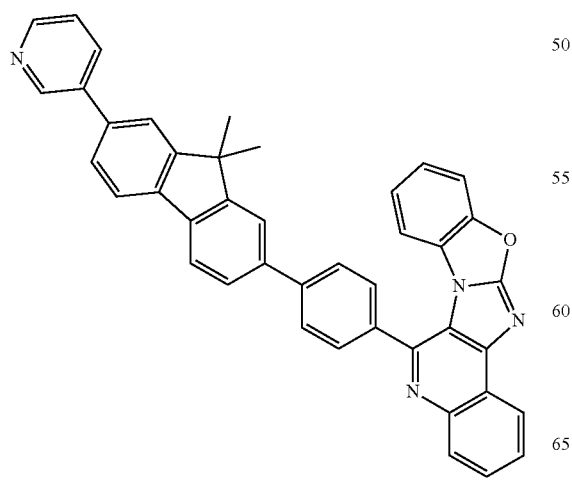
35
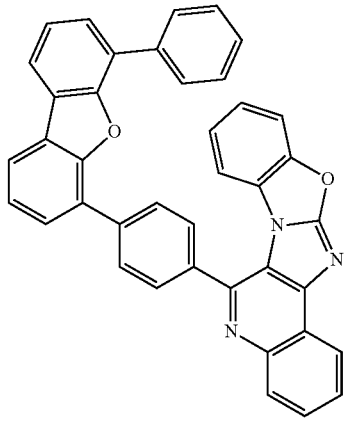
36
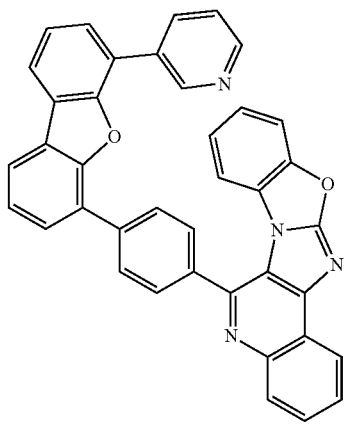
37
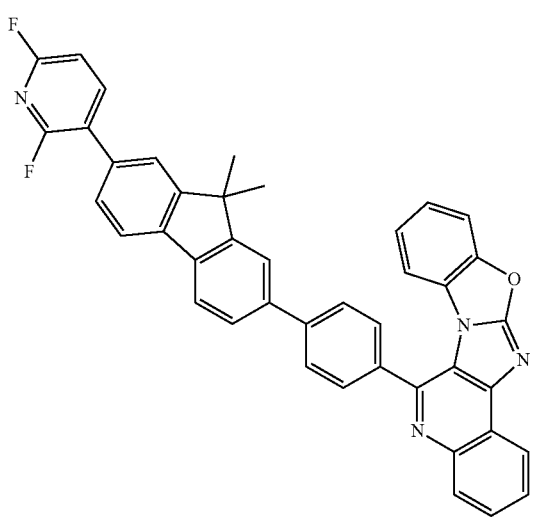

38
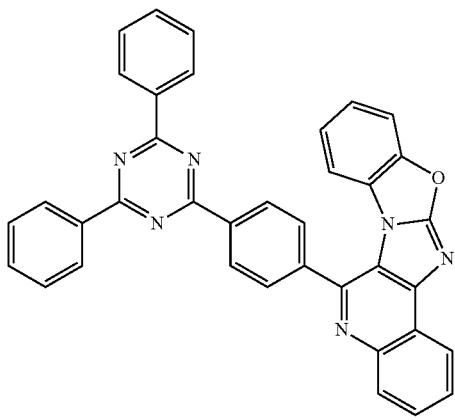
39
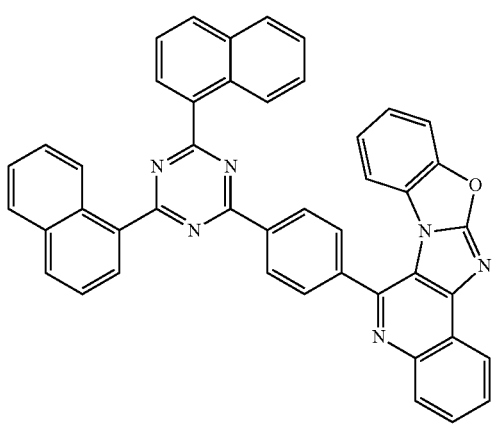
40
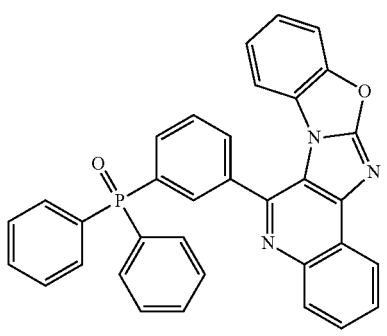
41
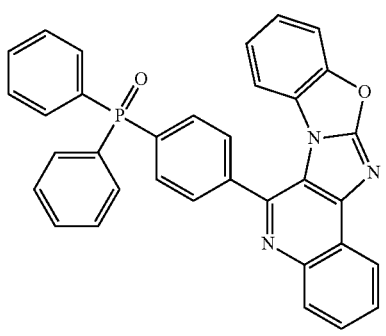
42
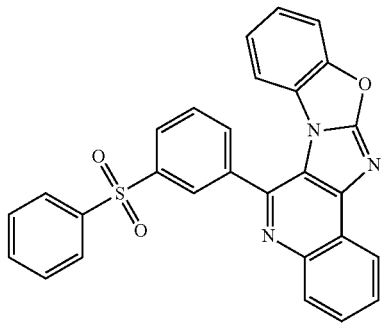
43
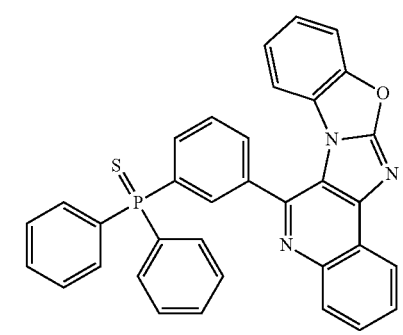
44
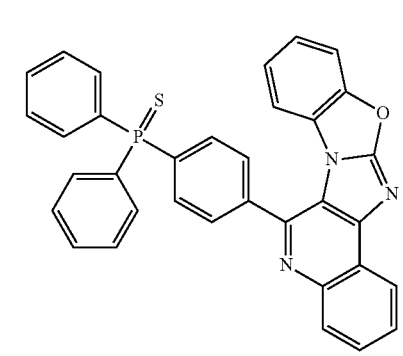
45
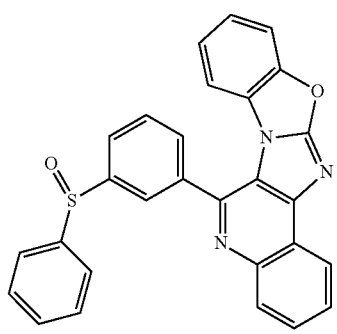

46
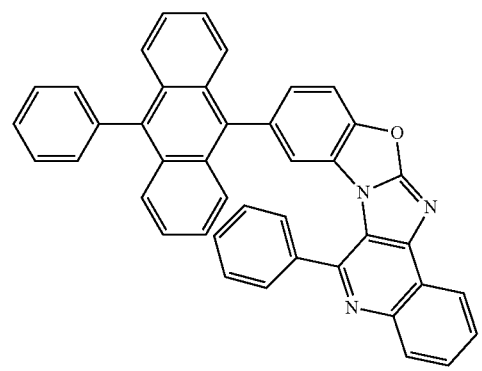
47
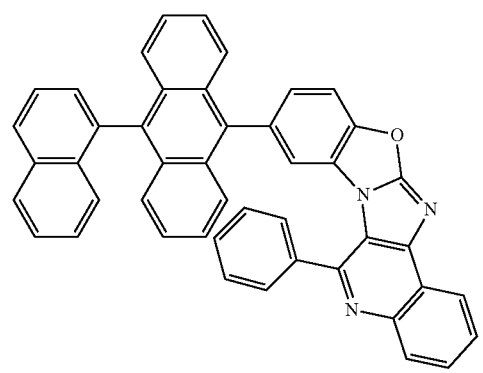
48
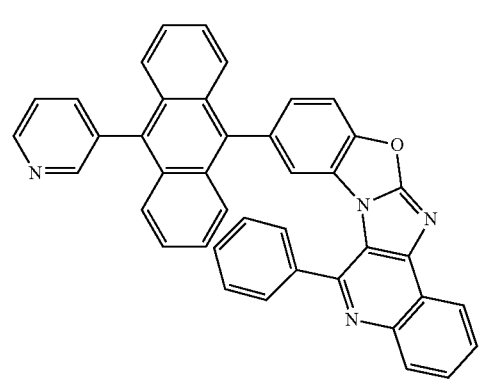
49
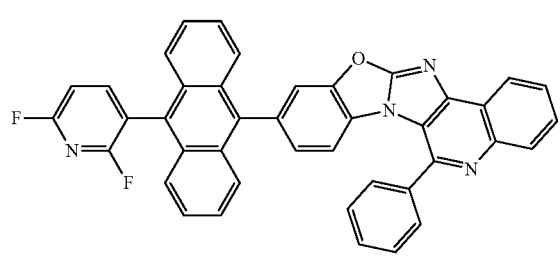
50
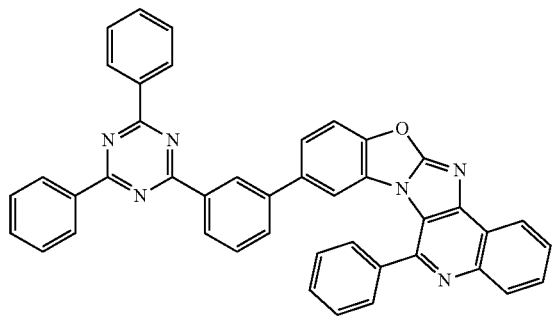
51
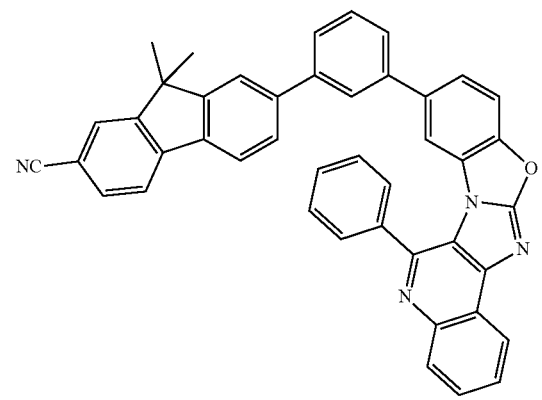
52
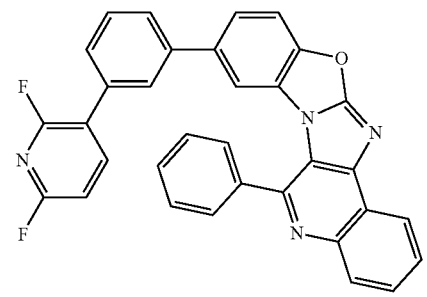
53
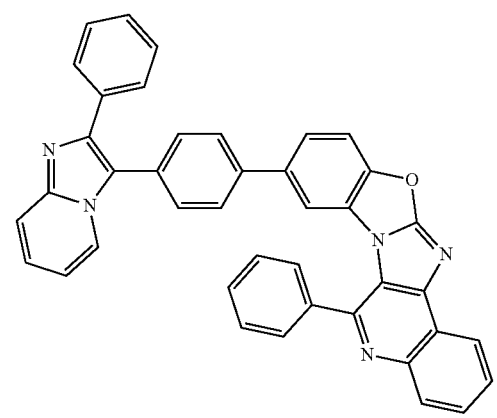

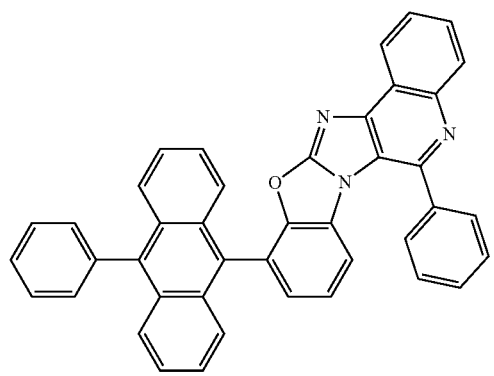
54
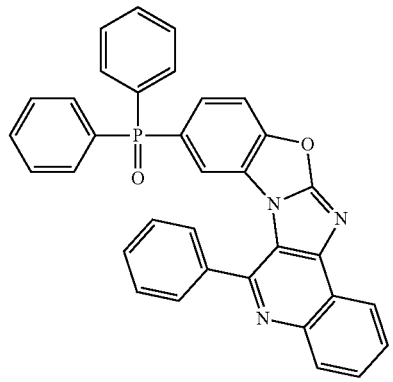
58
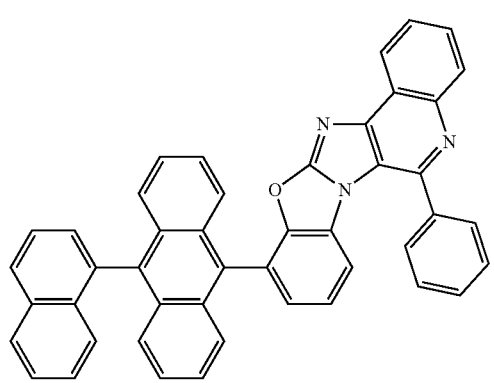
55
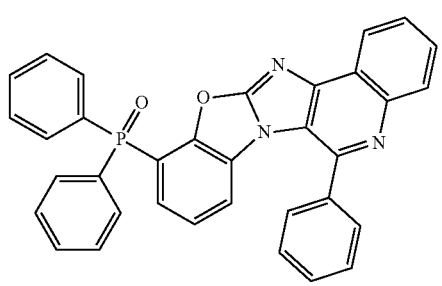
59
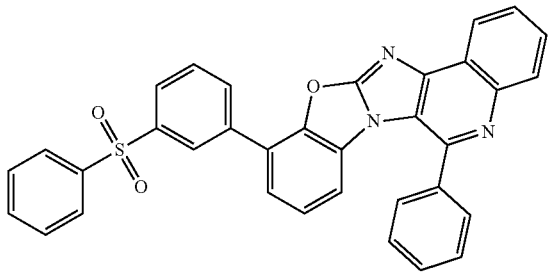
60
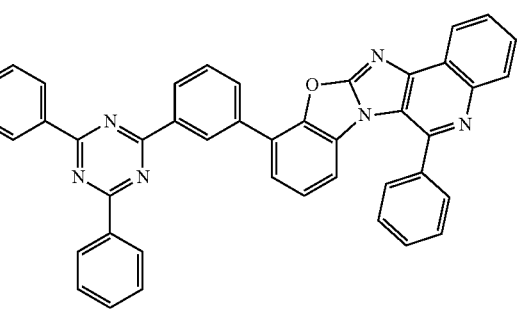
56
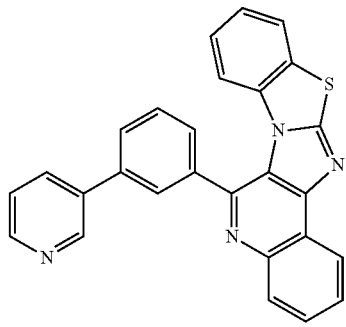
61
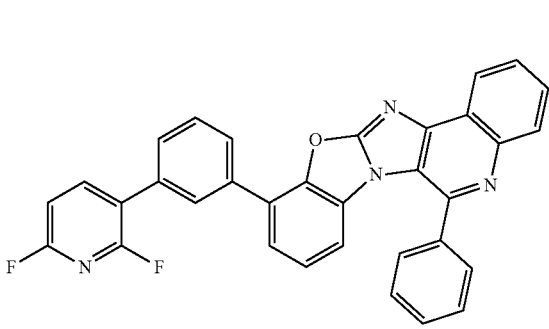
57
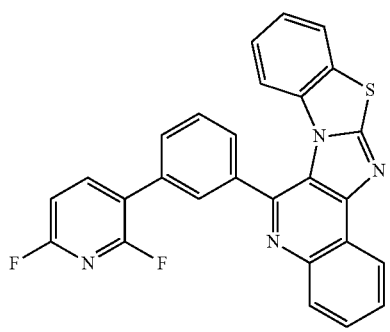
62

-continued
63
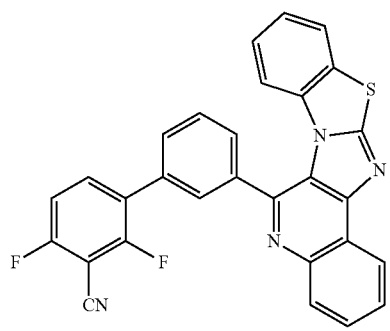
64
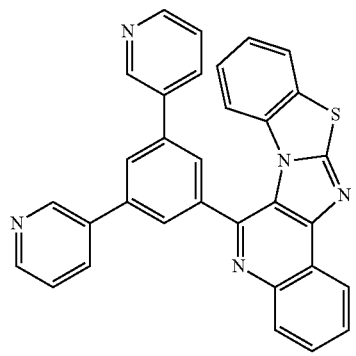
65
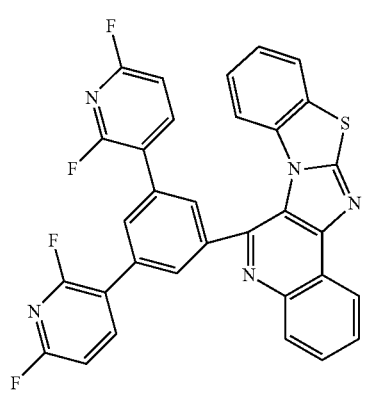
66
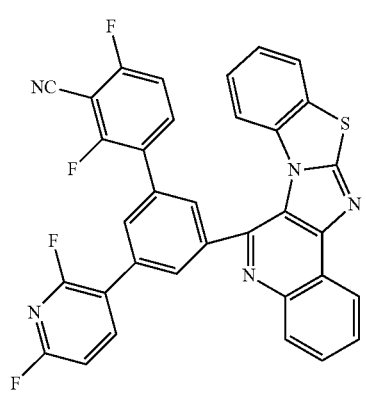
-continued
67
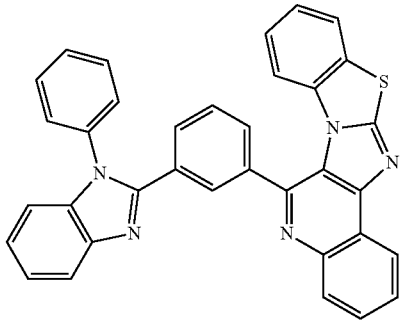
68
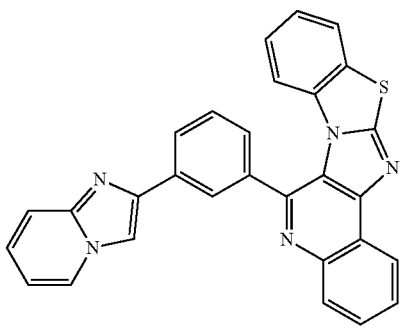
69
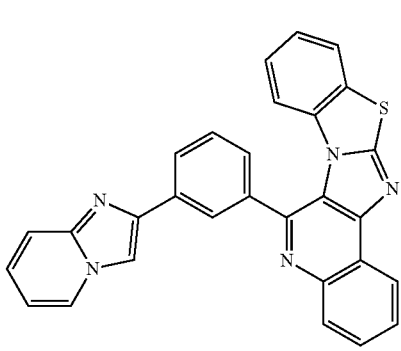
70
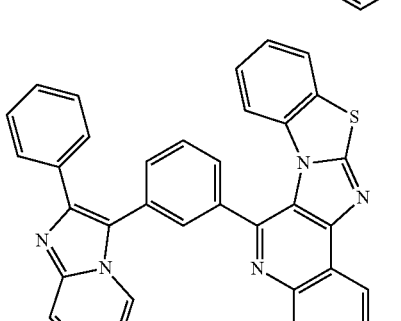
71
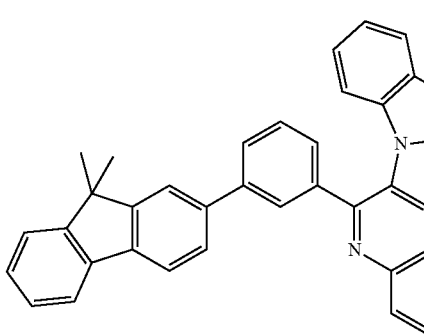

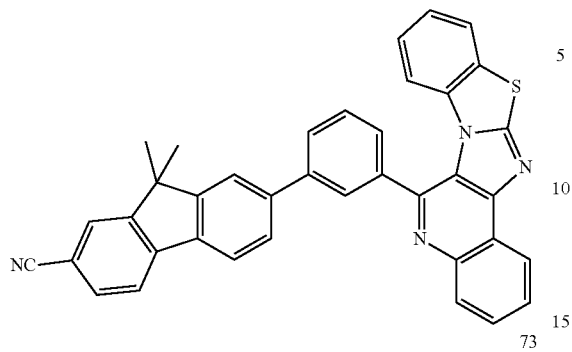
72
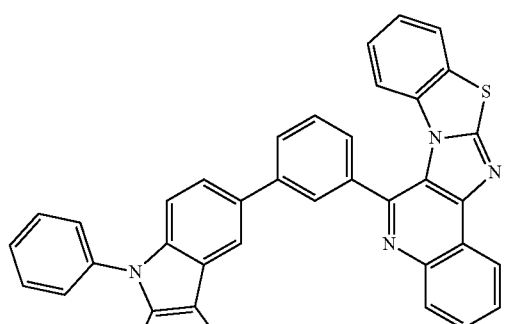
76
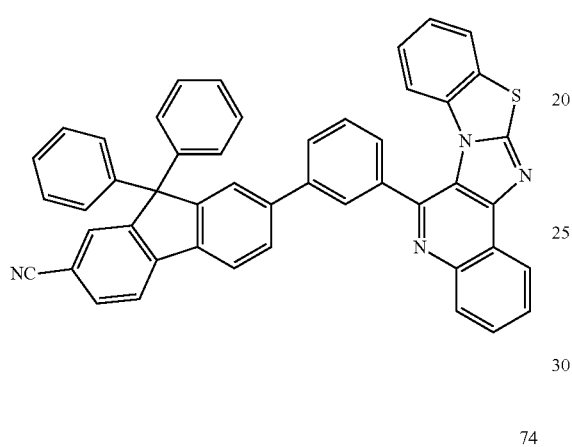
73
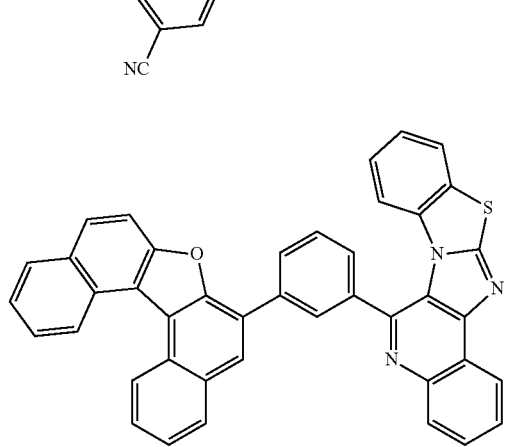
77
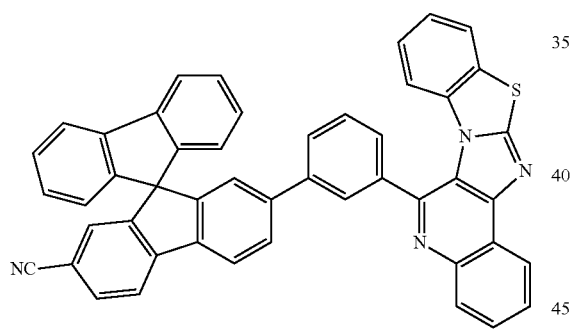
74
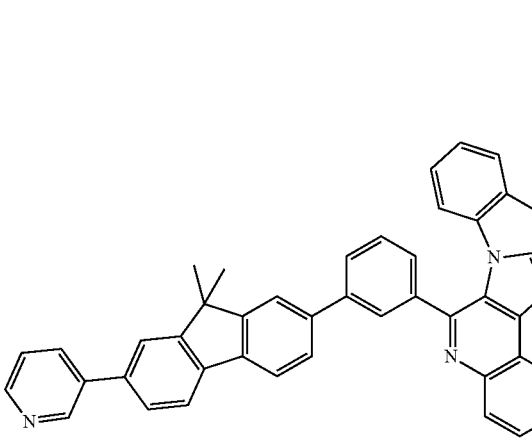
78
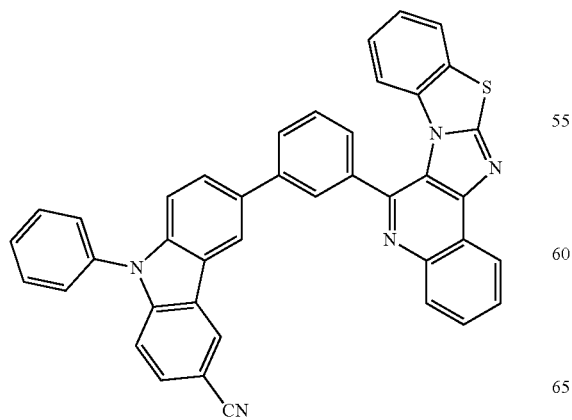
75
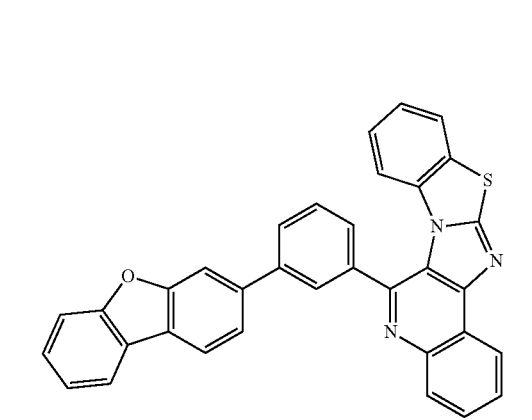
79

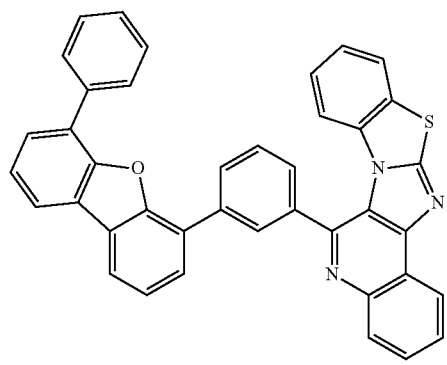
80
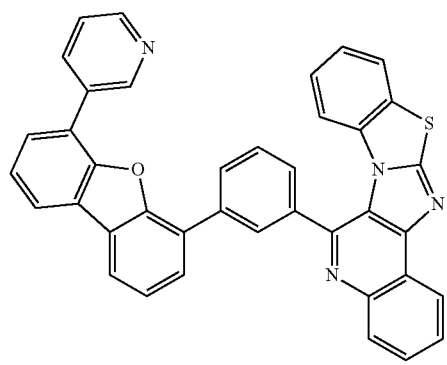
81
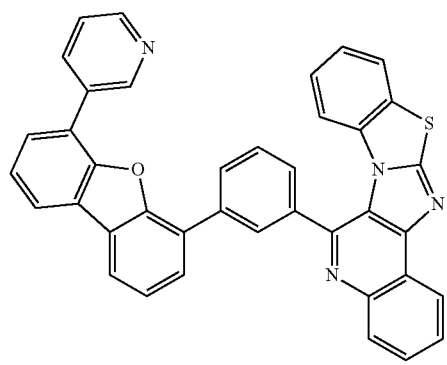
82
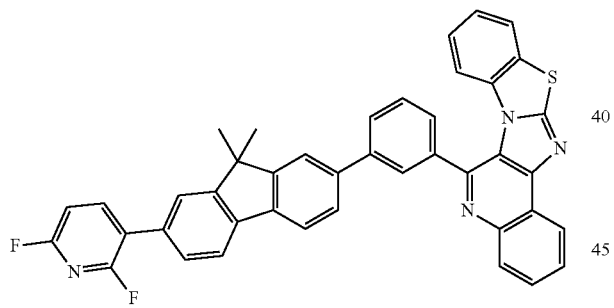
83
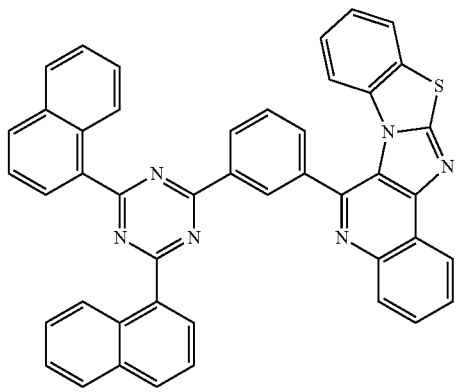
84
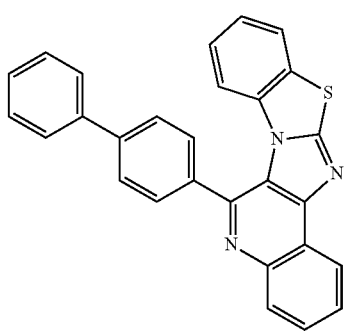
85
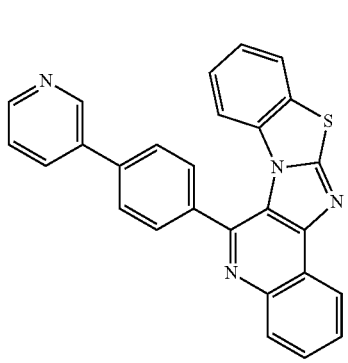
86
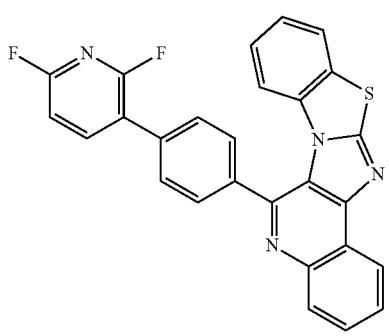
87

88
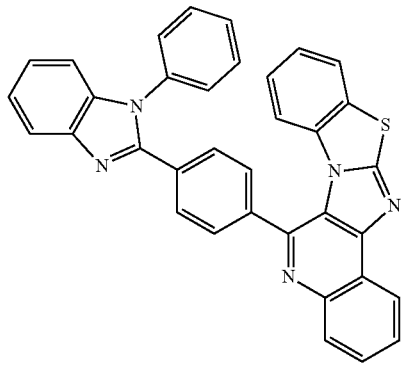
89
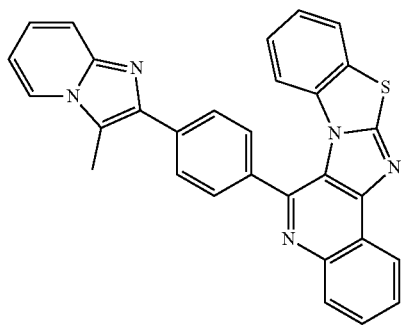
90
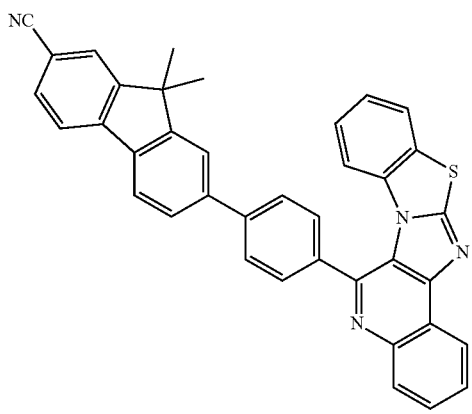
91
92
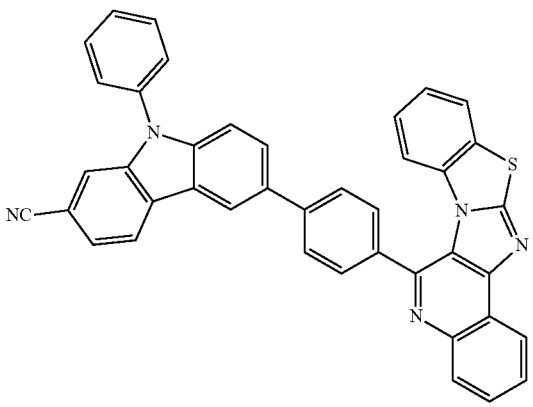
93
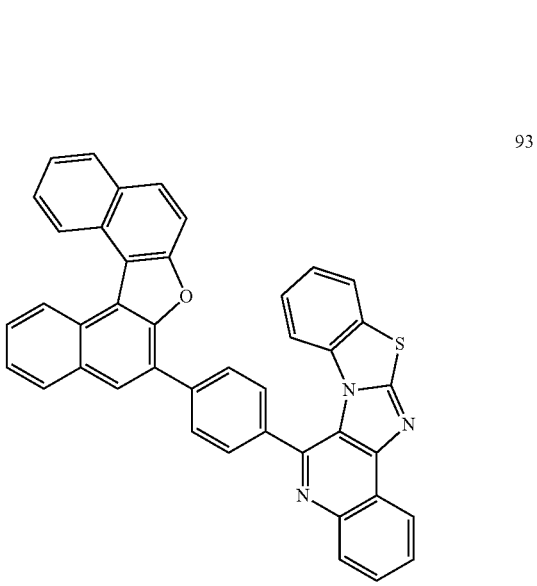
94
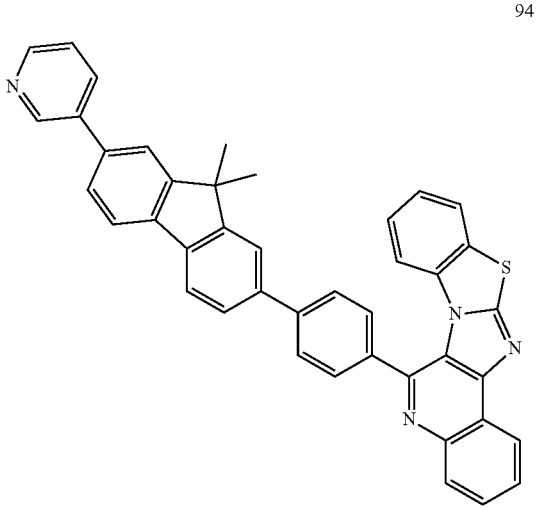

95
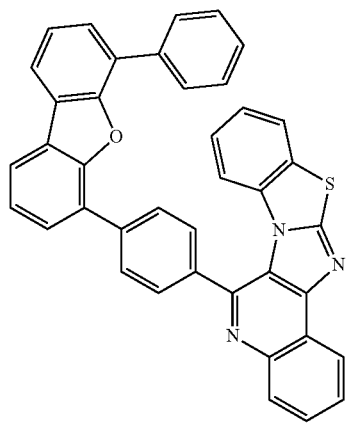
96
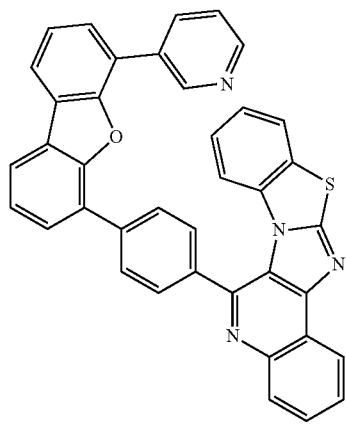
97
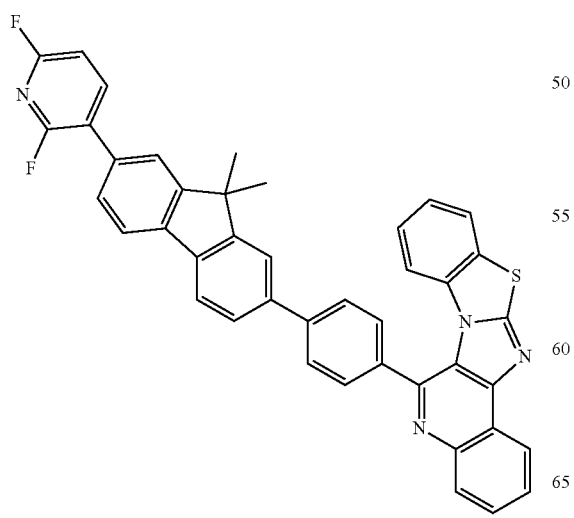
99
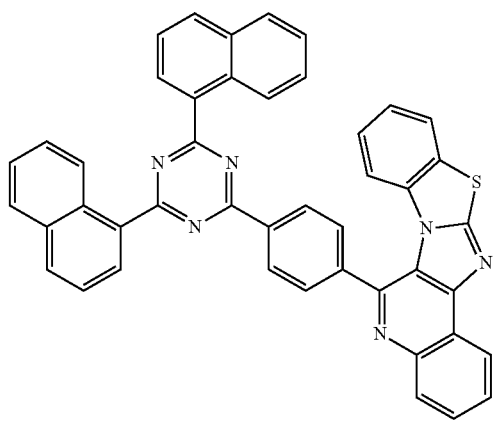
100
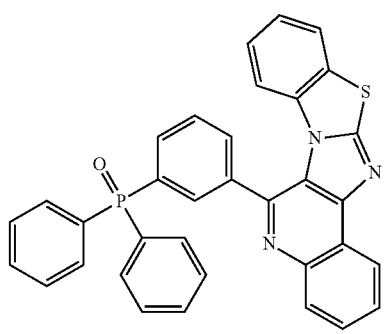
101
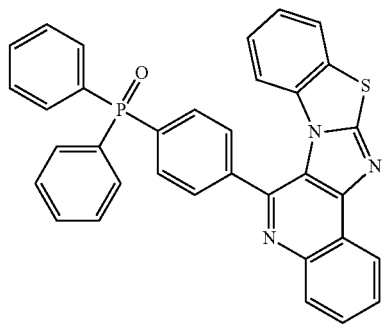
102
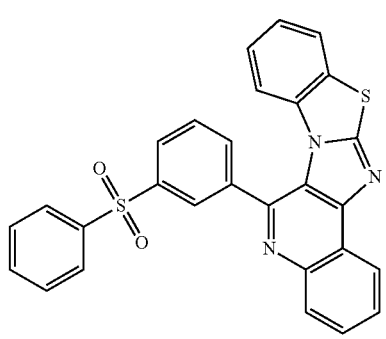

103
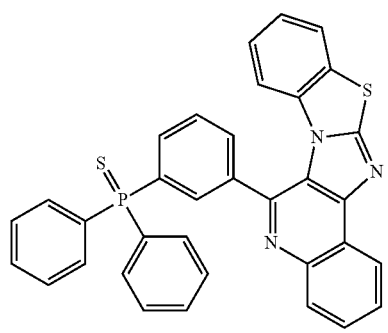
104
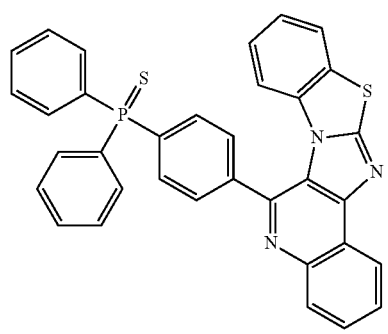
105
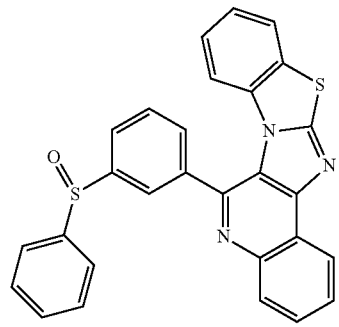
106
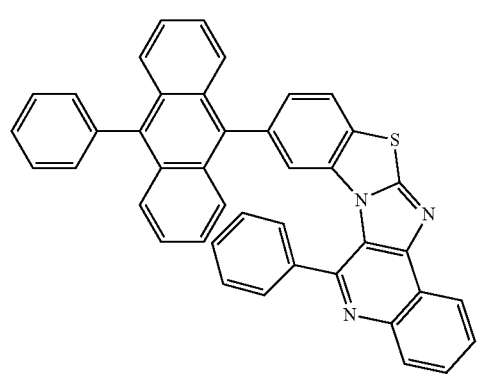
107
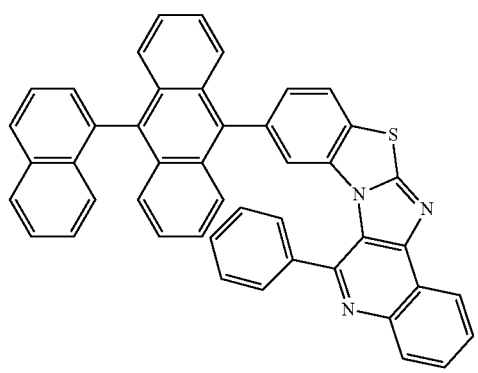
108
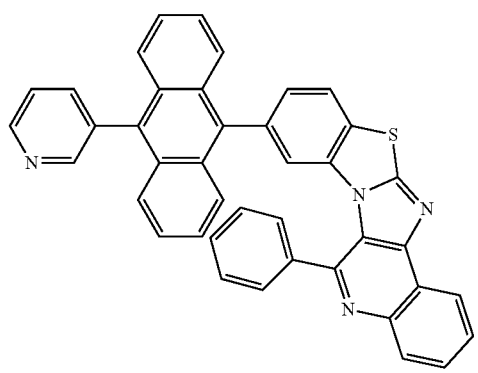
109
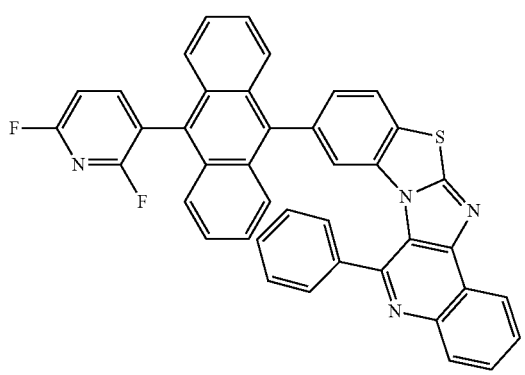
110
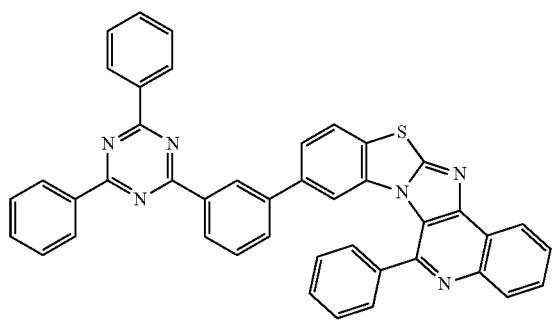

111
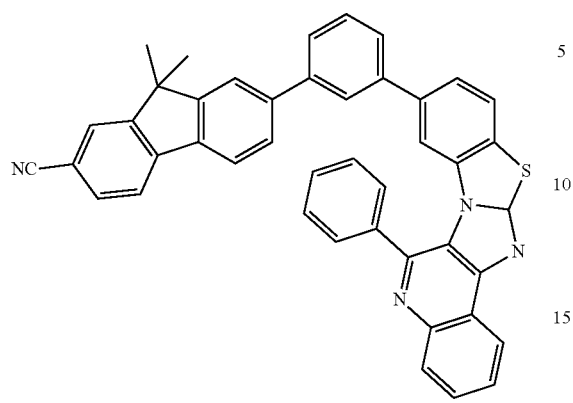
112
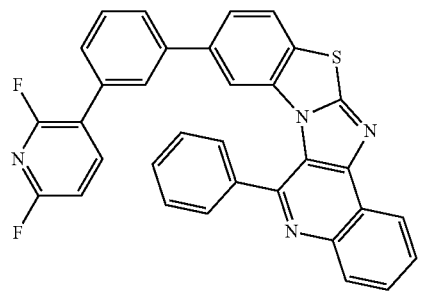
113
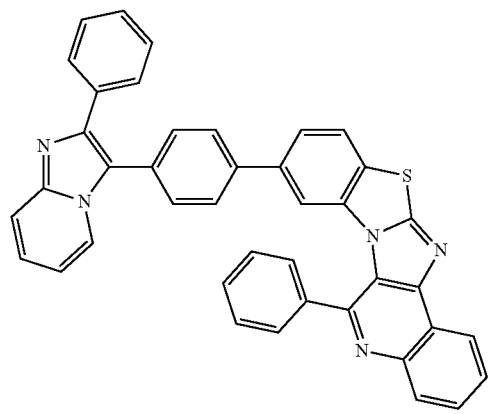
114
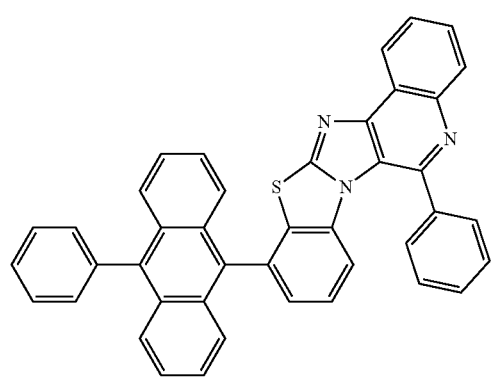
115
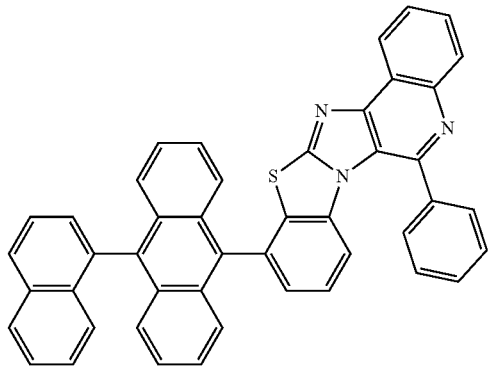
116
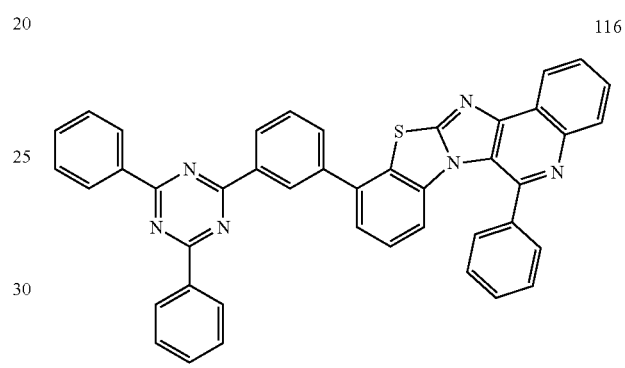
117
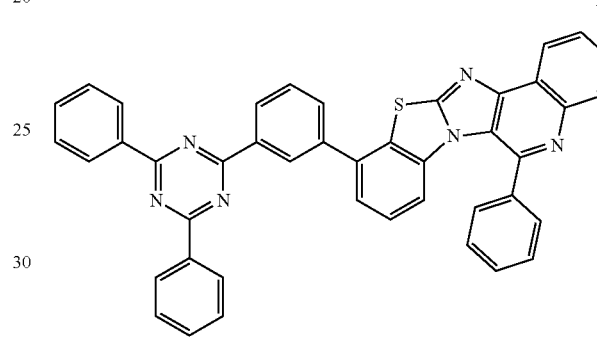
118
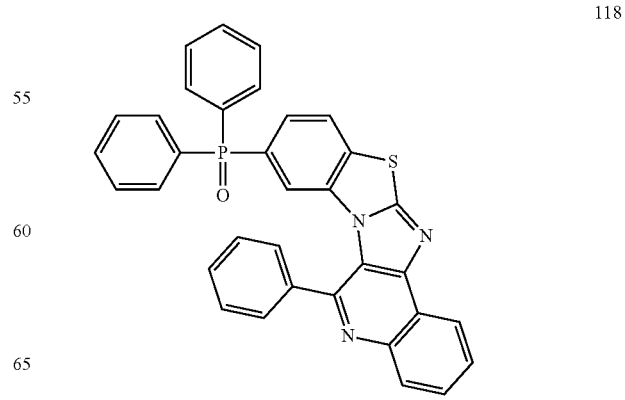

-continued
119
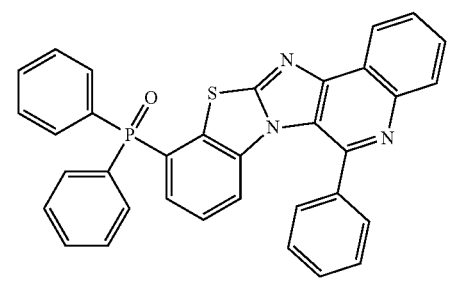
120
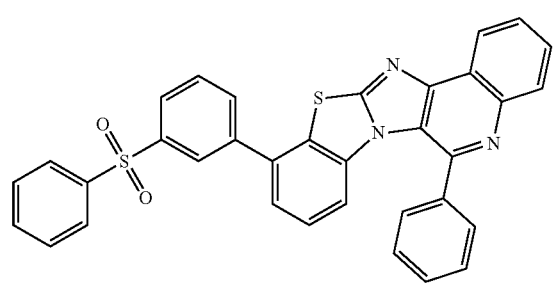
121
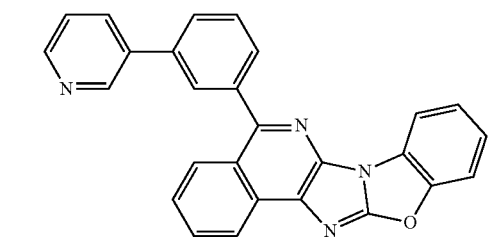
122
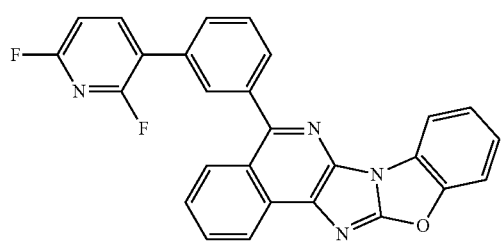
123
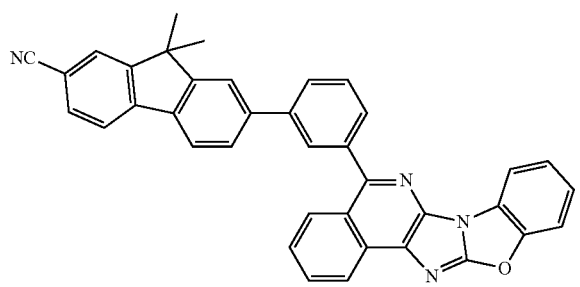
-continued
124
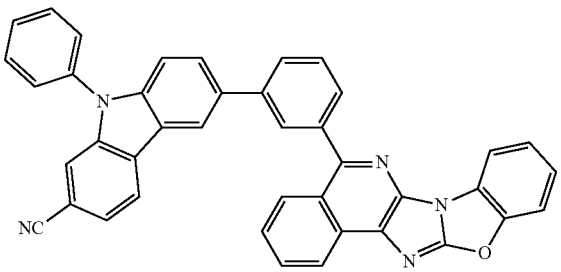
125
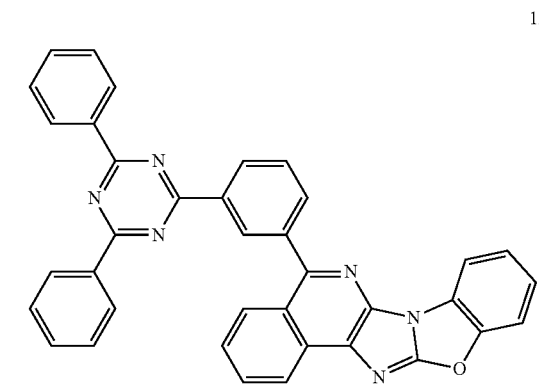
126
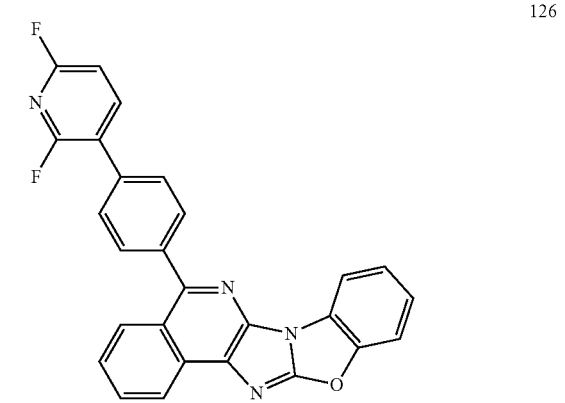
127
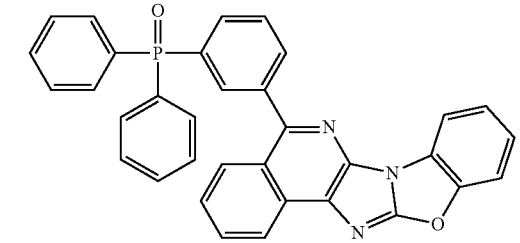
128
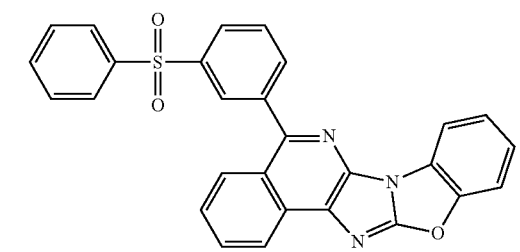

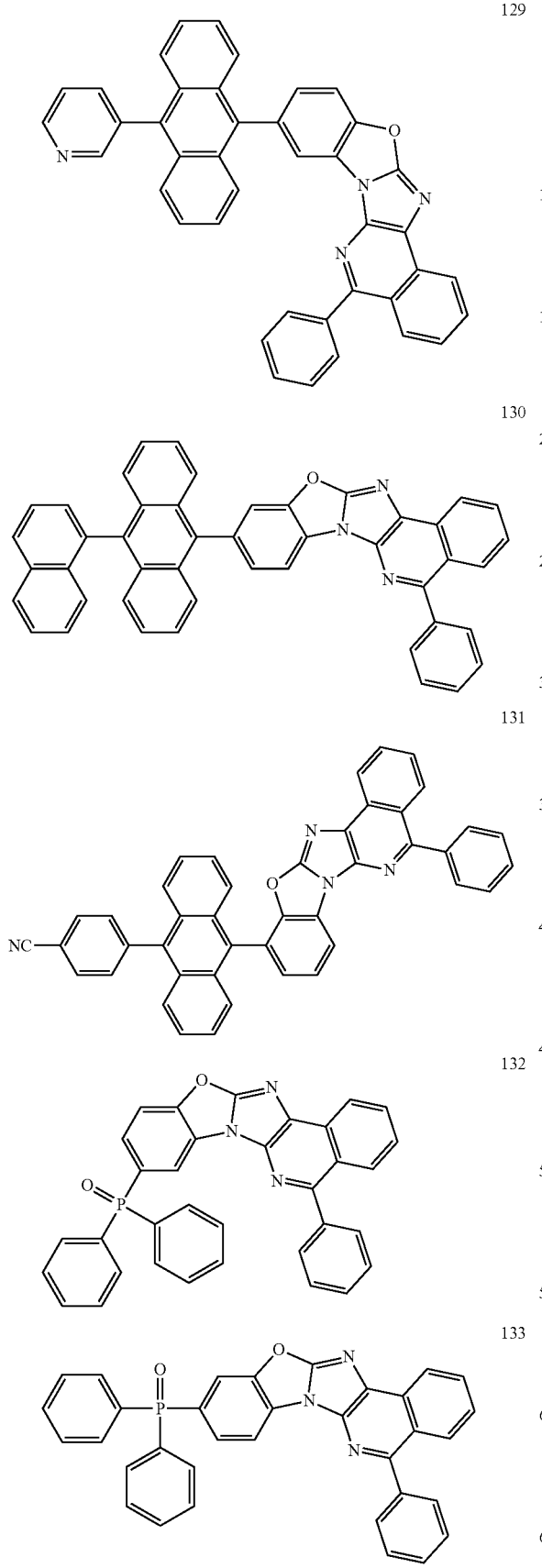
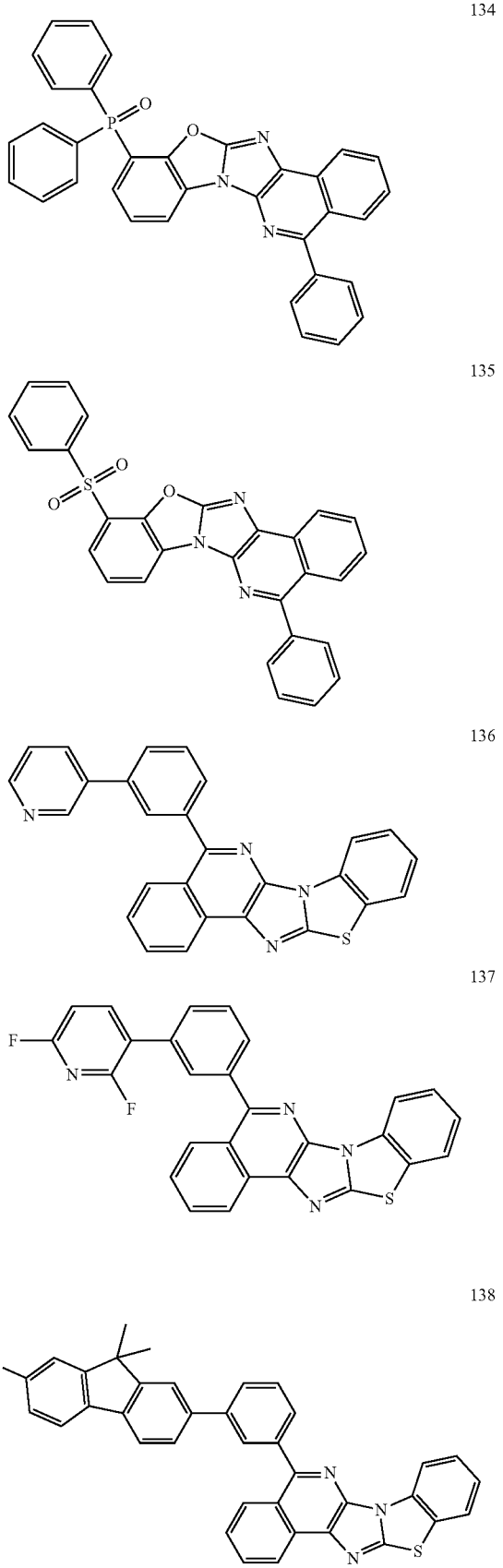

-continued
139
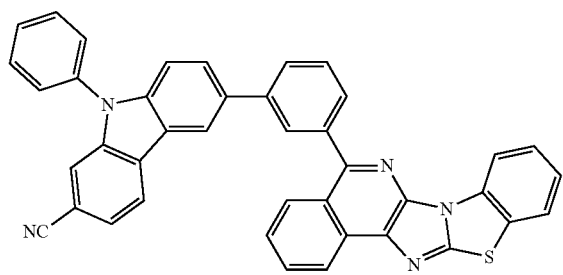
140
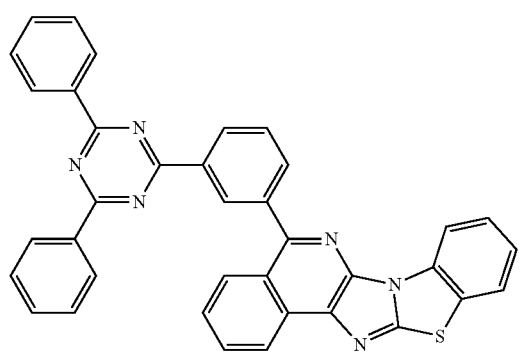
141
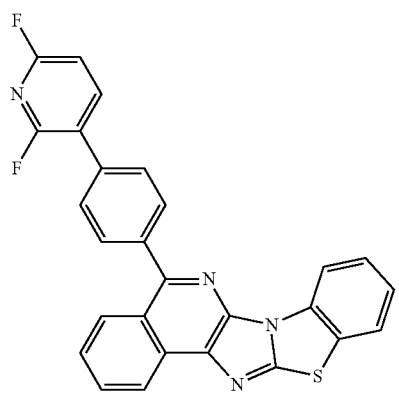
142
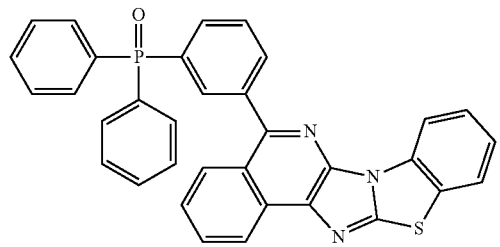
143
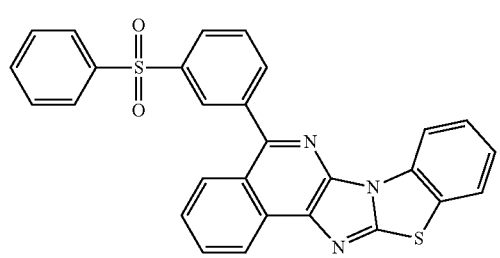
-continued
144
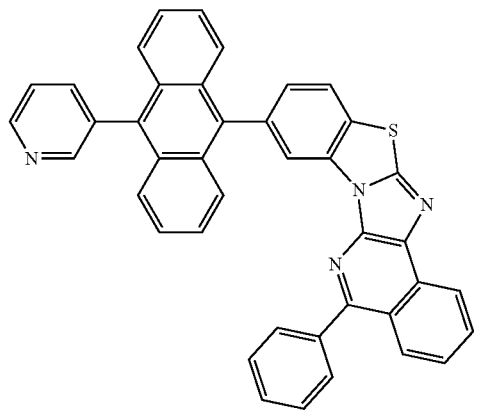
145
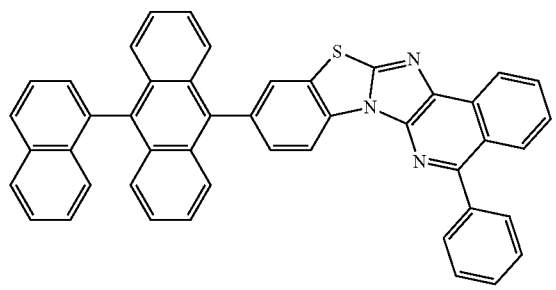
146
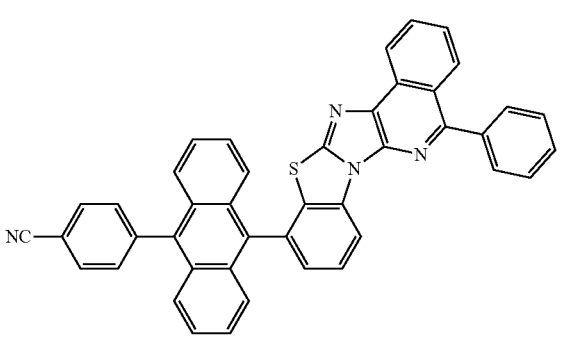
147
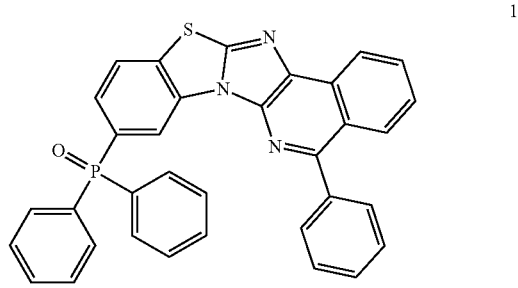
148
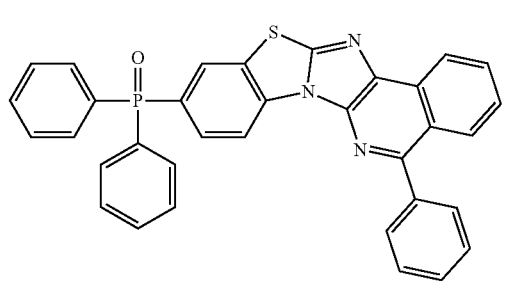

149
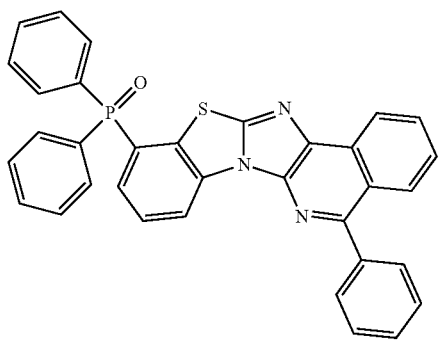

150
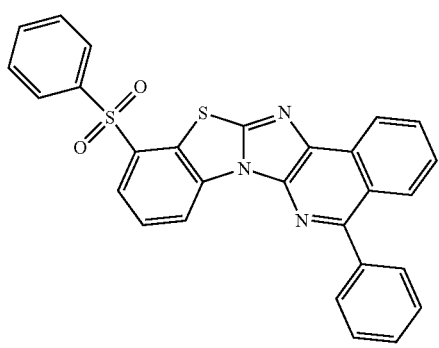

151
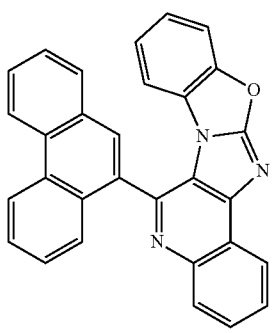

152
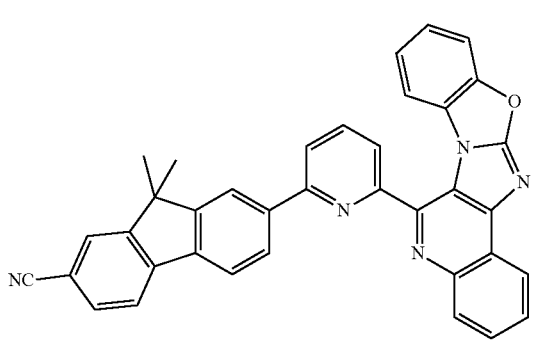

153
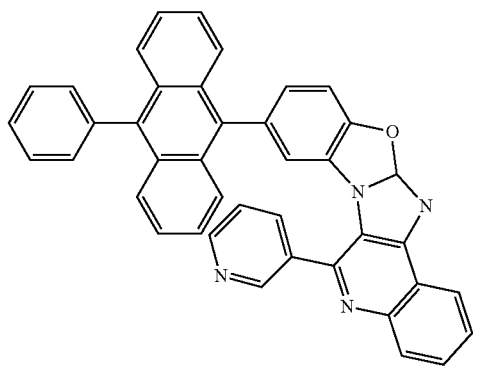

154
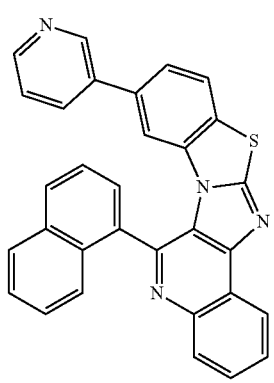

155
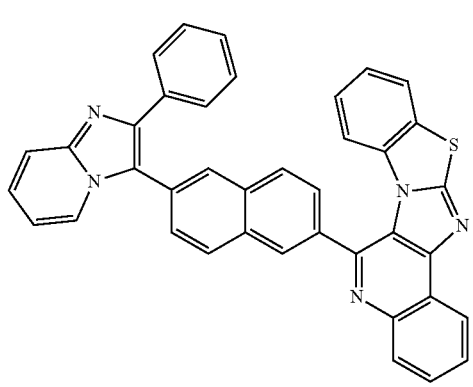

In Formula 1, a hetero ring including an oxygen atom or a sulfur atom may be condensed in a ring. The ring may include an imidazole and a quinoline. The imidazole and the quinoline may be condensed with each other. Thus, electron transport capability may be increased through a planar core structure.

Since the condensed cyclic compound may include a core represented by Formula 1, mobility of electrons may be increased by an increase in a dipole moment. The increase in the dipole moment may be due to at least one heteroatom and an increase in π-π orbital interaction due to a fused-aromatic ring.

Thus, an electronic device (e.g., an organic light-emitting device) which includes the condensed cyclic compound represented by Formula 1 may have a relatively high luminance, a relatively high efficiency, and a relatively long lifespan.

The condensed cyclic compound represented by Formula 1 may be synthesized by using a known organic synthesis method. The synthesis method for the condensed cyclic compound represented by Formula 1 may be recognizable to one of ordinary skill in the art, for example, by referring to the Examples described below.

At least one of the condensed cyclic compounds represented by Formula 1 may be positioned between a pair of electrodes of an organic light-emitting device. For example, the condensed cyclic compound represented by Formula 1 may be included in at least one layer selected from an electron transport region or an emission layer. According to an exemplary embodiment of the present invention, the condensed cyclic compound represented by Formula 1 may be included in a material for a capping layer. The capping layer may be positioned outside a pair of electrodes of an organic light-emitting device.

One or more exemplary embodiments of the present invention may provide an organic light-emitting device. The organic light-emitting device may include a first electrode, a second electrode facing the first electrode, and an organic layer. The organic layer may be disposed between the first electrode and the second electrode. The organic layer may include an emission layer. The organic layer may include at least one of the condensed cyclic compound represented by Formula 1.

The expression "(an organic layer) includes at least one condensed cyclic compound" as used herein may include a case in which "(an organic layer) includes the same compounds represented by Formula 1" and a case in which "(an organic layer) includes two or more different condensed cyclic compounds represented by Formula 1."

According to an exemplary embodiment of the present invention, the first electrode of the organic light-emitting device may be an anode. The second electrode of the organic light-emitting device may be a cathode. The organic layer may include a hole transport region and an electron transport region. The hole transport region may be disposed between the first electrode and the emission layer. The electron transport region may be disposed between the emission layer and the second electrode. The hole transport region may include at least one of a hole injection layer, a hole transport layer, a buffer layer, an emission auxiliary layer, an electron blocking layer. The electron transport region may include at least one of an emission auxiliary layer, a hole blocking layer, an electron transport layer, an electron injection layer.

According to an exemplary embodiment of the present invention, the electron transport region may include at least one of the condensed cyclic compounds represented by Formula 1. The electron transport region may include an electron transport layer. The electron transport layer may include at least one of the condensed cyclic compounds represented by Formula 1.

The emission layer may include at least one of the condensed cyclic compounds represented by Formula 1. The emission layer may include a dopant. An amount of the condensed cyclic compound represented by Formula 1 in the emission layer may be larger than an amount of the dopant. The condensed cyclic compound represented by Formula 1 in the emission layer may be configured to serve as a host. The dopant may be a phosphorescent dopant. Alternatively, the dopant may be a fluorescent dopant.

The electron transport region may include an emission auxiliary layer. The emission auxiliary layer may include the condensed cyclic compound represented by Formula 1.

The electron transport region may include an electron transport layer. The emission auxiliary layer may be disposed between the electron transport layer and the emission layer. The emission layer may include an anthracene-based compound.

The organic layer may include a hole transport region and/or an electron transport region. The hole transport region may be disposed between the first electrode and the emission layer. The first electrode may be an anode. The hole transport region may include at least one of a hole injection layer, a hole transport layer, a buffer layer, or an electron blocking layer. The electron transport region may be disposed between the emission layer and the second electrode. The second electrode may be a cathode. The electron transport region may include at least one of a hole blocking layer, an electron transport layer, or an electron injection layer. At least one of the condensed cyclic compounds represented by Formula 1 may be included in at least one of the hole transport region, the electron transport region, or the emission layer.

The organic light-emitting device may include a first capping layer and a second capping layer. The first capping layer may be disposed on a path where light generated from the emission layer is emitted to the outside through the first electrode. The second capping layer may be disposed on a path where the light generated from the emission layer is emitted to the outside through the second electrode. At least one of the first capping layer and the second capping layer may include at least one of the condensed cyclic compounds represented by Formula 1.

According to an exemplary embodiment of the present invention, the organic light-emitting device may include a structure in which the first electrode, the organic layer, the second electrode, and the second capping layer are sequentially stacked. The organic light-emitting device may also include a structure in which the first capping layer, the first electrode, the organic layer, and the second electrode are sequentially stacked. The organic light-emitting device may include a structure in which the first capping layer, the first electrode, the organic layer, the second electrode, and the second capping layer are sequentially stacked. The condensed cyclic compound may be included in at least one of the first capping layer and the second capping layer.

The term "organic layer" as used herein may refer to a single layer and/or a plurality of layers disposed between the first electrode and the second electrode of the organic light-emitting device. A material included in the "organic layer" is not limited to an organic material.

Figure 1:
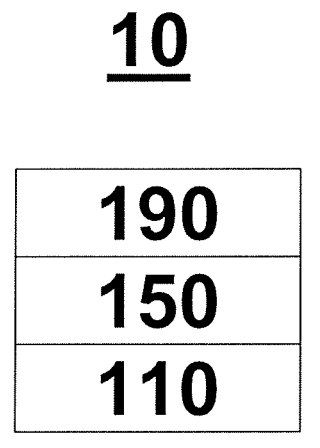

FIG. 1 is a schematic cross-sectional diagram illustrating an organic light-emitting device according to an exemplary embodiment of the present invention. Referring to FIG. 1, an organic light-emitting device 10 may include a first electrode 110, an organic layer 150, and a second electrode 190.

A structure of the organic light-emitting device 10 according to an exemplary embodiment of the present invention and a method of manufacturing the organic light-emitting device 10 according to an exemplary embodiment of the present invention will be described in more detail with reference to FIG. 1.

A substrate may be disposed below the first electrode 110. Alternatively, the substrate may be disposed above the second electrode 190. The substrate may include a glass substrate or a plastic substrate. The glass substrate or the plastic substrate may each have a relatively high mechanical strength, thermal stability, transparency, surface smoothness, ease of handling, and water-resistance.

The first electrode 110 may be formed by depositing or sputtering a material for forming the first electrode 110 on the substrate. When the first electrode 110 is an anode, the first electrode 110 may include at least one material with a relatively high work function, which may facilitate hole injection.

The first electrode 110 may be a reflective electrode, a semi-transmissive electrode, or a transmissive electrode. When the first electrode 110 is a transmissible electrode, the first electrode 110 may include indium tin oxide (ITO), indium zinc oxide (IZO), tin oxide (SnO$_2$), zinc oxide (ZnO), or any combinations thereof; however, exemplary embodiments of the present invention are not limited thereto. When the first electrode 110 is a semi-transmissible electrode or a reflectable electrode, the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combinations thereof; however, exemplary embodiments of the present invention are not limited thereto.

The first electrode 110 may have a single-layered structure. Alternatively, the first electrode 110 may have a multi-layered structure including two or more layers. For example, the first electrode 110 may have a three-layered structure of ITO/Ag/ITO; however, the structure of the first electrode 110 is not limited thereto.

The organic layer 150 may be disposed on the first electrode 110. The organic layer 150 may include an emission layer.

The organic layer 150 may include a hole transport region and an electron transport region. The hole transport region may be disposed between the first electrode 110 and the emission layer. The electron transport region may disposed be between the emission layer and the second electrode 190.

The hole transport region may have a single-layered structure including a single layer including a single material. The hole transport region may have a single-layered structure including a single layer including a plurality of different materials. The hole transport region may have a multi-layered structure including a plurality of layers, each including a plurality of different materials.

The hole transport region may include at least one layer selected from a hole injection layer (HIL), a hole transport layer (HTL), an emission auxiliary layer, or an electron blocking layer (EBL).

For example, the hole transport region may have a single-layered structure. The single-layered structure may include a single layer including a plurality of different materials. Alternatively, the hole transport region may include a multi-layered structure. The multi-layered structure may include a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure. For each structure, the layers may be sequentially stacked on the first electrode 110; however, the structure of the hole transport region is not limited thereto.

The hole transport region may include at least one of m-MTDATA, TDATA, 2-TNATA, NPB(NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, or a compound represented by Formula 202:

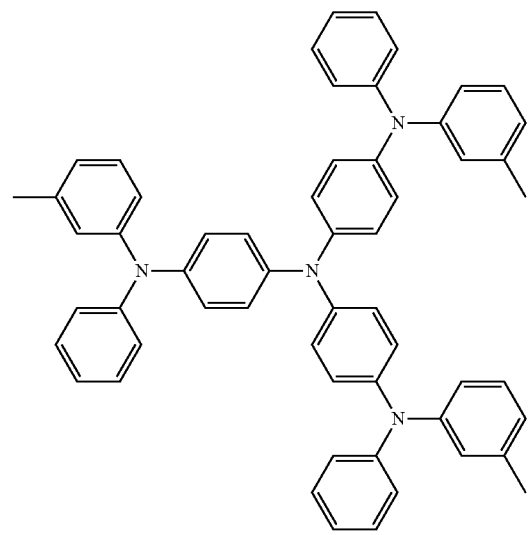

m-MTDATA

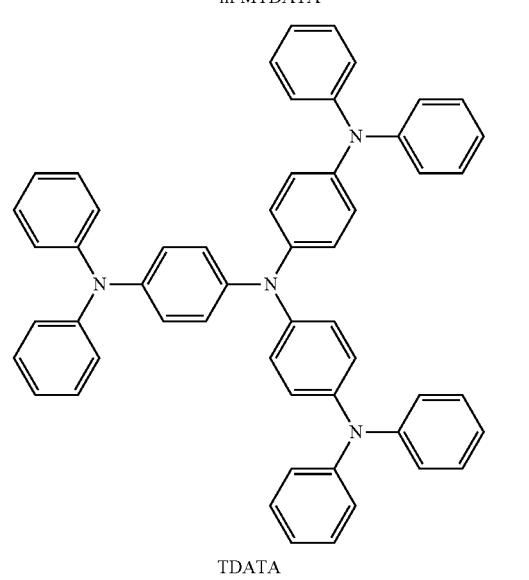

TDATA

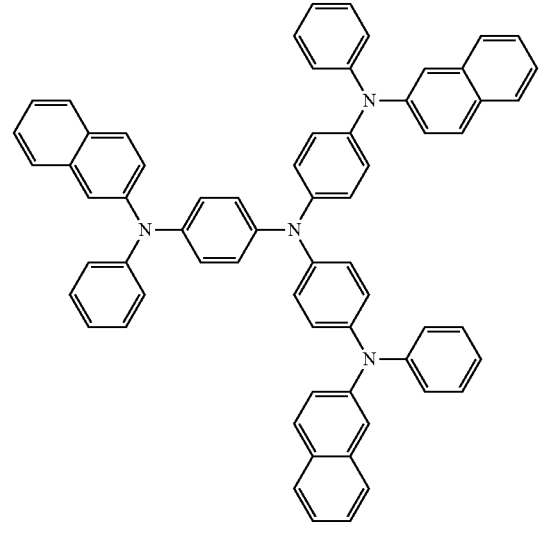

2-TNATA

-continued

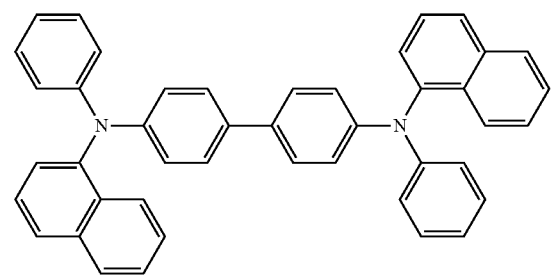

NPB

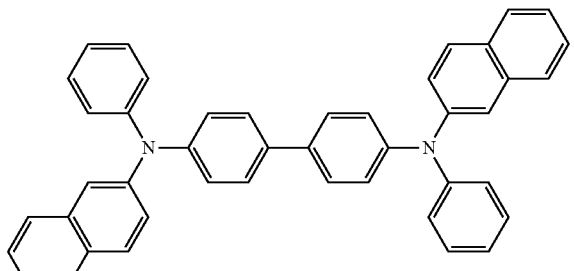

β-NPB

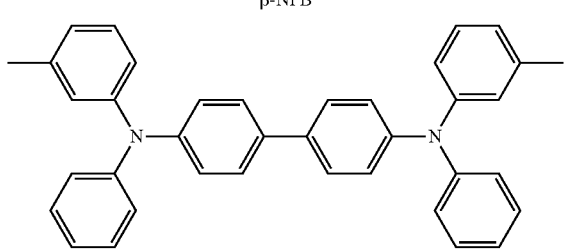

TPD

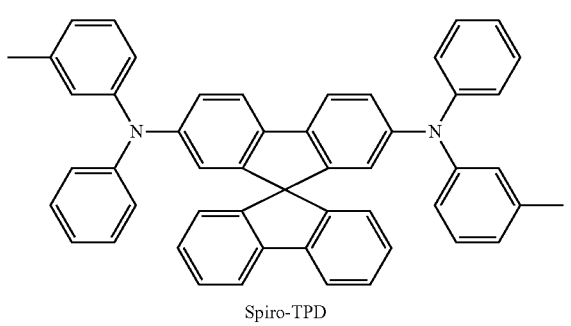

Spiro-TPD

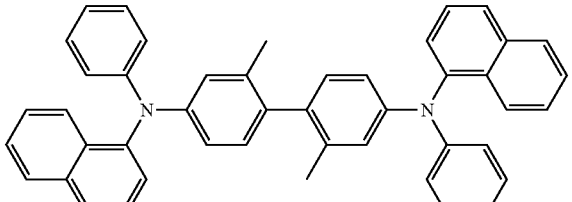

methylated NPB

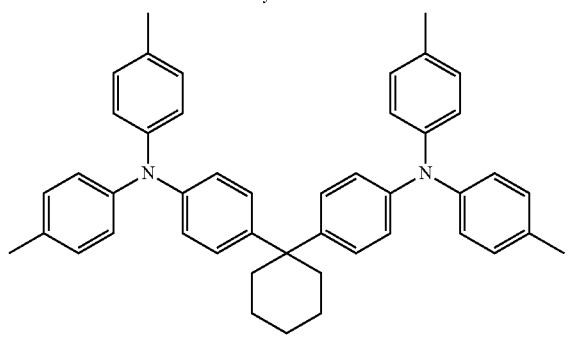

TAPC

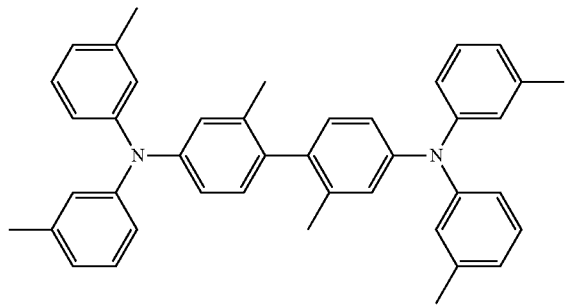

HMTPD

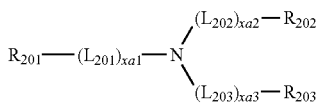

<Formula 201>

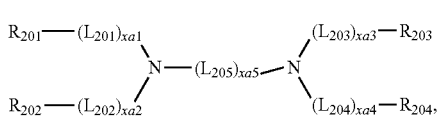

<Formula 202>

In Formulae 201 and 202:

$L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$

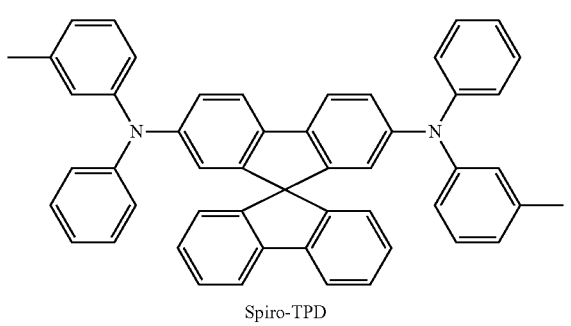

Spiro-NPB cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group, xa1 to xa4 may each independently be an integer selected from 0 to 3, xa5 may be an integer selected from 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

For example, in Formula 202, $R_{201}$ and $R_{202}$ may be linked via a single bond, a dimethyl-methylene group, or a diphenyl-methylene group, and $R_{203}$ and $R_{204}$ may be linked via a single bond, a dimethyl-methylene group, or a diphenyl-methylene group.

According to an exemplary embodiment of the present invention, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, or a pyridinylene group; or a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), or —N($Q_{31}$)($Q_{32}$).

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, or a naphthyl group.

According to an exemplary embodiment of the present invention, xa1 to xa4 in Formulae 201 and 202 may each independently be an integer selected from 0, 1, or 2.

According to an exemplary embodiment of the present invention, in Formulae 201 and 202, xa5 may be an integer selected from 1, 2, 3, or 4.

According to an exemplary embodiment of the present invention, in Formulae 201 and 202, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, or a pyridinyl group; or a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), or —N($Q_{31}$)($Q_{32}$).

$Q_{31}$ to $Q_{33}$ may be the same as described above.

According to an exemplary embodiment of the present invention, at least one of $R_{201}$ to $R_{203}$ in Formula 201 may each independently be selected from:

a fluorenyl group, a spiro-bifluorenyl group, a carbazolyl group, a dibenzofuranyl group, or a dibenzothiophenyl group; or a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, or a dibenzothiophenyl group; however, exemplary embodiments of the present invention are not limited thereto.

According to an exemplary embodiment of the present invention, in Formula 202, $R_{201}$ and $R_{202}$ may be linked via a single bond and/or $R_{203}$ and $R_{204}$ may be linked via a single bond.

According to an exemplary embodiment of the present invention, at least one of $R_{201}$ to $R_{204}$ in Formula 202 may be selected from:

a carbazolyl group; or a carbazolyl group, substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, or a dibenzothiophenyl group; however, exemplary embodiments of the present invention are not limited thereto.

The compound represented by Formula 201 may be represented by Formula 201A; however, exemplary embodiments of the present invention are not limited thereto:

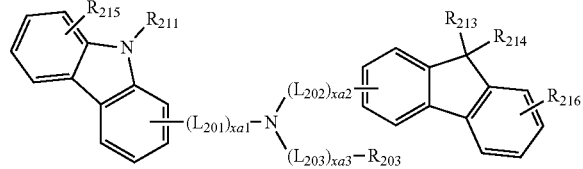

<Formula 201A>

The compound represented by Formula 201 may be represented by Formula 201A(1); however, exemplary embodiments of the present invention are not limited thereto:

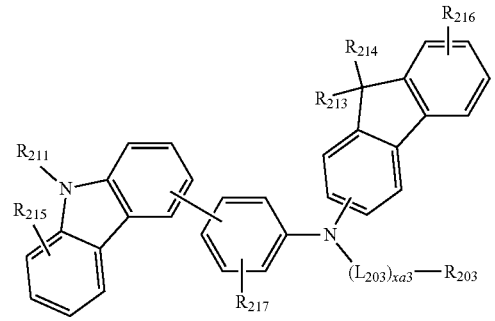

<Formula 201A(1)>

The compound represented by Formula 201 may be represented by Formula 201A-1; however, exemplary embodiments of the present invention are not limited thereto:

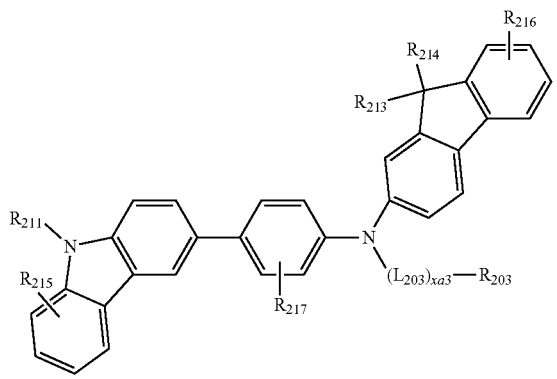

<Formula 201A-1>

According to an exemplary embodiment of the present invention, the compound represented by Formula 202 may be represented by Formula 202A:

<Formula 202A>

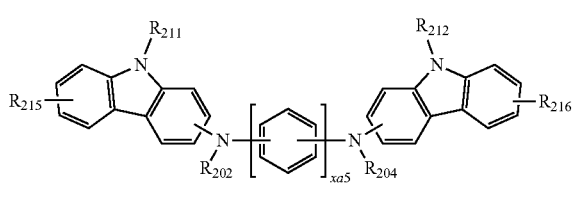

According to an exemplary embodiment of the present invention, the compound represented by Formula 202 may be represented by Formula 202A-1:

<Formula 202A-1>

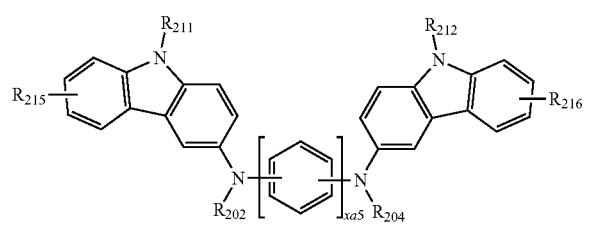

In Formulae 201A, 201A(1), 201A-1, 202A, and 202A-1:

$L_{201}$ to $L_{203}$, xa1 to xa3, xa5, $R_{202}$ to $R_{204}$, $R_{211}$, and $R_{212}$ may be the same as described above.

In Formulae 201A, 201A(1), 201A-1, 202A, and 202A-1, $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, or a pyridinyl group.

The hole transport region may include at least one compound selected from Compounds HT1 to HT39; however, exemplary embodiments of the present invention are not limited thereto:

HT1

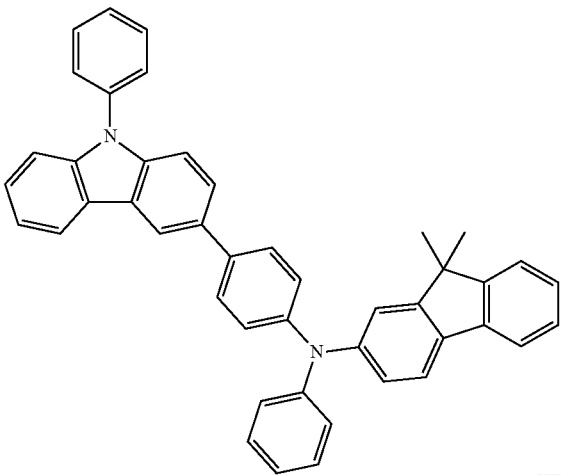

HT2

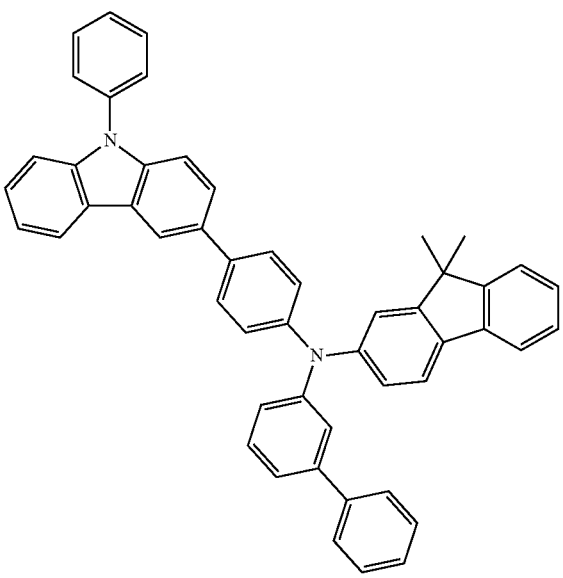

HT3

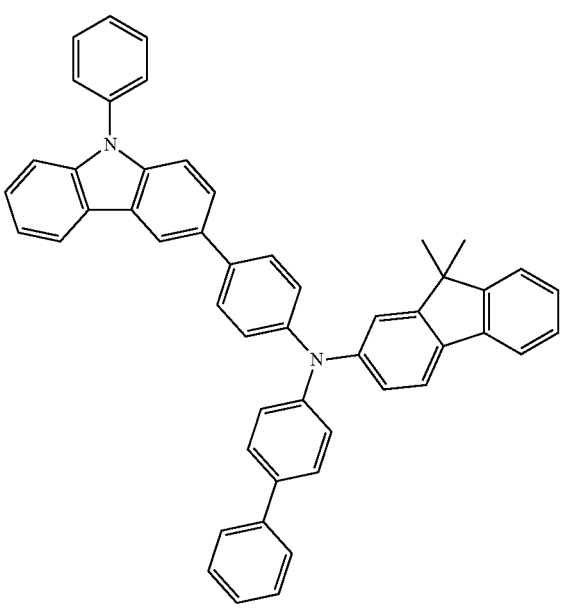

HT4
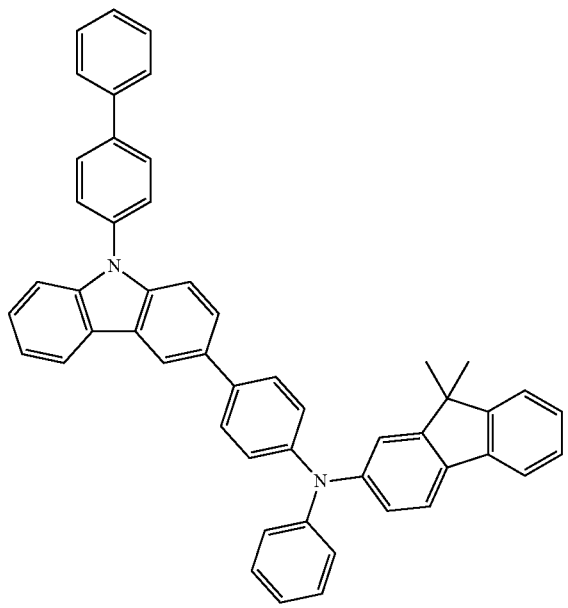
HT6
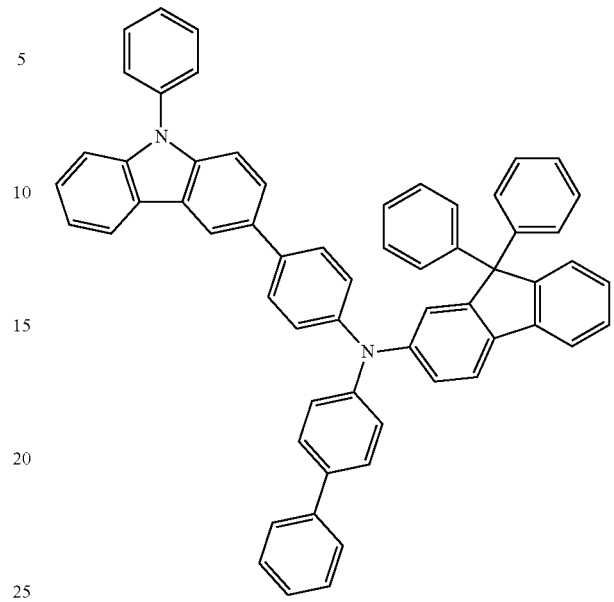
HT5
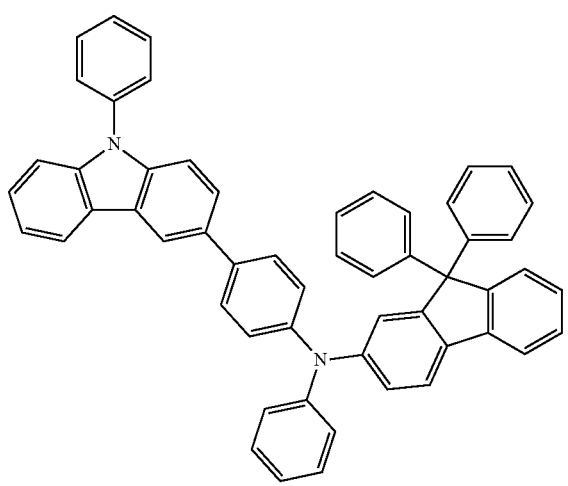
HT7
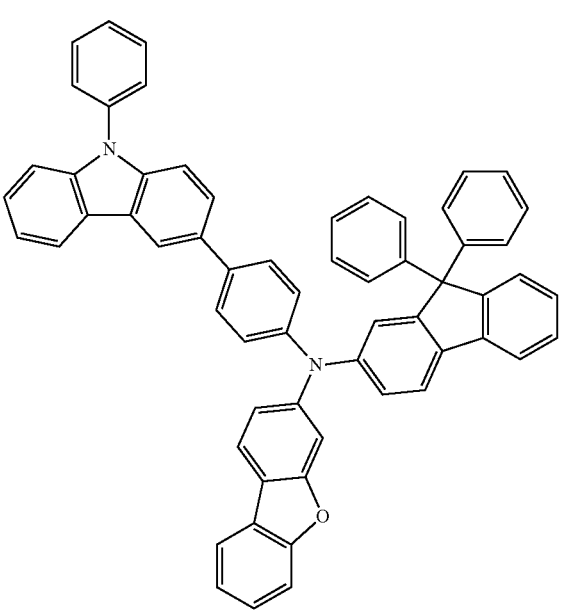

-continued
HT8
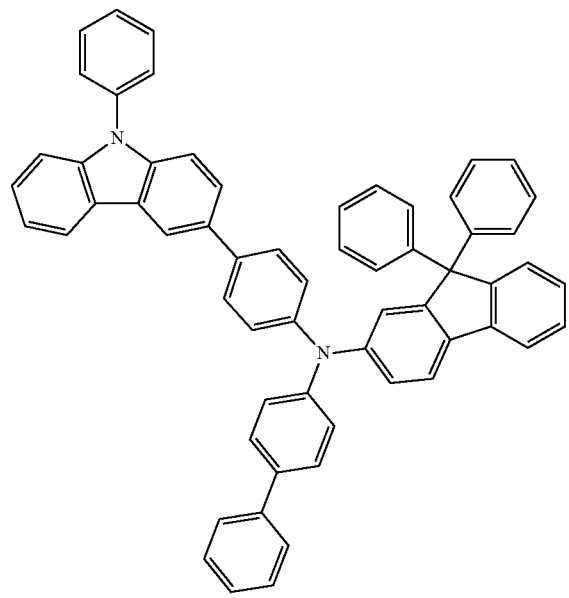
HT9
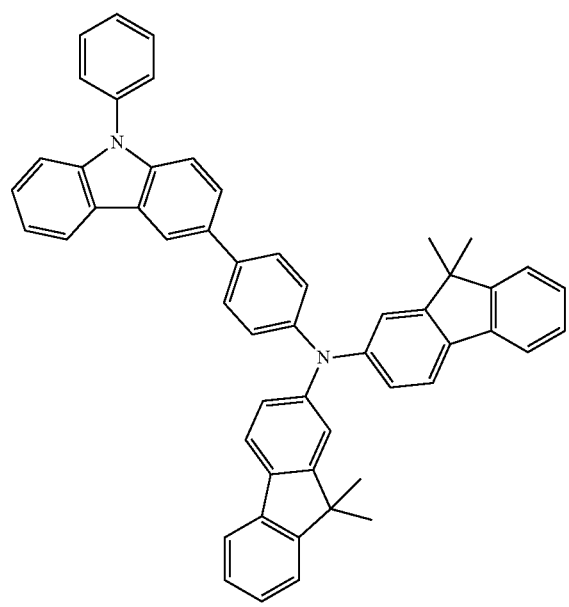
HT10
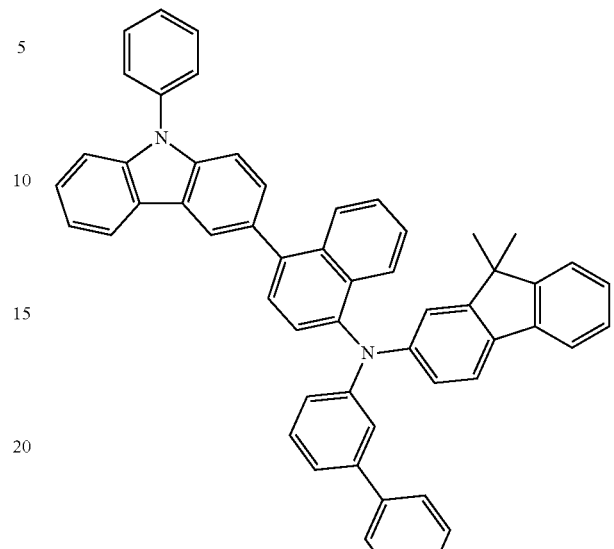
HT11
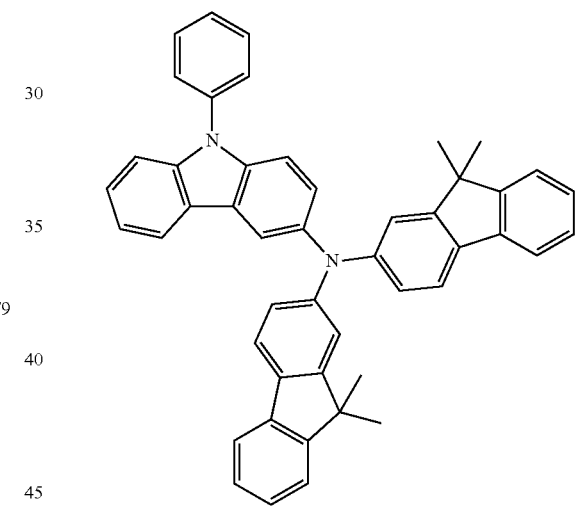
HT12
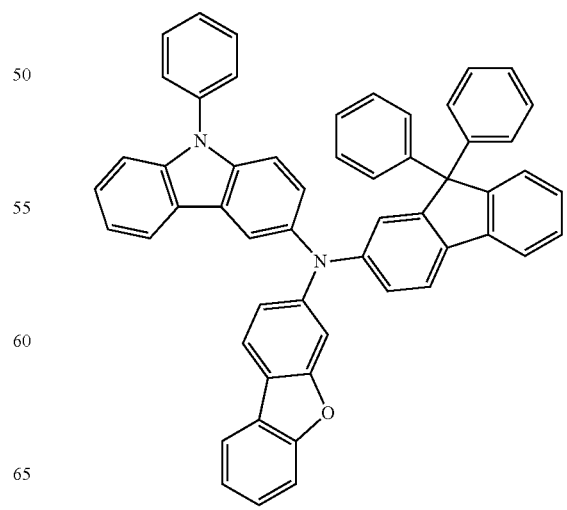

HT13
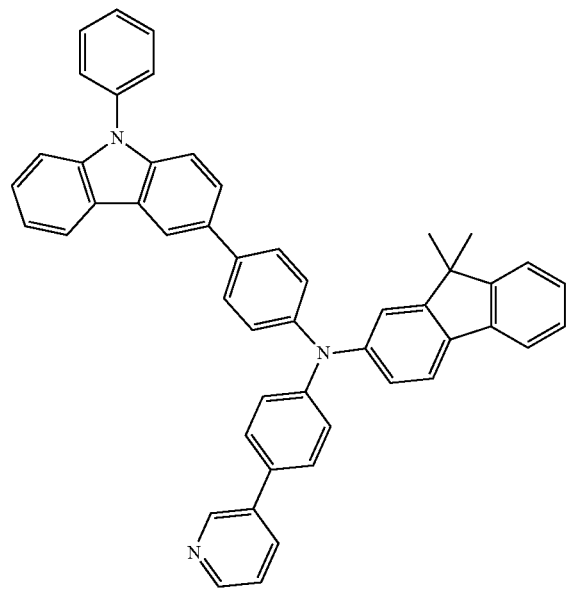
HT15
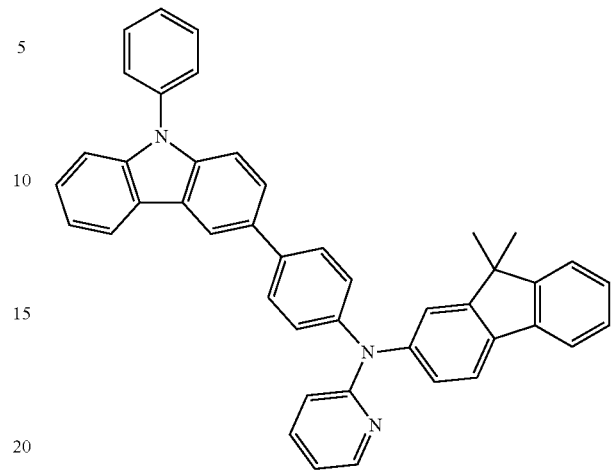
HT16
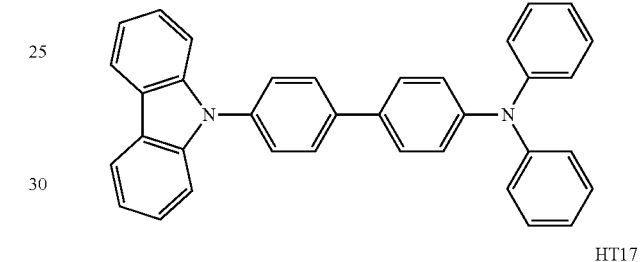
HT17
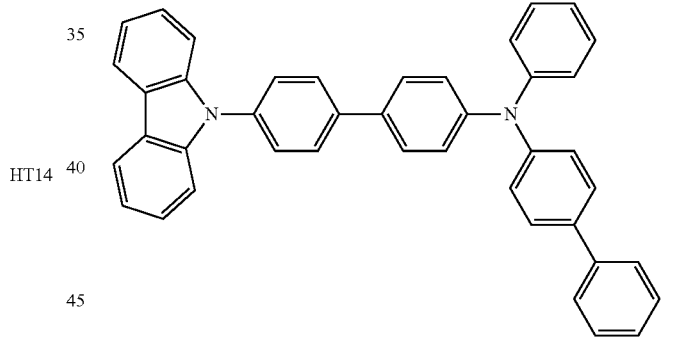
HT14
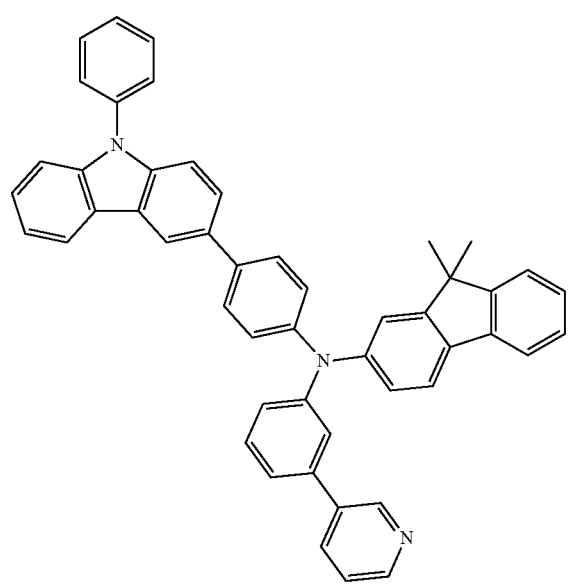
HT18
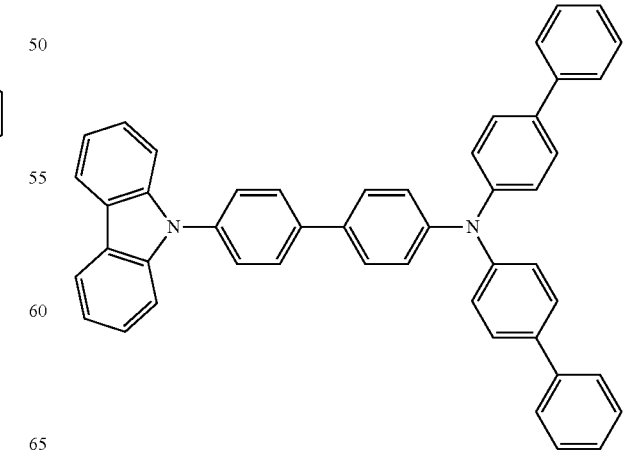

HT19
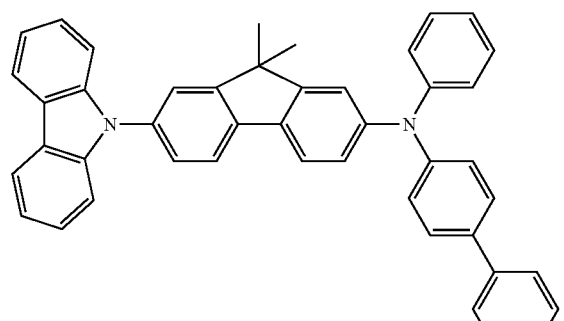
HT22
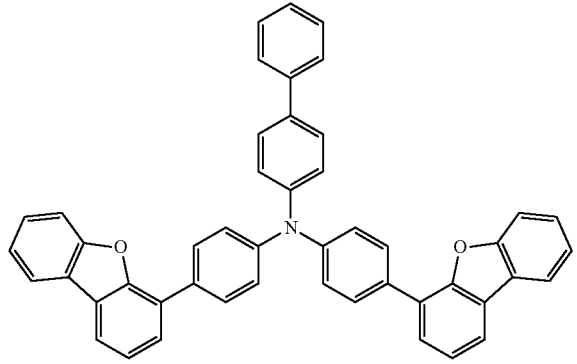
HT20
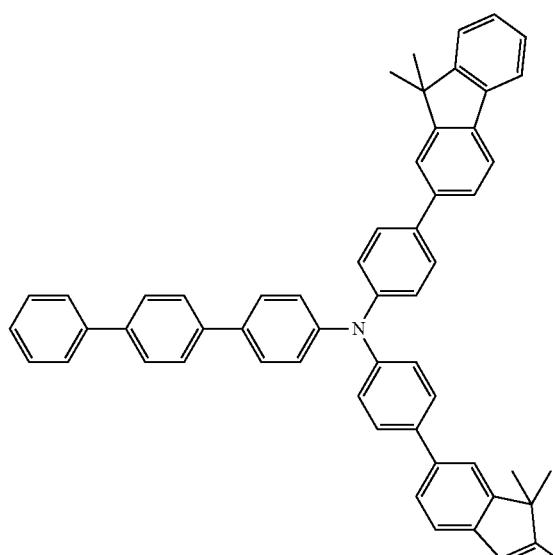
HT23
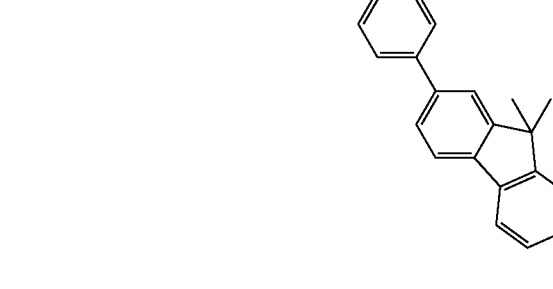
HT24
HT21
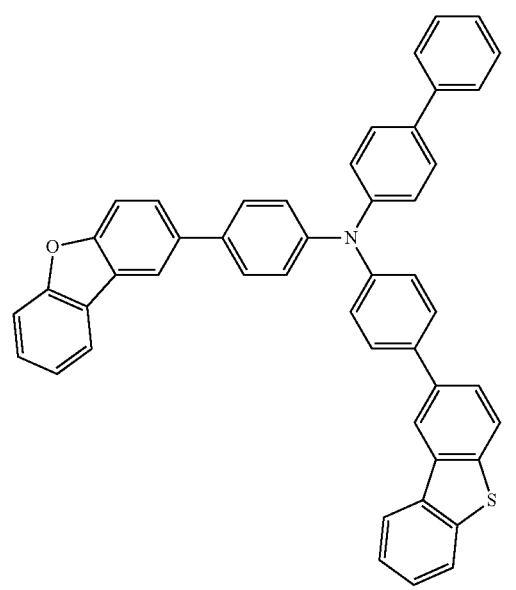
HT25
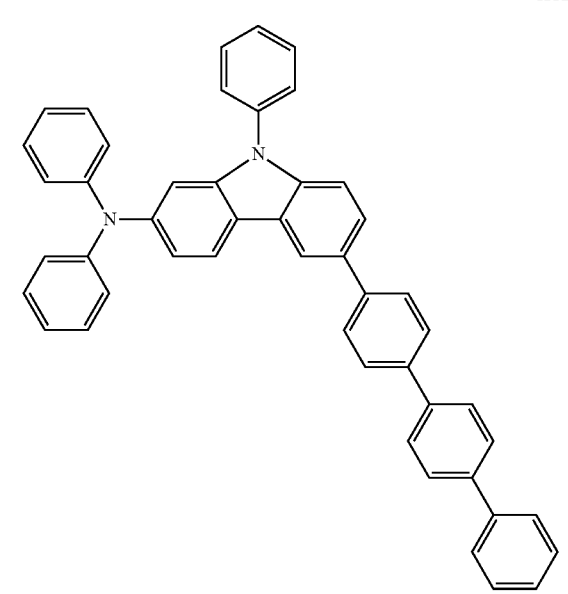

HT26
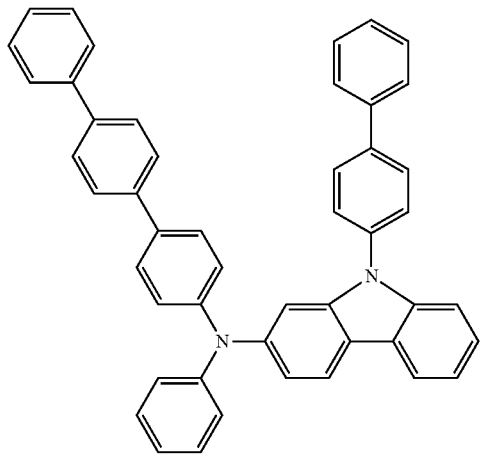
HT29
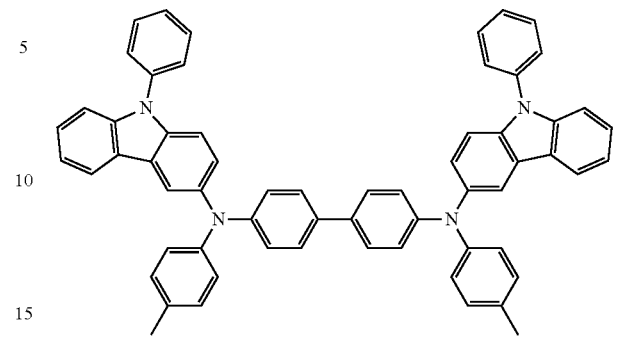
HT30
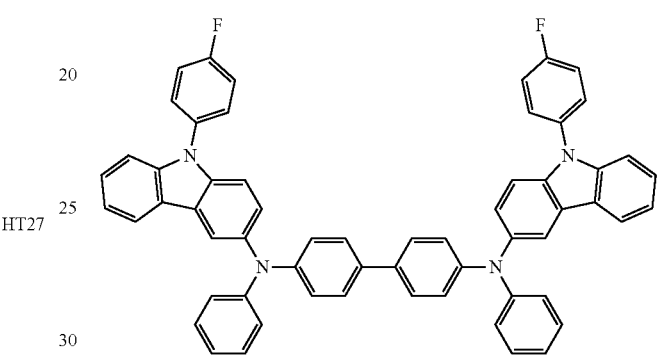
HT27
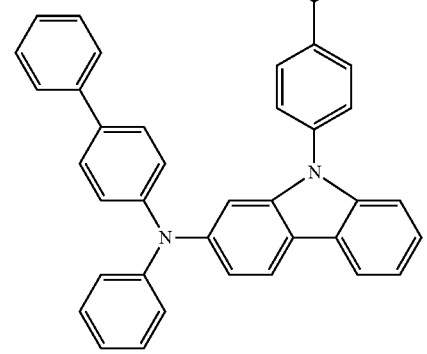
HT31
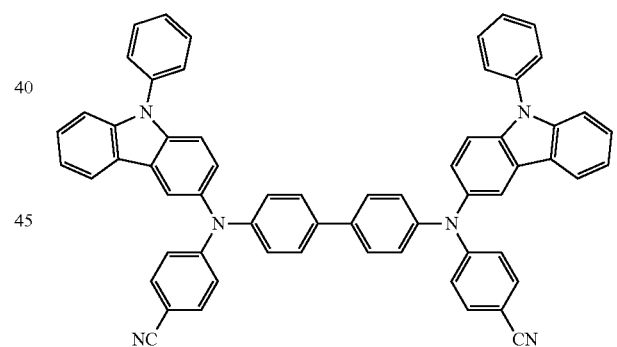
HT28
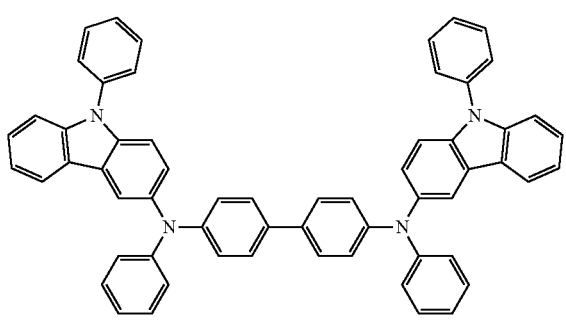
HT32

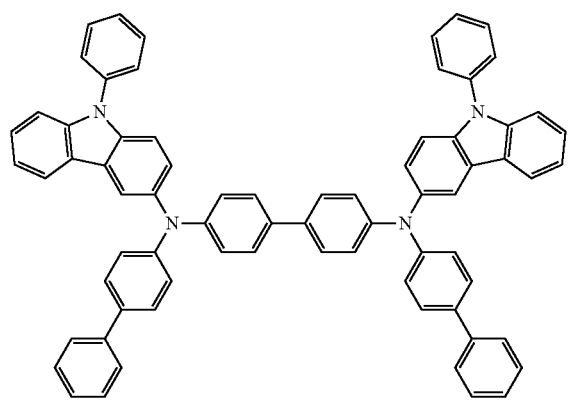
HT33
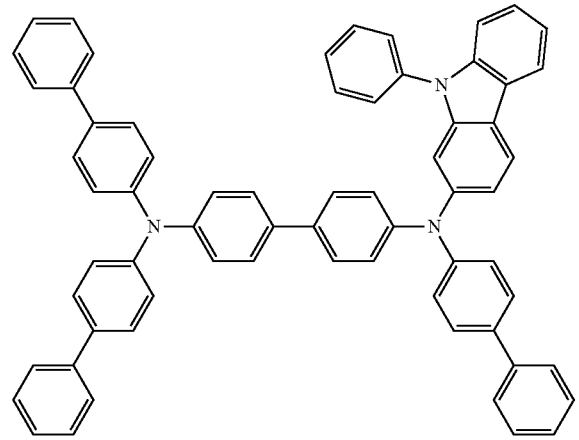
HT36
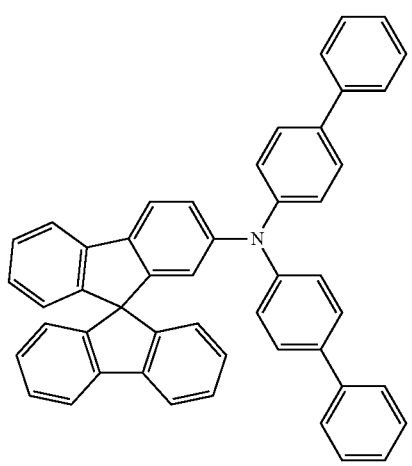
HT34
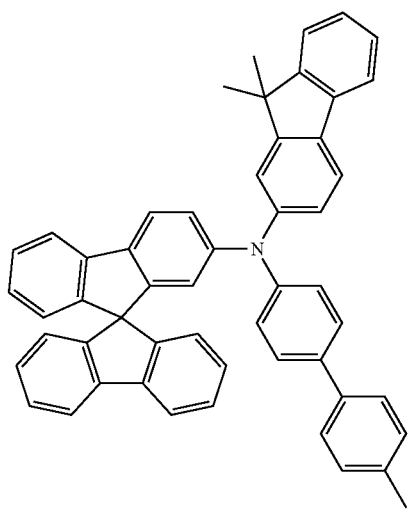
HT35
HT37
HT38

HT39

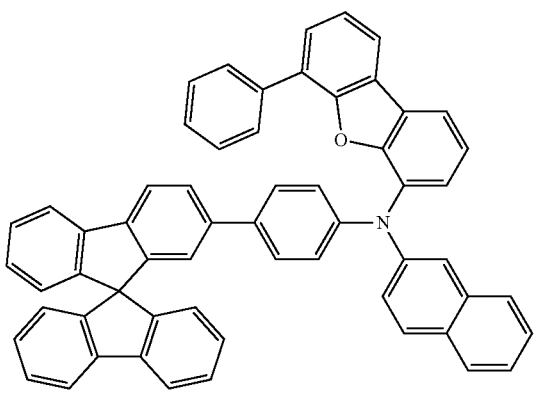

A thickness of the hole transport region may be in a range of from about 100 Å to about 10,000 Å, for example, from about 100 Å to about 1,000 Å. When the hole transport region includes at least one of a hole injection layer and a hole transport layer, the thickness of the hole injection layer may be in a range of from about 100 Å to about 9,000 Å, for example, from about 100 Å to about 1,000 Å, and the thickness of the hole transport layer may be in a range of from about 50 Å to about 2,000 Å, for example, from about 100 Å to about 1,500 Å. When the thickness of the hole transport region, the hole injection layer and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer. The electron blocking layer may reduce or eliminate the flow of electrons from an electron transport region. The emission auxiliary layer and the electron blocking layer may include materials as described herein.

The hole transport region may include a charge-generation material. The charge-generation material may increase conductive properties of the hole transport region. The charge-generation material may be substantially homogeneously or non-homogeneously dispersed in the hole transport region.

The charge-generation material may include, for example, a p-dopant.

According to an exemplary embodiment of the present invention, a lowest unoccupied molecular orbital (LUMO) of the p-dopant may be about −3.5 eV or less.

The p-dopant may include at least one of a quinone derivative, a metal oxide, or a compound including a cyano group; however, exemplary embodiments of the present invention are not limited thereto.

For example, the p-dopant may include at least one of:

a quinone derivative, such as tetracyanoquinodimethane (TCNQ) and 2,3,5,6-tetrafluoro-7,7,8,8-tetracyanoquinodimethane (F4-TCNQ);

a metal oxide, such as a tungsten oxide or a molybdenum oxide;

1,4,5,8,9,11-hexaazatriphenylene-hexacarbonitrile (HAT-CN); or a compound represented by Formula 221 below; however, exemplary embodiments of the present invention are not limited thereto:

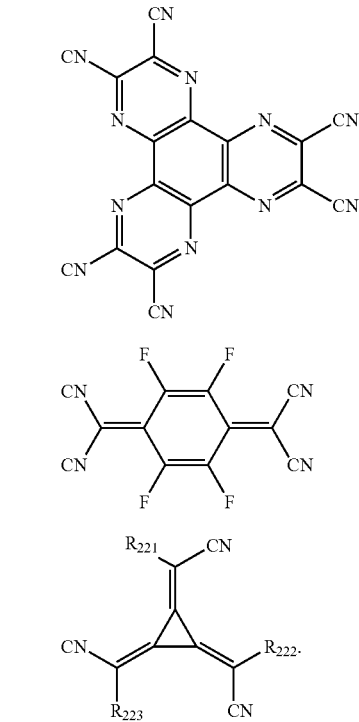

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, or a $C_1$-$C_{20}$ alkyl group substituted with —I.

When the organic light-emitting device 10 is a full color organic light-emitting device, the emission layer may be patterned into a red emission layer, a green emission layer, or a blue emission layer, according to a sub pixel. According to an exemplary embodiment of the present invention, the emission layer may have a stacked structure. The stacked structure may include two or more layers selected from a red emission layer, a green emission layer, or a blue emission layer. The two or more layers may be in direct contact with each other. Alternatively, the two or more layers may be separated from each other. According to an exemplary embodiment of the present invention, the emission layer may include two or more materials. The two or more materials may include a red-light emission material, a green-light emission material, or a blue-light emission material. The two or more materials may be mixed with each other in a single layer. The two or more materials mixed with each other in the single layer may emit white light.

The emission layer may include a host and a dopant. The dopant may include at least one of a phosphorescent dopant or a fluorescent dopant.

An amount of the dopant in the emission layer may be in a range of from about 0.01 to about 15 parts by weight based on 100 parts by weight of the host; however, exemplary embodiments of the present invention are not limited thereto.

A thickness of the emission layer may be in a range of from about 100 Å to about 1,000 Å, for example, from about 200 Å to about 600 Å. When the thickness of the emission layer is within this range, increased light-emission characteristics may be obtained without a substantial increase in driving voltage.

The host may include the condensed cyclic compound represented by Formula 1; however, exemplary embodiments of the present invention are not limited thereto. The host may include a compound represented by Formula 301.

$$[Ar_{301}]_{xb11}\text{-}[(L_{301})_{xb1}\text{-}R_{301}]_{xb21} \quad \text{<Formula 301>}$$

In Formula 301:

$Ar_{301}$ may be a substituted or unsubstituted $C_5$-$C_{60}$ carbocyclic group or a substituted or unsubstituted $C_1$-$C_{60}$ heterocyclic group, $xb11$ may be an integer selected from 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group, $xb1$ may be an integer selected from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), or —P(=O)($Q_{301}$)($Q_{302}$), and $xb21$ may be an integer selected from 1 to 5.

$Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, or a naphthyl group; however, exemplary embodiments of the present invention are not limited thereto.

According to an exemplary embodiment of the present invention, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, or a dibenzothiophene group; or a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, or a naphthyl group; however, exemplary embodiments of the present invention are not limited thereto.

When $xb11$ in Formula 301 is 2 or greater, at least two $Ar_{301}(s)$ may be linked via a single bond.

According to an exemplary embodiment of the present invention, the compound represented by Formula 301 may be represented by Formula 301-1 or 301-2:

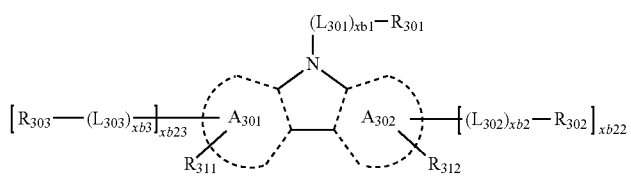

<Formula 301-1>

-continued

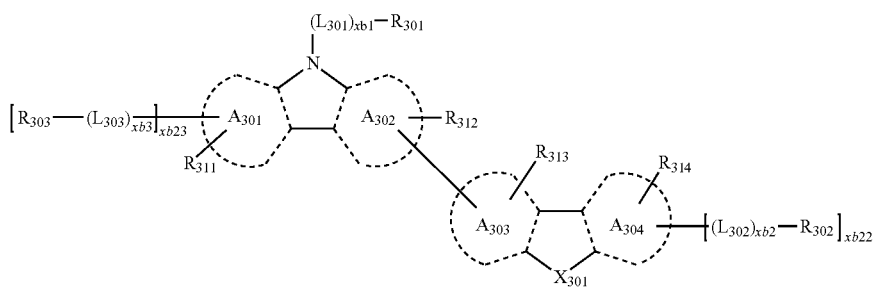

<Formula 301-2>

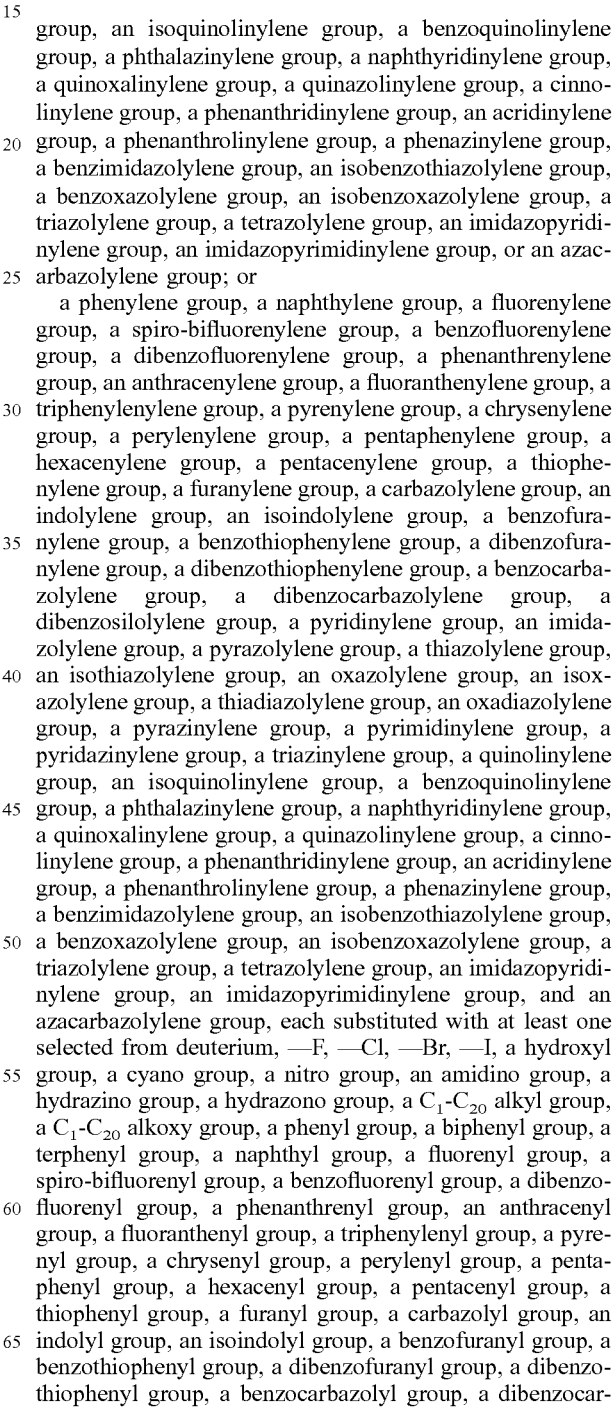

In Formulae 301-1 to 301-2:

$A_{301}$ to $A_{304}$ may each independently be selected from a benzene, a naphthalene, a phenanthrene, a fluoranthene, a triphenylene, a pyrene, a chrysene, a pyridine, a pyrimidine, an indene, a fluorene, a spiro-bifluorene, a benzofluorene, a dibenzofluorene, an indole, a carbazole, a benzocarbazole, a dibenzocarbazole, a furan, a benzofuran, a dibenzofuran, a naphthofuran, a benzonaphthofuran, a dinaphthofuran, a thiophene, a benzothiophene, a dibenzothiophene, a naphthothiophene, a benzonaphthothiophene, or a dinaphthothiophene.

$X_{301}$ may be oxygen (O), sulfur (S), or N-[$(L_{304})_{xb4}$-$R_{304}$].

$R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

xb22 and xb23 may each independently be an integer selected from 0, 1, or 2.

$L_{301}$, xb1, $R_{301}$, and $Q_{31}$ to $Q_{33}$ may be the same as described above.

$L_{302}$ to $L_{304}$ may be the same as described above with reference to $L_{301}$.

Xb2 to xb4 may be the same as described above with reference to xb1.

$R_{302}$ to $R_{304}$ may be the same as described above with reference to $R_{301}$.

According to an exemplary embodiment of the present invention, $L_{301}$ to $L_{304}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, or an azacarbazolylene group; or a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$)

$Q_{31}$ to $Q_{33}$ may be the same as described above.

According to an exemplary embodiment of the present invention, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, or an azacarbazolyl group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

$Q_{31}$ to $Q_{33}$ may be the same as described above.

According to an exemplary embodiment of the present invention, the host may include an alkaline earth-metal complex. For example, the host may include a beryllium (Be) complex, for example, Compound H55, a magnesium (Mg) complex, or a zinc (Zn) complex.

The host may include at least one of 9,10-di(2-naphthyl) anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), or Compounds H1 to H55; however exemplary embodiments of the present invention are not limited thereto.

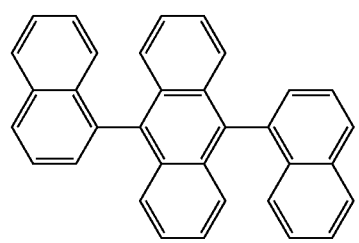

H1

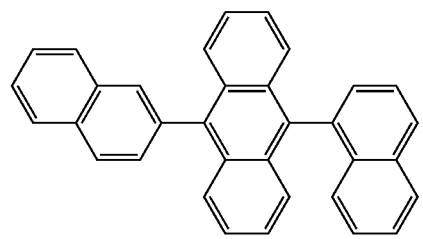

H2

H3
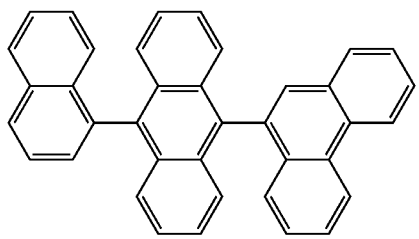
H4
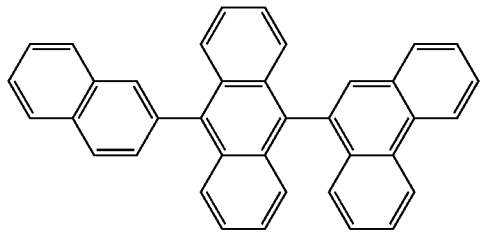
H5
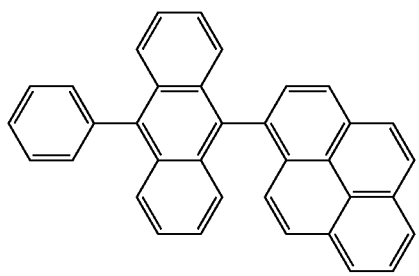
H6
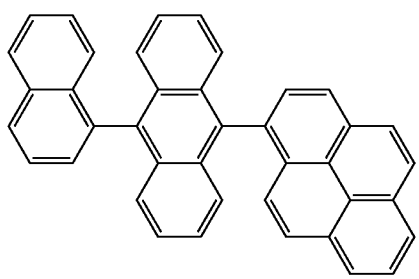
H7
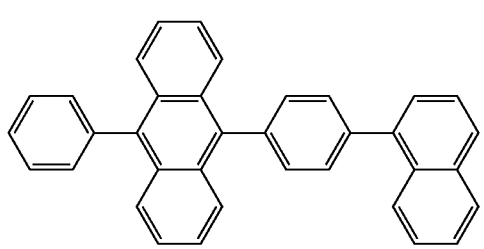
H8
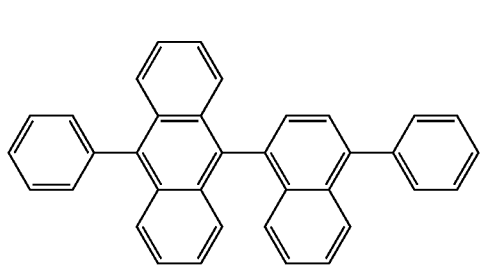
H9
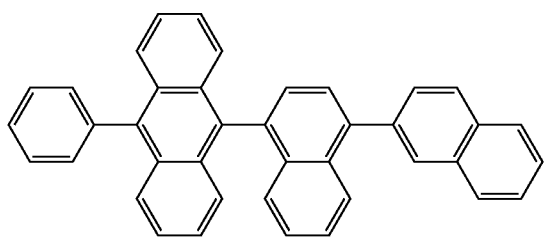
H10
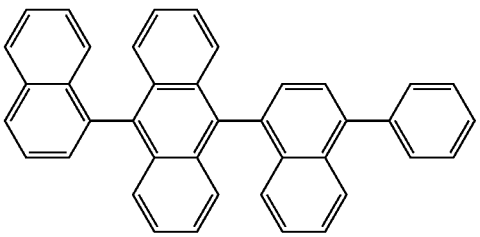
H11
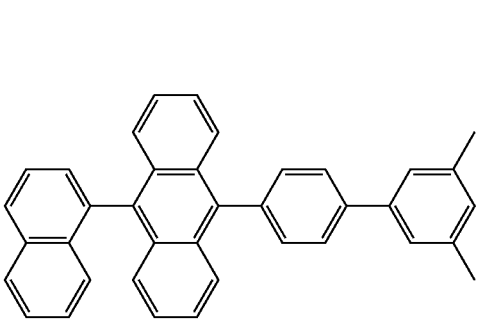
H12
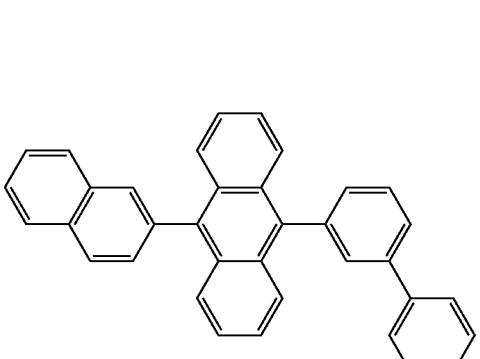
H13
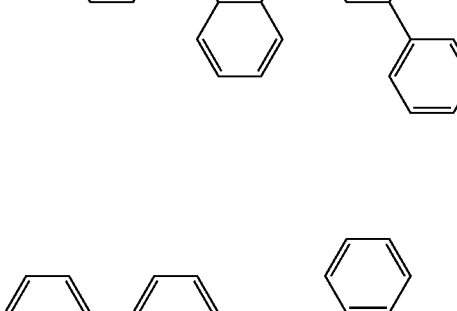

H14
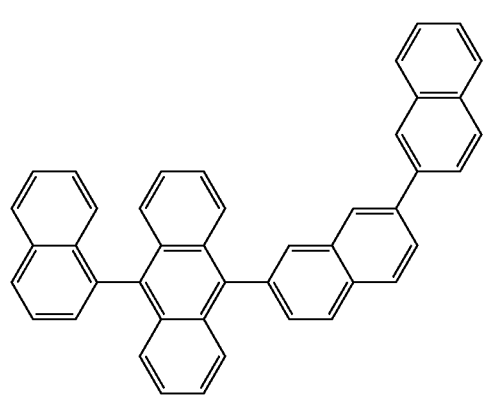
H15
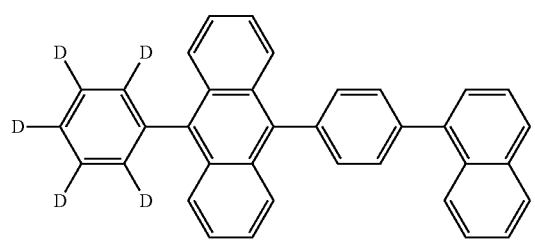
H16
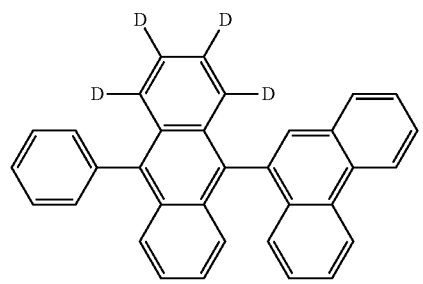
H17
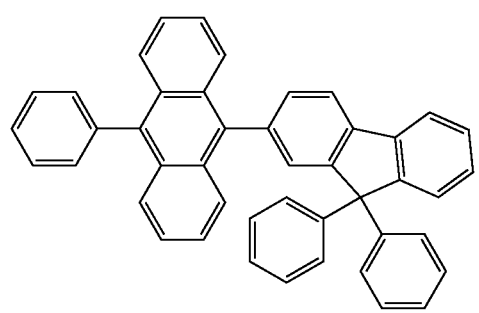
H18
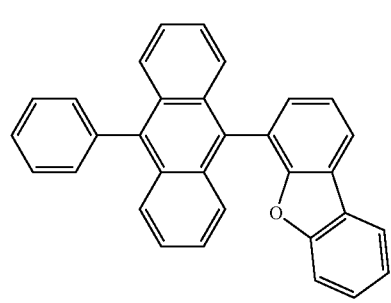
H19
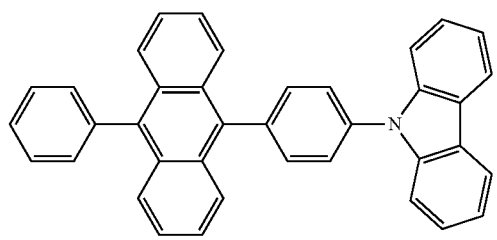
H20
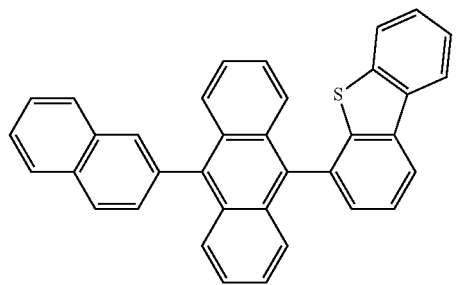
H21
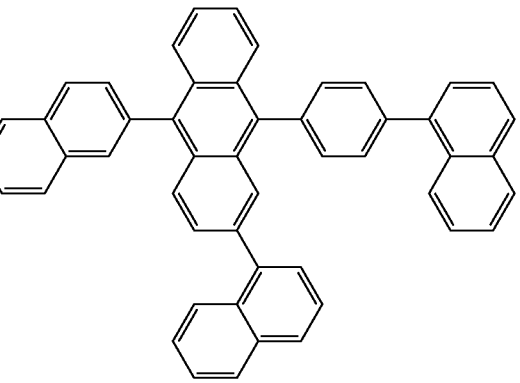
H22
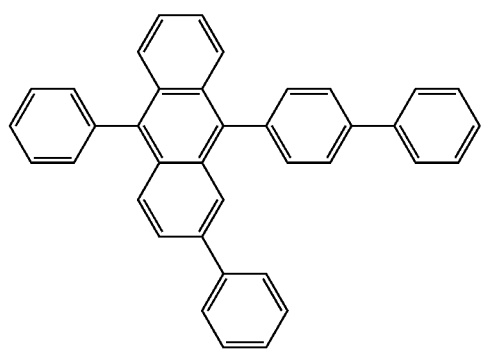

H23
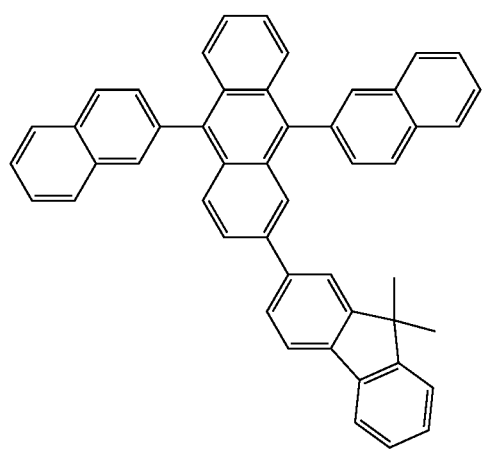
H24
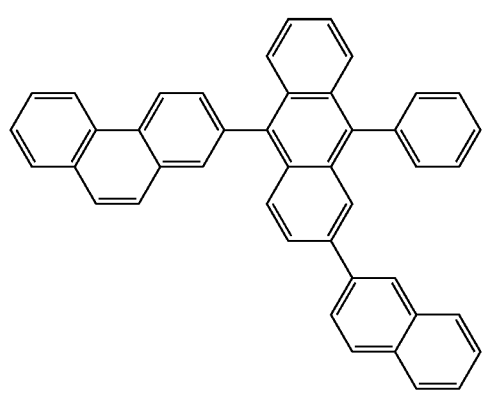
H25
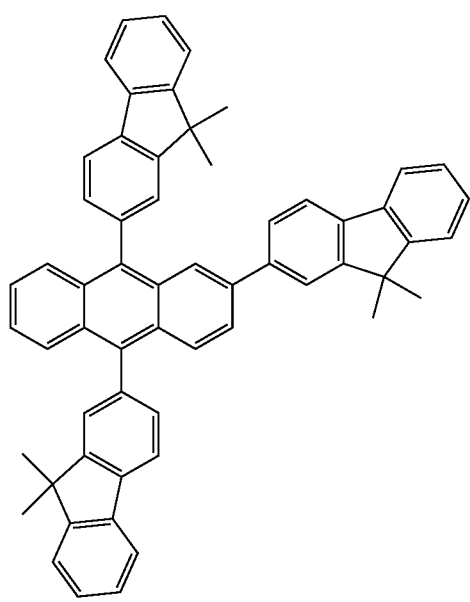
H26
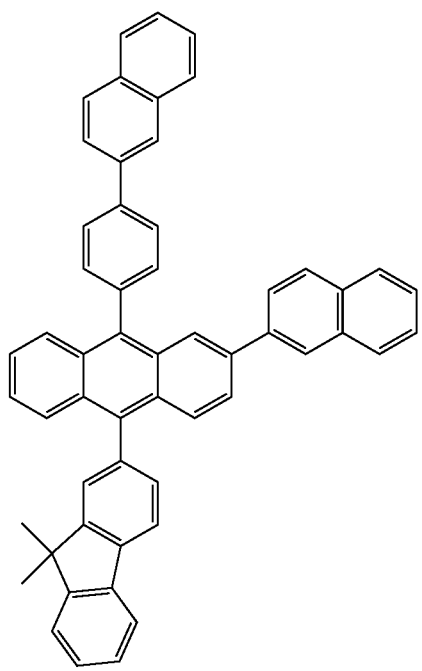
H27
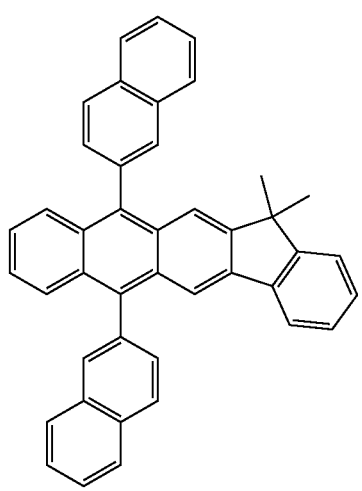
H28
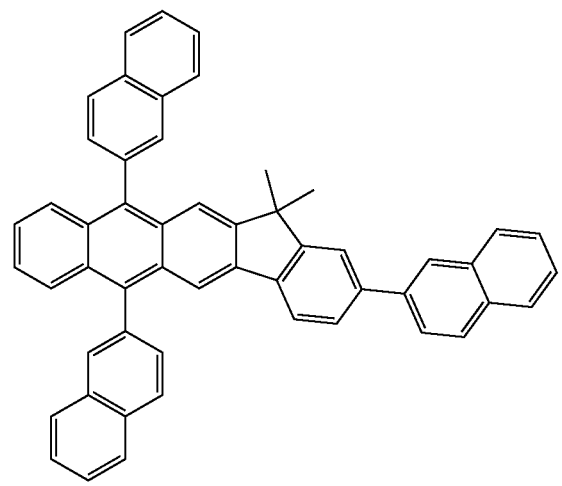

H29
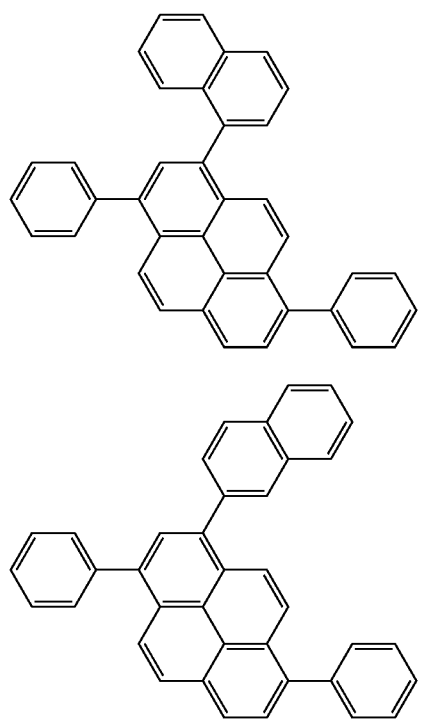
H30
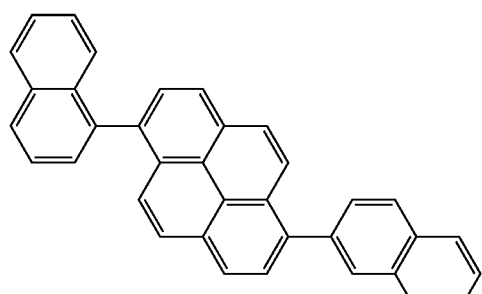
H31
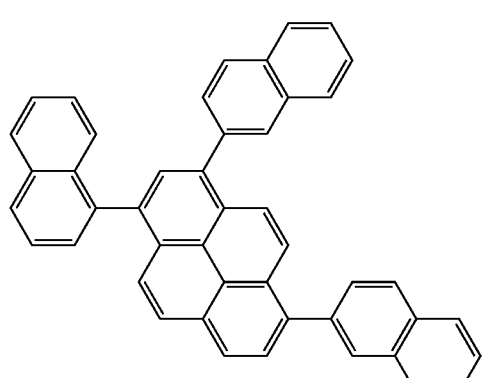
H32
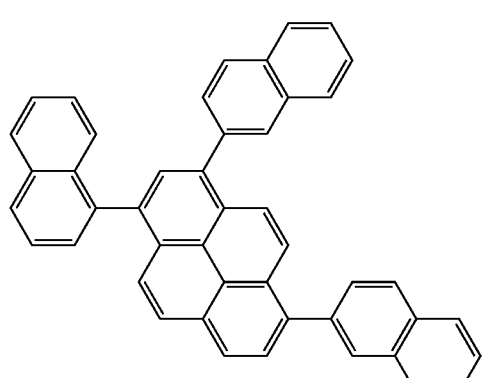
H33
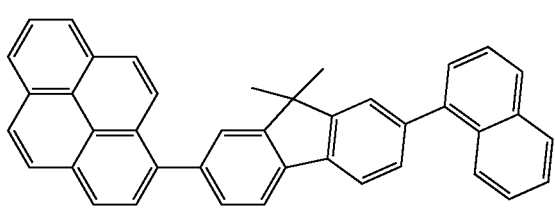
H34
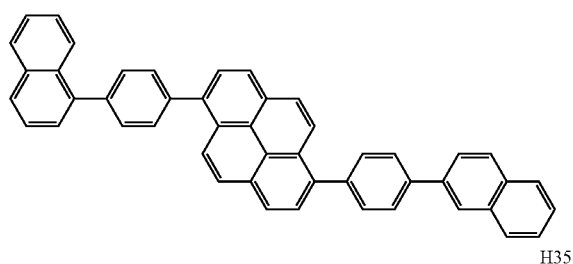
H35
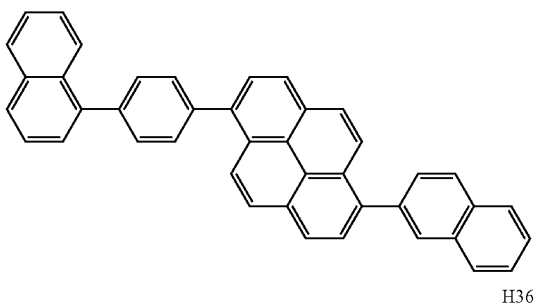
H36
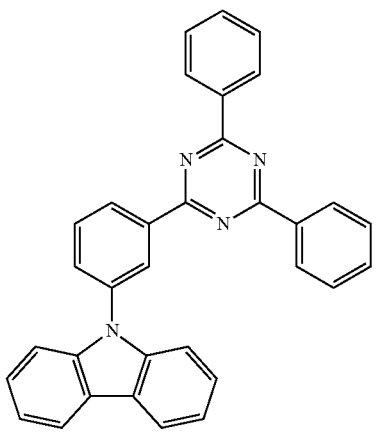
H37
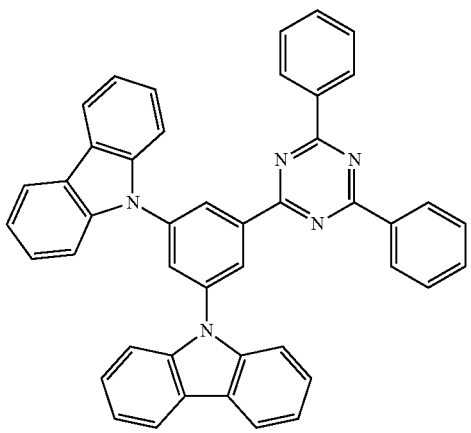
H38
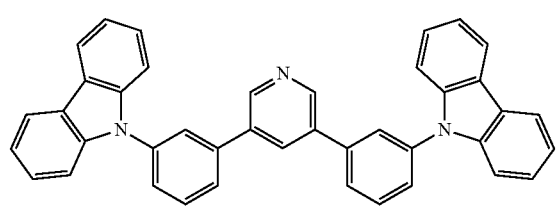

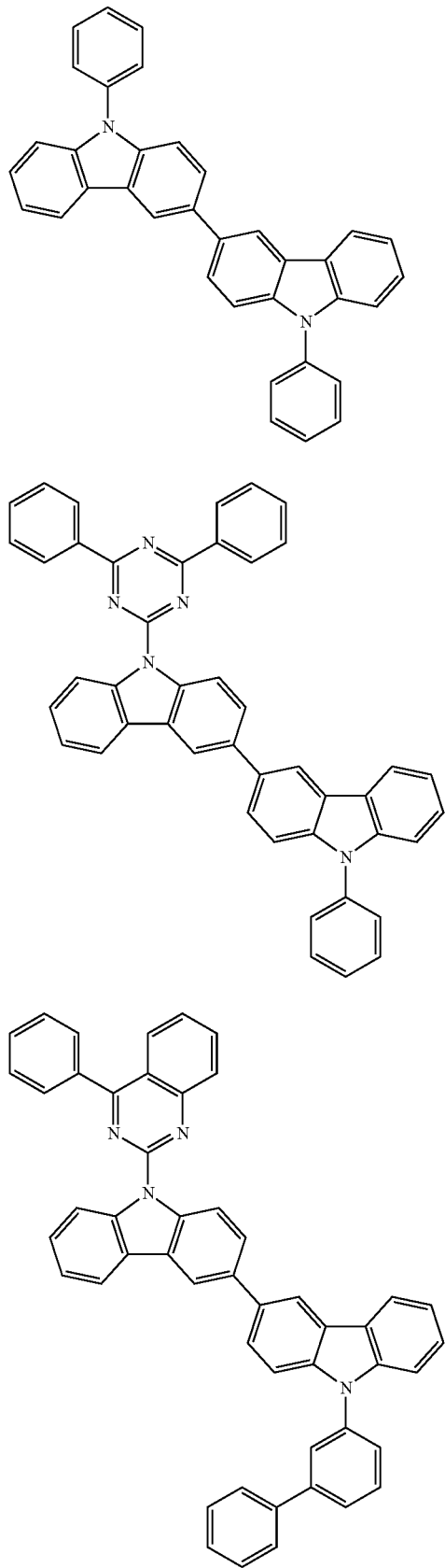
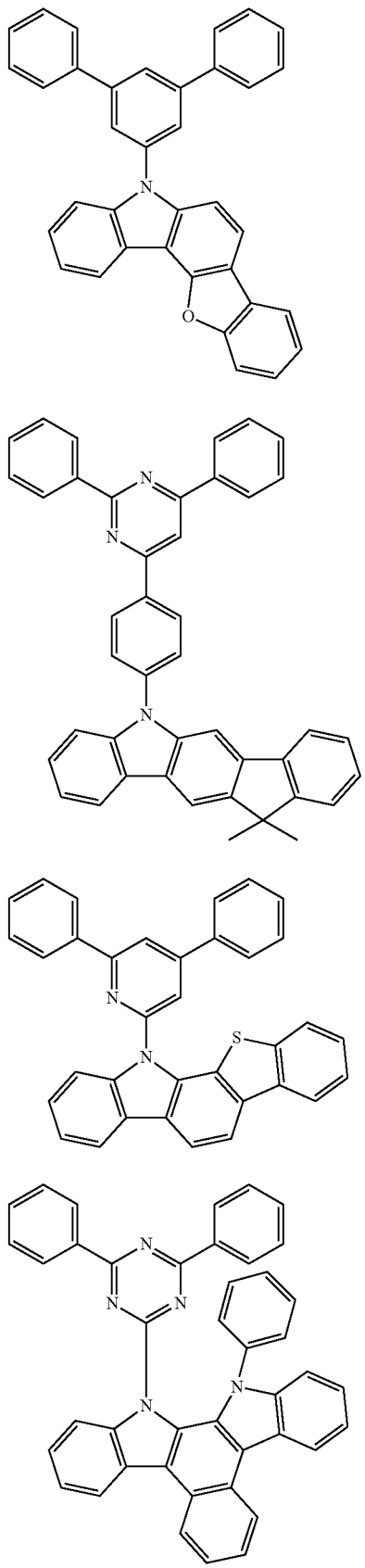

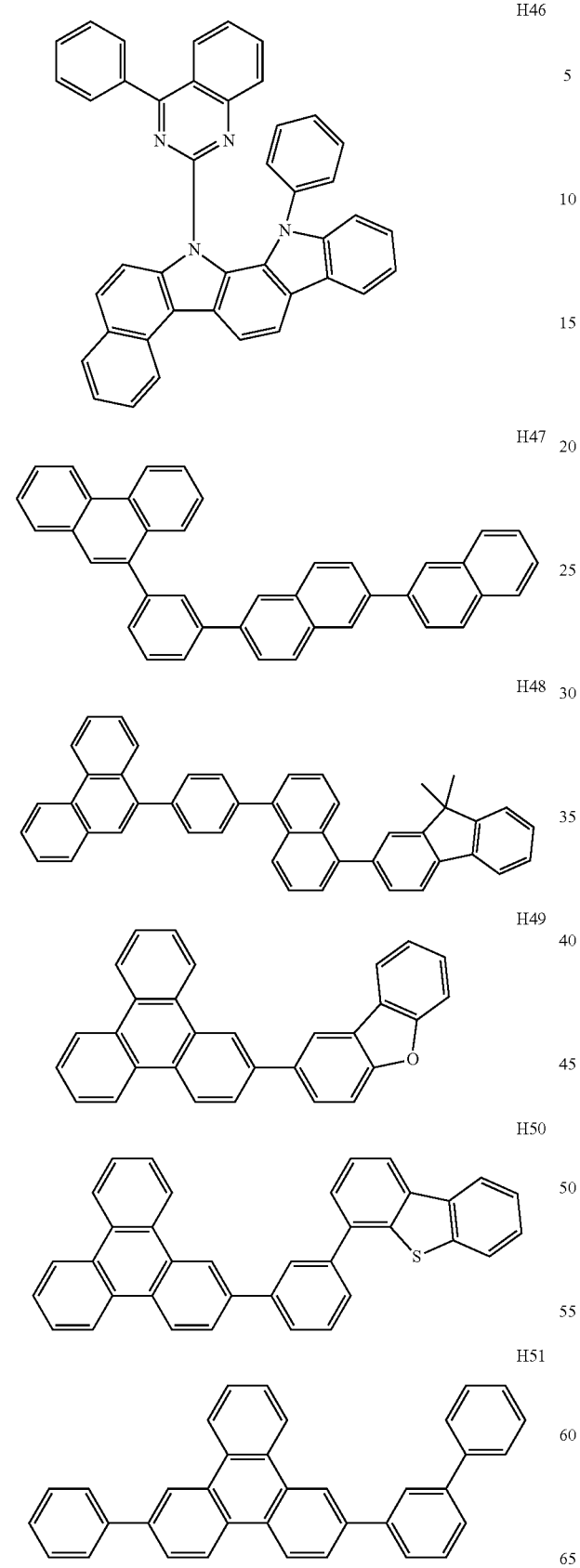
The phosphorescent dopant may include an organometallic complex represented by Formula 401:
$$M(L_{401})_{xc1}(L_{402})_{xc2}$$ <Formula 401>

<Formula 402>

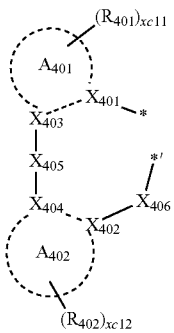

In Formulae 401 and 402:

M may be selected from iridium (Ir), platinum (Pt), palladium (Pd), osmium (Os), titanium (Ti), zirconium (Zr), hafnium (Hf), europium (Eu), terbium (Tb), rhodium (Rh), or thulium (Tm).

$L_{401}$ may be selected from ligands represented by Formula 402. xc1 may be an integer selected from 1, 2, or 3. When xc1 is 2 or greater, at least two $L_{401}$(s) may be the same or different from each other.

$L_{402}$ may be an organic ligand. xc2 may be an integer selected from 0 to 4. When xc2 is 2 or greater, at least two $L_{402}$(s) may be the same or different from each other.

$X_{401}$ to $X_{404}$ may each independently be selected from nitrogen (N) or carbon (C).

$X_{401}$ and $X_{403}$ may be linked via a single bond or a double bond. $X_{402}$ and $X_{404}$ may be linked via a single bond or a double bond.

$A_{401}$ and $A_{402}$ may each independently be selected from a $C_5$-$C_{60}$ carbocyclic group or a $C_1$-$C_{60}$ heterocyclic group.

$X_{405}$ may be selected from a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=*'. $Q_{411}$ and $Q_{412}$ may be selected from hydrogen, deuterium, a $C_1$-$C_{20}$ alkyl group, a $C_1$-$C_{20}$ alkoxy group, a phenyl group, a biphenyl group, a terphenyl group, or a naphthyl group.

$X_{406}$ may be selected from a single bond, oxygen (O), or sulfur (S).

$R_{401}$ and $R_{402}$ may each independently be selected from hydrogen (H), deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, or a $C_1$-$C_{20}$ heteroaryl group.

xc11 and xc12 may each independently be an integer selected from 0 to 10.

* and *' in Formula 402 may each indicate a binding site to M in Formula 401.

According to an exemplary embodiment of the present invention, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, or a dibenzothiophene group.

In Formula 402, $X_{401}$ may be nitrogen (N) and $X_{402}$ may be carbon (C). Alternatively, $X_{401}$ and $X_{402}$ may each be nitrogen (N).

According to an exemplary embodiment of the present invention, $R_{401}$ and $R_{402}$ in Formula 402 may each independently be selected from:

Hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, or a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, or a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, or a dibenzothiophenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, or a dibenzothiophenyl group; or —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)

$(Q_{401})(Q_{402})$. $Q_{401}$ to $Q_{403}$ may each independently be selected from a $C_1$-$C_{10}$ alkyl group, a $C_1$-$C_{10}$ alkoxy group, a phenyl group, a biphenyl group, or a naphthyl group; however, exemplary embodiments of the present invention are not limited thereto.

According to an exemplary embodiment of the present invention, when xc1 in Formula 401 is 2 or greater, two $A_{401}$(s) in at least two $L_{401}$(s) may be linked via $X_{407}$, which is a linking group. Alternatively, two $A_{402}$(s) in two or more $L_{401}$(s) may be linked via $X_{408}$, which is a linking group (see, e.g., Compounds PD1 to PD4 and PD7). $X_{407}$ and $X_{408}$ may each independently be selected from a single bond, *—O—*', *—S—*', *—C(=O)—*', *—N($Q_{413}$)-*', *—C($Q_{413}$)($Q_{414}$)-*' or *—C($Q_{413}$)=C($Q_{414}$)-*', in which $Q_{413}$ and $Q_{414}$ may each independently be selected from hydrogen, deuterium, a $C_1$-$C_{20}$ alkyl group, a $C_1$-$C_{20}$ alkoxy group, a phenyl group, a biphenyl group, a terphenyl group, or a naphthyl group; however, exemplary embodiments of the present invention are not limited thereto.

$L_{402}$ in Formula 401 may be a monovalent, divalent, or trivalent organic ligand.

For example, $L_{402}$ may be selected from a halogen, a diketone (for example, acetylacetonate), a carboxylic acid (for example, picolinate), —C(=O), an isonitrile, —CN, or phosphorus (for example, phosphine or phosphite); however, exemplary embodiments of the present invention are not limited thereto.

According to an exemplary embodiment of the present invention, the phosphorescent dopant may be selected from, for example, Compounds PD1 to PD25; however, exemplary embodiments of the present invention are not limited thereto:

PD1

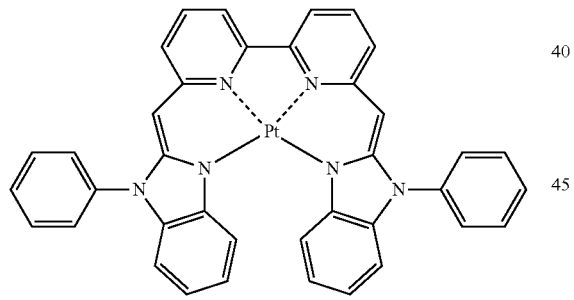

PD2

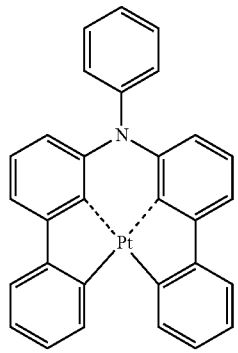

PD3

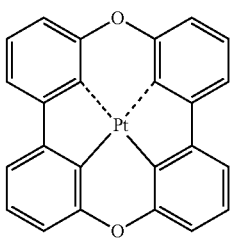

PD4

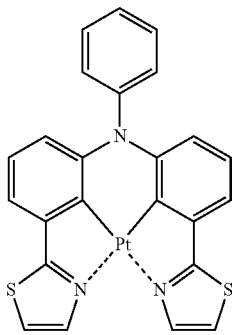

PD5

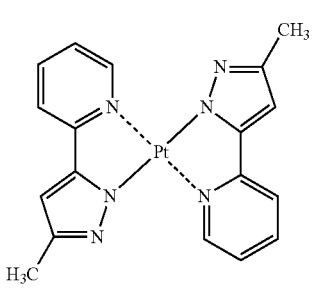

PD6

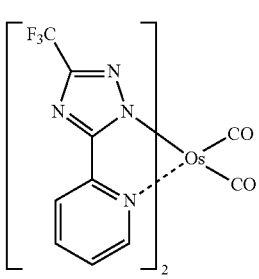

PD7

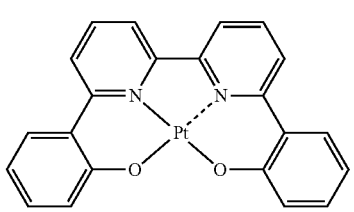

PD8

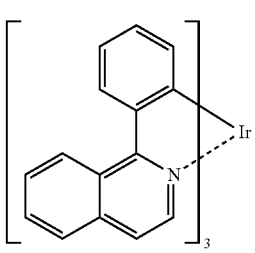

PD9
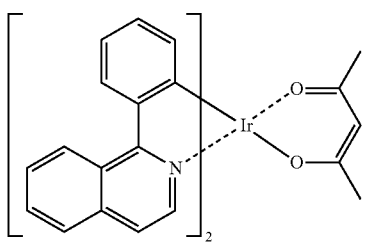
PD10
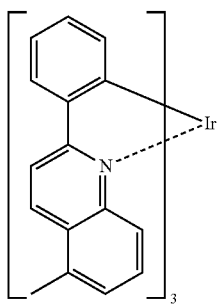
PD11
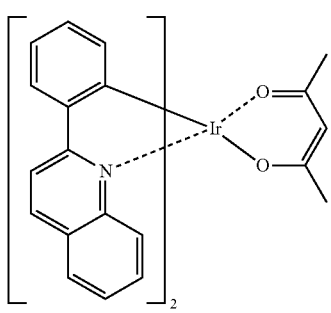
PD12
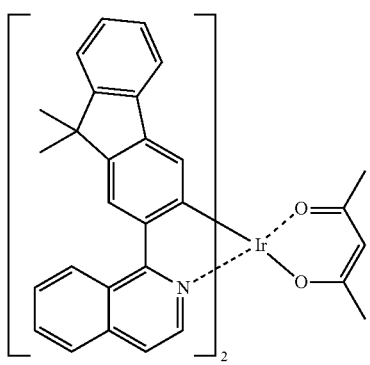
PD13
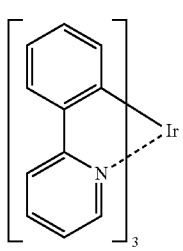
PD14
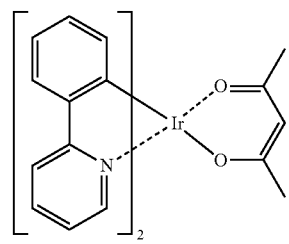
PD15
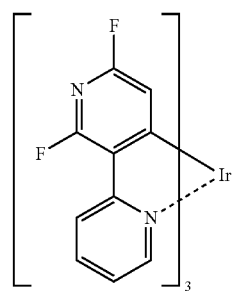
PD16
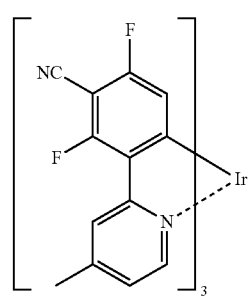
PD17
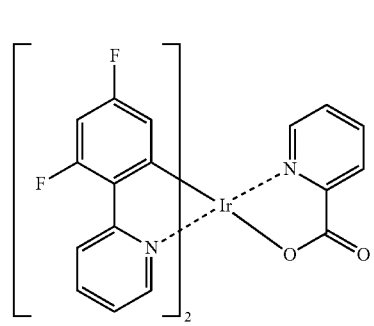
PD18
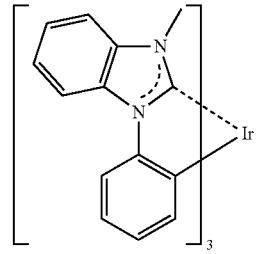

PD19 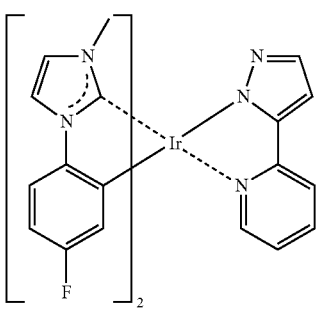

PD20 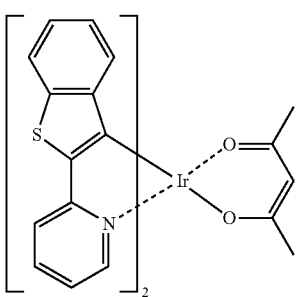

PD21 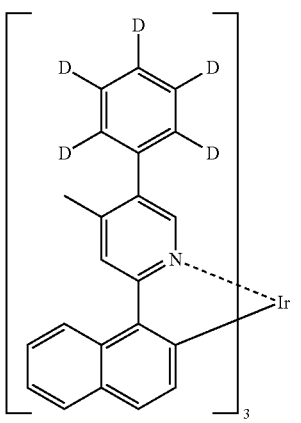

PD22 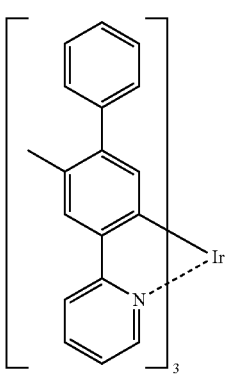

PD23 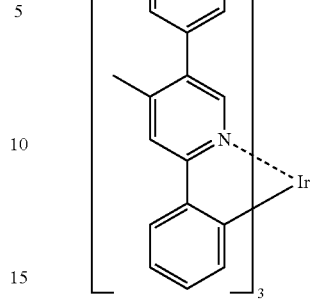

PD24 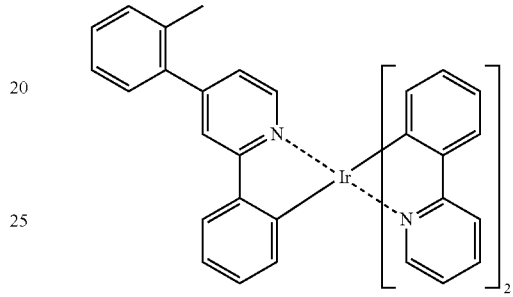

PD25 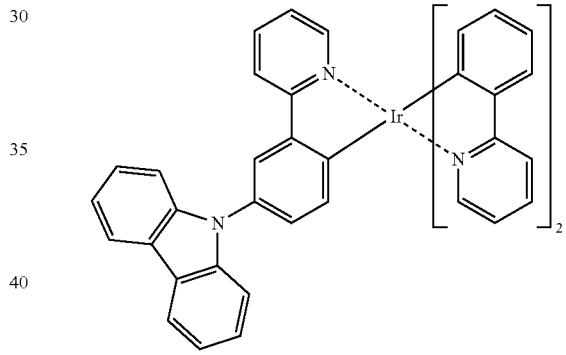

According to one or more exemplary embodiments of the present invention, the fluorescent dopant may include an arylamine compound or a styrylamine compound.

The fluorescent dopant may include a compound represented by Formula 501:

<Formula 501>

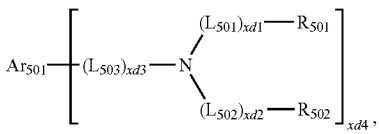

In Formula 501:

$Ar_{501}$ may be selected from a substituted or unsubstituted $C_5$-$C_{60}$ carbocyclic group or a substituted or unsubstituted $C_1$-$C_{60}$ heterocyclic group.

$L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group.

xd1 to xd3 may each independently be an integer selected from 0 to 3.

$R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

xd4 may be an integer selected from 1 to 6.

According to an exemplary embodiment of the present invention, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, or an indenophenanthrene group; or a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, or a naphthyl group.

According to an exemplary embodiment of the present invention, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, or a pyridinylene group; or a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, or a pyridinyl group.

According to an exemplary embodiment of the present invention, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, or a pyridinyl group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, or —Si($Q_{31}$)($Q_{32}$)($Q_{33}$).

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, or a naphthyl group.

xd4 in Formula 501 may be 2; however, exemplary embodiments of the present invention are not limited thereto.
For example, the fluorescent dopant may be selected from Compounds FD1 to FD22:
FD1
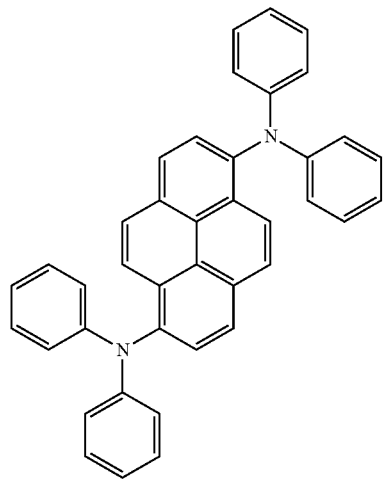
FD2
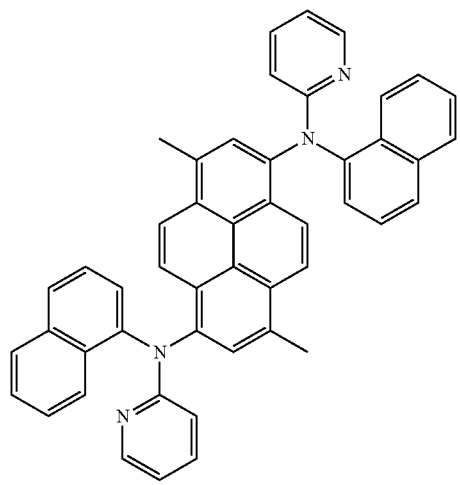
FD3
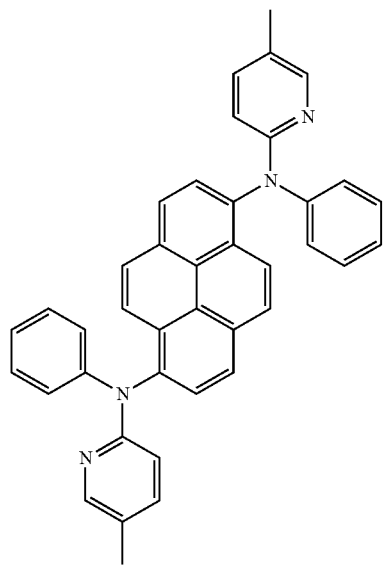
FD4
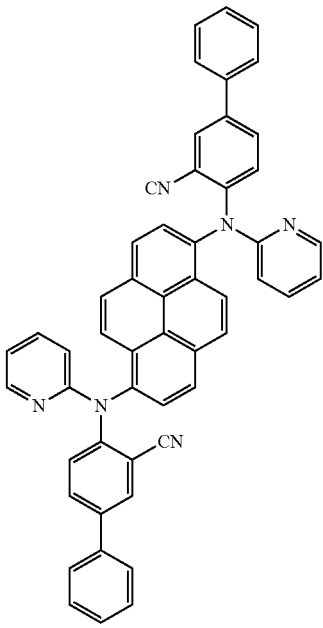
FD5
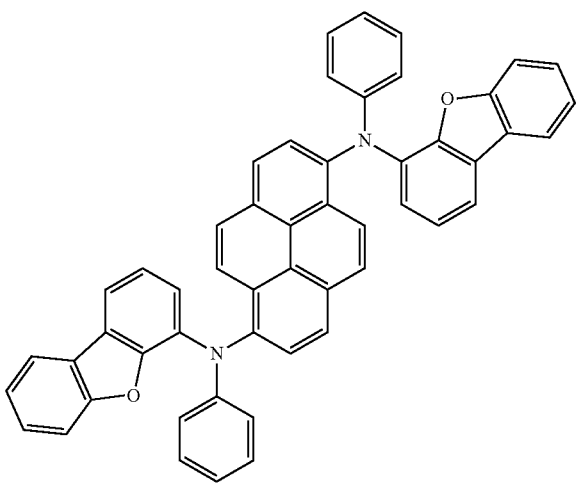
FD6
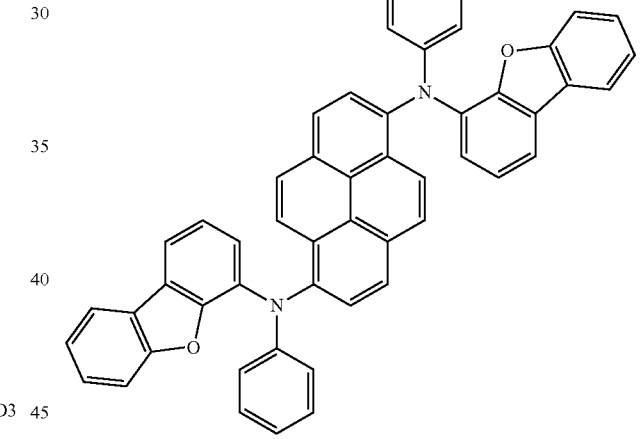

FD7
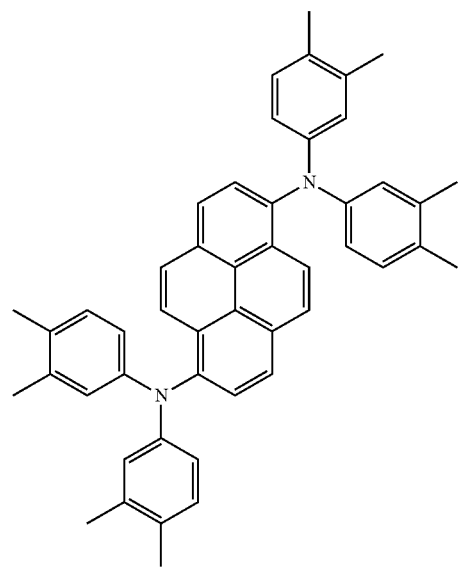
FD10
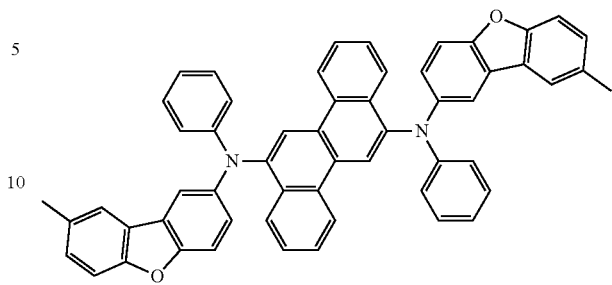
FD11
FD8
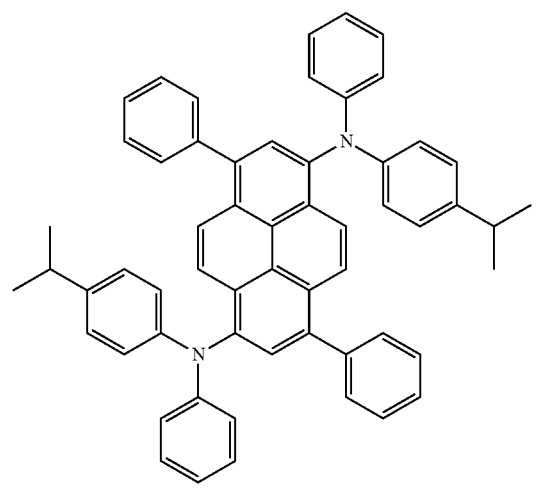
FD12
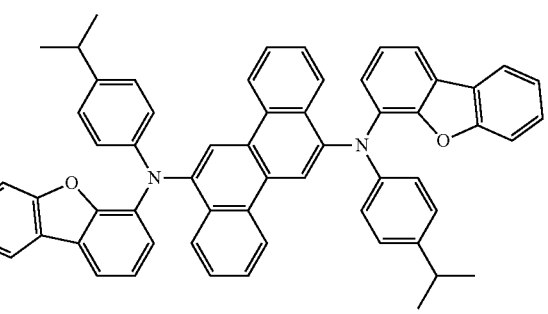
FD9
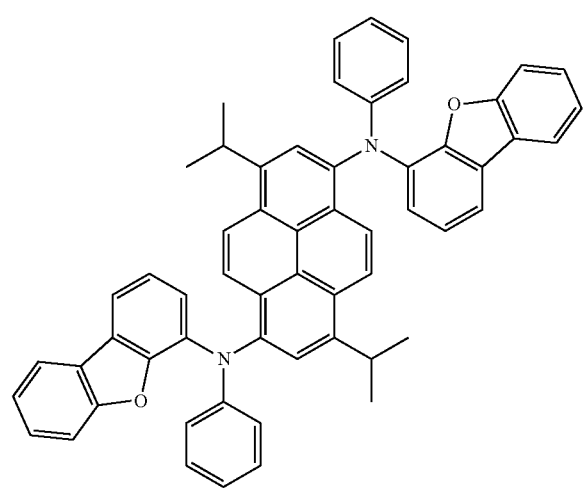
FD13
FD14
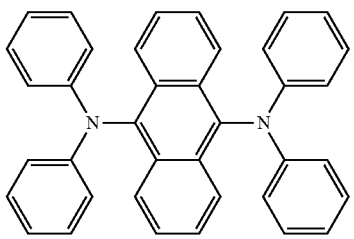

FD15
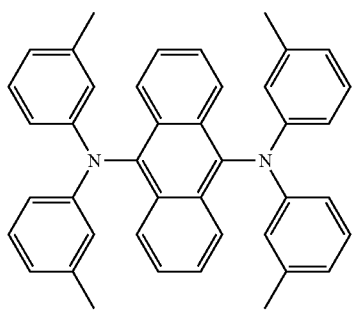
FD16
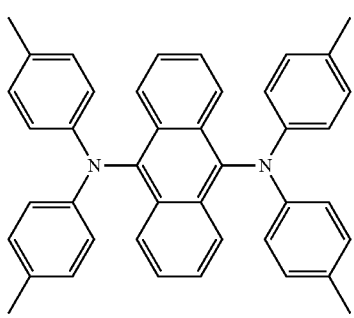
FD17
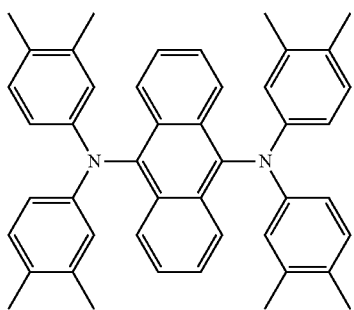
FD18
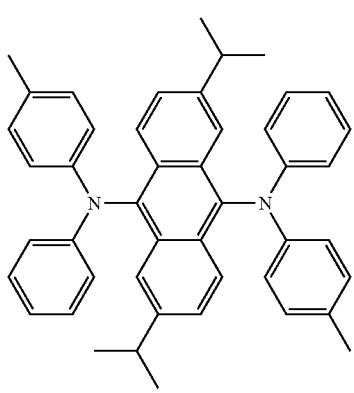
FD19
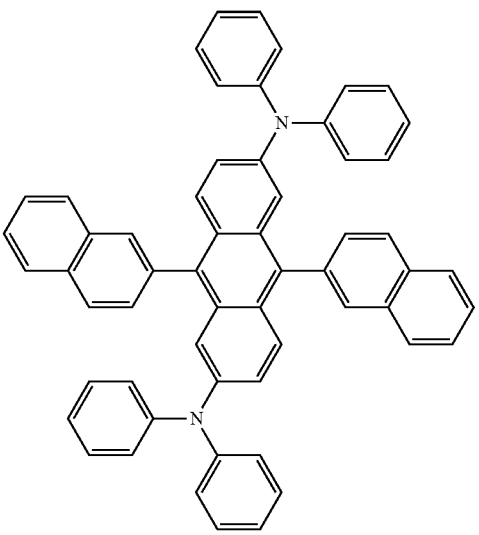
FD20
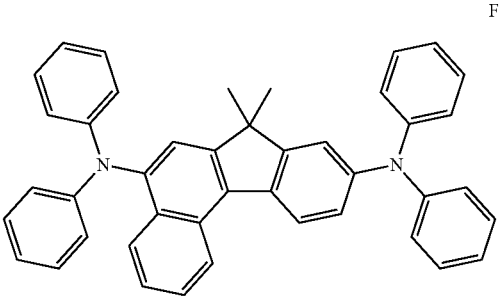
FD21
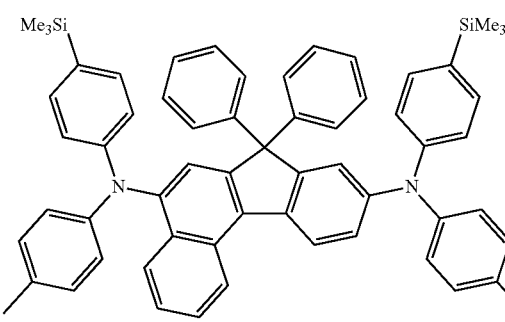
FD22
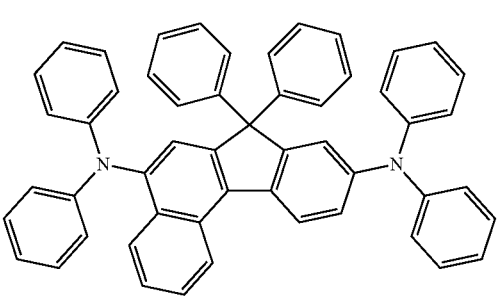
The fluorescent dopant may be selected from the following compounds, however, exemplary embodiments of the present invention are not limited thereto.

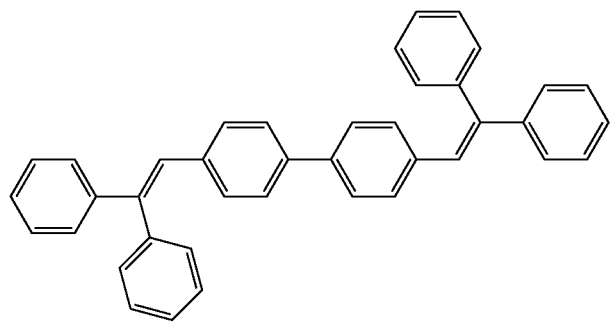
DPVBi
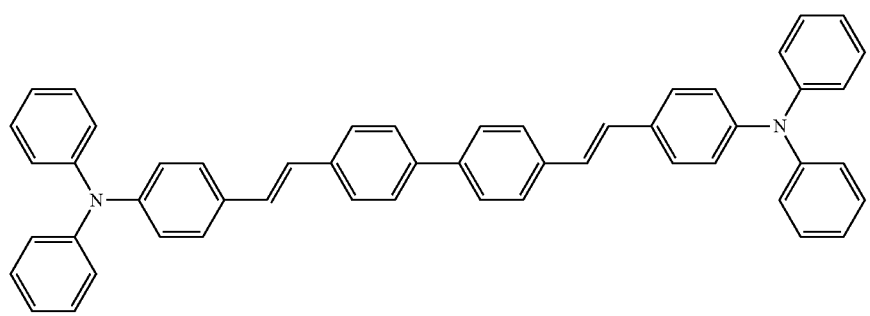
DPAVBi
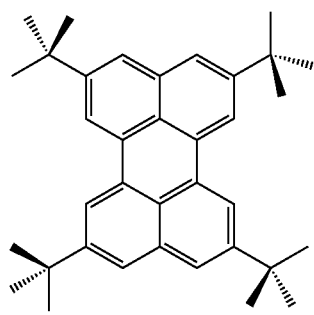
TBPe
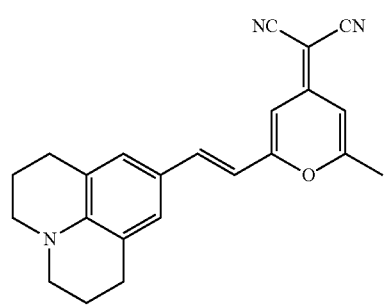
DCM
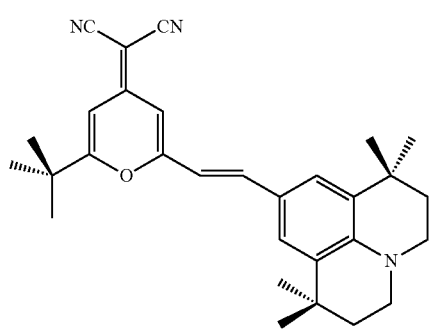
DCJTB
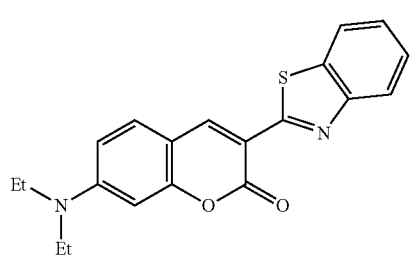
Coumarin 6

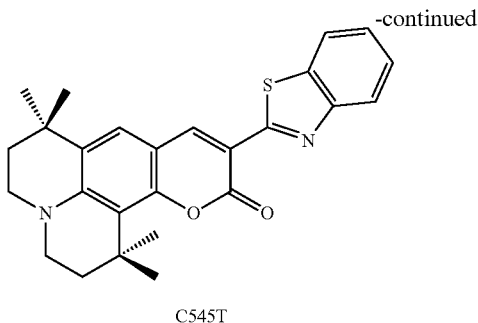

C545T

The electron transport region may have a single-layered structure including a single layer including a single material. The electron transport region may have a single-layered structure including a single layer including a plurality of different materials. The electron transport region may have a multi-layered structure each having a plurality of layers, each including a plurality of different materials.

The electron transport region may include at least one of a buffer layer, a hole blocking layer, an electron control layer, an electron transport layer, or an electron injection layer; however, exemplary embodiments of the present invention are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure. For each structure, the layers may be sequentially stacked on an emission layer. However, exemplary embodiments of the structure of the electron transport region are not limited thereto.

The electron transport region, for example, a buffer layer, a hole blocking layer, an electron control layer, or an electron transport layer in the electron transport region, may include a metal-free compound. The metal-free compound may include at least one π electron-depleted nitrogen-containing ring.

The π electron-depleted nitrogen-containing ring may indicate a $C_1$-$C_{60}$ heterocyclic group having at least one *—N=*' moiety as a ring-forming moiety.

For example, the π electron-depleted nitrogen-containing ring may be a 5-membered to 7-membered hetero monocyclic group having at least one *—N=*' moiety. The π electron-depleted nitrogen-containing ring may be a heteropoly cyclic group in which two or more 5-membered to 7-membered hetero monocyclic groups each having at least one *—N=*' moiety are condensed with each other. The π electron-depleted nitrogen-containing ring may be a heteropoly cyclic group in which at least one of 5-membered to 7-membered hetero monocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, or an azacarbazole; however, exemplary embodiments of the present invention are not limited thereto.

The condensed cyclic compound represented by Formula 1 may be included in the electron transport region. According to an exemplary embodiment of the present invention, the electron transport region may include an emission auxiliary layer. The condensed cyclic compound may be included in the emission auxiliary layer; however, exemplary embodiments of the present invention are not limited thereto.

According to an exemplary embodiment of the present invention, the electron transport region may include, in addition to the condensed cyclic compound represented by Formula 1, a compound represented by Formula 601.

$$[Ar_{601}]_{xe11}\text{-}[(L_{601})_{xe1}\text{-}R_{601}]_{xe21}. \quad \text{<Formula 601>}$$

In Formula 601:

$Ar_{601}$ may be selected from a substituted or unsubstituted $C_5$-$C_{60}$ carbocyclic group or a substituted or unsubstituted $C_1$-$C_{60}$ heterocyclic group.

xe11 may be an integer selected from 1, 2, or 3.

$L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group.

xe1 may be an integer selected from 0 to 5.

$R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), or —P(=O)($Q_{601}$)($Q_{602}$).

$Q_{601}$ to $Q_{603}$ may each independently be selected from a $C_1$-$C_{10}$ alkyl group, a $C_1$-$C_{10}$ alkoxy group, a phenyl group, a biphenyl group, a terphenyl group, or a naphthyl group.

xe21 may be an integer selected from 1 to 5.

According to an exemplary embodiment of the present invention, at least one of $Ar_{601}$(s) in the number of xe11 and/or at least one of $R_{601}$ (S) in the number of xe21 may include the π electron-depleted nitrogen-containing ring.

According to an exemplary embodiment of the present invention, the ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, or an azacarbazole group; or a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), or —P(=O)($Q_{31}$)($Q_{32}$).

$Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, or a naphthyl group.

When xe11 in Formula 601 is 2 or greater, at least two $Ar_{601}$(s) may be linked via a single bond.

According to an exemplary embodiment of the present invention, $Ar_{601}$ in Formula 601 may be an anthracene group.

According to an exemplary embodiment of the present invention, the compound represented by Formula 601 may be represented by Formula 601-1:

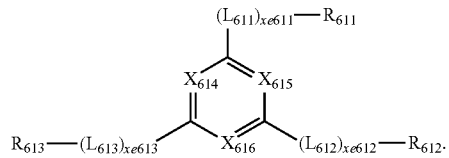

<Formula 601-1>

In Formula 601-1:

$X_{614}$ may be nitrogen (N) or C($R_{614}$), $X_{615}$ may be nitrogen (N) or C($R_{615}$), $X_{616}$ may be nitrogen (N) or C($R_{616}$), and at least one selected from $X_{614}$ to $X_{616}$ may be nitrogen (N).

$L_{611}$ to $L_{613}$ may each be the same as $L_{601}$.

xe611 to xe613 may each be the same as xe1.

$R_{611}$ to $R_{613}$ may each be the same as $R_{601}$.

$R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, or a naphthyl group.

According to an exemplary embodiment of the present invention, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, or an azacarbazolylene group; or a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, or an azacarbazolyl group; however, exemplary embodiments of the present invention are not limited thereto.

According to an exemplary embodiment of the present invention, xe1 and xe611 to xe613 in Formulae 601 and 601-1 may each independently be an integer selected from 0, 1, or 2.

According to an exemplary embodiment of the present invention, $R_{601}$ and $R_{611}$ to $R_{613}$ in Formulae 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, or an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, or an azacarbazolyl group; or —S(=O)$_2$(Q$_{601}$) and —P(=O)(Q$_{601}$)(Q$_{602}$). Q$_{601}$ and Q$_{602}$ may be the same as described above.

The electron transport region may include at least one compound selected from Compounds ET1 to ET36; however, exemplary embodiments of the present invention are not limited thereto:
ET1
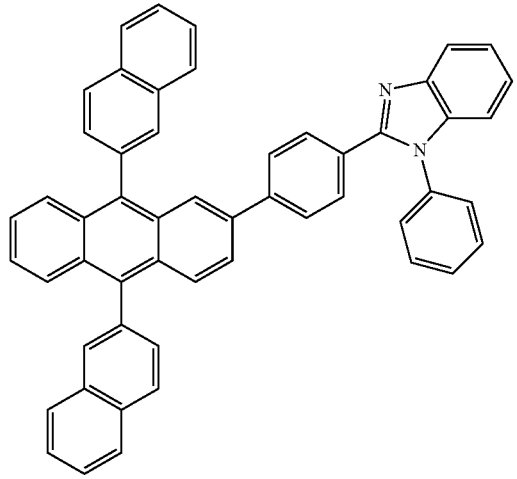
ET2
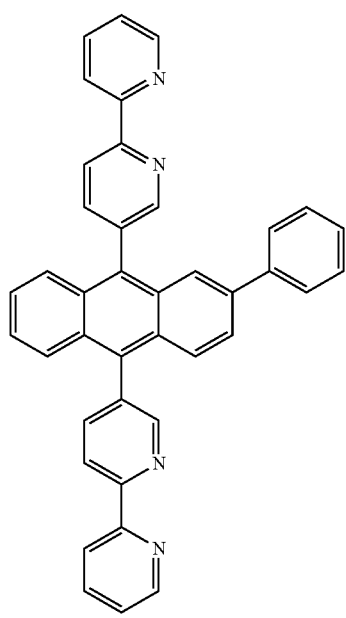
ET3
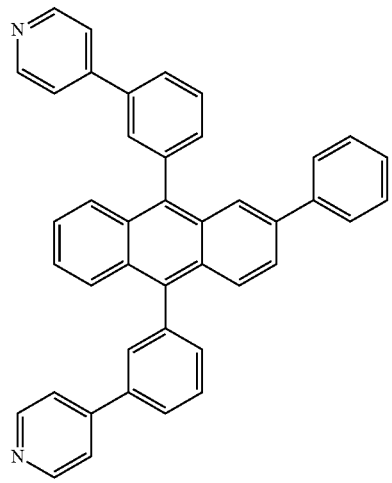
ET4
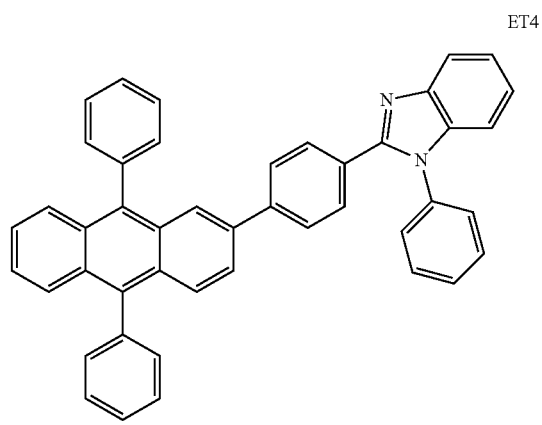
ET5
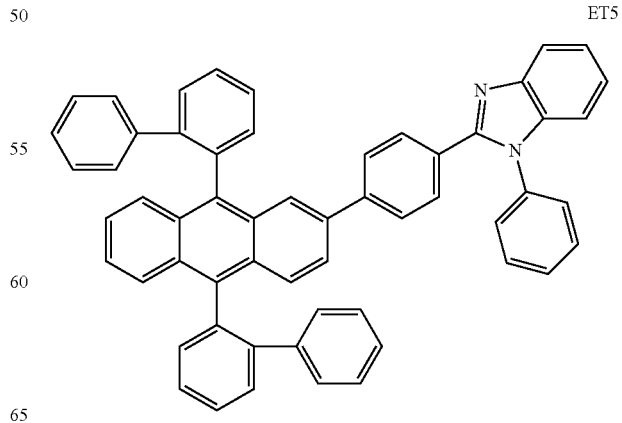

ET6
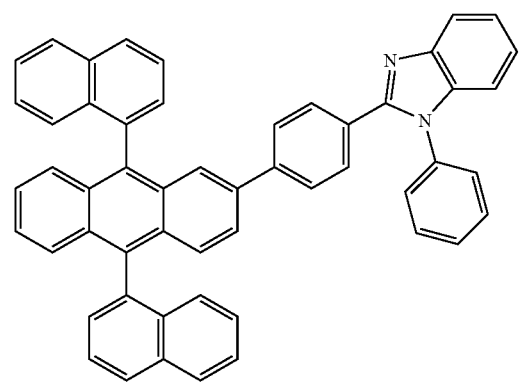
ET7
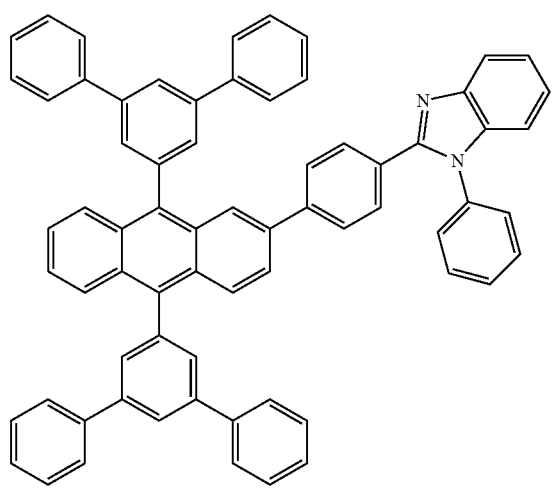
ET8
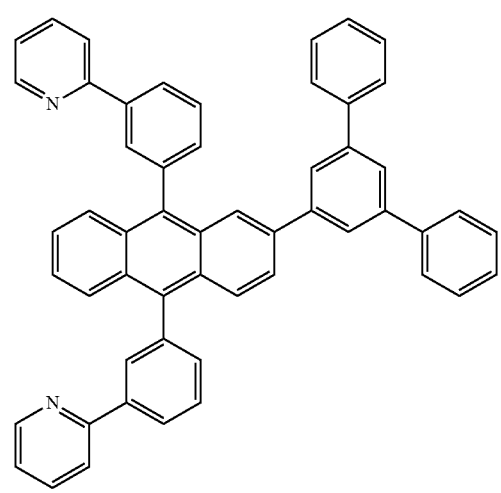
ET9
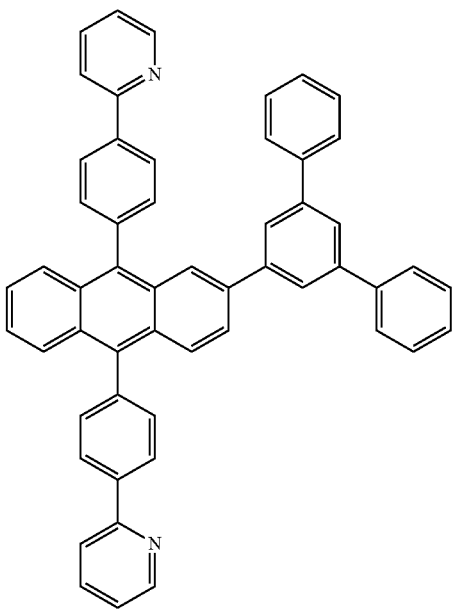
ET10
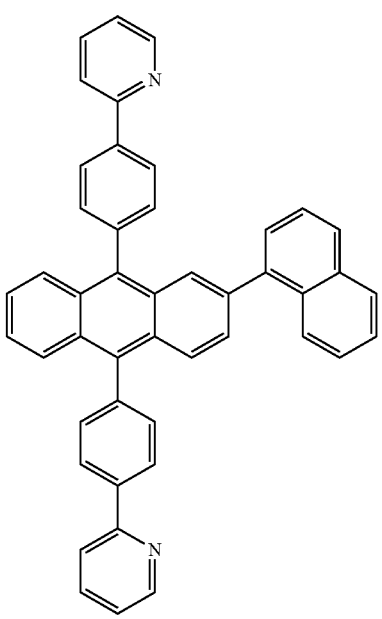

ET11
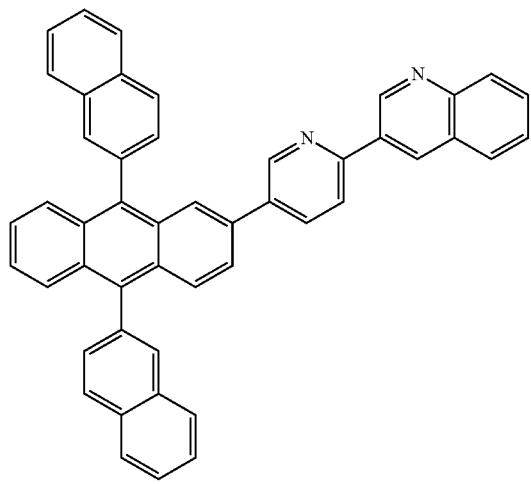
ET14
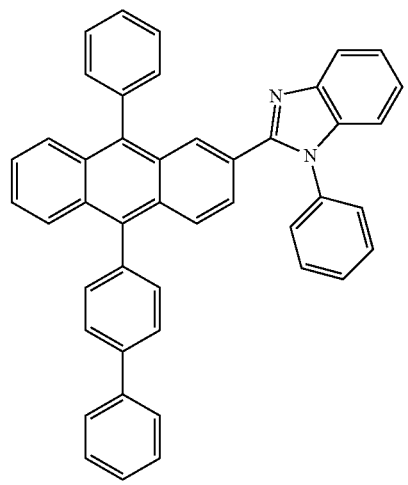
ET12
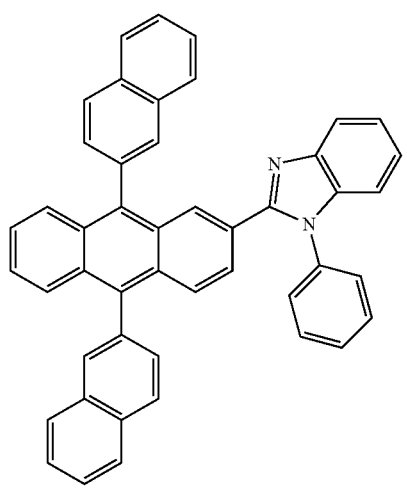
ET15
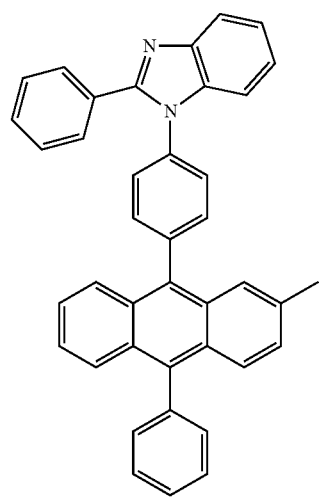
ET13
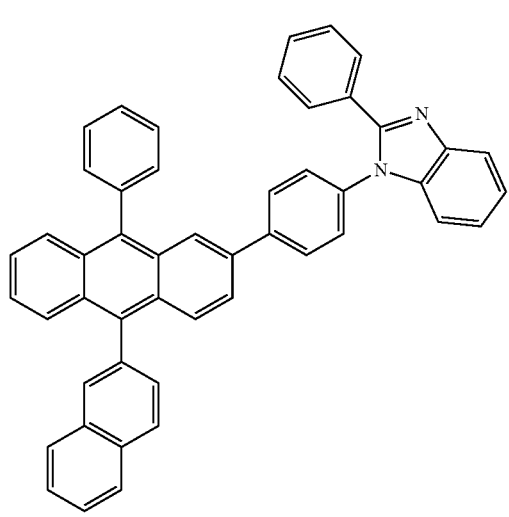
ET16
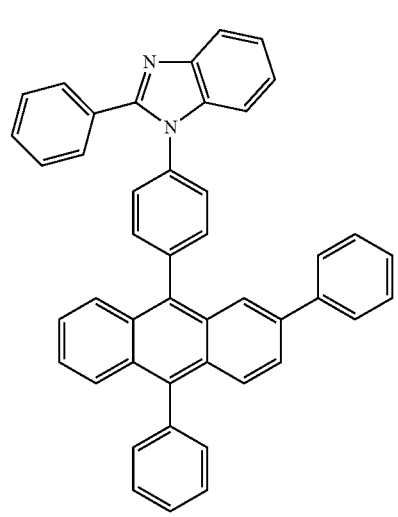

ET17
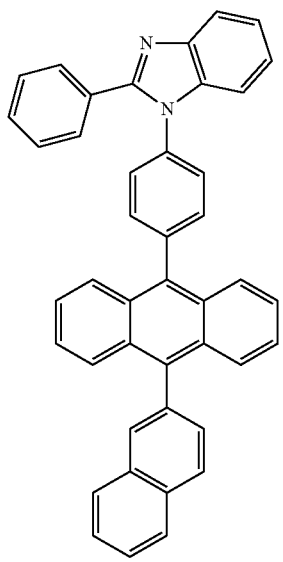
ET18
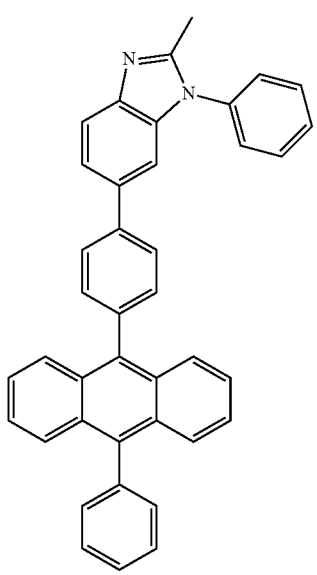
ET19
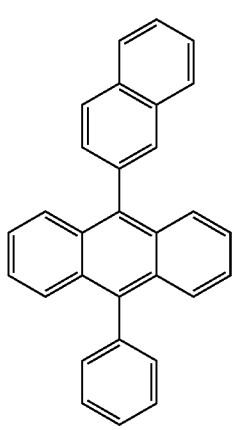
ET20
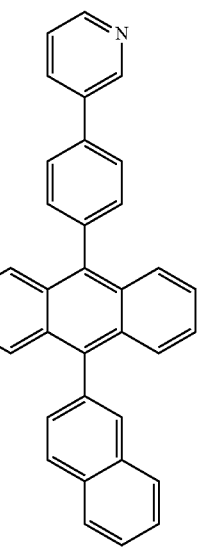
ET21
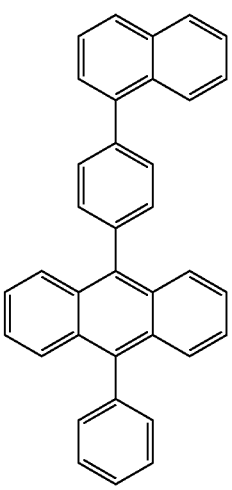
ET22
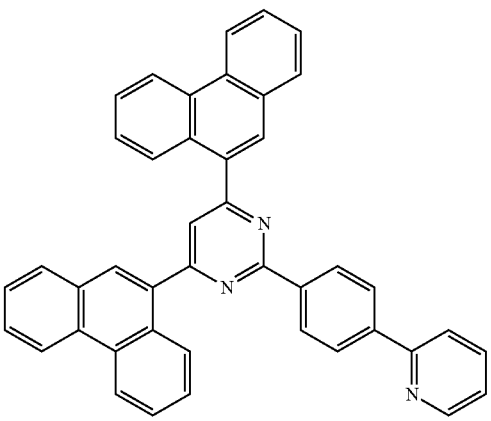

ET23
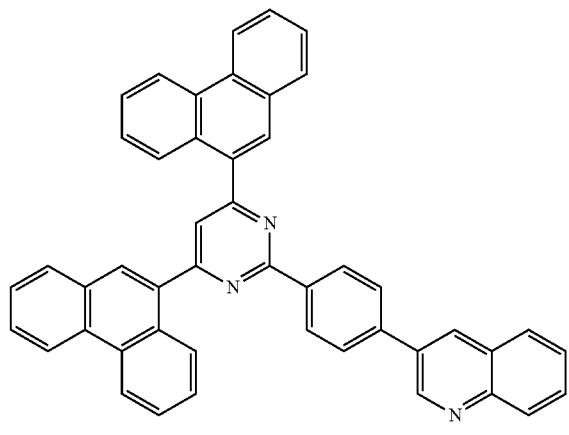
ET24
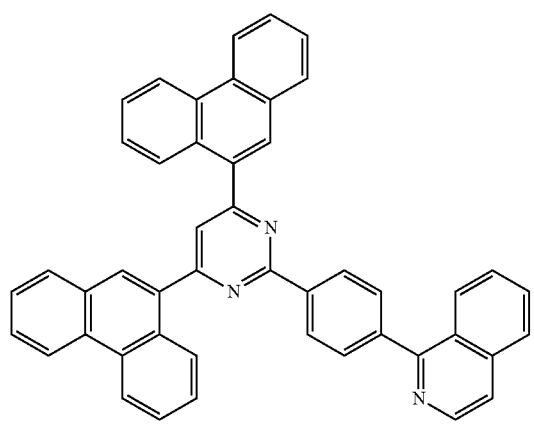
ET25
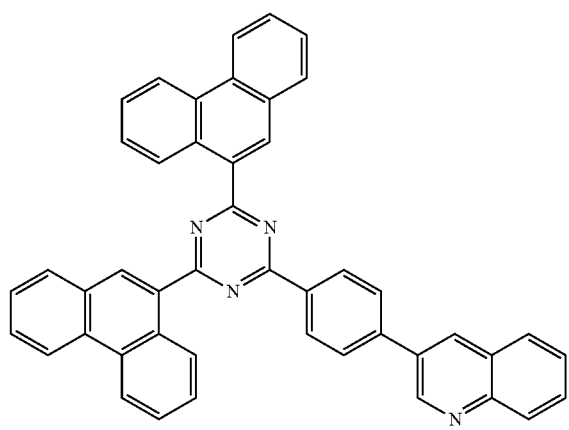
ET26
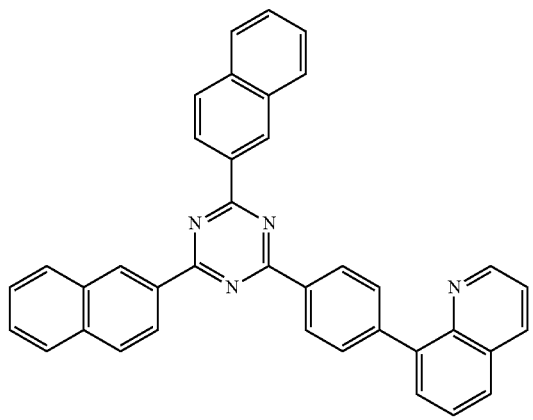
ET27
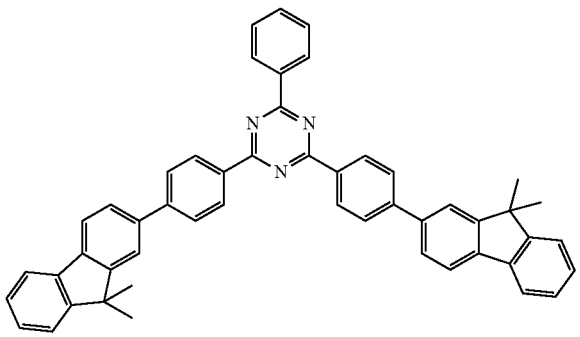
ET28

ET29
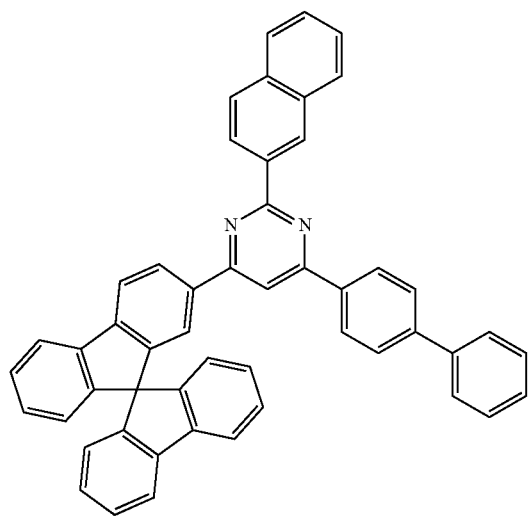
ET32
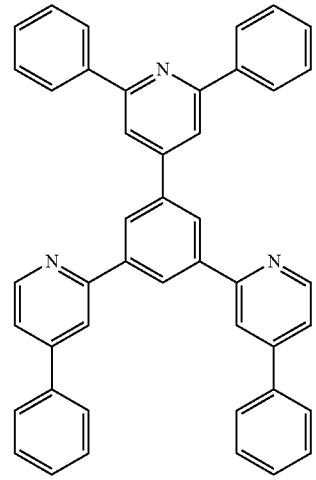
ET30
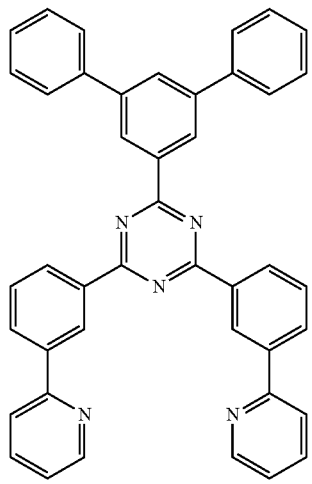
ET33
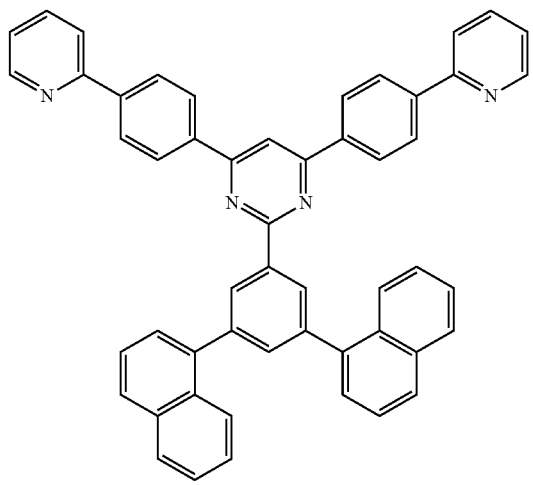
ET31
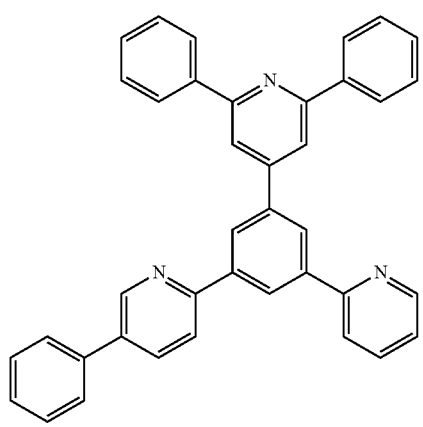
ET34

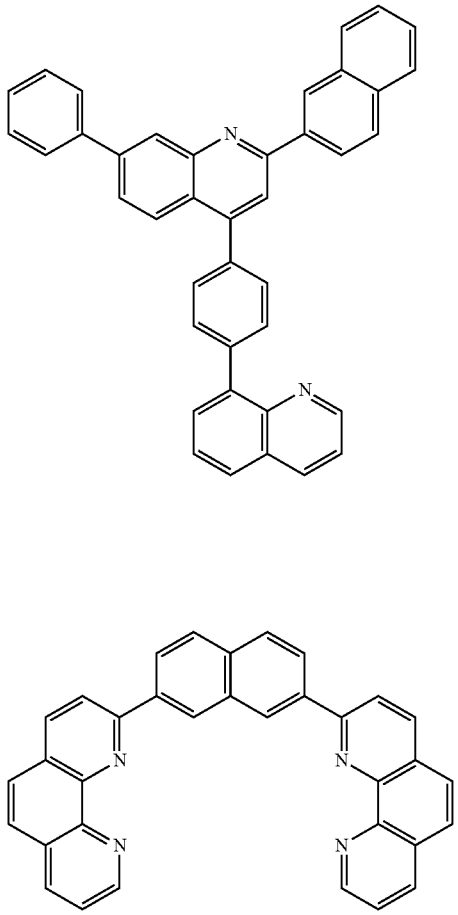

ET35

ET36

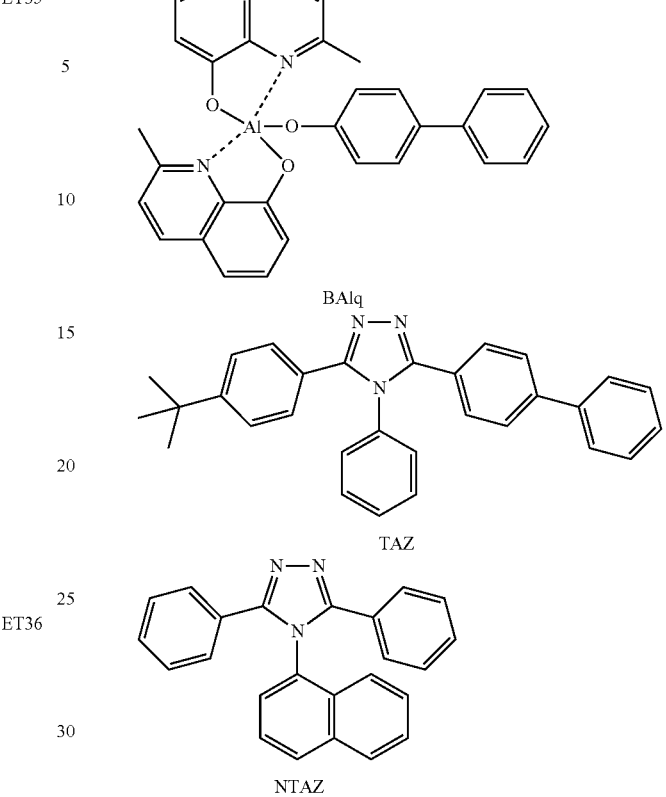

BAlq

TAZ

NTAZ

A thicknesses of the buffer layer, the hole blocking layer, and the electron control layer may each be in a range of from about 20 Å to about 1,000 Å, for example, from about 30 Å to about 300 Å. When the thicknesses of the buffer layer, the hole blocking layer, and the electron control layer are within these ranges, the electron blocking layer may have relatively high electron blocking characteristics or electron control characteristics without a substantial increase in driving voltage.

A thickness of the electron transport layer may be in a range of from about 100 Å to about 1,000 Å, for example, from about 150 Å to about 500 Å. When the thickness of the electron transport layer is within the range described above, the electron transport layer may have satisfactory electron transport characteristics without a substantial increase in driving voltage.

The electron transport region, for example, the electron transport layer in the electron transport region, may include, in addition to the materials described above, a material including metal.

The material including metal may include at least one selected from an alkali metal complex or an alkaline earth-metal complex. The alkali metal complex may include a metal ion selected from an lithium (Li) ion, a sodium (Na) ion, a potassium (K) ion, a rubidium (Rb) ion, and a caesium (Cs) ion. The alkaline earth-metal complex may include a metal ion selected from a beryllium (Be) ion, a magnesium (Mg) ion, a calcium (Ca) ion, an strontium (Sr) ion, and a barium (Ba) ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenylan oxazole, a According to an exemplary embodiment of the present invention, the electron transport region may include at least one selected from 2,9-dimethyl-4,7-diphenyl-1,10-phenanthroline (BCP), 4,7-dphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), or NTAZ.

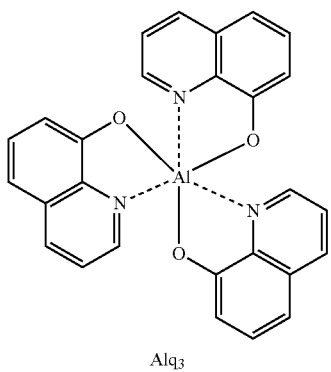

Alq$_3$ hydroxy phenylthiazole, a hydroxy diphenylan oxadiazole, a hydroxy diphenylthiadiazol, a hydroxy phenylpyridine, a hydroxy phenylbenzimidazole, a hydroxy phenylbenzothiazole, a bipyridine, a phenanthroline, or a cyclopentadiene; however, exemplary embodiments of the present invention are not limited thereto.

For example, the material including metal may include a lithium (Li) complex. The lithium (Li) complex may include, for example, Compound ET-D1 (lithium quinolate, LiQ) or ET-D2.

ET-D1

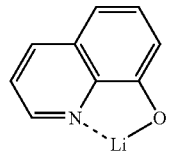

ET-D2

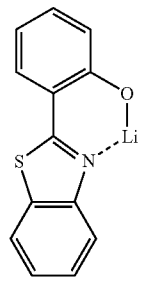

The electron transport region may include an electron injection layer. The electron injection layer may be configured to facilitate injection of electrons from the second electrode 190. The electron injection layer may be in direct contact with the second electrode 190.

The electron injection layer may have a single-layered structure including a single layer including a single material. The electron injection layer may have a single-layered structure including a single layer including a plurality of different materials. The electron injection layer may have a multi-layered structure having a plurality of layers, each including a plurality of different materials.

The electron injection layer may include an alkali metal, an alkaline earth metal, a rare-earth metal, an alkali metal compound, an alkaline earth-metal compound, a rare-earth metal compound, an alkali metal complex, an alkaline earth-metal complex, a rare-earth metal complex or any combinations thereof.

The alkali metal may include Li, Na, K, Rb, or Cs. According to an exemplary embodiment of the present invention, the alkali metal may be Li, Na, or Cs. The alkali metal may be Li or Cs; however, exemplary embodiments of the present invention are not limited thereto.

The alkaline earth metal may be selected from Mg, Ca, Sr, or Ba.

The rare-earth metal may be selected from Sc, Y, Ce, Yb, Gd, or Tb.

The alkali metal compound, the alkaline earth-metal compound, and the rare-earth metal compound may be selected from oxides and halides (for example, fluorides, chlorides, bromides, or iodines) of the alkali metal, the alkaline earth-metal or the rare-earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. According to an exemplary embodiment of the present invention, the alkali metal compound may include LiF, $Li_2O$, NaF, LiI, NaI, CsI, or KI; however, exemplary embodiments of the present invention are not limited thereto.

The alkaline earth-metal compound may be selected from alkaline earth-metal compounds, such as BaO, SrO, CaO, $Ba_xSr_{1-x}O$ (0<x<1), or $Ba_xCa_{1-x}O$ (0<x<1). According to an exemplary embodiment of the present invention, the alkaline earth-metal compound may be selected from BaO, SrO, or CaO; however, exemplary embodiments of the present invention are not limited thereto.

The rare-earth metal compound may be selected from $YbF_3$, $ScF_3$, $ScO_3$, $Y_2O_3$, $Ce_2O_3$, $GdF_3$, or $TbF_3$. According to an exemplary embodiment of the present invention, the rare-earth metal compound may include $YbF_3$, $ScF_3$, $TbF_3$, $YbF_3$, $ScI_3$, or $TbI_3$; however, exemplary embodiments of the present invention are not limited thereto.

The alkali metal complex, the alkaline earth-metal complex, and the rare-earth metal complex may include an ion of alkali metal, alkaline earth-metal, or rare-earth metal as described above. A ligand coordinated with a metal ion of the alkali metal complex, the alkaline earth-metal complex, and the rare-earth metal complex may each independently be selected from hydroxy quinoline, hydroxy isoquinoline, hydroxy benzoquinoline, hydroxy acridine, hydroxy phenanthridine, hydroxy phenylan oxazole, hydroxy phenylthiazole, hydroxy diphenylan oxadiazole, hydroxy diphenylthiadiazol, hydroxy phenylpyridine, hydroxy phenylbenzimidazole, hydroxy phenylbenzothiazole, bipyridine, phenanthroline, or cyclopentadiene; however, exemplary embodiments of the present invention are not limited thereto.

The electron injection layer may include an alkali metal, an alkaline earth metal, a rare-earth metal, an alkali metal compound, an alkaline earth-metal compound, a rare-earth metal compound, an alkali metal complex, an alkaline earth-metal complex, a rare-earth metal complex, or any combinations thereof. According to an exemplary embodiment of the present invention, the electron injection layer may include an organic material. When the electron injection layer includes an organic material, an alkali metal, an alkaline earth metal, a rare-earth metal, an alkali metal compound, an alkaline earth-metal compound, a rare-earth metal compound, an alkali metal complex, an alkaline earth-metal complex, a rare-earth metal complex, or any combinations thereof may be substantially homogeneously or non-homogeneously dispersed in a matrix including the organic material.

A thickness of the electron injection layer may be in a range of from about 1 Å to about 100 Å, for example, from about 3 Å to about 90 Å. When the thickness of the electron injection layer is within the range described above, the electron injection layer may have satisfactory electron injection characteristics without a substantial increase in driving voltage.

The second electrode 190 may be disposed on the organic layer 150. The second electrode 190 may be a cathode. The cathode may be an electron injection electrode. Accordingly, the second electrode 190 may include a metal, an alloy, an electrically conductive compound, or a combination thereof, which may have a relatively low work function.

The second electrode 190 may include at least one of lithium (Li), silver (Ag), magnesium (Mg), aluminum (Al), aluminum-lithium (Al—Li), calcium (Ca), magnesium-indium (Mg—In), magnesium-silver (Mg—Ag), indium tin oxide (ITO), or indium zinc oxide (IZO); however, exemplary embodiments of the present invention are not limited thereto. The second electrode 190 may be a transmissive electrode, a semi-transmissive electrode, or a reflective electrode.

The second electrode 190 may have a single-layered structure. Alternatively, the second electrode 190 may have a multi-layered structure including two or more layers.

Figure 2:
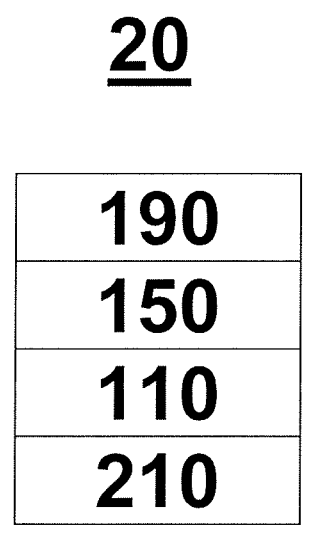

FIG. 2 is a schematic cross-sectional diagram illustrating an organic light-emitting device according to an exemplary embodiment of the present invention. Referring to FIG. 2, an organic light-emitting device 20 may include a first capping layer 210, the first electrode 110, the organic layer 150, and the second electrode 190. The first electrode 110, the organic layer 150, and the second electrode 190 may be sequentially stacked.

Figure 3:
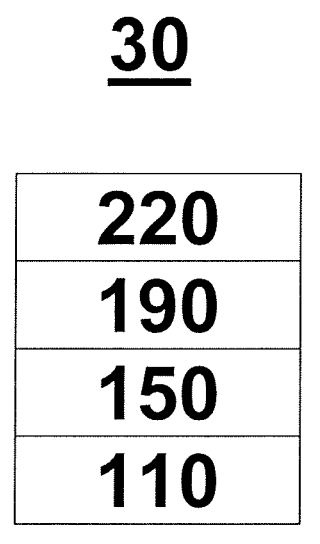

FIG. 3 is a schematic cross-sectional diagram illustrating an organic light-emitting device according to an exemplary embodiment of the present invention. Referring to FIG. 3, an organic light-emitting device 30 may include the first electrode 110, the organic layer 150, the second electrode 190, and a second capping layer 220. The first electrode 110, the organic layer 150, the second electrode 190, and the second capping layer 220 may be sequentially stacked.

Figure 4:
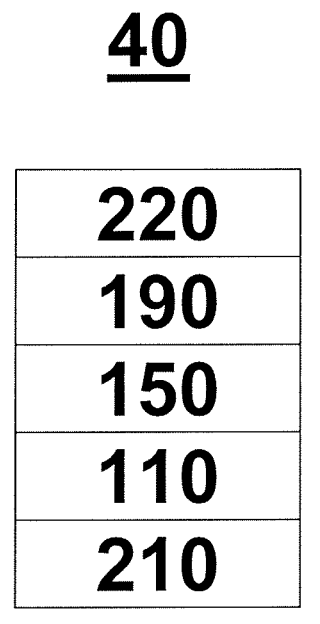

FIG. 4 is a schematic cross-sectional diagram illustrating an organic light emitting device according to an exemplary embodiment of the present invention. Referring to FIG. 4, the organic light-emitting device 40 may include the first capping layer 210, the first electrode 110, the organic layer 150, the second electrode 190, and the second capping layer 220. The first electrode 110, the organic layer 150, the second electrode 190, and the second capping layer 200 may be sequentially stacked.

In the organic layer 150 of each of the organic light-emitting devices 20 and 40, light generated in an emission layer may pass through the first electrode 110 and the first capping layer 210 toward the outside. The first electrode 110 may be a semi-transmissive or a transmissive electrode. In the organic layer 150 of each of the organic light-emitting devices 30 and 40, light generated in an emission layer may pass through the second electrode 190 and the second capping layer 220 toward the outside. The second electrode 190 may be a semi-transmissive electrode or a transmissive electrode.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one of the first capping layer 210 and the second capping layer 220 may include at least one material selected from carbocyclic compounds, heterocyclic compounds, amine-based compounds, porphyrine derivatives, phthalocyanine derivatives, naphthalocyanine derivatives, alkali metal complexes, or alkaline earth-based complexes. The carbocyclic compound, the heterocyclic compound, and the amine-based compound may be optionally substituted with a substituent including at least one element selected from O, N, S, Se, Si, F, Cl, Br, or I. According to an exemplary embodiment of the present invention, at least one of the first capping layer 210 and the second capping layer 220 may include an amine-based compound.

According to an exemplary embodiment of the present invention, at least one of the first capping layer 210 and the second capping layer 220 may include the compound represented by Formula 201 or the compound represented by Formula 202.

According to an exemplary embodiment of the present invention, at least one of the first capping layer 210 and the second capping layer 220 may include a compound selected from Compounds HT28 to HT33 and Compounds CP1 to CP5; however, exemplary embodiments of the present invention are not limited thereto.

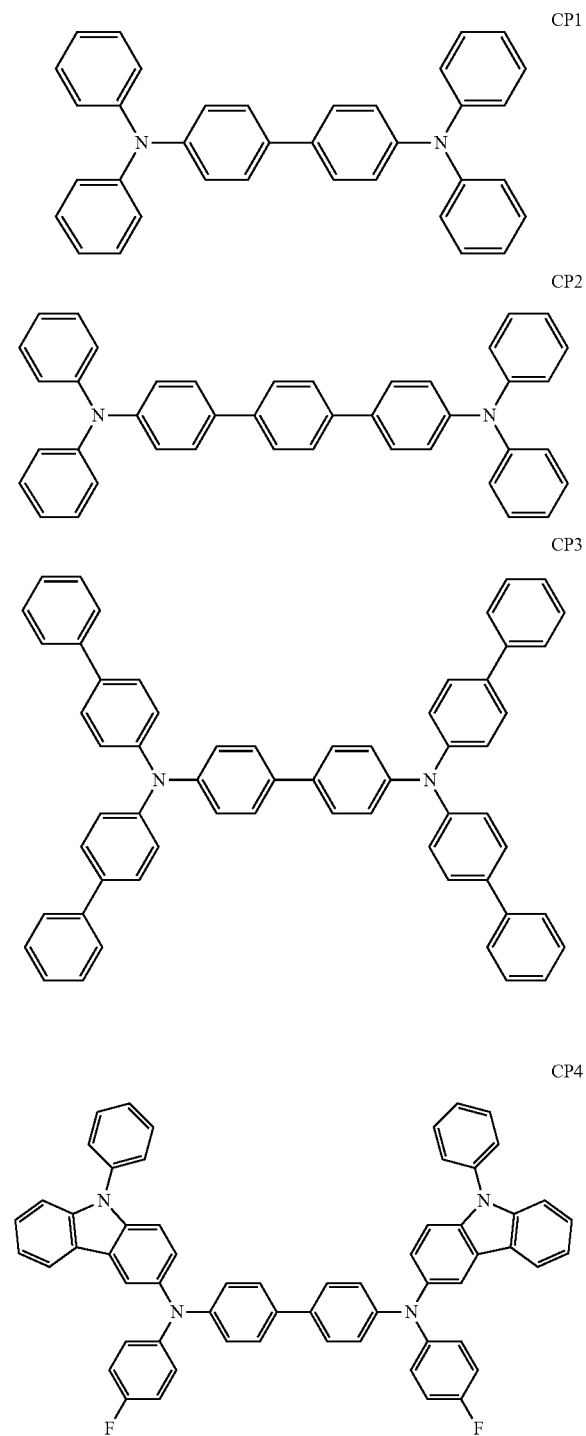

CP5

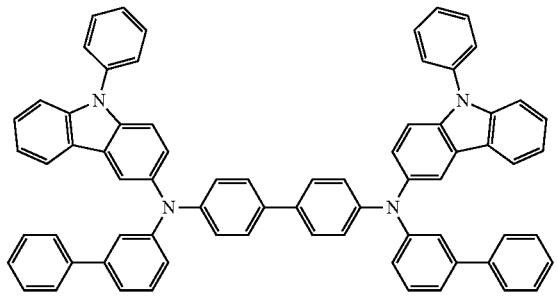

Layers included in the hole transport region, the emission layer, and layers included in the electron transport region may be formed in a certain region by using one or more suitable methods selected from vacuum deposition, spin coating, casting, langmuir-blodgett (LB) deposition, ink-jet printing, laser-printing, or laser-induced thermal imaging.

When layers included in the hole transport region, the emission layer, and layers constituting the electron transport region are formed by vacuum deposition, for example, the vacuum deposition may be performed at a deposition temperature of from about 100° C. to about 500° C., at a vacuum degree of from about $10^{-8}$ torr to about $10^{-3}$ torr, and at a deposition rate of from about 0.01 Å/sec to about 100 Å/sec by taking into account a material to be included in a layer to be formed, and the structure of a layer to be formed.

When layers included in the hole transport region, the emission layer, and layers included in the electron transport region are formed by spin coating, the spin coating may be performed at a coating speed of from about 2,000 rpm to about 5,000 rpm and at a heat treatment temperature of from about 80° C. to about 200° C. by taking into account a material to be included in a layer to be formed, and the structure of a layer to be formed.

The term "$C_1$-$C_{60}$ alkyl group" as used herein refers to a linear or branched aliphatic saturated hydrocarbon monovalent group having 1 to 60 carbon atoms. Examples thereof include a methyl group, an ethyl group, a propyl group, an isobutyl group, a sec-butyl group, a tert-butyl group, a pentyl group, an iso-amyl group, or a hexyl group. The term "$C_1$-$C_{60}$ alkylene group" as used herein refers to a divalent group having substantially the same structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group. Examples thereof include an ethenyl group, a propenyl group, or a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group. Examples thereof include an ethynyl group or a propynyl group. The term "$C_2$-$C_{60}$ alkynylene group" as used herein refers to a divalent group having substantially the same structure as the $C_2$-$C_{60}$ alkynyl group.

The term "$C_1$-$C_{60}$ alkoxy group" as used herein refers to a monovalent group represented by —$OA_{101}$, in which $A_{101}$ is the $C_1$-$C_{60}$ alkyl group. Examples thereof include a methoxy group, an ethoxy group, or an isopropyloxy group.

The term "$C_3$-$C_{10}$ cycloalkyl group" as used herein refers to a monovalent saturated hydrocarbon monocyclic group having 3 to 10 carbon atoms. Examples thereof include a cyclopropyl group, a cyclobutyl group, a cyclopentyl group, a cyclohexyl group, or a cycloheptyl group. The term "$C_3$-$C_{10}$ cycloalkylene group" as used herein refers to a divalent group having substantially the same structure as the $C_3$-$C_{10}$ cycloalkyl group.

The term "$C_1$-$C_{10}$ heterocycloalkyl group" as used herein refers to a monovalent monocyclic group having at least one heteroatom selected from N, O, Si, P, or S as a ring-forming atom and 1 to 10 carbon atoms. Examples thereof include a 1,2,3,4-oxatriazolidinyl group, a tetrahydrofuranyl group, or a tetrahydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and does not have aromaticity. Examples thereof include a cyclopentenyl group, a cyclohexenyl group, or a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Examples thereof include a 4,5-dihydro-1,2,3,4-oxatriazolyl group, a 2,3-dihydrofuranyl group and a 2,3-dihydrothiophenyl group. The term "$C_1$-$C_1°$ heterocycloalkenylene group" as used herein refers to a divalent group having substantially the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms. A "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, or a chrysenyl group. When the $C_6$-$C_{60}$ aryl group and the $C_6$-$C_{60}$ arylene group each include two or more rings, the rings may be chemically bonded to each other.

The term "$C_1$-$C_{60}$ heteroaryl group" as used herein refers to a monovalent group having a carbocyclic aromatic system that has at least one heteroatom selected from N, O, Si, P, or S as a ring-forming atom, in addition to 1 to 60 carbon atoms. A "$C_1$-$C_{60}$ heteroarylene group" as used herein refers to a divalent group having a carbocyclic aromatic system that has at least one heteroatom selected from N, O, Si, P, or S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, or an isoquinolinyl group. When the $C_1$-$C_{60}$ heteroaryl group and the $C_1$-$C_{60}$ heteroarylene group each include two or more rings, the rings may be condensed with each other.

The term "$C_6$-$C_{60}$ aryloxy group" as used herein refers to —$OA_{102}$, in which $A_{102}$ is the $C_6$-$C_{60}$ aryl group. The term "$C_6$-$C_{60}$ arylthio group" as used herein refers to —$SA_{103}$, in which $A_{103}$ is the $C_6$-$C_{60}$ aryl group.

The term "monovalent non-aromatic condensed polycyclic group" as used herein refers to a monovalent group, for example, having 8 to 60 carbon atoms, that has two or more rings condensed with each other, only carbon atoms as a ring-forming atom, and non-aromaticity in the entire molecular structure. An example of the monovalent non-aromatic condensed polycyclic group is a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group, for example, having 1 to 60 carbon atoms, that has two or more rings condensed to each other, at least one heteroatom selected from N, O, Si, P, or S, other than carbon atoms as a ring-forming atom, and has non-aromaticity in the entire molecular structure. An example of the monovalent non-aromatic condensed heteropolycyclic group is a carbazolyl group. The term "divalent non-aromatic condensed heteropolycyclic group" as used herein refers to a divalent group having substantially the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The term "$C_5$-$C_{60}$ carbocyclic group" as used herein refers to a ring, such as a benzene, a monovalent group, such as a phenyl group, or a divalent group, such as a phenylene group. According to some exemplary embodiments of the present invention, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having substantially the same structure as the $C_1$-$C_{60}$ carbocyclic group, except that as a ring-forming atom, at least one heteroatom selected from N, O, Si, P, or S is used in addition to carbon. The number of carbon atoms may be in a range of 1 to 60.

At least one substituent selected from a substituent(s) of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), or —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), or —P(=O)($Q_{21}$)($Q_{22}$); or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$). $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, or a terphenyl group.

The term "Ph" used herein refers to a phenyl group, the term "Me" used herein refers to a methyl group, the term "Et" used herein refers to an ethyl group, the term "ter-Bu" or "Bu$^t$" used herein refers to a tert-butyl, and the term "OMe" used herein refers to a methoxy group.

The term "biphenyl group" as used therein refers to "a phenyl group substituted with a phenyl group." As an example, a "biphenyl group" is a substituted phenyl group having a $C_6$-$C_{60}$ aryl group as a substituent.

The term "terphenyl group" as used herein refers to "a phenyl group substituted with a biphenyl group." As an example, the "terphenyl group" is a substituted phenyl group having, as a substituent, a $C_6$-$C_{60}$ aryl group substituted with a $C_6$-$C_{60}$ aryl group.

*, *', and *" used herein, unless defined otherwise, each refer to a binding site to a neighboring atom in a corresponding formula.

A compound according to some exemplary embodiments of the present invention and an organic light-emitting device according to some exemplary embodiments of the present invention will be described in more detail with reference to Synthesis Examples and Examples. However, exemplary embodiments of the present invention are not limited to the Examples described herein. The wording "B was used instead of A" as used in describing Synthesis Examples refers to an example in which a molar equivalent of B was used in place of A.

EXAMPLES

Synthesis Example 1: Synthesis of Compound 2

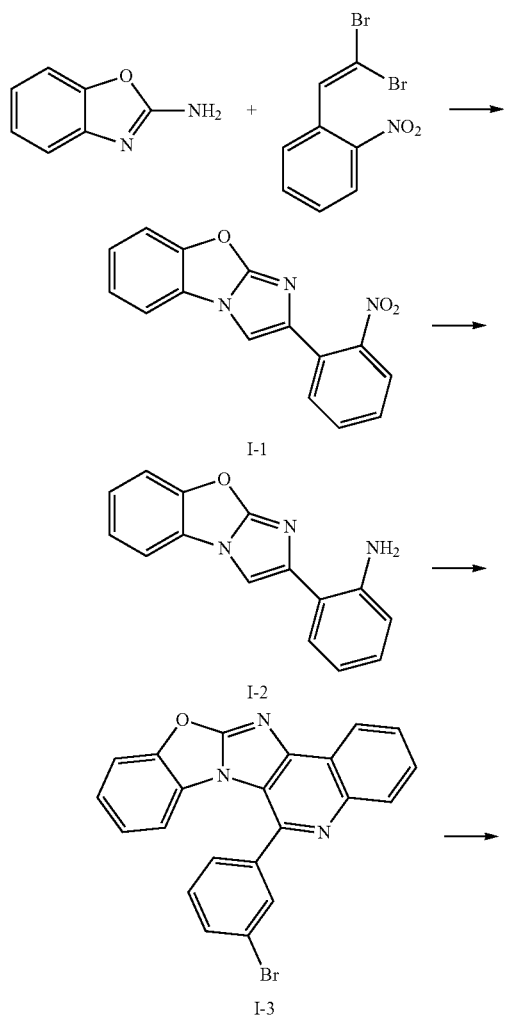

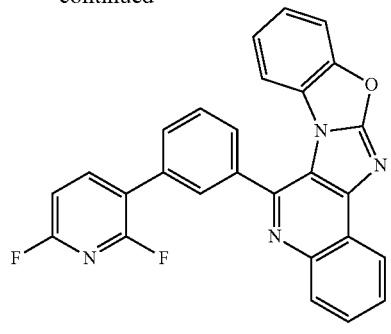

2

Synthesis of Intermediate I-1

1.34 g (10 mmol) of benzo[d]oxazol-2-amine and 3.07 g (10 mmol) of 1-(2,2-dibromovinyl)-2-nitrobenzene were dissolved in 80 mL of dimethylformamide (DMF) and were then stirred at a temperature of 120° C. for about 12 hours. The obtained reacting solution was cooled to room temperature. Then, organic layers were extracted three times by using 30 mL of water and 30 mL of ethyl acetate. The collected organic layers were dried by using magnesium sulfate and the solvent was evaporated. The obtained residue was separated and purified by silica gel column chromatography, thus completing the preparation of 1.87 g (75%) of Intermediate I-1. Intermediate I-1 was confirmed through LC-MS. $C_{15}H_9N_3O_3$: M+1 279.1.

Synthesis of Intermediate I-2

2.79 g (10 mmol) of Intermediate I-1 and 2.79 g (50 mmol) of Fe powder were dissolved in 60 mL of AcOH and were then stirred at a temperature of 90° C. for about 2 hours. The obtained reacting solution was cooled to room temperature and was then neutralized with $NaHCO_3$ (aq). Then, organic layers were extracted three times by using 50 mL of ethyl acetate. The collected organic layers were dried by using magnesium sulfate and the solvent was evaporated. The obtained residue was separated and purified by silica gel column chromatography, thus completing the preparation of 1.62 g (65%) of Intermediate I-2. Intermediate I-2 was confirmed through LC-MS. $C_{15}H_{11}N_3O$: M+1 249.3.

Synthesis of Intermediate I-3

2.49 g (10 mmol) of Intermediate I-2, 1.85 g (10 mmol) of 3-bromo-benzaldehyde, and 0.200 g (1.0 mmol) of p-TsOH were dissolved in 70 mL of toluene and were then stirred at a temperature of 100 t for about 8 hours. The reacting solution was cooled to room temperature. Then, organic layers were extracted three times by using 30 mL of water and 30 mL of ethyl acetate. The collected organic layers were dried by using magnesium sulfate and the solvent was evaporated. The obtained residue was separated and purified by silica gel column chromatography, thus completing the preparation of 2.49 g (60%) of Intermediate I-3. Intermediate I-3 was confirmed through LC-MS. $C_{22}H_{12}BrN_3O$: M+1 413.0.

Synthesis of Compound 2

4.13 g (10 mmol) of Intermediate I-3, 1.59 g (10 mmol) of (2,6-difluoropyridin-3-yl)boronic acid, 0.578 g (0.50 mmol) of Pd(PPh$_3$)$_4$, and 4.15 g (30 mmol) of K$_2$CO$_3$ were dissolved in 60 mL of a mixed solution of tetrahydrofuran (THF) and H$_2$O (a volume ratio of 2:1) and were then stirred at a temperature of 80° C. for about 12 hours. The obtained reacting solution was cooled to room temperature. Then, organic layers were extracted three times by using 30 mL of water and 30 mL of ethyl acetate. The collected organic layers were dried by using magnesium sulfate and the solvent was evaporated. The obtained residue was separated and purified by silica gel column chromatography, thus completing the preparation of 3.23 g (72%) of Compound 2. Compound 2 was confirmed through MS/FAB and $^1$H NMR. C$_{27}$H$_{14}$F$_2$N$_4$O cal. 448.11, found 448.12.

Synthesis Example 2: Synthesis of Compound 12

3.87 g (70%) of Compound 12 was prepared in substantially the same manner as in Synthesis of Compound 2, except that 9,9-dimethyl-7-(4,4,5,5-tetramethyl-1,3,2-dioxaborolan-2-yl)-9H-fluorene-2-carbonitrile was used instead of (2,6-difluoropyridin-3-yl)boronic acid in Synthesis of Compound 2. Compound 12 was confirmed through MS/FAB and $^1$H NMR. C$_{38}$H$_{24}$N$_5$O cal. 552.20, found 552.21.

Synthesis Example 3: Synthesis of Compound 38

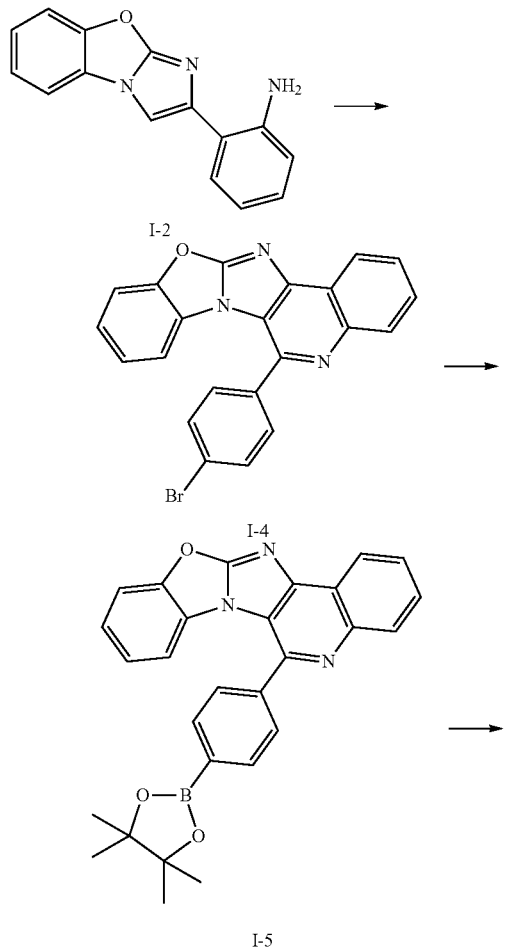

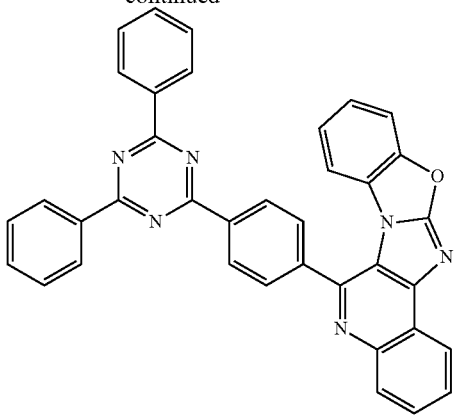

38

Synthesis of Intermediate I-4

2.61 g (63%) of Intermediate I-4 was prepared in substantially the same manner as in Synthesis of Intermediate I-3, except that 4-bromo-benzaldehyde was used instead of 3-bromo-benzaldehyde in synthesizing Intermediate I-3. Intermediate I-4 was confirmed through LC-MS. C$_{22}$H$_{12}$BrN$_3$O: M+1 413.1.

Synthesis of Intermediate I-5

4.13 g (10 mmol) of Intermediate I-4 was dissolved in 60 mL of THF and 4.0 mL (2.5 M in hexane) of nBuLi was added thereto at a temperature of −78° C. After 1 hour, 1.86 g (10 mmol) of 2-isopropoxy-4,4,5,5-tetramethyl-1,3,2-dioxaborolane was added thereto at a temperature of −78° C. The resultant solution was stirred at room temperature for about 12 hours and water was added thereto. Then, organic layers were extracted three times by using 30 mL of diethylether. The collected organic layers were dried by using magnesium sulfate and the solvent was evaporated. The obtained residue was separated and purified by silica gel column chromatography, thereby completing the preparation of 3.55 g (77%) of Intermediate I-5. Intermediate I-5 was confirmed through LC-MS. C$_{28}$H$_{24}$BrN$_3$O$_3$: M+1 461.2.

Synthesis of Compound 38

4.25 g (75%) of Compound 38 was prepared in substantially the same manner as in Synthesis of Compound 2, except that 2-chloro-4,6-diphenyl-1,3,5-triazine was used instead of (2,6-difluoropyridin-3-yl)boronic acid in synthesizing Compound 2. Compound 38 was confirmed through MS/FAB and $^1$H NMR. C$_{37}$H$_{22}$N$_6$O cal. 566.19, found 566.20.

Synthesis Example 4: Synthesis of Compound 46

3.53 g (60%) of Compound 46 was prepared in substantially the same manner as in Synthesis of Compound 2, except that 5-bromobenzo[d]oxazol-2-amine was used instead of benzo[d]oxazol-2-amine in synthesizing Intermediate I-1 and 4,4,5,5-tetramethyl-2-(10-phenylanthracen-9-yl)-1,3,2-dioxaborolane was used instead of (2,6-difluoropyridin-3-yl)boronic acid in synthesizing Compound 2.

Compound 46 was confirmed through MS/FAB and ¹H NMR. $C_{42}H_{25}N_3O$ cal. 587.20, found 587.22.

Synthesis Example 5: Synthesis of Compound 59

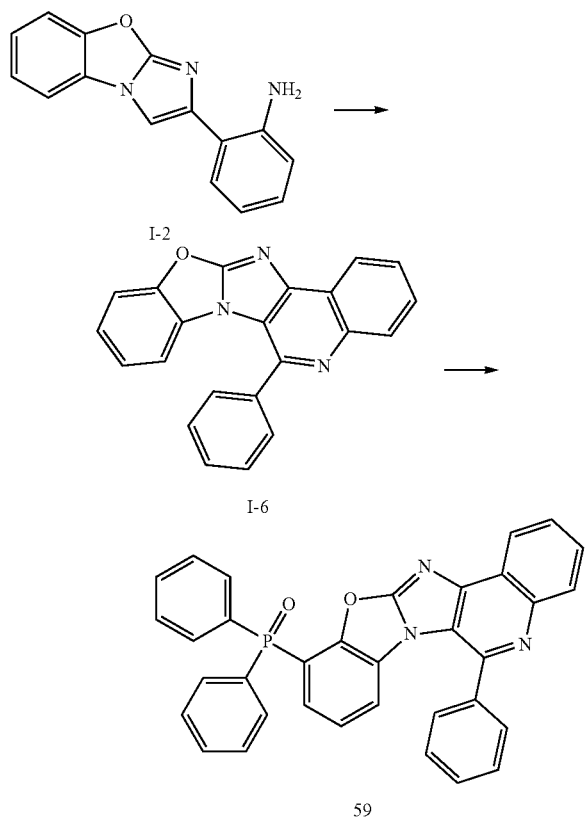

Synthesis of Intermediate I-6

2.35 g (70%) of Intermediate I-6 was prepared in substantially the same manner as in Synthesis of Intermediate I-3, except that benzaldehyde was used instead of 3-bromobenzaldehyde in synthesizing Intermediate I-3. Intermediate I-6 was confirmed through LC-MS. $C_{22}H_{13}N_3O$: M+1 335.2

Synthesis of Compound 59

3.35 g (10 mmol) of Intermediate I-6 was dissolved in 60 mL of THF and 4.0 mL (2.5 M in hexane) of nBuLi was added thereto at a temperature of −78° C. After 1 hour, 2.20 g (10 mmol) of chloro-diphenyl phosphine was added thereto at a temperature of −78° C. The resultant solution was stirred at room temperature for about 12 hours and water was added thereto. Then, organic layers were extracted three times by using 30 mL of diethylether. The collected organic layers were dried by using magnesium sulfate and the solvent was evaporated. The obtained residue was dissolved in 60 mL of dichloromethane and 4 mL of $H_2O_2$ was added thereto. The resultant solution was stirred at room temperature for about 5 hours. 30 mL of water was added thereto. Then, organic layers were extracted three times by using 30 mL of dichloromethane. The collected organic layers were dried by using magnesium sulfate and the solvent was evaporated. The obtained residue was separated and purified by silica gel column chromatography, thus completing the preparation of 3.86 g (72%) of Compound 59. Compound 59 was confirmed through MS/FAB and ¹H NMR. $C_{34}H_{22}N_3O_2P$ cal. 535.14, found 535.15.

Synthesis Example 6: Synthesis of Compound 73

4.36 g (63%) of Compound 73 was prepared in substantially the same manner as in Synthesis of Compound 2, except that benzo[d]thiazol-2-amine was used instead of benzo[d]oxazol-2-amine in synthesizing Intermediate I-1 and 9,9-diphenyl-7-(4,4,5,5-tetramethyl-1,3,2-dioxaborolan-2-yl)-9H-fluorene-2-carbonitrile was used instead of (2,6-difluoropyridin-3-yl)boronic acid in synthesizing Compound 2. Compound 73 was confirmed through MS/FAB and ¹H NMR. $C_{48}H_{28}N_4S$ cal. 692.20, found 692.21.

Synthesis Example 7: Synthesis of Compound 100

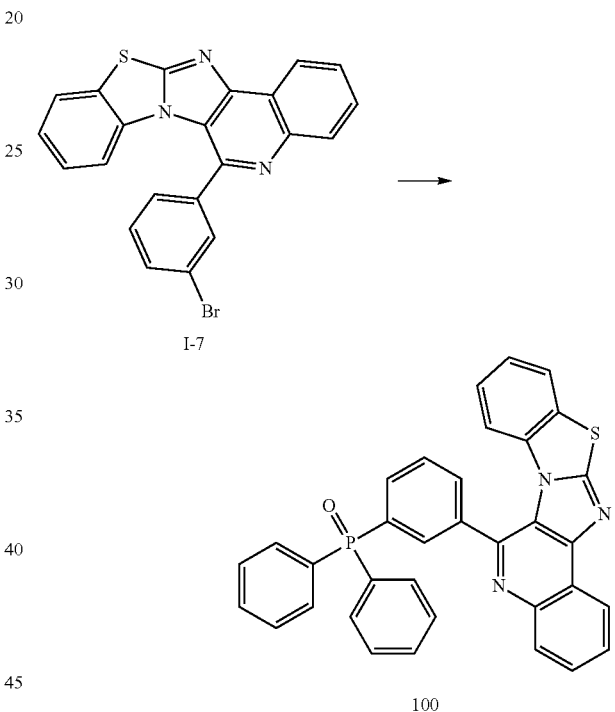

3.75 g (68%) of Compound 100 was prepared in substantially the same manner as in Synthesis of Compound 59, except that Intermediate I-7 was used instead of Intermediate I-6 in synthesizing Compound 59. Compound 100 was confirmed through MS/FAB and ¹H NMR. $C_{34}H_{22}N_3OPS$ cal. 551.12, found 551.13.

Synthesis Example 8: Synthesis of Compound 123

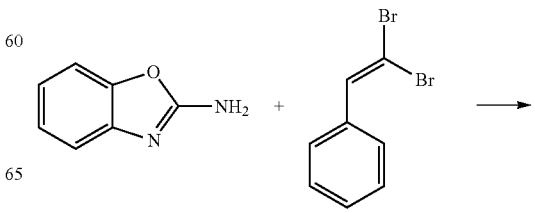

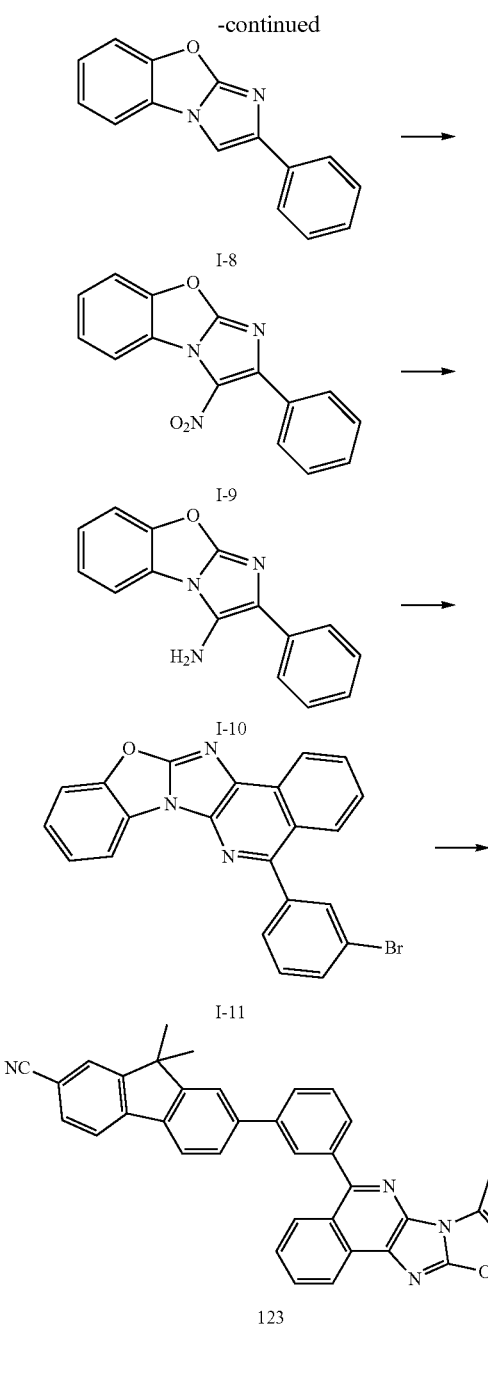

mixed with 10 mL of water and the precipitated solid was filtered. The obtained solid was dissolved in ethyl acetate and water was added thereto. Then, organic layers were extracted three times by using 30 mL of diethylether. The collected organic layers were dried by using magnesium sulfate and the solvent was evaporated. The obtained residue was separated and purified by silica gel column chromatography, thereby completing the preparation of 1.82 g (65%) of Intermediate I-9. Intermediate I-9 was confirmed through LC-MS. $C_{15}H_9N_3O_3$: M+1 279.1

Synthesis of Intermediate I-10

1.64 g (66%) of Intermediate I-10 was prepared in substantially the same manner as in Synthesis of Intermediate I-2, except that Intermediate I-9 was used instead of Intermediate I-1 in synthesizing Intermediate I-2. Intermediate I-10 was confirmed through LC-MS. $C_{15}H_{11}N_3O$: M+1 249.1

Synthesis of Intermediate I-11

2.86 g (69%) of Intermediate I-11 was prepared in substantially the same manner as in Synthesis of Intermediate I-3, except that Intermediate I-10 was used instead of Intermediate I-2 in synthesizing Intermediate I-3. Intermediate I-11 was confirmed through LC-MS. $C_{22}H_{12}BrN_3O$: M+1 413.1

Synthesis of Compound 123

3.98 g (72%) of Compound 123 was prepared in substantially the same manner as in Synthesis of Compound 12, except that Intermediate I-11 was used instead of Intermediate I-3 in synthesizing Compound 12. Compound 123 was confirmed through MS/FAB and $^1$H NMR. $C_{38}H_{24}N_4O$ cal. 552.20, found 552.21.

Synthesis Example 9: Synthesis of Compound 142

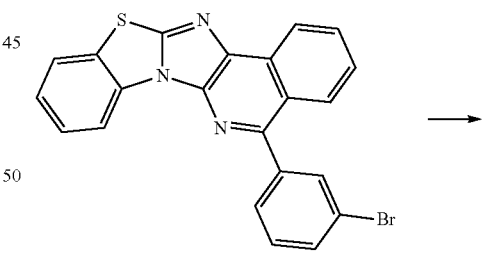

Synthesis of Intermediate I-8

1.64 g (70%) of Intermediate I-8 was prepared in substantially the same manner as in Synthesis of Intermediate I-1, except that (2,2-dibromovinyl)benzene was used instead of 1-(2,2-dibromovinyl)-2-nitrobenzene in synthesizing Intermediate I-1. Intermediate I-8 was confirmed through LC-MS. $C_{15}H_{10}N_2O$: M+1 234.1

Synthesis of Intermediate I-9

2.34 g (10 mmol) of Intermediate I-8 was dissolved in 100 mL of AcOH and 1.03 g (15 mmol) of $NaNO_2$ was saturated in water and slowly added thereto. The resultant solution was stirred for 12 hours. The obtained reacting solution was

Synthesis of Intermediate I-11

3.27 g (76%) of Intermediate I-12 was prepared in substantially the same manner as in Synthesis of Intermediate I-8, except that benzo[d]thiazol-2-amine was used instead of benzo[d]oxazol-2-amine in synthesizing Intermediate I-8. Intermediate I-12 was confirmed through LC-MS. $C_{22}H_{12}BrN_3S$: M+1 429.0

Synthesis of Compound 142

3.92 g (71%) of Compound 142 was prepared in substantially the same manner as in Synthesis of Compound 100, except that Intermediate I-12 was used instead of Intermediate I-7 in synthesizing Compound 100. Compound 142 was confirmed through MS/FAB and $^1$H NMR. $C_{34}H_{22}N_3OPS$ cal. 551.12, found 551.13.

Synthesis Example 10: Synthesis of Compound 144

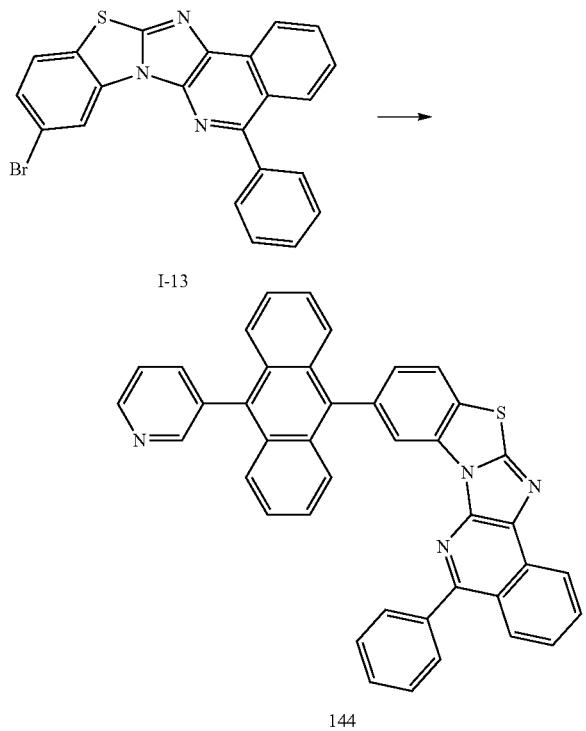

Synthesis of Intermediate I-13

2.58 g (60%) of Intermediate I-13 was prepared in substantially the same manner as in Synthesis of Intermediate I-11, except that 5-bromobenzo[d]thiazol-2-amine was used instead of benzo[d]oxazol-2-amine in synthesizing Intermediate I-8. Intermediate I-13 was confirmed through LC-MS. $C_{22}H_{12}BrN_3S$: M+1 429.0

Synthesis of Compound 144

4.35 g (72%) of Compound 144 was prepared in substantially the same manner as in Synthesis of Compound 123, except that, in synthesizing Compound 123, Intermediate I-13 was used instead of Intermediate I-11 and 3-(10-(4,4,5,5-tetramethyl-1,3,2-dioxaborolan-2-yl)anthracen-9-yl)pyridine was used instead of 9,9-dimethyl-7-(4,4,5,5-tetramethyl-1,3,2-dioxaborolan-2-yl)-9H-fluorene-2-carbonitrile. Compound 144 was confirmed through MS/FAB and $^1$H NMR. $C_{41}H_{24}N_4S$ cal. 604.17, found 604.18.

$^1$H NMR and MS/FAB of synthesized Compounds are shown in Table 1 below. Methods of synthesizing compounds other than Compounds shown in Table 1 are recognizable by one of ordinary skill in the art by referring to the synthesis paths and source materials described above.

TABLE 1

| Compound | $^1$H NMR (CDCl$_3$, 400 MHz) | MS/FAB found | MS/FAB calc. |
|---|---|---|---|
| 2 | δ = 8.67-8.65 (m, 1H), 8.75-8.36 (m, 2H), 8.20-8.14 (m, 2H), 8.00-7.95 (m, 1H), 7.86-7.82 (m, 1H), 7.71-7.64 (m, 4H), 7.26 (t, 1H), 7.12 (d, 1H), 7.02 (d, 1H) | 448.12 | 448.11 |
| 12 | δ = 8.67 (d, 1H), 8.37 (t, 1H), 8.15 (d, 1H), 8.00-7.95 (m, 2H), 7.90 (d, 1H), 7.86-7.80 (m, 2H), 7.72-7.64 (m, 5H), 7.51-7.45 (m, 3H), 7.26 (t, 1H), 7.12 (d, 1H), 1.59 (s, 6H) | 552.21 | 552.20 |
| 38 | δ = 8.81-8.75 (m, 6H), 8.68-8.65 (d, 1H), 8.58-8.55 (m, 2H), 8.16 (d, 1H), 7.99 (t, 1H), 7.83 (t, 1H), 7.71-7.59 (m, 6H), 7.42-7.38 (t, 2H), 7.26 (t, 1H), 7.13 (d, 1H) | 566.20 | 566.19 |
| 46 | δ = 8.69-8.63 (m, 3H), 8.17 (d, 1H), 7.98 (t, 1H), 7.90 (d, 1H), 7.85-7.76 (m, 6H), 7.71-7.68 (m, 3H), 7.53-7.45 (m, 5H), 7.41-7.28 (m, 5H) | 587.22 | 587.20 |
| 59 | δ = 8.69-8.63 (m, 3H), 8.18 (d, 1H), 7.97 (t, 1H), 7.86-7.76 (m, 6H), 7.56-7.45 (m, 6H), 7.42-7.33 (m, 5H) | 535.15 | 535.14 |
| 73 | δ = 8.69 (m, 1H), 8.49 (t, 1H), 8.46 (d, 1H), 8.07-7.96 (m, 3H), 7.85-7.78 (m, 3H), 7.70 (d, 1H), 7.66-7.47 (m, 5H), 7.38-7.30 (m, 7H) | 692.21 | 692.20 |
| 100 | δ = 8.67 (d, 1H), 8.46 (d, 1H), 8.42-8.39 (m, 1H), 8.07-8.05 (m, 1H), 8.00-7.96 (m, 2H), 7.89-7.71 (m, 4H), 7.67-7.56 (m, 5H), 7.52-7.34 (m, 7H) | 551.13 | 551.12 |
| 123 | δ = 9.07 (d, 1H), 8.54 (d, 1H), 8.37 (t, 1H), 8.00 (dd, 1H), 7.90-7.65 (m, 8H), 7.60-7.56 (m, 1H), 7.51-5.45 (m, 2H), 7.40-7.33 (m, 2H), 7.22 (d, 1H), 1.61 (s, 6H) | 552.21 | 552.20 |
| 142 | δ = 9.11 (d, 1H), 8.47-8.40 (m, 2H), 8.15-8.09 (m, 2H), 7.88 (d, 1H), 7.84-7.78 (m, 2H), 7.68-7.63 (m, 4H), 7.60-7.56 (m, 2H), 7.52-7.39 (m, 8H) | 551.13 | 551.12 |
| 144 | δ = 9.11-9.08 (m, 2H), 8.59 (dd, 1H), 8.50 (d, 1H), 8.42 (d, 1H), 8.23-8.18 (m, 3H), 7.99-7.90 (m, 5H), 7.82 (t, 1H), 7.70-7.56 (m, 5H), 7.39-7.30 (m, 5H) | 604.18 | 604.17 |

Example 1

An anode was prepared by cutting an ITO glass substrate (manufactured by Corning), on which an ITO layer was deposited to a thickness of 15 Ω/cm² (1,200 Å), to a size of 50 mm×50 mm×0.7 mm, ultrasonically cleaning the ITO glass substrate (anode) using isopropyl alcohol and pure water each for about 5 minutes, and exposing the ITO glass substrate (anode) to irradiation of UV for about 30 minutes and ozone to clean. Then, the glass substrate (anode) was loaded into a vacuum deposition apparatus.

2-TNATA was vacuum-deposited on the ITO glass substrate (anode) to form a hole injection layer having a thickness of about 600 Å. 4,4'-bis[N-(1-naphthyl)-N-phenylamino]bisphenyl (NPB) was vacuum-deposited on the hole injection layer to form a hole transport layer having a thickness of about 300 Å.

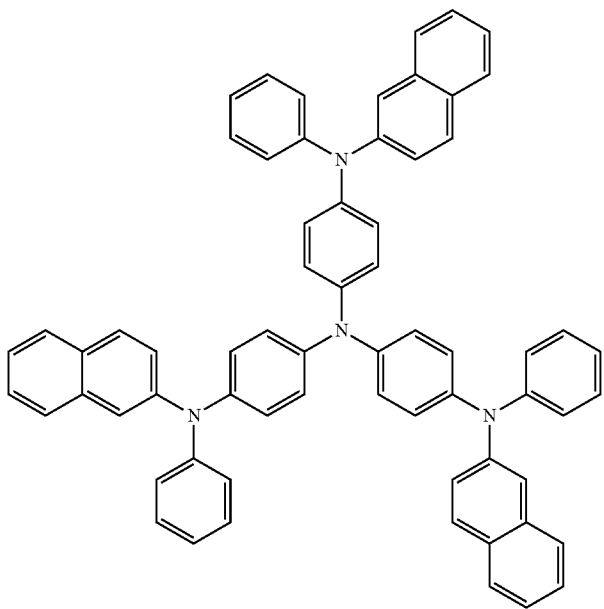

2-TNATA

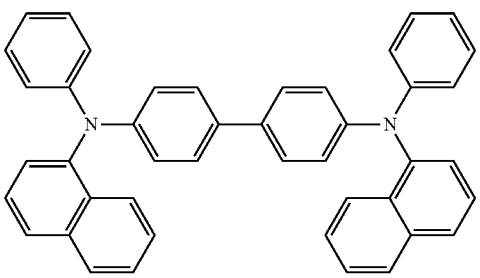

NPB

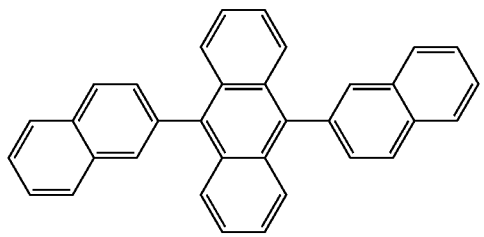

ADN

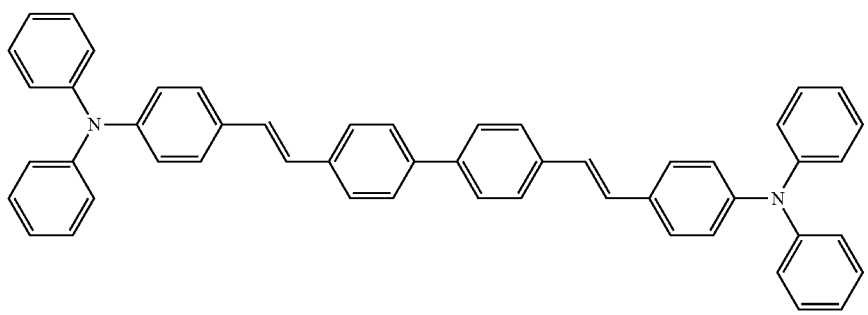

DPAVBi 9,10-di-naphthalene-2-yl-anthracene (ADN) (blue fluorescent host) and 4,4'-bis[2-(4-(N,N-diphenylamino)phenyl)vinyl]biphenyl (DPAVBi) (blue fluorescent dopant) were co-deposited on the hole transport layer at a weight ratio of 98:2 to form an emission layer having a thickness of about 300 Å.

Compound 2 was deposited on the emission layer to form an electron transport layer having a thickness of about 300 Å. LiF (alkali metal halide) was deposited on the electron transport layer to form an electron injection layer having a thickness of about 10 Å. Al was vacuum-deposited on the electron injection layer to form an LiF/Al electrode (cathode electrode) having a thickness of about 3,000 Å. Thus, an organic light-emitting device was formed.

Examples 2 to 10 and Comparative Examples 1 and 2

Organic light-emitting devices of Examples 2 to 10 and Comparative Examples 1 and 2 were manufactured in substantially the same manner as in Example 1, except that Compounds shown in Table 2 were each used instead of Compound 2 in forming an electron transport layer.

TABLE 2

| | Material | Driving voltage (V) | Current density (mA/cm$^2$) | luminance (cd/m$^2$) | Efficiency (cd/A) | Emission color | Half lifespan (hr @100 mA/cm$^2$) |
|---|---|---|---|---|---|---|---|
| Example 1 | Compound 2 | 3.22 | 50 | 3,775 | 7.55 | blue | 690 hr |
| Example 2 | Compound 12 | 3.15 | 50 | 3,830 | 7.66 | blue | 702 hr |
| Example 3 | Compound 38 | 3.37 | 50 | 3,625 | 7.25 | blue | 655 hr |
| Example 4 | Compound 46 | 3.35 | 50 | 3,480 | 6.96 | blue | 736 hr |
| Example 5 | Compound 59 | 3.79 | 50 | 3,430 | 6.86 | blue | 839 hr |
| Example 6 | Compound 73 | 3.26 | 50 | 3,865 | 7.73 | blue | 672 hr |
| Example 7 | Compound 100 | 3.71 | 50 | 3,410 | 6.82 | blue | 856 hr |
| Example 8 | Compound 123 | 3.30 | 50 | 3,810 | 7.62 | blue | 723 hr |
| Example 9 | Compound 142 | 3.82 | 50 | 3,500 | 7.00 | blue | 812 hr |
| Example 10 | Compound 144 | 3.37 | 50 | 3,630 | 7.26 | blue | 705 hr |
| Comparative Example 1 | Compound 200 | 5.06 | 50 | 3,010 | 6.02 | blue | 325 hr |
| Comparative Example 2 | Compound A | 4.82 | 50 | 3,150 | 6.30 | blue | 436 hr |

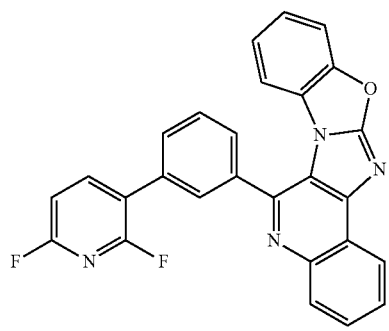

2

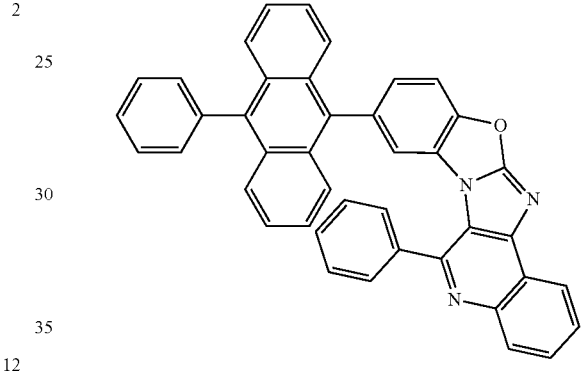

46

-continued

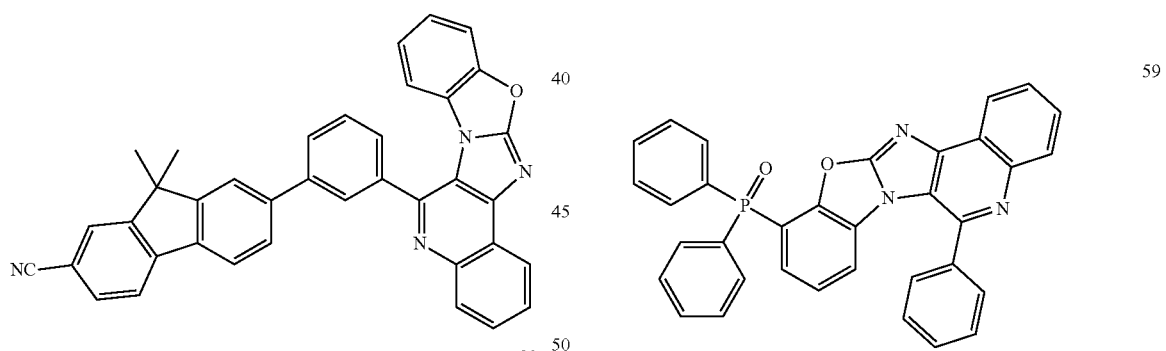

12

59

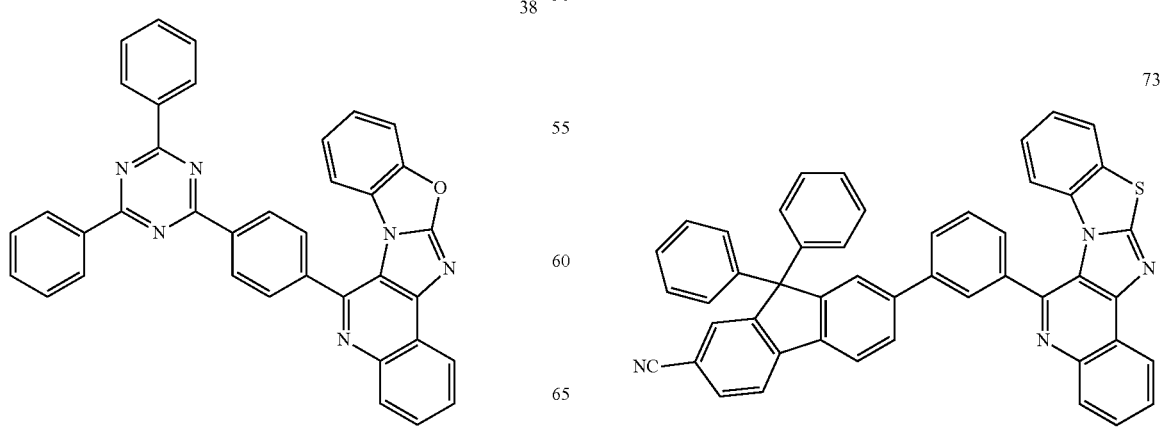

38

73

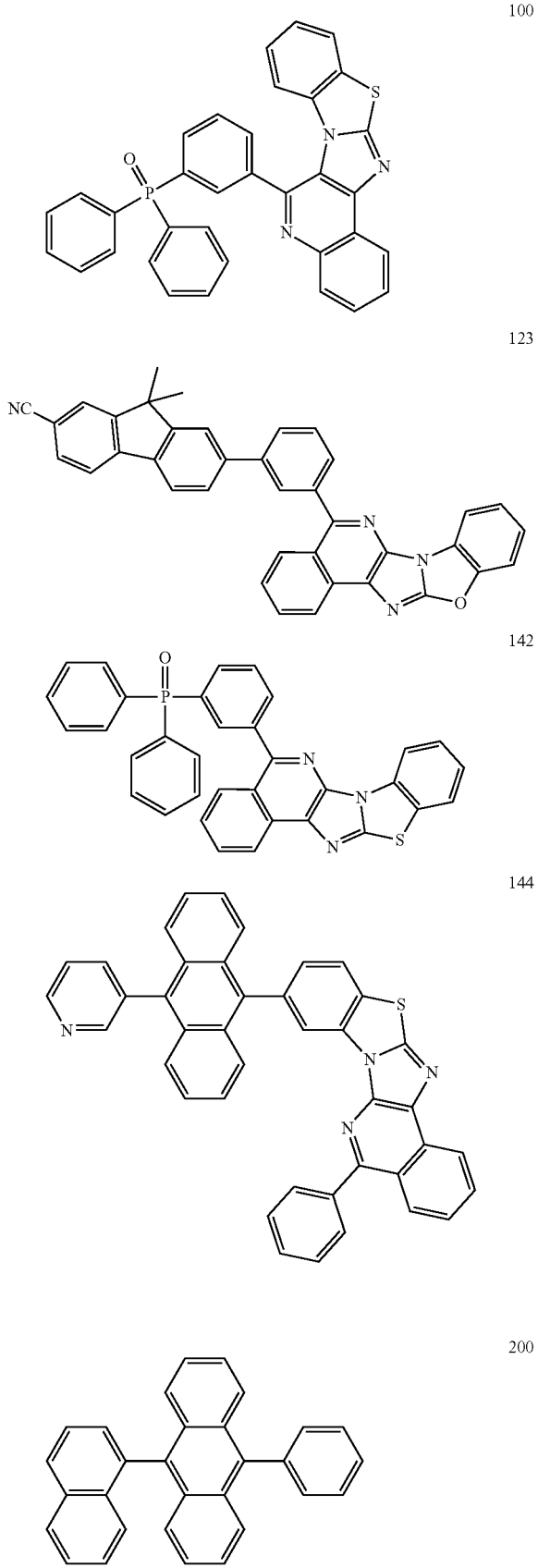

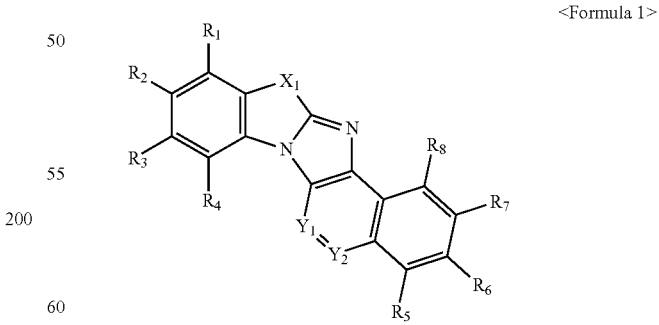

Referring to Table 2, the organic light-emitting devices of Examples 1 to 10 had relatively high efficiency, luminance, and lifespan characteristics, compared to those of Comparative Examples 1 and 2.

According to an exemplary embodiment of the present invention, the organic light-emitting device including the condensed cyclic compound may have increased efficiency, relatively high luminance, and a relatively long lifespan.

It should be understood that exemplary embodiments of the present invention described herein should be considered in a descriptive sense only and not for purposes of limitation. Descriptions of features or aspects within each embodiment should typically be considered as available for other similar features or aspects in other exemplary embodiments of the present invention.

While one or more exemplary embodiments of the present invention have been described with reference to the figures, it will be understood by those of ordinary skill in the art that various changes in form and details may be made therein without departing from the spirit and scope of the present invention as defined by the following claims.

What is claimed is:

1. A condensed cyclic compound represented by Formula 1:

<Formula 1>

$*-(L_1)_{a1}-(Ar_1)_{b1}$,   <Formula 2> wherein, in Formulae 1 and 2,
$X_1$ is O or S,
$Y_1$ is $C(R_9)$ or N,
$Y_2$ is $C(R_{10})$ or N, $L_1$ is selected from a substituted or unsubstituted $C_3$-$C_{60}$ carbocyclic group, a substituted or unsubstituted $C_1$-$C_{60}$ heterocyclic group, *—S(=O)($Q_1$)-*', *—S(=O)$_2$—*', *—P(=O)($Q_1$)-*', *—P(=O)$_2$—*', *—P(=S)($Q_1$)-*', or *—P(=S)$_2$—*', a1 is an integer selected from 0 to 4, wherein when a1 is 2 or greater, at least two $L_1$(s) are the same or different from each other, $Ar_1$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —S(=O)($Q_1$)($Q_2$), —S(=O)$_2$($Q_1$), —P(=O)($Q_1$)($Q_2$), —P(=O)$_2$($Q_1$), —P(=S)($Q_1$)($Q_2$), or —P(=S)$_2$($Q_1$), b1 is an integer selected from 1 to 4, wherein when b1 is 2 or greater, at least two $Ar_1$(s) are the same or different from each other, $R_1$ to $R_{10}$ are each independently selected from a group represented by Formula 2, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), at least one of $R_1$ to $R_{10}$ is the group represented by Formula 2, and at least one substituent selected from a substituent(s) of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group is selected from:

deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), or —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, or a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ hetcrocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), or —P(=O)($Q_{21}$)($Q_{22}$); or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_1$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, or a terphenyl group, and

* and *' each indicate a binding site to a neighboring atom, wherein if a1 is 0, $Y_1$ is $C(R_9)$ and $Y_2$ is N, then the condensed cyclic compound includes at least one of the following: $X_1$ is O and $R_9$ is not an aryl group.

2. The condensed cyclic compound of claim 1, wherein $L_1$ is selected from:

a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzofuran group, a dibenzothiophene group, a dibenzosilole group, a carbazole group, a benzocarbazole group, a dibenzocarbazole group, a benzimidazole group, or an imidazopyridine group;

a benzene group, a pentalene group, an indene group, a naphthalene group, an azulene group, a heptalene group, an indacene group, an acenaphthalene group, a fluorene group, a spiro-bifluorene group, a spiro-benzofluorene-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pyrrole group, a thiophene group, a furan group, a silole group, an imidazole group, a pyrazole group, a thiazole group, an isothiazole group, an oxazole group, an isoxazole group, a pyridine group, a pyrazine group, a pyrimidine group, a pyridazine group, a triazine group, a benzofuran group, a benzothiophene group, a benzosilole group, a dibenzofuran group, a dibenzothiophene group, a dibenzosilole group, a carbazole group, a benzocarbazole group, a dibenzocarbazole group, a benzimidazole group, and an imidazopyridine group, each substituted with at least one selected from deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a carbazolyl group, a pyridinyl group, a pyrazinyl group, a pyrimidinyl group, a pyridazinyl group, a benzofuranyl group, a benzothiophenyl group, a dibenzofuranyl group, a dibenzothiophenyl group, a benzocarbazolyl group, a dibenzocarbazolyl group, —Si($Q_{31}$)($Q_{32}$)($Q_{33}$), —N($Q_{31}$)($Q_{32}$), or —B($Q_{31}$)($Q_{32}$); or

*—S(=O)($Q_1$)-*', *—S(=O)$_2$—*', *—P(=O)($Q_1$)-*', *—P(=O)$_2$—*', *—P(=S)(Q)-*', or *—P(=S)$_2$—*', wherein $Q_1$ and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, or a pyridinyl group, and

* and *' each indicate a binding site to a neighboring atom.

3. The condensed cyclic compound of claim 1, wherein $L_1$ is selected from:

a benzene group, an anthracene group, a dibenzofuran group, a benzimidazole group, an imidazopyridine group, or a triazine group;

a benzene group, a fluorene group, and a carbazole group, each substituted with at least one selected from a cyano group, a $C_1$-$C_{20}$ alkyl group, a phenyl group, a biphenyl group, or a pyridinyl group; and

*—S(=O)($Q_1$)-*', *—S(=O)$_2$—*', *—P(=O)($Q_1$)-*', *—P(=O)$_2$—*', *—P(=S)($Q_1$)-*', or *—P(=S)$_2$—*', wherein * and *' each indicate a binding site to a neighboring atom.

4. The condensed cyclic compound of claim 1, wherein $L_1$ is selected from groups represented by Formulae 3-1 to 3-50:

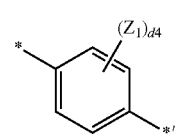

Formula 3-1

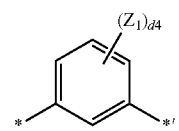

Formula 3-2

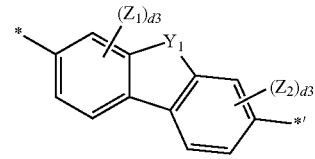

Formula 3-3

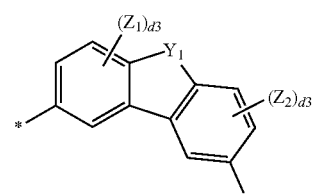

Formula 3-4

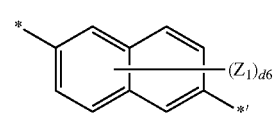

Formula 3-5

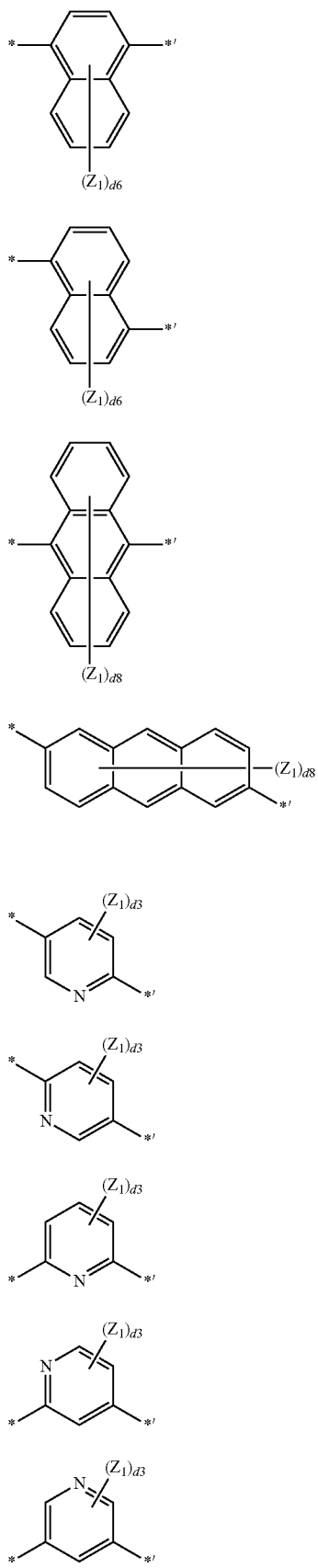
Formula 3-6
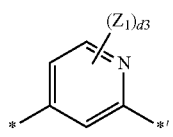
Formula 3-7
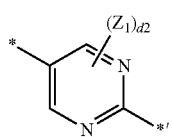
Formula 3-8
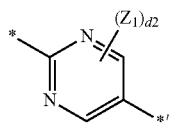
Formula 3-9
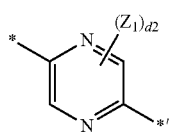
Formula 3-10
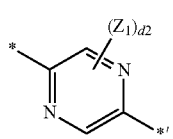
Formula 3-11
Formula 3-12
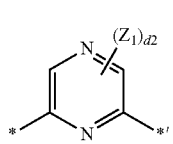
Formula 3-13
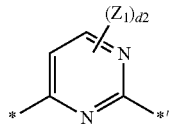
Formula 3-14
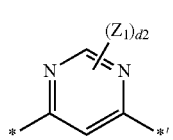
Formula 3-15
Formula 3-16
Formula 3-17
Formula 3-18
Formula 3-19
Formula 3-20
Formula 3-21
Formula 3-22
Formula 3-23
Formula 3-24
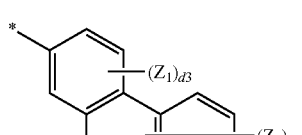
Formula 3-25
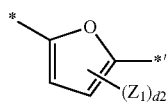

-continued
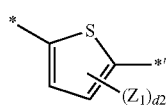
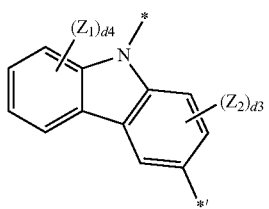
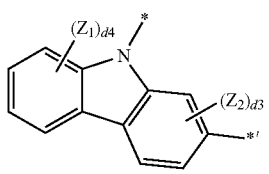
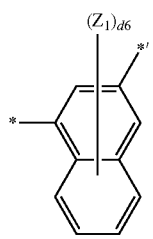
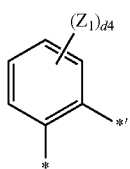
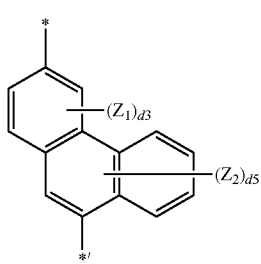
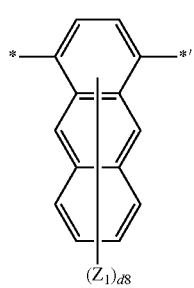
-continued
Formula 3-26
Formula 3-27
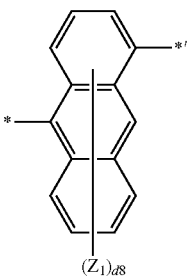
Formula 3-28
Formula 3-29
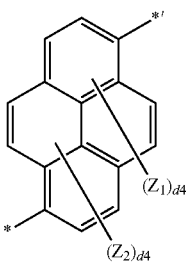
Formula 3-30
Formula 3-31
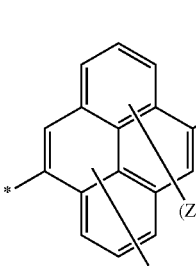
Formula 3-32
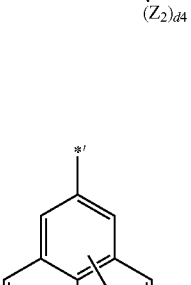
Formula 3-33
Formula 3-34
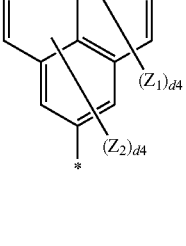
Formula 3-35
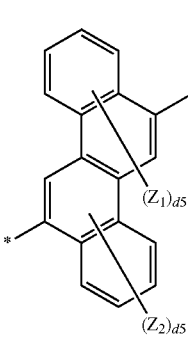
Formula 3-36
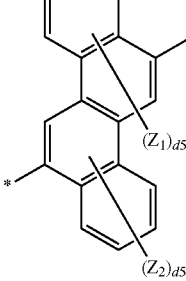
Formula 3-37

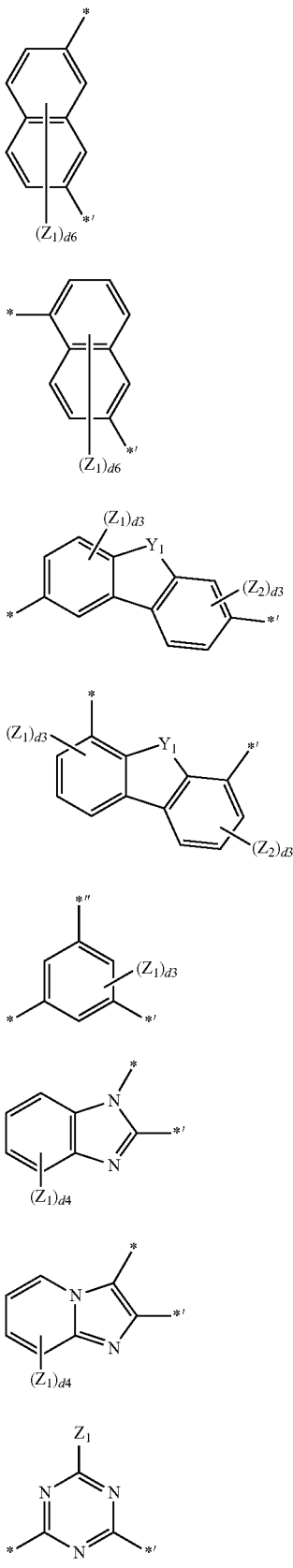

Formula 3-38

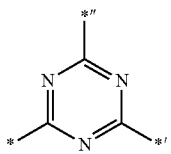

Formula 3-39

*—S(=O)—*'

Formula 3-40

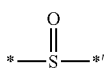

Formula 3-41

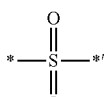

Formula 3-42

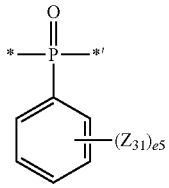

Formula 3-43

Formula 3-44

Formula 3-45

Formula 3-46

Formula 3-47

Formula 3-48

Formula 3-49

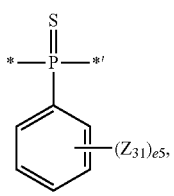

Formula 3-50 wherein, in Formulae 3-1 to 3-50, $Y_1$ is O, S, $C(Z_3)(Z_4)$, $N(Z_5)$, or $Si(Z_6)(Z_7)$, $Z_1$ to $Z_7$ are each independently selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, or —$Si(Q_{31})(Q_{32})(Q_{33})$, wherein $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, or a pyridinyl group, d2 is an integer selected from 0 to 2, d3 is an integer selected from 0 to 3, d4 is an integer selected from 0 to 4, d5 is an integer selected from 0 to 5, d6 is an integer selected from 0 to 6, d8 is an integer selected from 0 to 8, and
*, *', and *" each indicate a binding site to a neighboring atom.

5. The condensed cyclic compound of claim 1, wherein a1 is an integer selected from 0 to 2.

6. The condensed cyclic compound of claim 1, wherein $Ar_1$ is selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a carbazolyl group, a benzofuranyl group, a benzothiophenyl group, a dibenzofuranyl group, a dibenzothiophenyl group, a benzonaphthofuranyl group, a dinaphthofuranyl group, a benzocarbazolyl group, a dibenzocarbazolyl group, a dibenzosilolyl group, a benzonaphthosilolyl group, a dinaphthosilolyl group, a benzimidazolyl group, or an imidazopyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a carbazolyl group, a benzofuranyl group, a benzothiophenyl group, a dibenzofuranyl group, a dibenzothiophenyl group, a benzonaphthofuranyl group, a dinaphthofuranyl group, a benzocarbazolyl group, a dibenzocarbazolyl group, a dibenzosilolyl group, a benzonaphthosilolyl group, a dinaphthosilolyl group, a benzimidazolyl group, and an imidazopyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyridinyl group, a pyrazinyl group, a pyrimidinyl group, a pyridazinyl group, a triazinyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, a dibenzosilolyl group, —N($Q_{31}$)($Q_{32}$), or —Si($Q_{31}$)($Q_{32}$)($Q_{33}$); and —S(=O)($Q_1$)($Q_2$), —S(=O)$_2$($Q_1$), —P(=O)($Q_1$)($Q_2$), —P(=O)$_2$($Q_1$), —P(=S)($Q_1$)($Q_2$), or —P(=S)$_2$($Q_1$), wherein $Q_1$, $Q_2$, and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, or a pyridinyl group.

7. The condensed cyclic compound of claim 6, wherein $Ar_1$ is selected from:

a phenyl group, a biphenyl group, a terphenyl group, a fluorenyl group, a spiro-bifluorenyl group, a pyridinyl group, a triazinyl group, a carbazolyl group, a dibenzofuranyl group, a dinaphthofuranyl group, a benzimidazolyl group, or an imidazopyridinyl group;

a phenyl group, a terphenyl group, a fluorenyl group, a spiro-bifluorenyl group, a pyridinyl group, a triazinyl group, a carbazolyl group, a dibenzofuranyl group, a dinaphthofuranyl group, a benzimidazolyl group, and an imidazopyridinyl group, each substituted with at least one selected from deuterium, —F, a cyano group, a $C_1$-$C_{20}$ alkyl group, a phenyl group, a biphenyl group, a terphenyl group, a fluorenyl group, a spiro-bifluorenyl group, a pyridinyl group, a carbazolyl group, a dibenzofuranyl group, —N($Q_{31}$)($Q_{32}$), or —Si($Q_{31}$)($Q_{32}$)($Q_{33}$); and —S(=O)($Q_1$)($Q_2$), —S(=O)$_2$($Q_1$), —P(=O)($Q_1$)($Q_2$), —P(=O)$_2$($Q_1$), —P(=S)($Q_1$)($Q_2$), and —P(=S)$_2$($Q_1$), wherein $Q_1$, $Q_2$, and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, or a pyridinyl group.

8. The condensed cyclic compound of claim 1, wherein $Ar_1$ is selected from groups represented by Formulas 5-1 to 5-30, —S(=O)($Q_1$)($Q_2$), —S(=O)$_2$($Q_1$), —P(=O)($Q_1$)($Q_2$), —P(=O)$_2$($Q_1$), —P(=S)($Q_1$)($Q_2$), or —P(=S)$_2$($Q_1$):

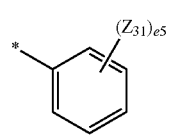

Formula 5-1

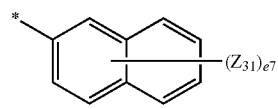

Formula 5-2

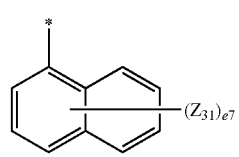

Formula 5-3

-continued
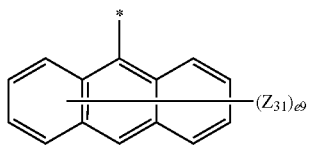
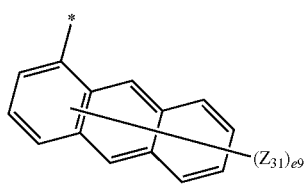
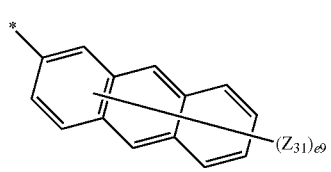
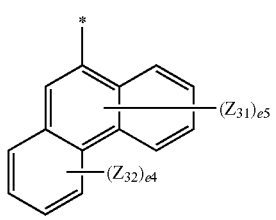
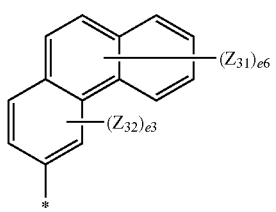
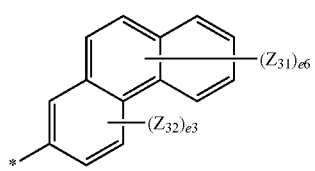
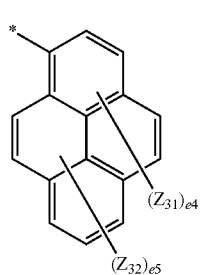
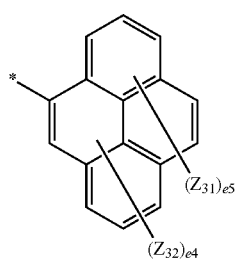
Formula 5-4
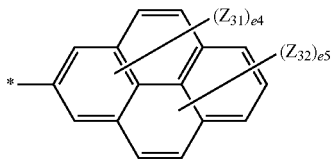
Formula 5-5
Formula 5-6
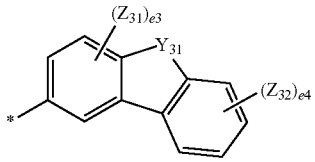
Formula 5-7
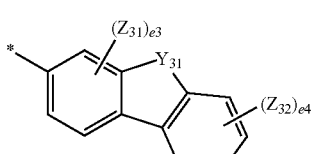
Formula 5-8
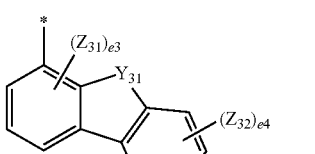
Formula 5-9
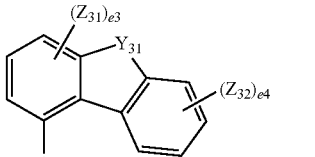
Formula 5-10
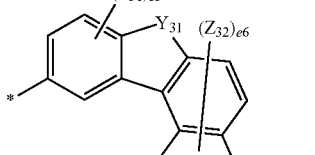
Formula 5-11
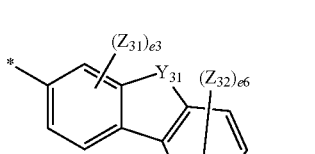
Formula 5-12
Formula 5-13
Formula 5-14
Formula 5-15
Formula 5-16
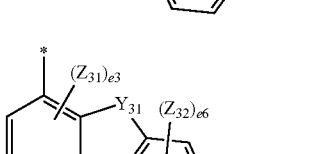
Formula 5-17
Formula 5-18
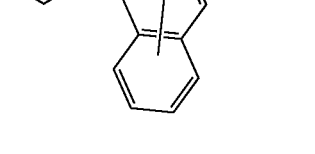
Formula 5-19
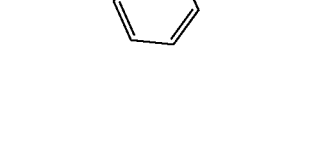

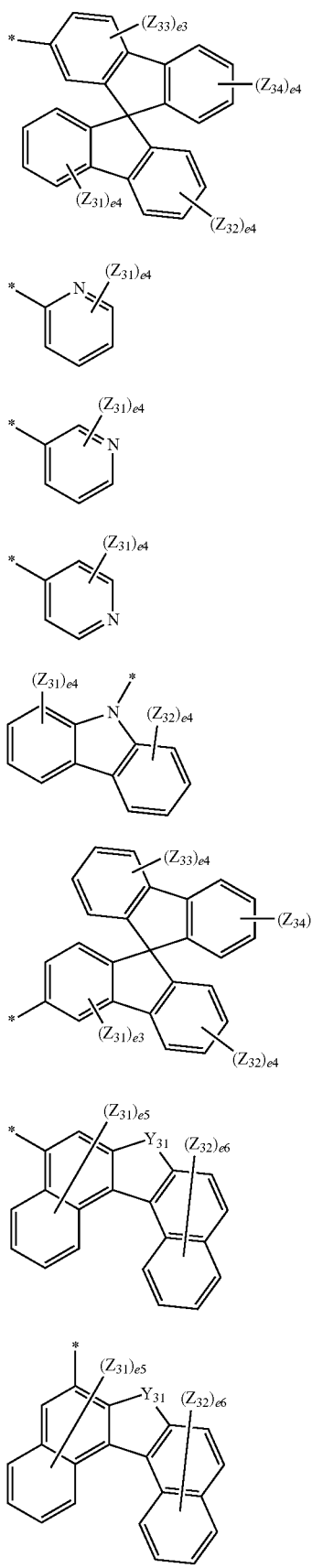

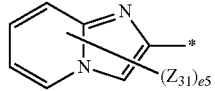
Formula 5-20

Formula 5-21

Formula 5-22

Formula 5-23

Formula 5-24

Formula 5-25

Formula 5-26

Formula 5-27

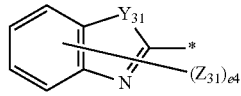
Formula 5-28

Formula 5-29

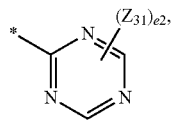
Formula 5-30 wherein, in Formulae 5-1 to 5-30, $Y_{31}$ is O, S, $C(Z_{33})(Z_{34})$, $N(Z_{35})$, or $Si(Z_{36})(Z_{37})$, $Z_{31}$ to $Z_{37}$ are each independently selected from hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, a silolyl group, a pyridinyl group, an indolyl group, an isoindolyl group, a benzofuranyl group, a benzothiophenyl group, a benzosilolyl group, a dibenzofuranyl group, a dibenzothiophenyl group, a dibenzosilolyl group, a carbazolyl group, a benzocarbazolyl group, a dibenzocarbazolyl group, or —$Si(Q_{31})(Q_{32})(Q_{33})$, wherein $Q_1$, $Q_2$, and $Q_{31}$ to $Q_{33}$ are each independently selected from a $C_1$-$C_{20}$ alkyl group, a $C_1$-$C_{20}$ alkoxy group, a phenyl group, a biphenyl group, a terphenyl group, a naphthyl group, or a pyridinyl group, e3 is an integer selected from 0 to 3,
e4 is an integer selected from 0 to 4,
e5 is an integer selected from 0 to 5,
e6 is an integer selected from 0 to 6,
e7 is an integer selected from 0 to 7,
e9 is an integer selected from 0 to 9, and
* indicates a binding site to a neighboring atom.

9. The condensed cyclic compound of claim 8, wherein $Ar_1$ is selected from groups represented by Formulae 5-1, 5-3, 5-4, 5-7, 5-13, 5-14, 5-22, and 5-27 to 5-30.

10. The condensed cyclic compound of claim 1, wherein $Ar_1$ is selected from groups represented by Formulae 6-1 to 6-143 and groups represented by Formulae 10-1 to 10-7:

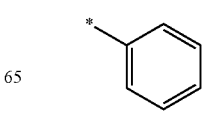
Formula 6-1

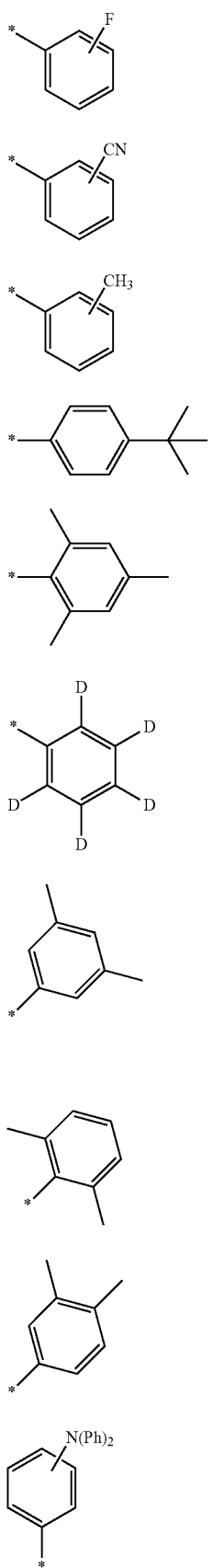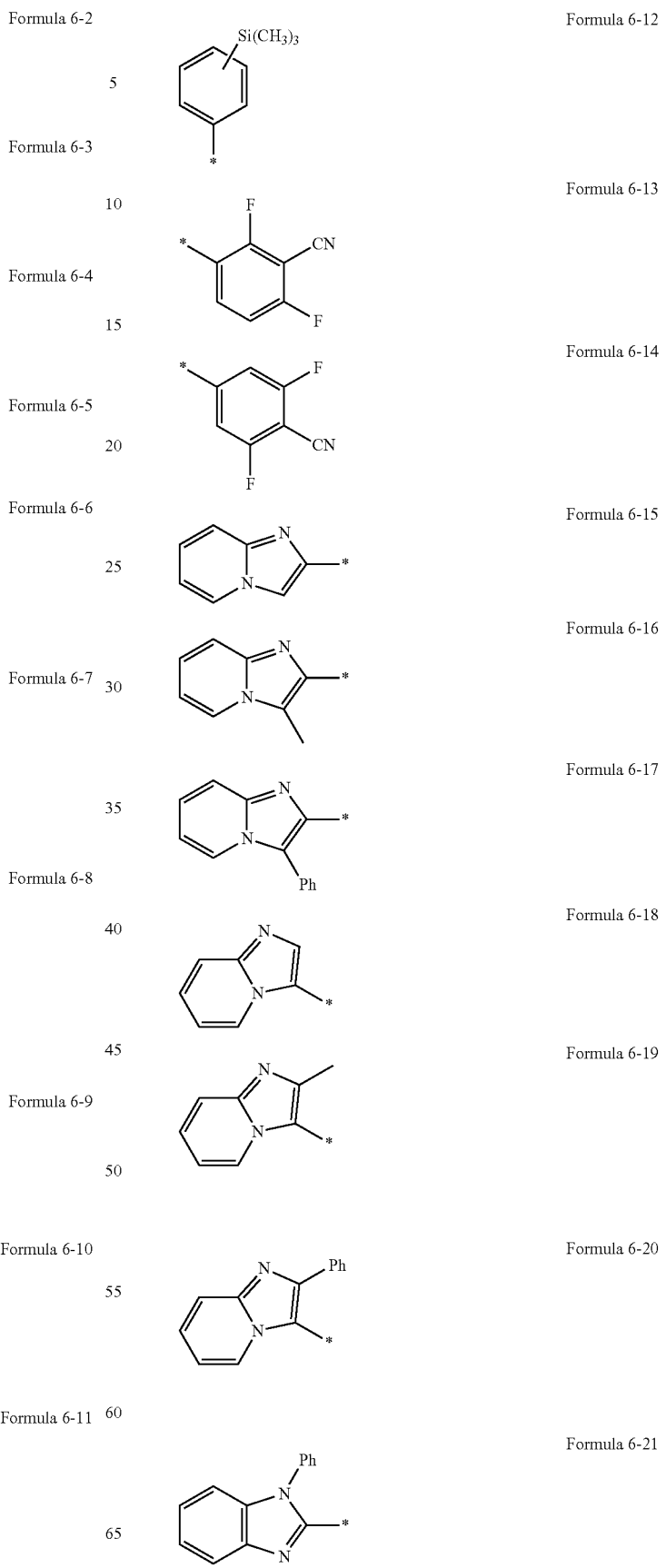

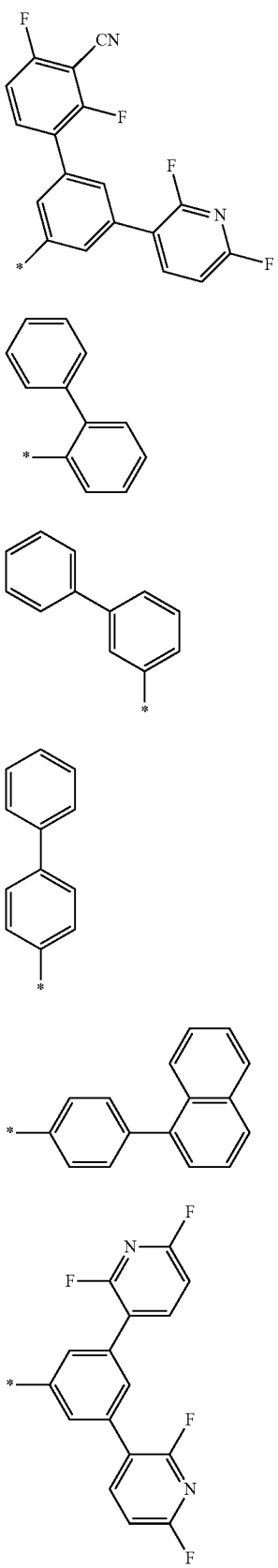
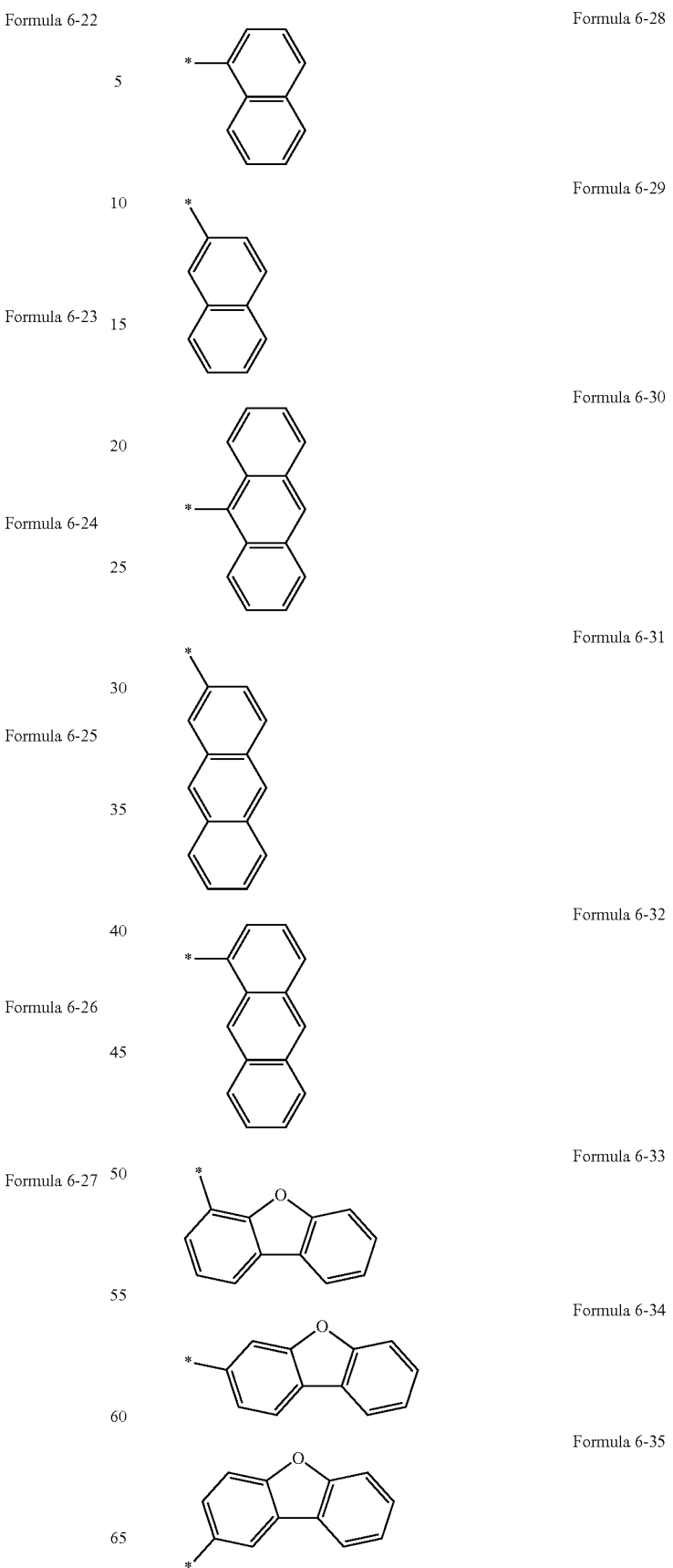

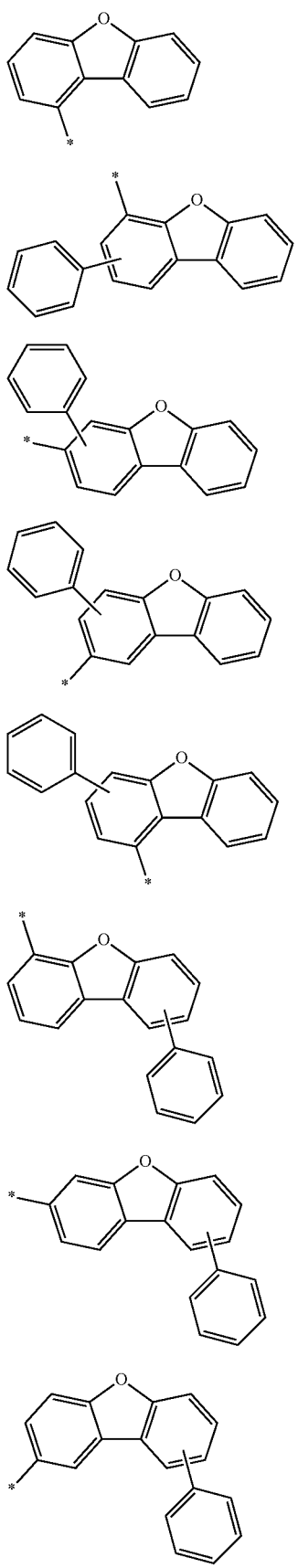
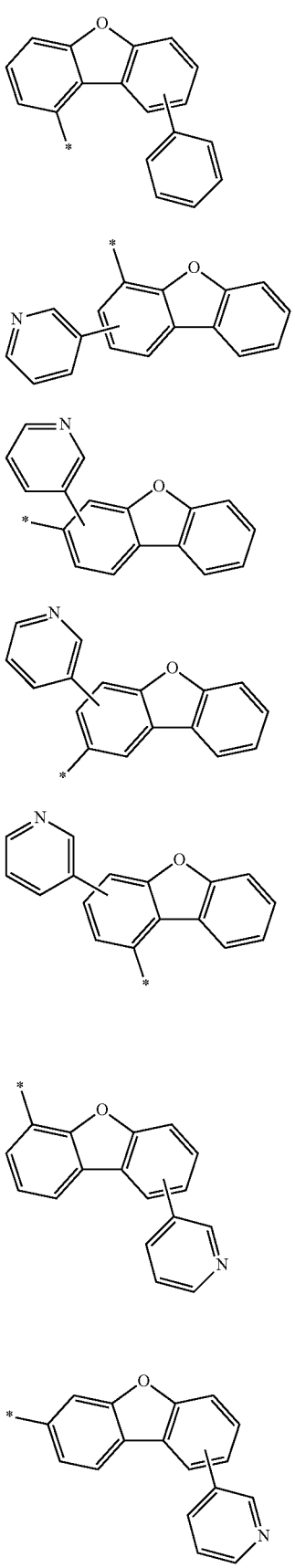

-continued
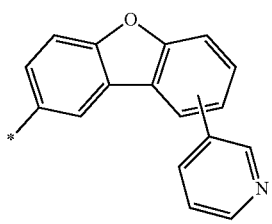
Formula 6-51
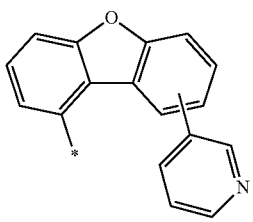
Formula 6-52
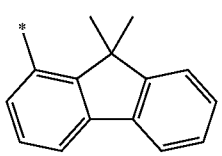
Formula 6-53
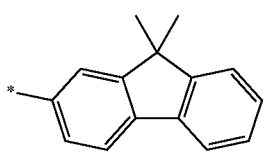
Formula 6-54
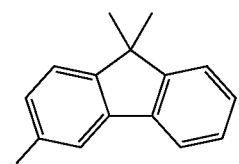
Formula 6-55
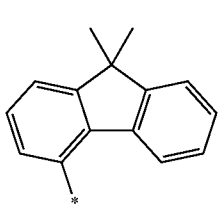
Formula 6-56
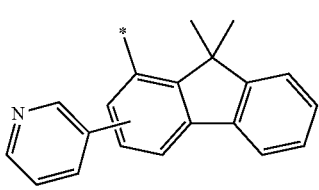
Formula 6-57
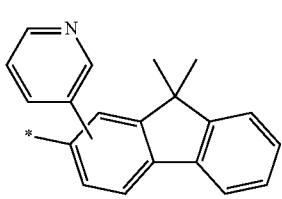
Formula 6-58
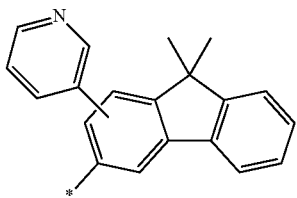
Formula 6-59
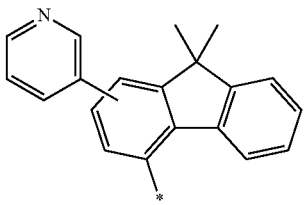
Formula 6-60
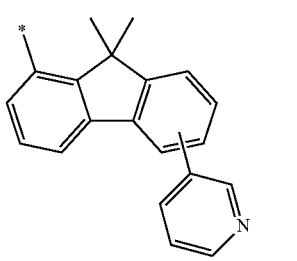
Formula 6-61
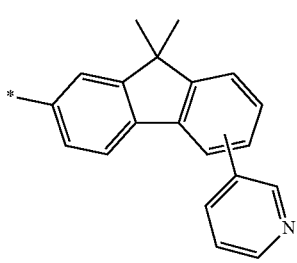
Formula 6-62
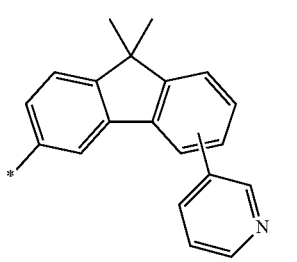
Formula 6-63
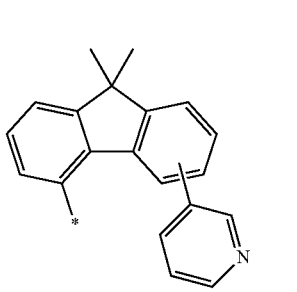
Formula 6-64

Formula 6-65
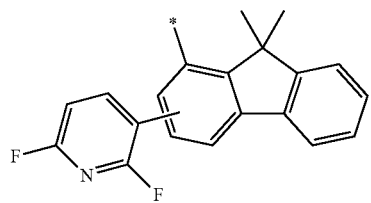
Formula 6-66
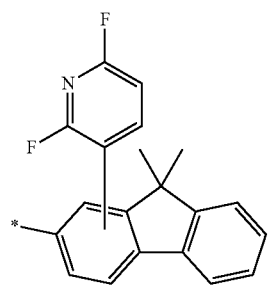
Formula 6-67
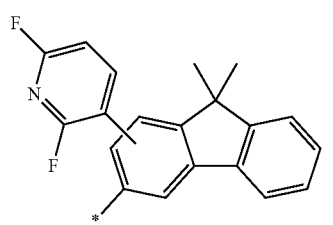
Formula 6-68
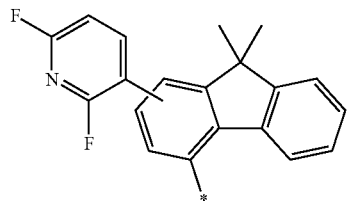
Formula 6-69
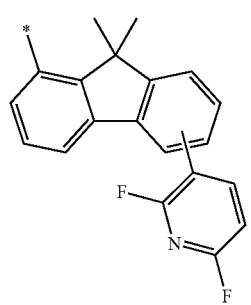
Formula 6-70
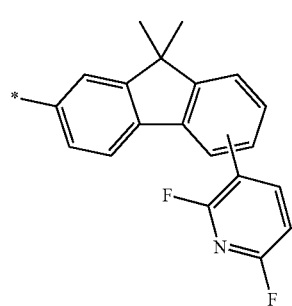
Formula 6-71
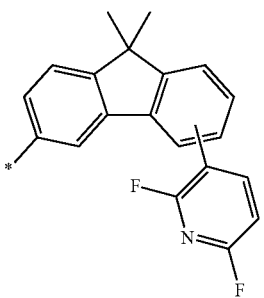
Formula 6-72
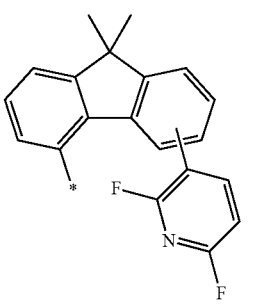
Formula 6-73
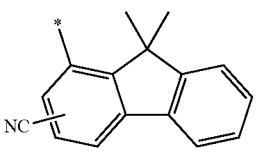
Formula 6-74
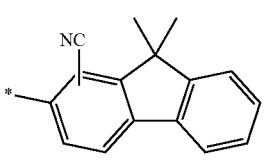
Formula 6-75
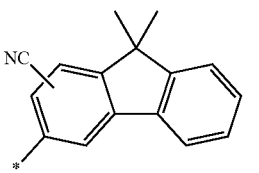
Formula 6-76
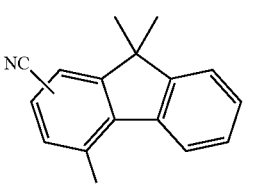
Formula 6-77
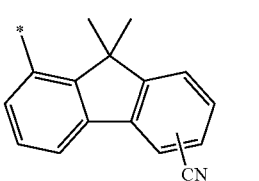

| Formula 6-78 |
| Formula 6-79 |
| Formula 6-80 |
| Formula 6-81 |
| Formula 6-82 |
| Formula 6-83 |
| Formula 6-84 |
| Formula 6-85 |
| Formula 6-86 |
| Formula 6-87 |
| Formula 6-88 |
| Formula 6-89 |
| Formula 6-90 |
| Formula 6-91 |
| Formula 6-92 |
| Formula 6-93 |
| Formula 6-94 |

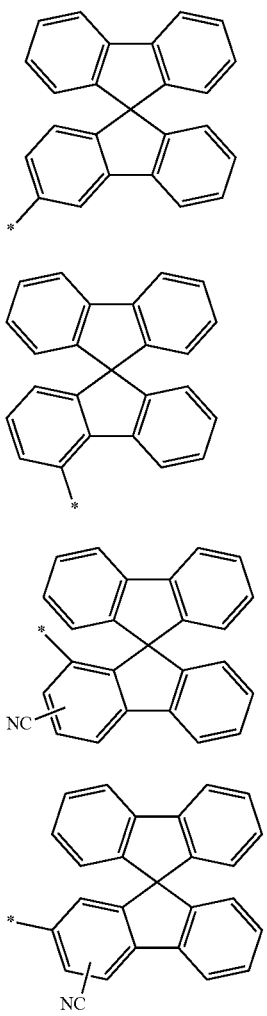
Formula 6-95
Formula 6-96
Formula 6-97
Formula 6-98
Formula 6-99
Formula 6-100
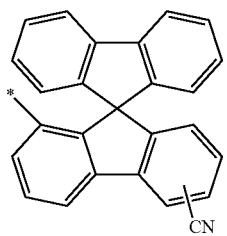
Formula 6-101
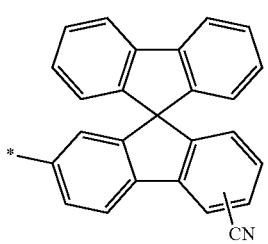
Formula 6-102
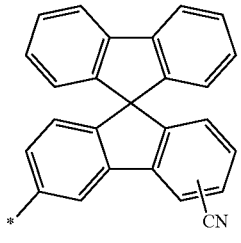
Formula 6-103
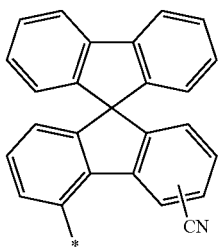
Formula 6-104
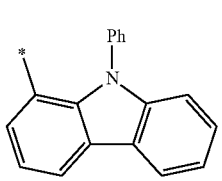
Formula 6-105
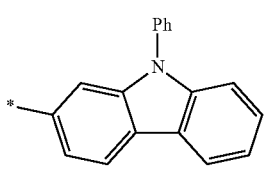
Formula 6-106
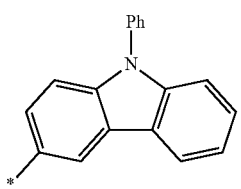
Formula 6-107

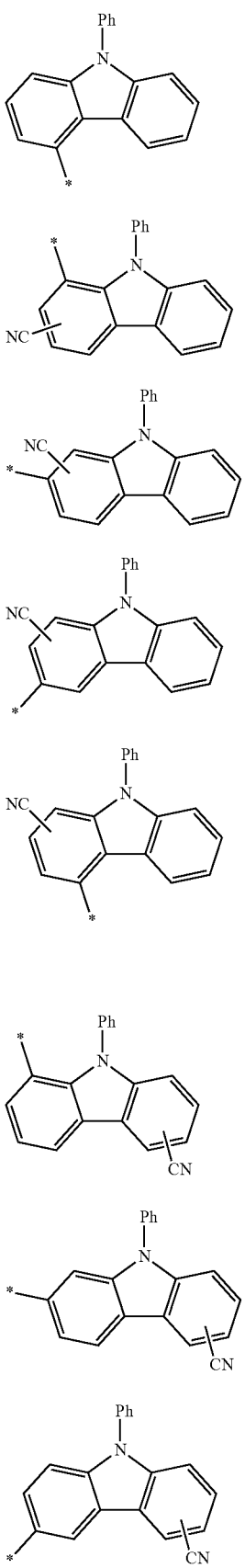
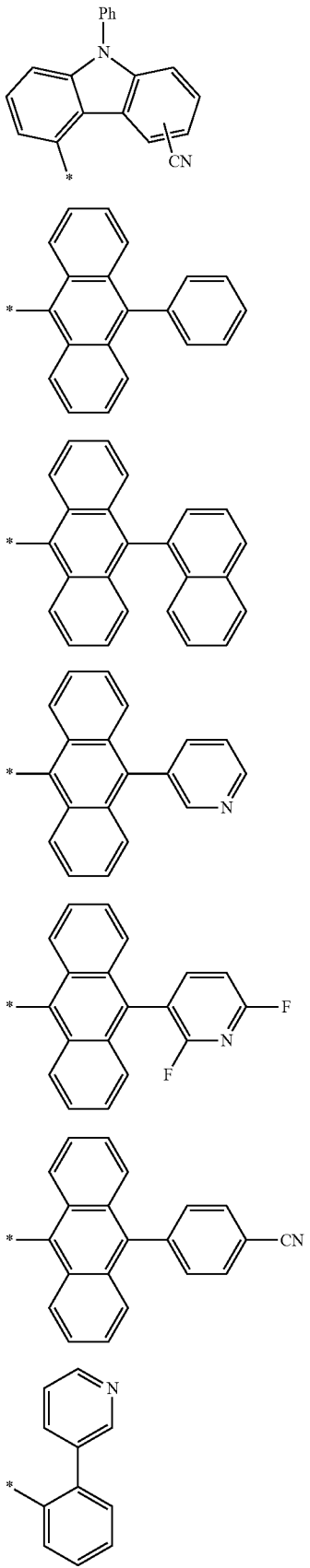
Formula 6-108
Formula 6-109
Formula 6-110
Formula 6-111
Formula 6-112
Formula 6-113
Formula 6-114
Formula 6-115
Formula 6-116
Formula 6-117
Formula 6-118
Formula 6-119
Formula 6-120
Formula 6-121
Formula 6-122

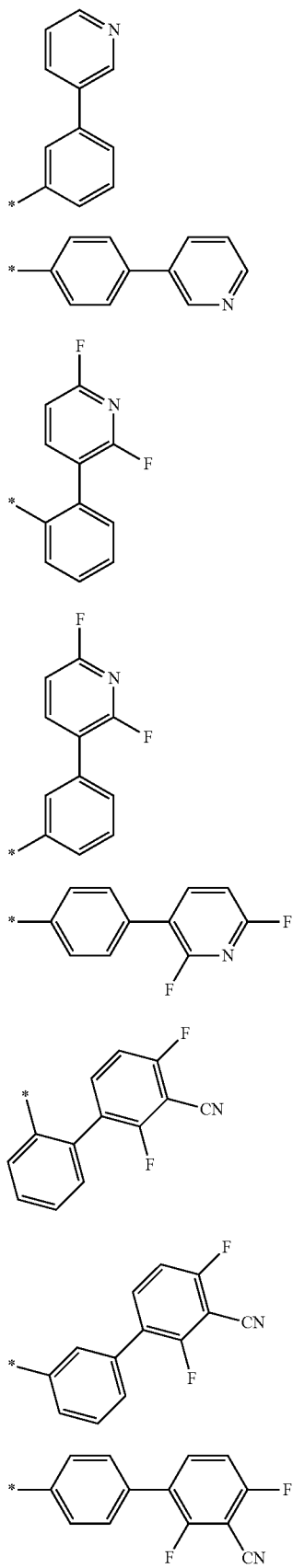
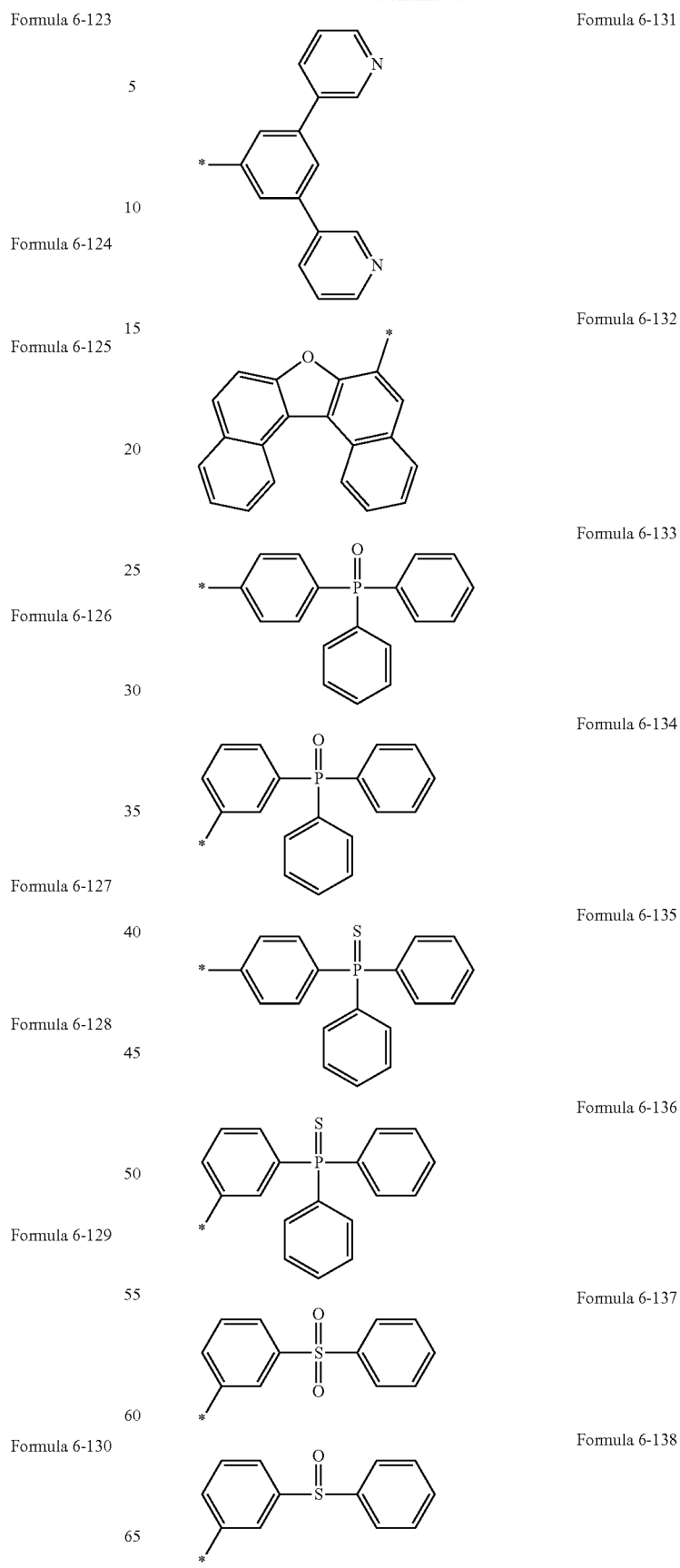
Formula 6-123
Formula 6-124
Formula 6-125
Formula 6-126
Formula 6-127
Formula 6-128
Formula 6-129
Formula 6-130
Formula 6-131
Formula 6-132
Formula 6-133
Formula 6-134
Formula 6-135
Formula 6-136
Formula 6-137
Formula 6-138

Formula 6-139
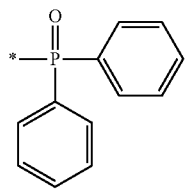

Formula 6-140
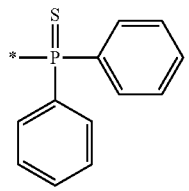

Formula 6-141
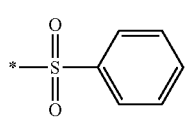

Formula 6-142
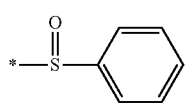

Formula 6-143
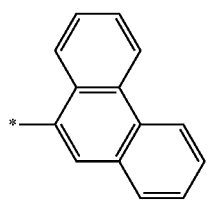

Formula 10-1
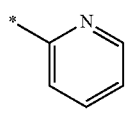

Formula 10-2

Formula 10-3
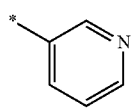

Formula 10-4

Formula 10-5
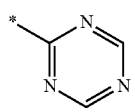

Formula 10-6
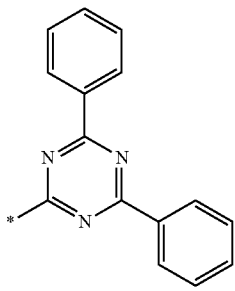

Formula 10-7
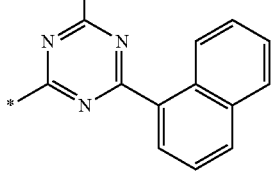

wherein Ph in Formulae 6-1 to 6-143 and 10-1 to 10-7 refers to a phenyl group, and * indicates a binding site to a neighboring atom.

11. The condensed cyclic compound of claim 1, wherein
  i) $Y_1=C(R_9)$ and at least one selected from $R_1$ to $R_3$ and $R_9$ is represented by Formula 2; or
  ii) $Y_2=C(R_{10})$ and at least one selected from $R_1$ to $R_3$ and $R_{10}$ is represented by Formula 2.

12. A condensed cyclic compound selected from Compounds 1 to 155:

1
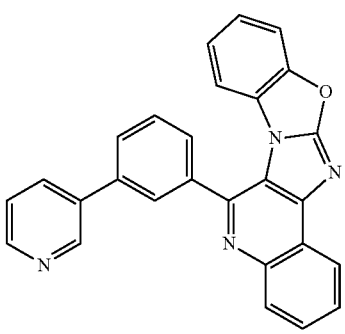

2
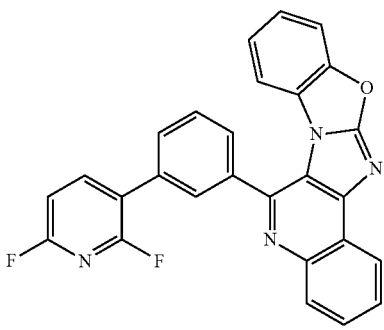

| 219 -continued | 220 -continued |
|---|---|
| 3 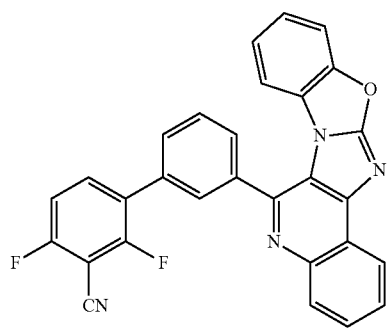 | 7 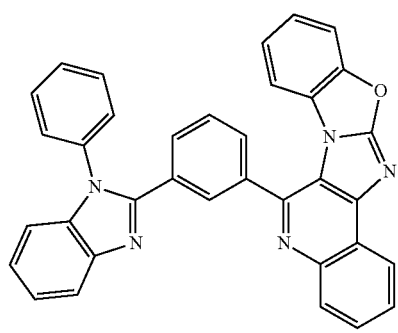 |
| 4 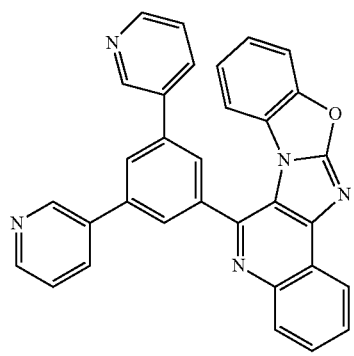 | 8 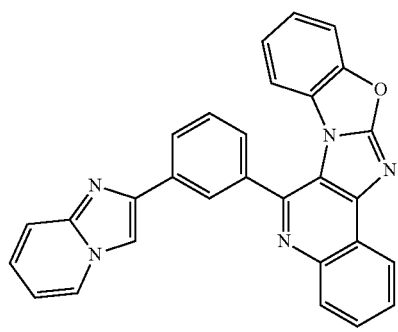 |
| 5 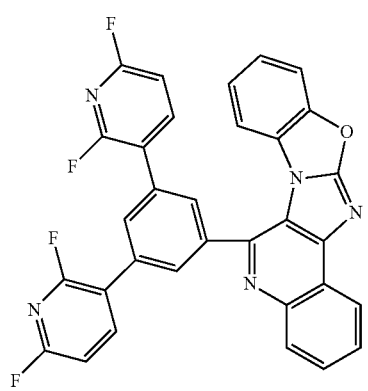 | 9 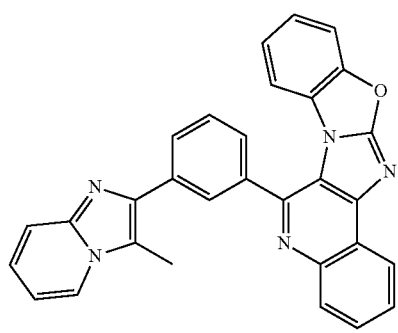 |
| 6 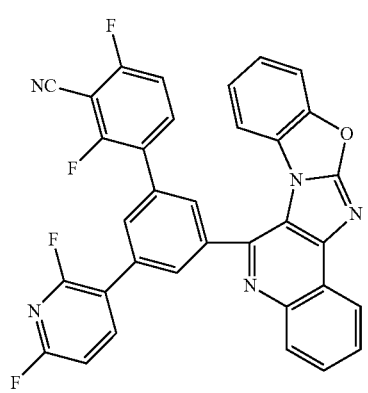 | 10 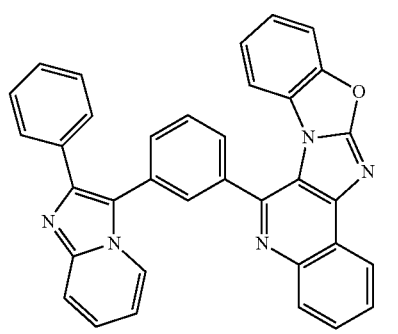 |
| | 11 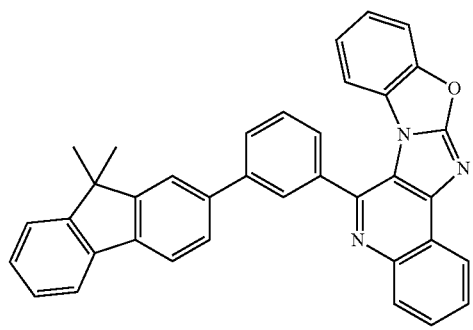 |

-continued
12
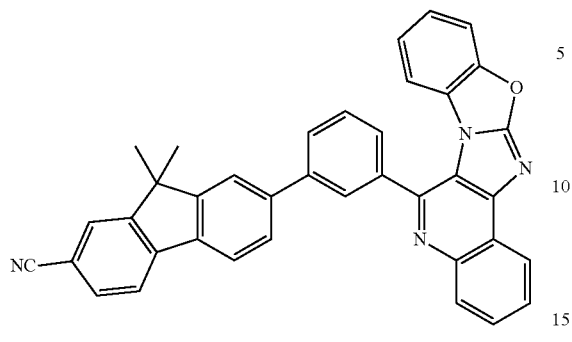
13
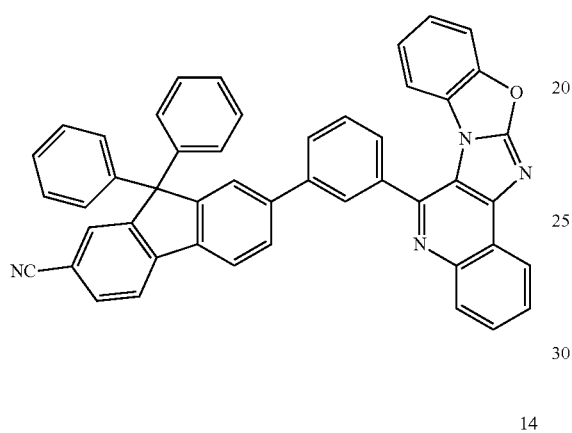
14
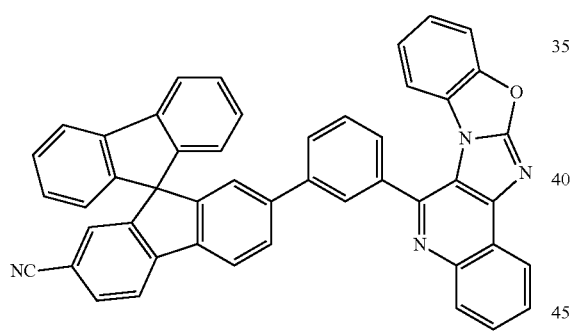
15
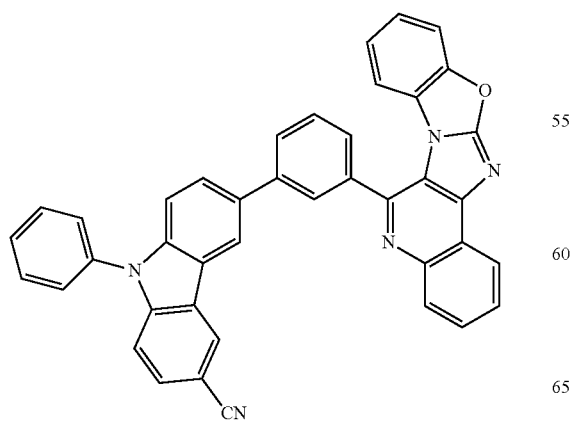
-continued
16
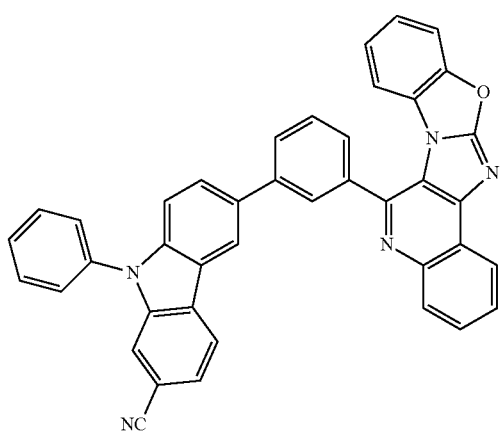
17
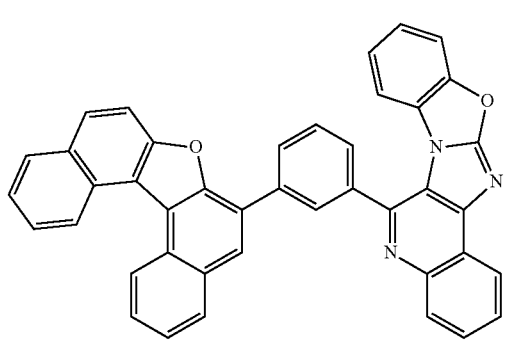
18
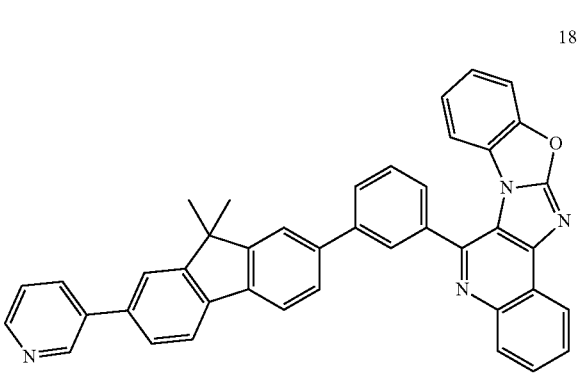
19
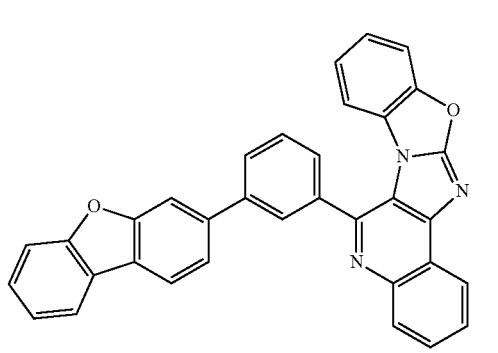

20
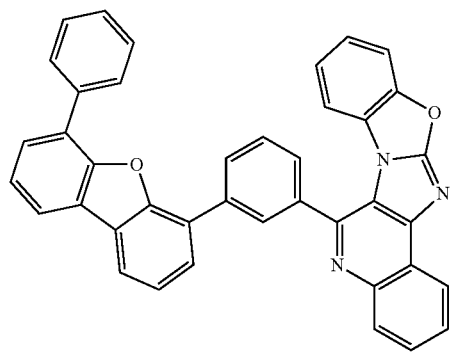
21
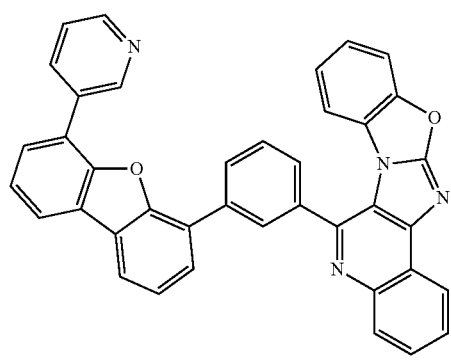
22
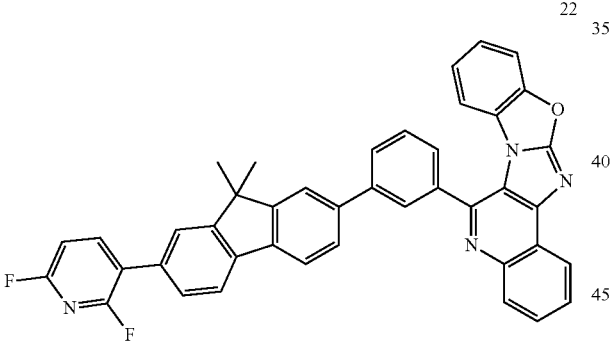
23
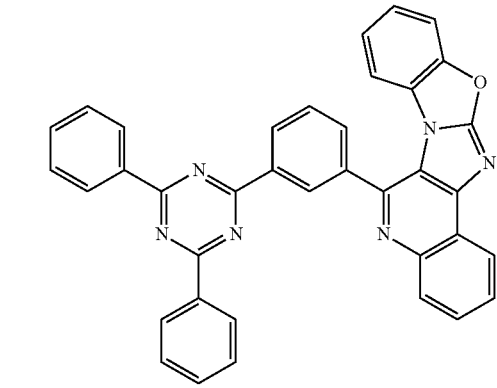
24
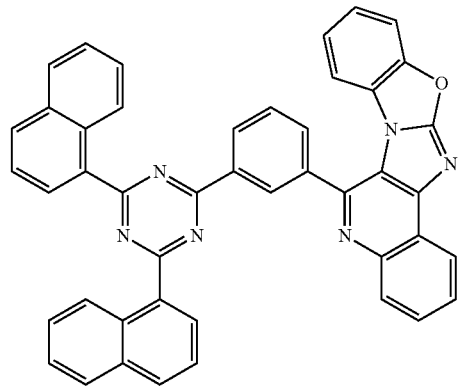
25
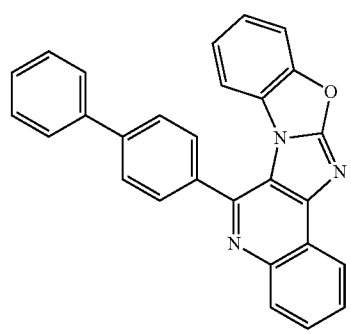
26
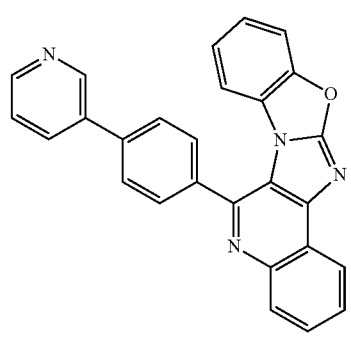
27
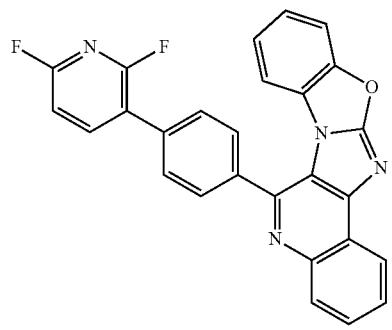

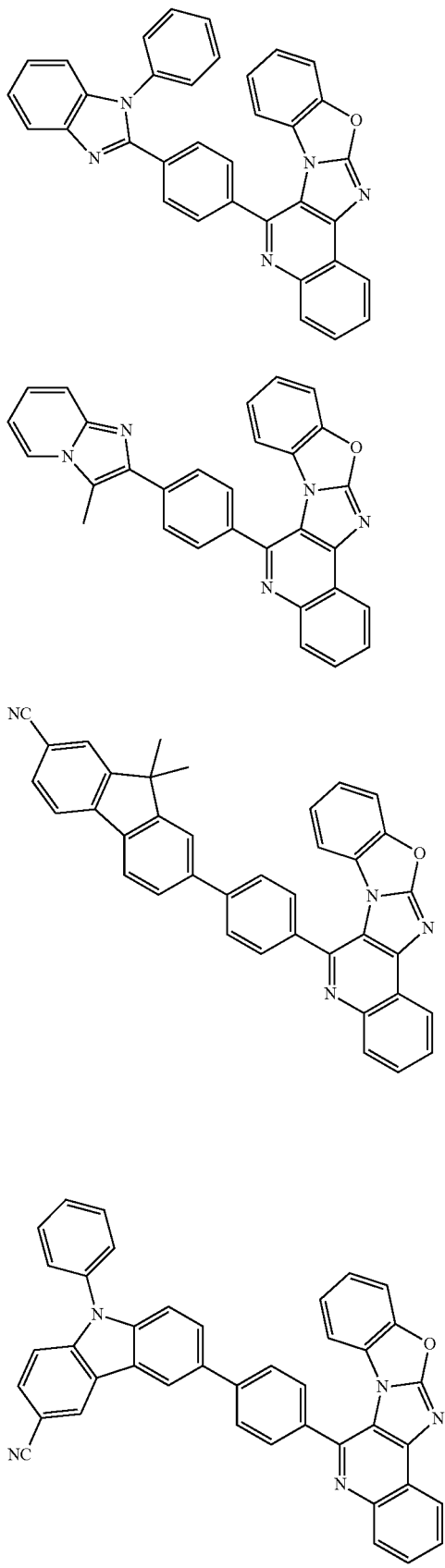
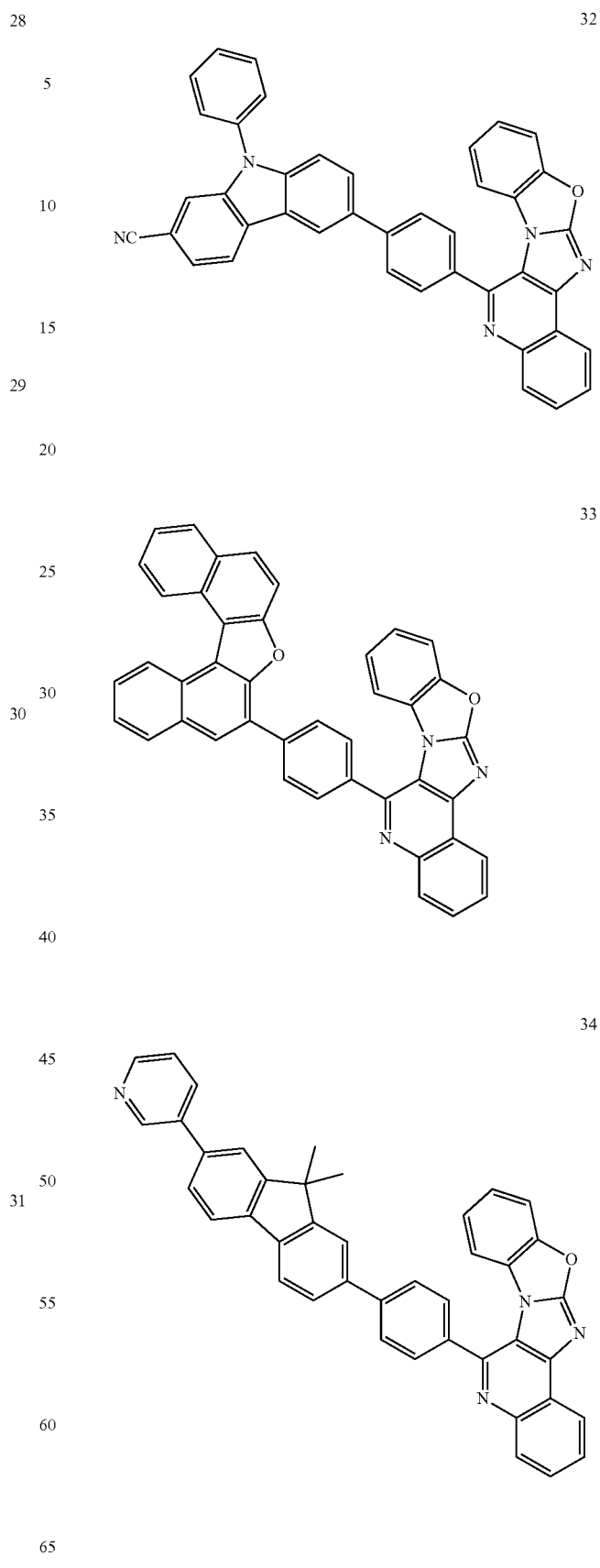

227
-continued
35
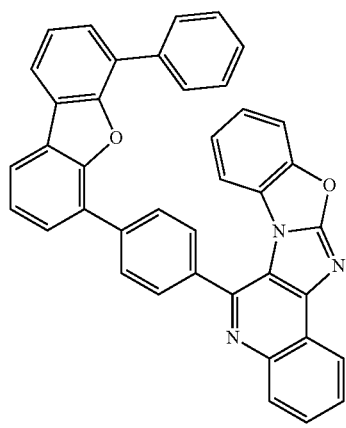
36
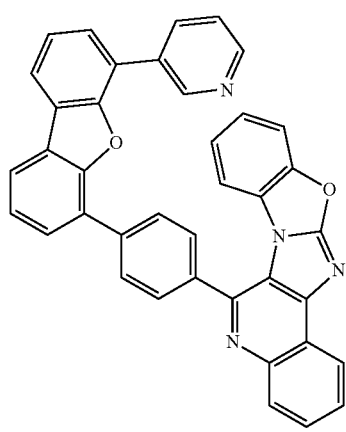
37
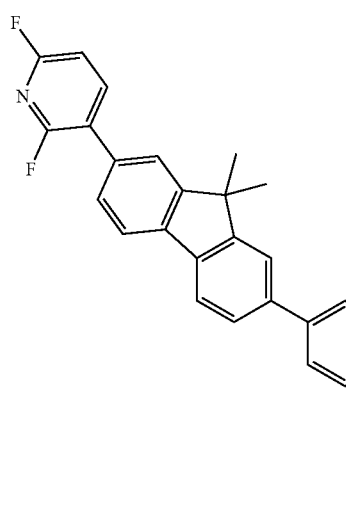
228
-continued
38
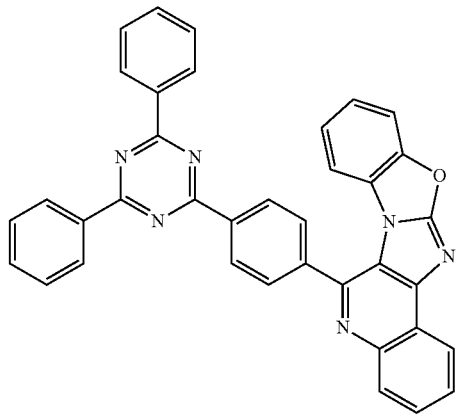
39
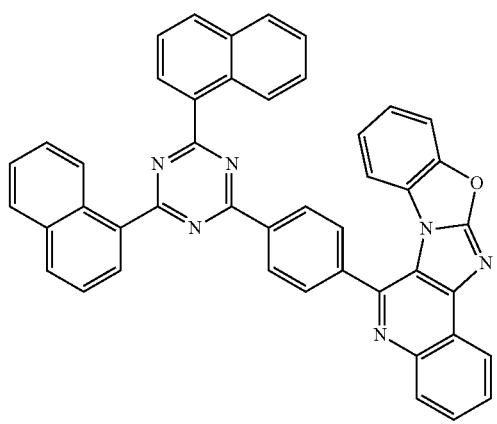
40
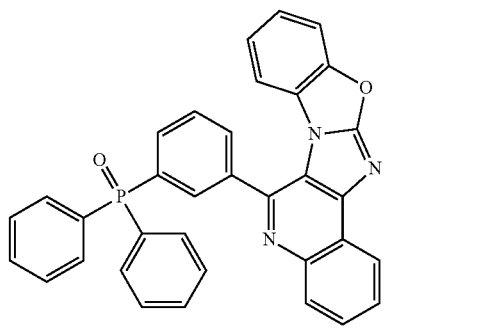
41
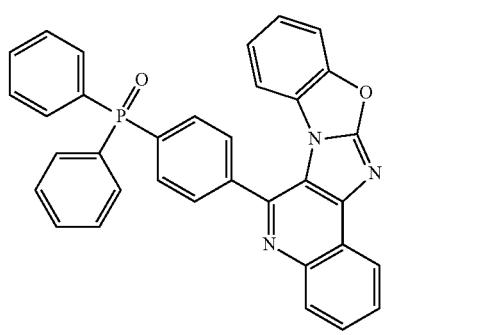

42
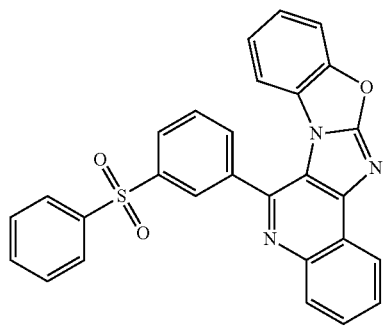
43
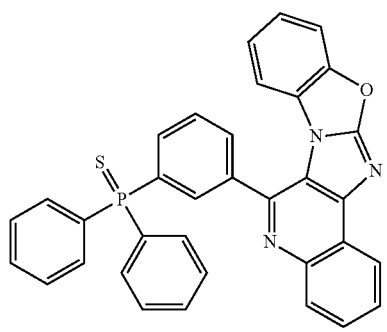
44
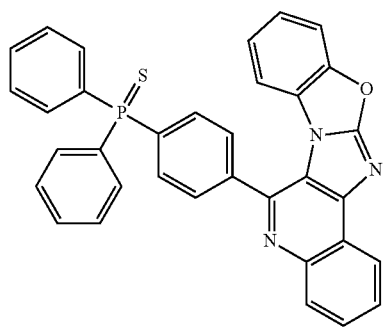
45
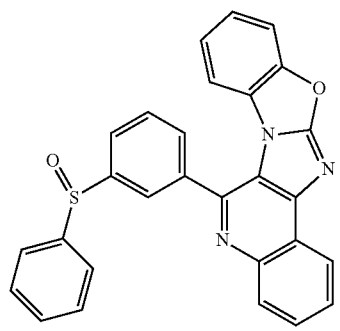
46
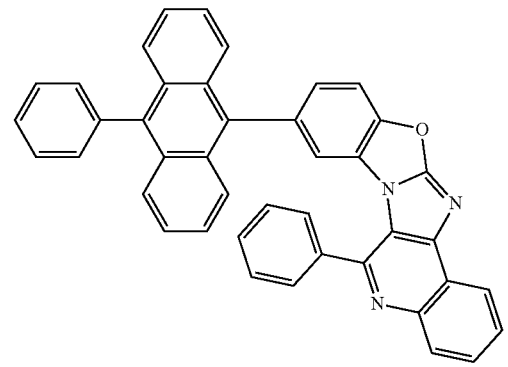
47
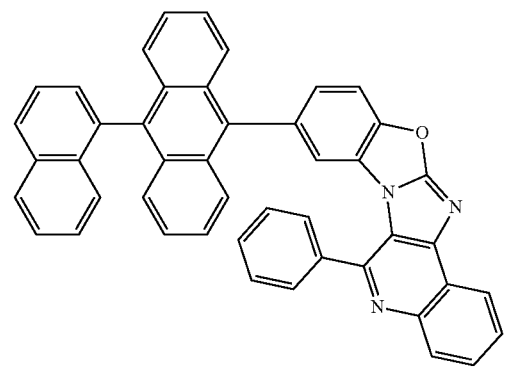
48
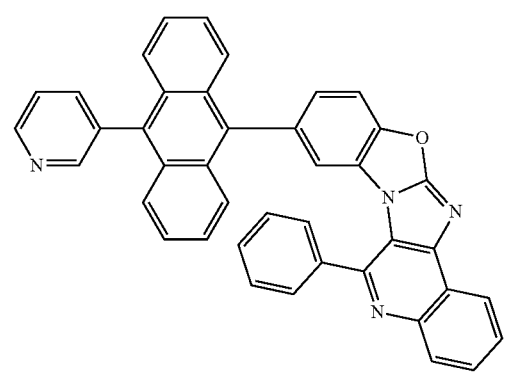
49
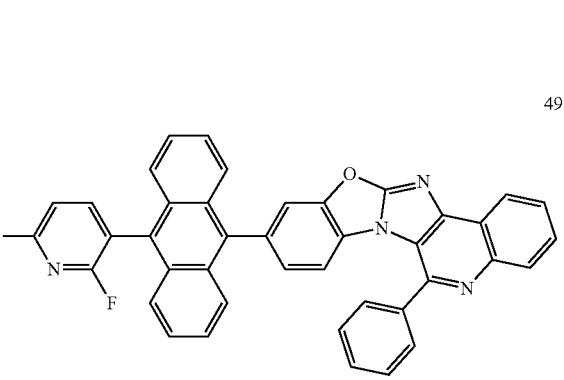

231
-continued
50
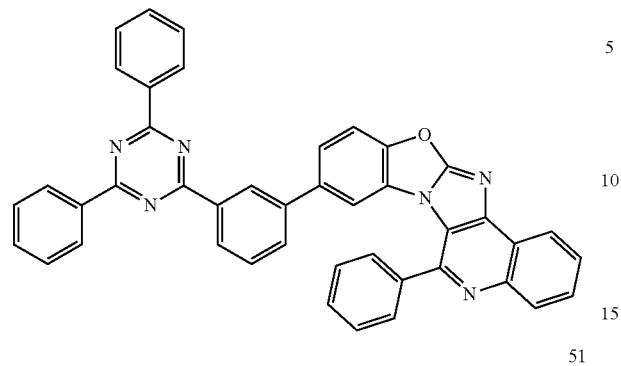
51
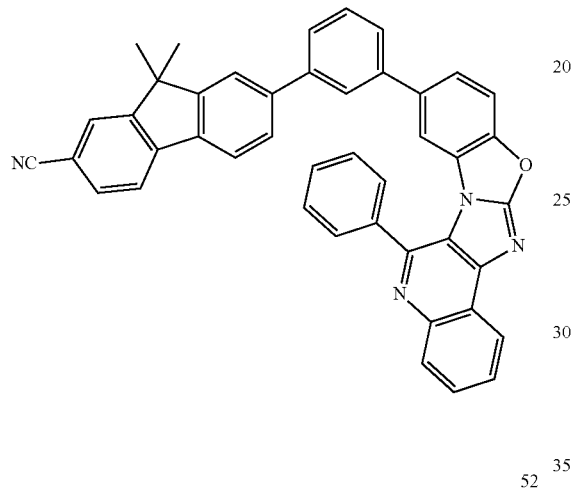
52
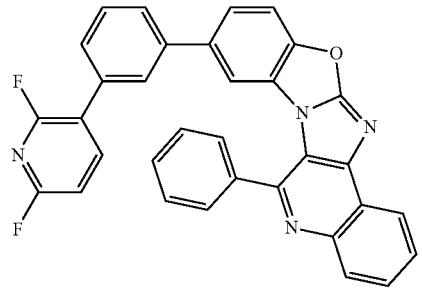
53
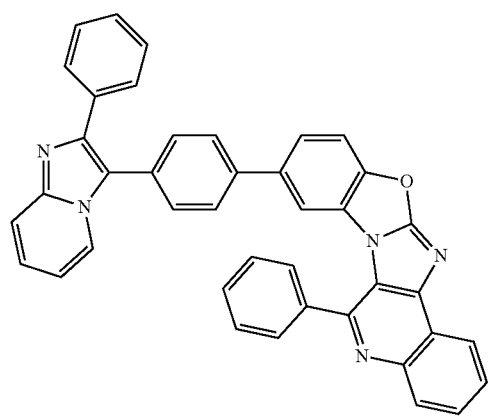
232
-continued
54
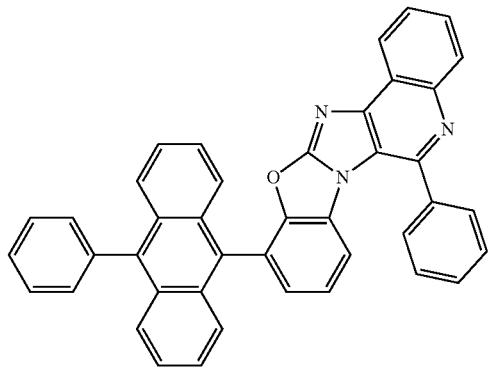
55
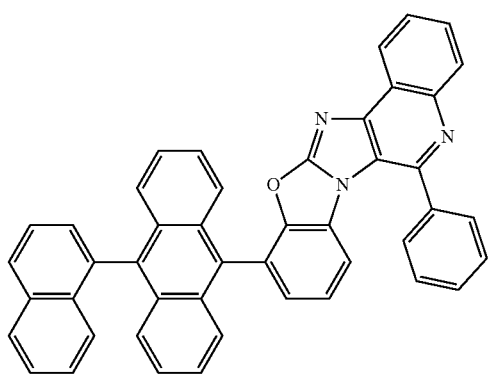
56
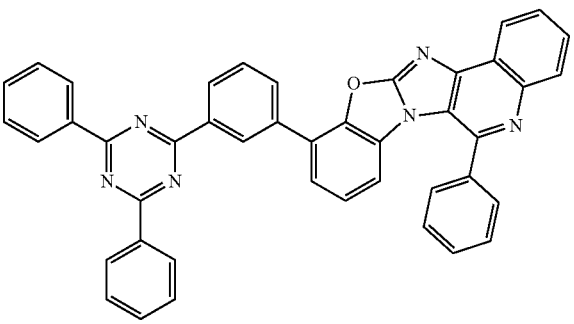
57
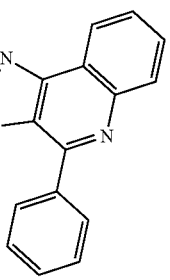

58
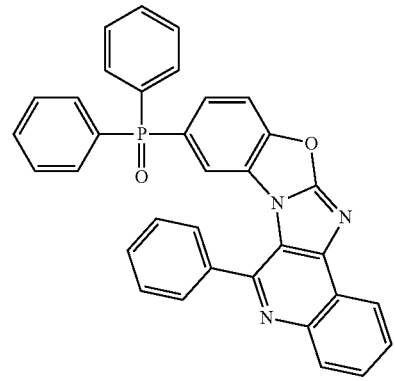
59
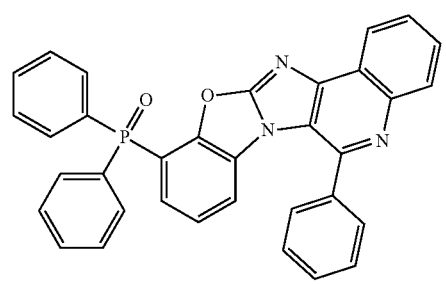
60
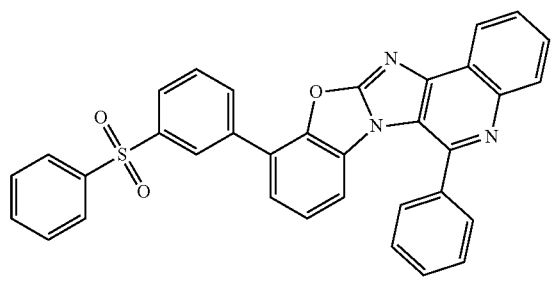
61
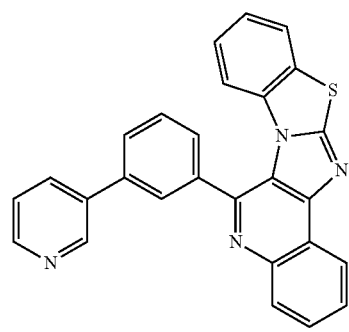
62
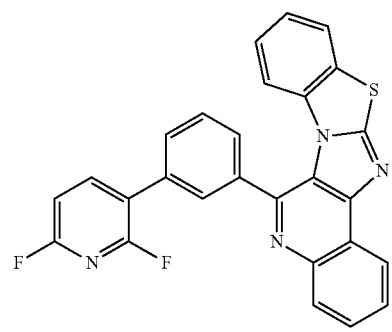
63
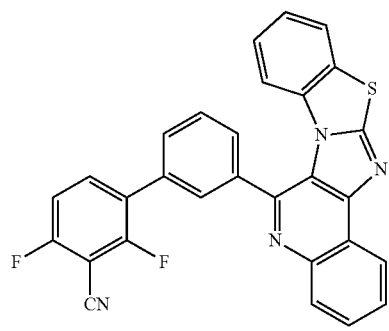
64
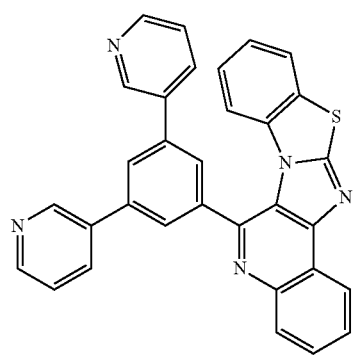
65
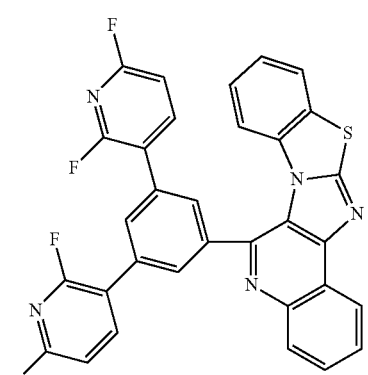
66
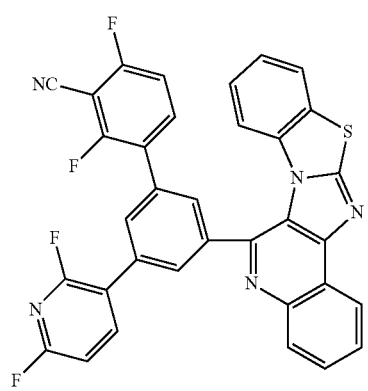

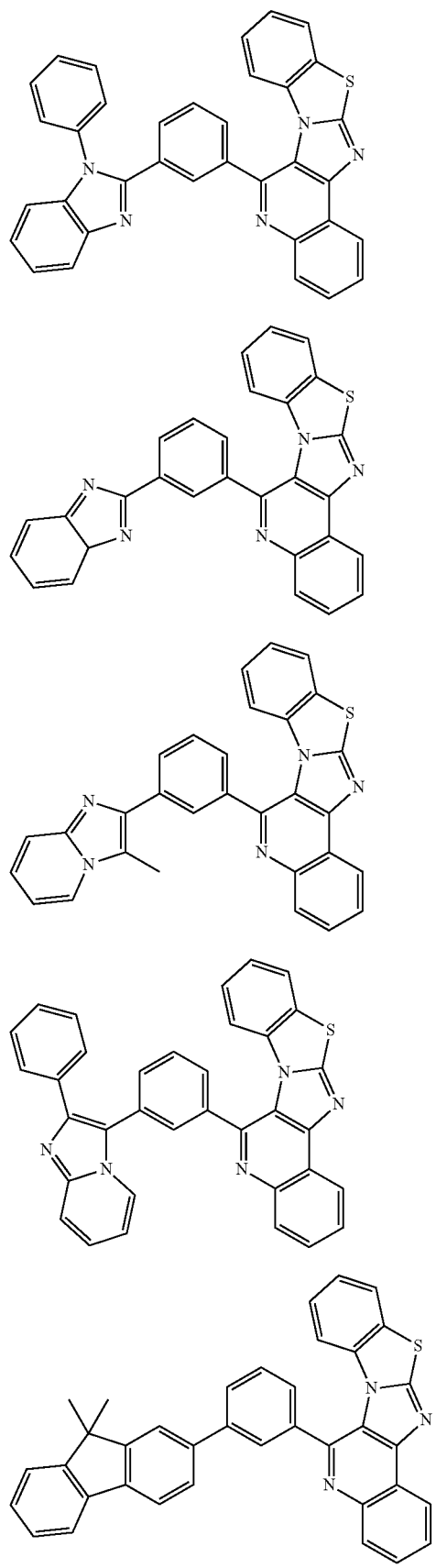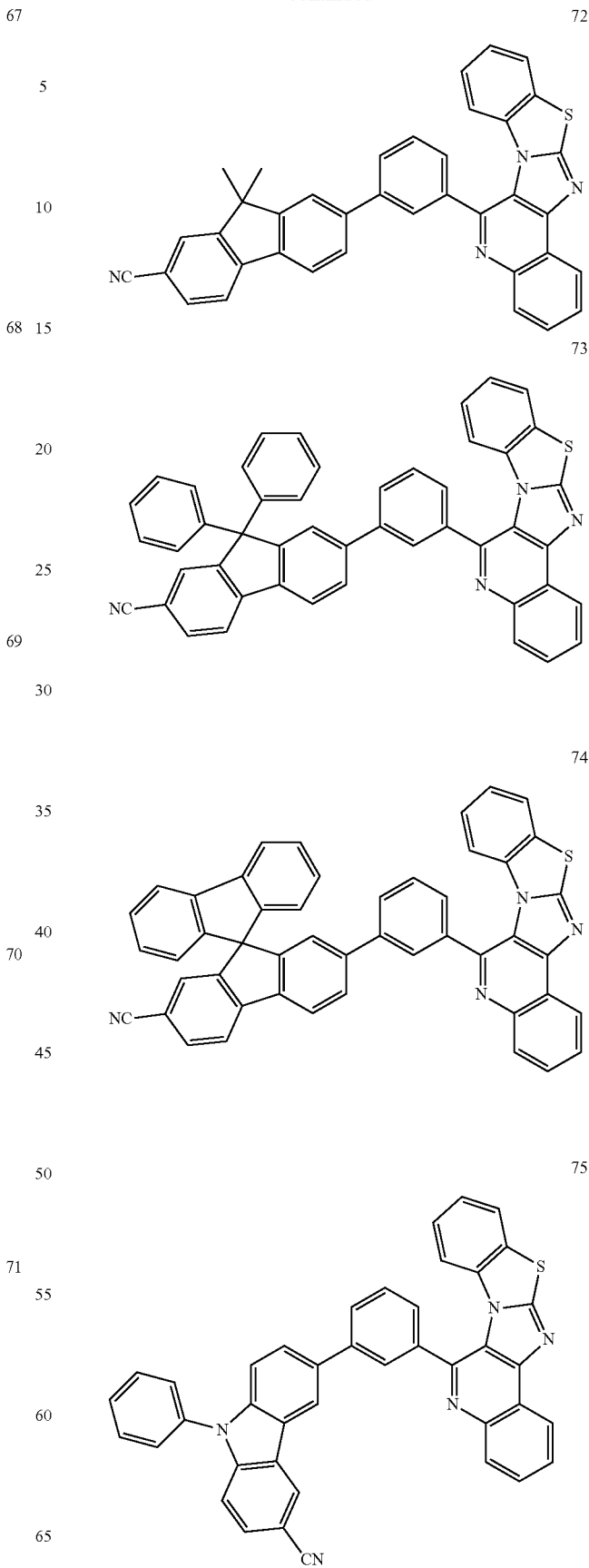

76
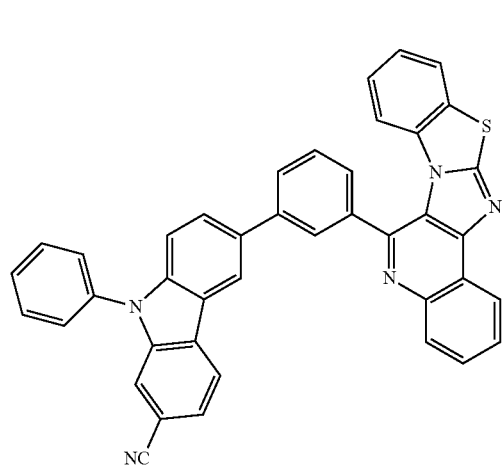
77
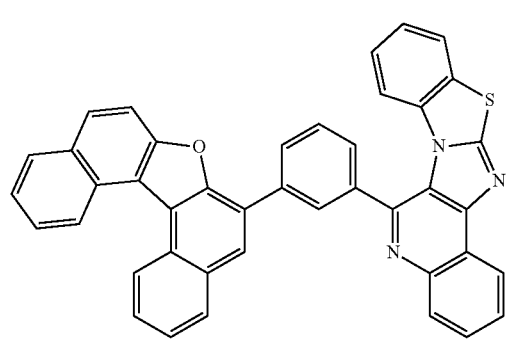
78
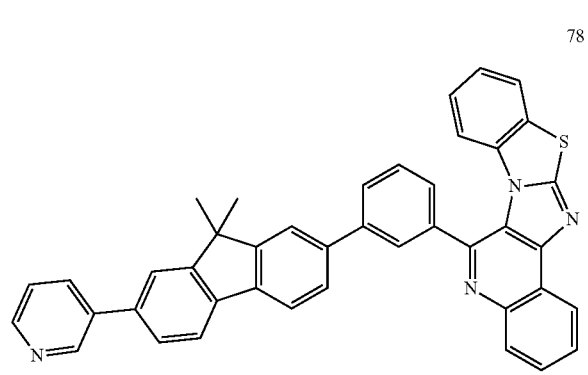
79
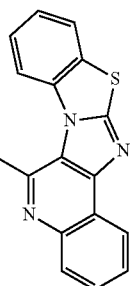
80
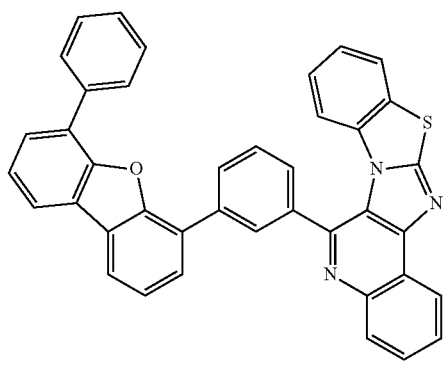
81
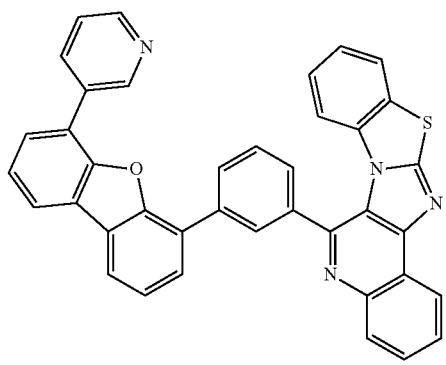
82
83
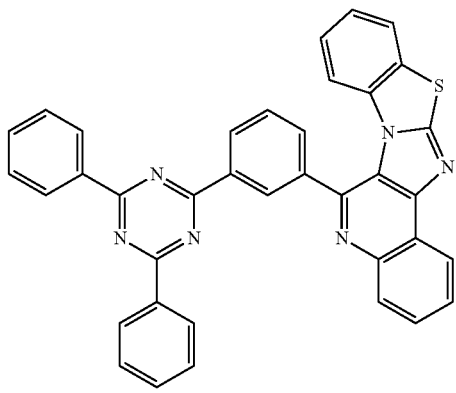

84
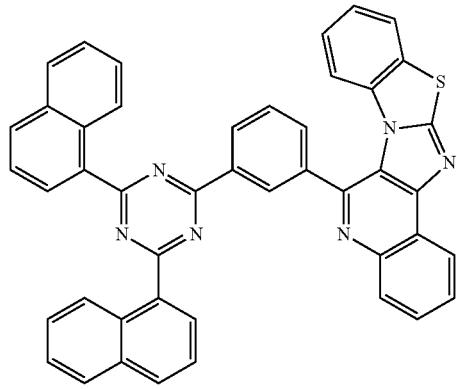
85
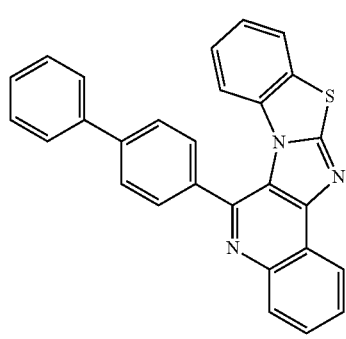
86
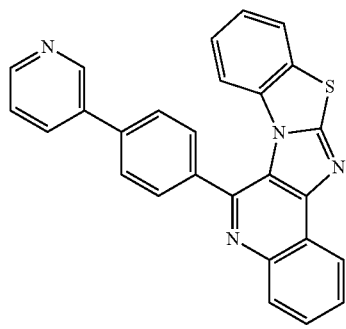
87
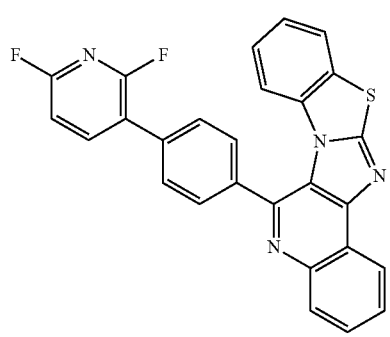
88
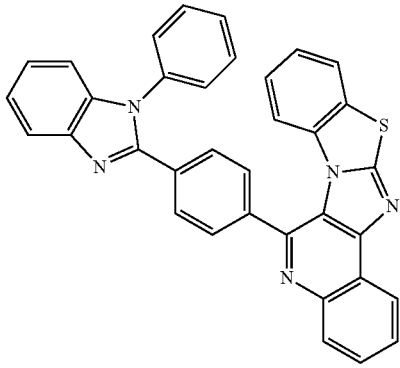
89
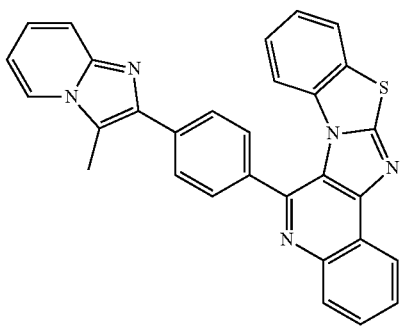
90
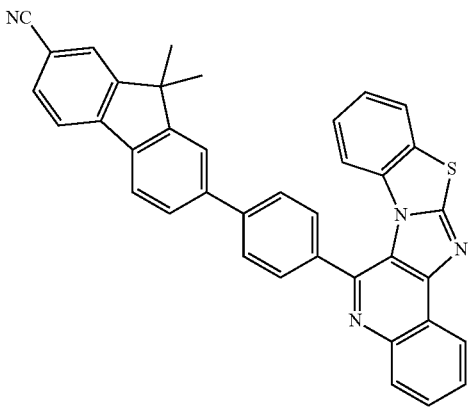
91
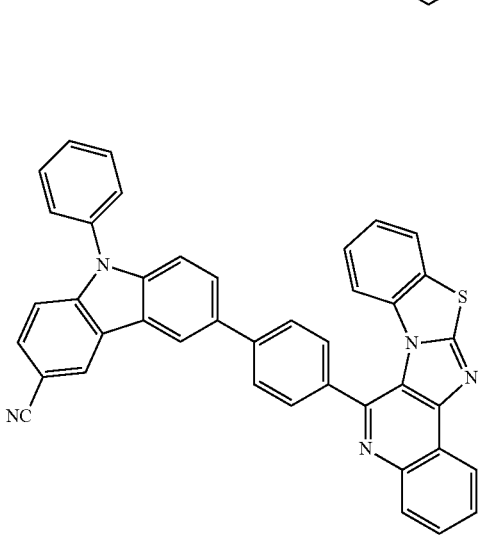

92
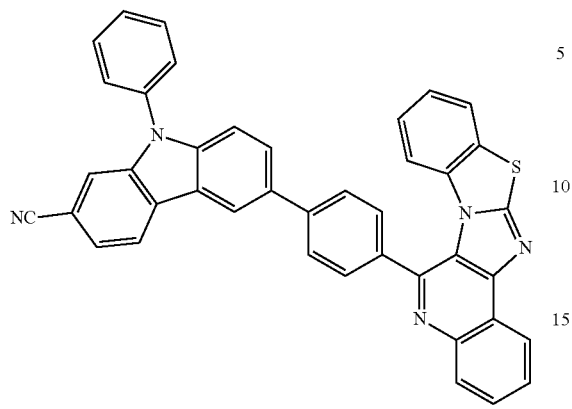
95
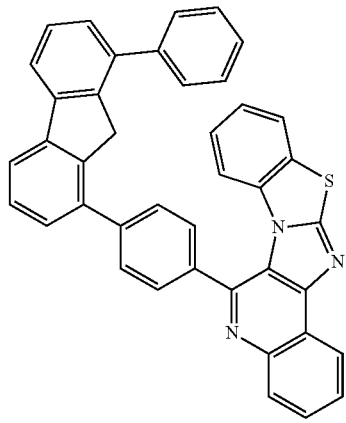
93
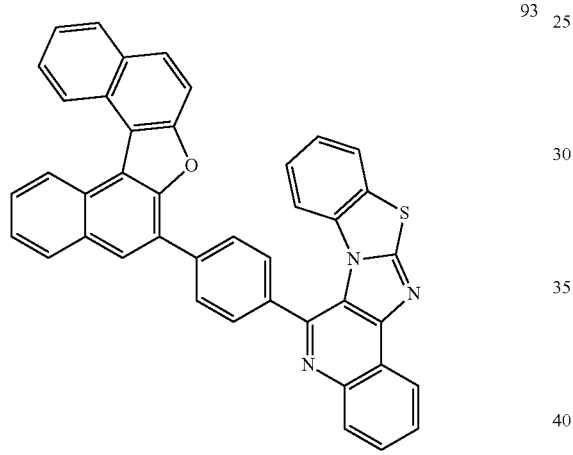
96
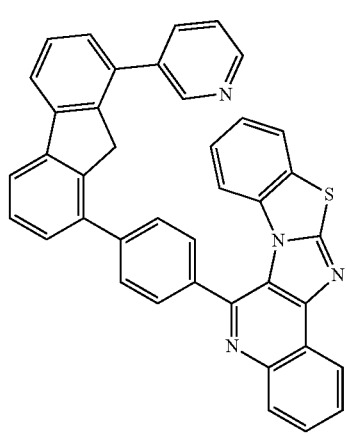
94
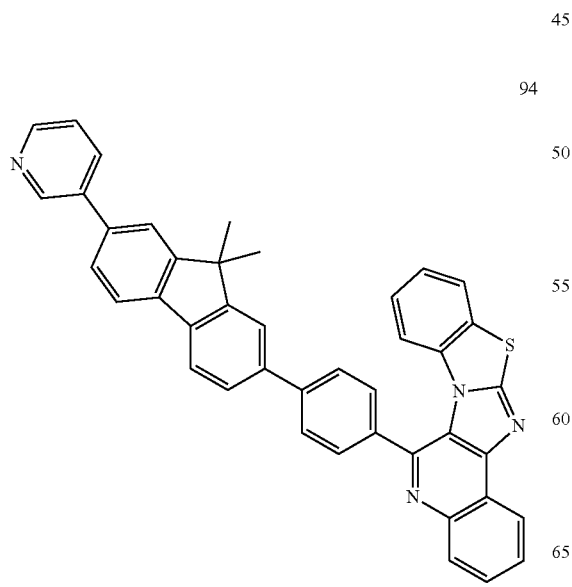
97
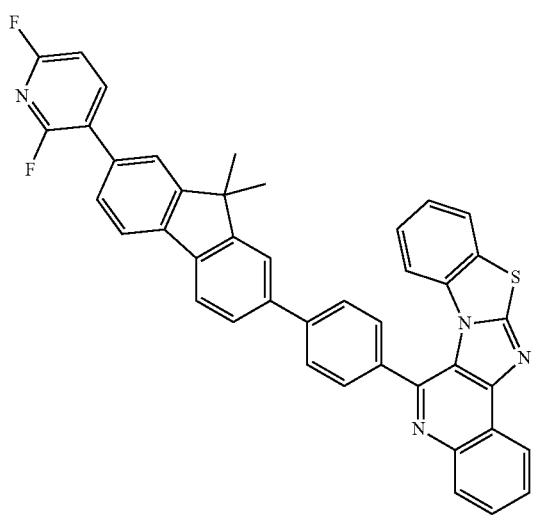

98
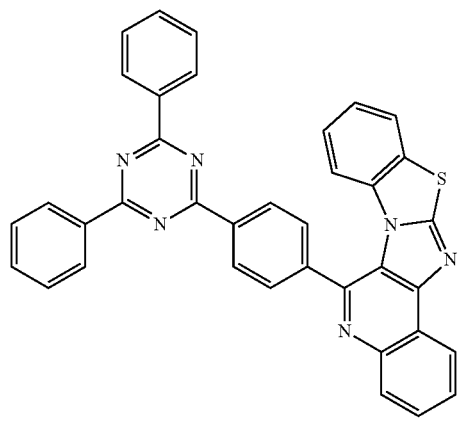
99
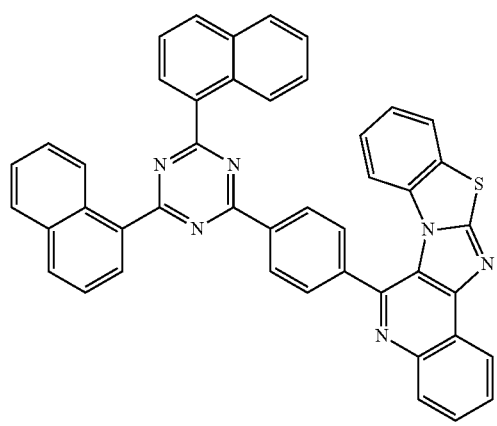
100
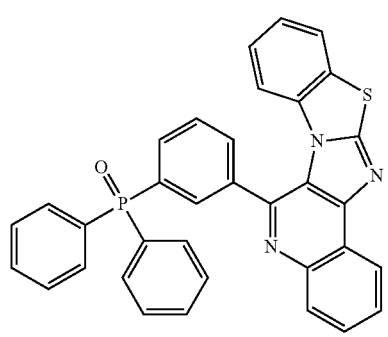
101
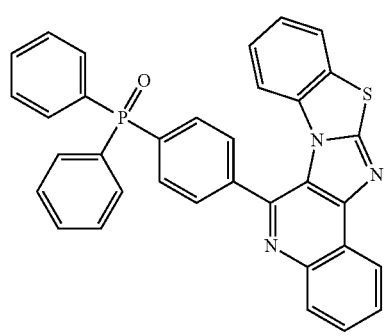
102
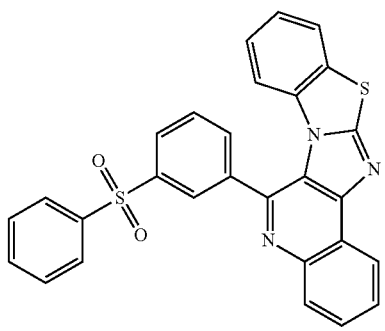
103
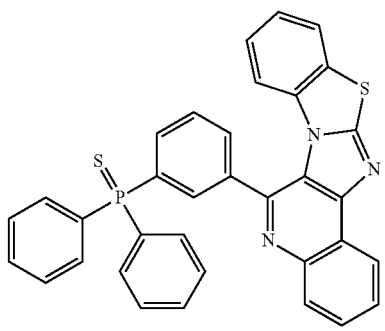
104
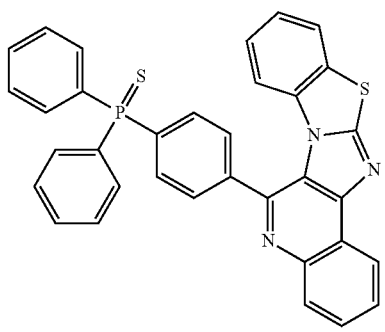
105
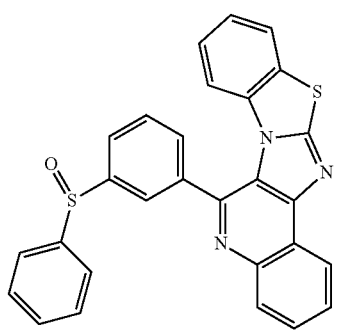

-continued
106
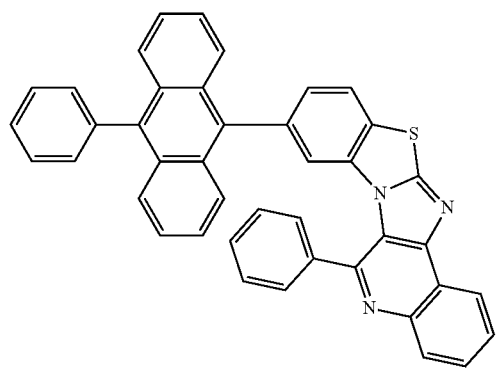
107
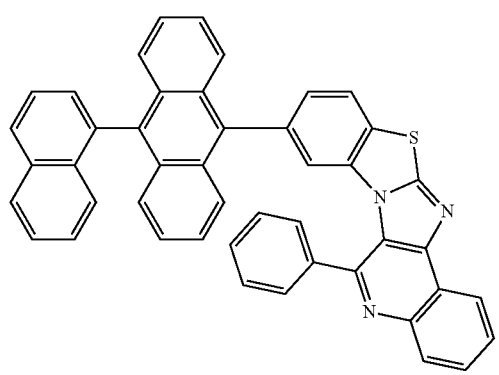
108
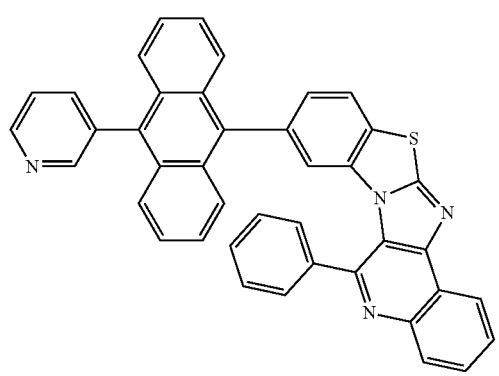
109
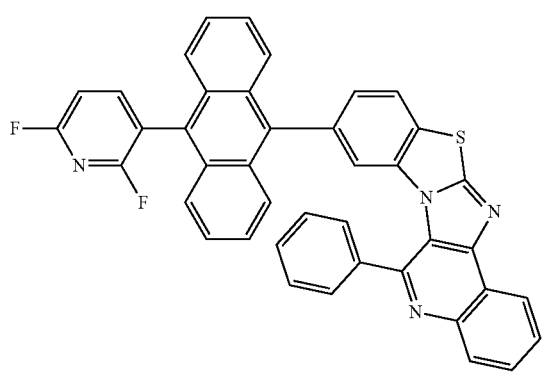
-continued
110
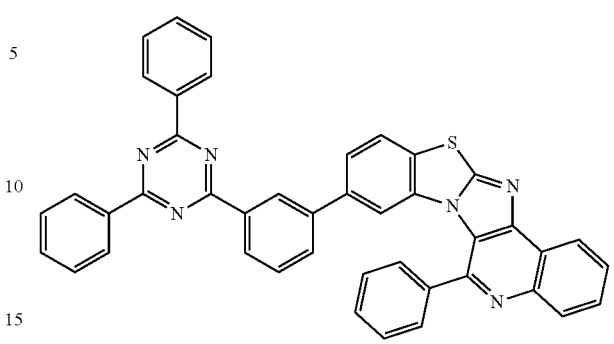
111
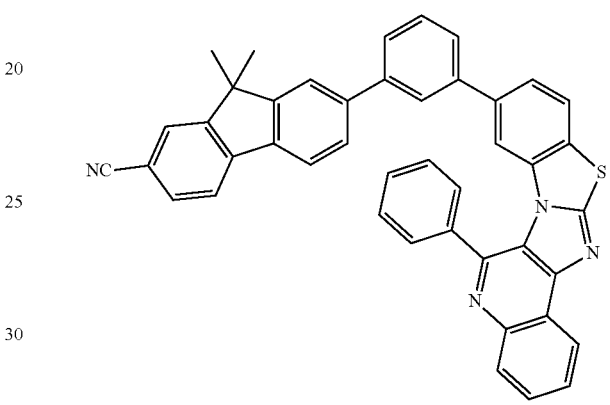
112
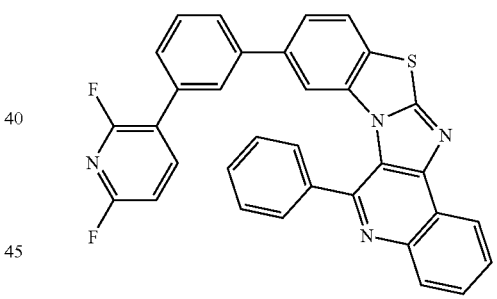
113
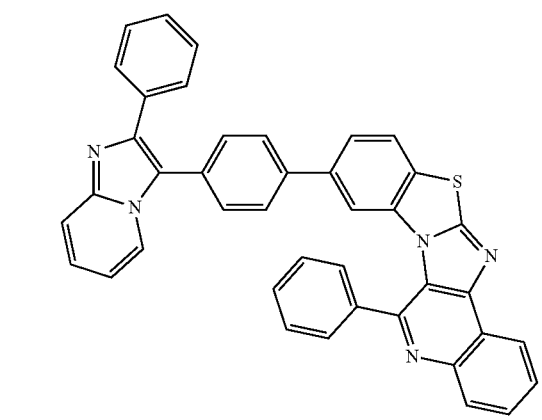

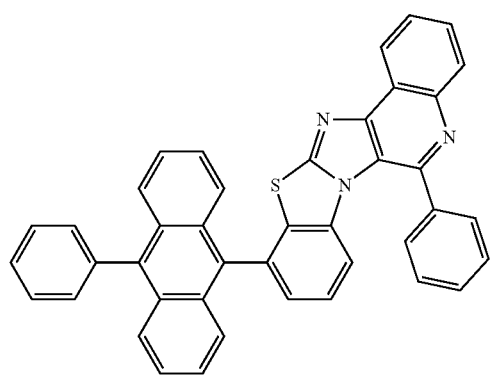
114
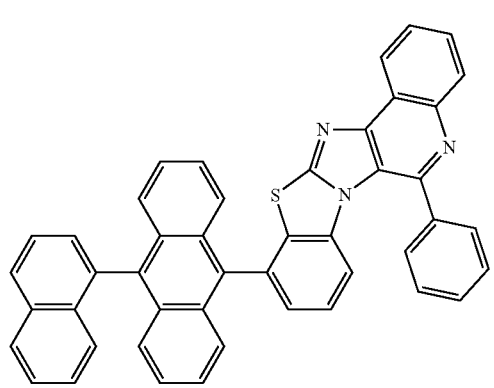
115
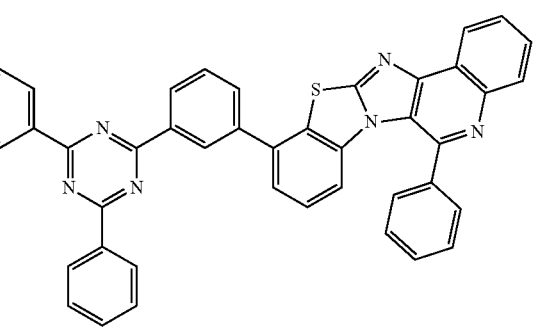
116
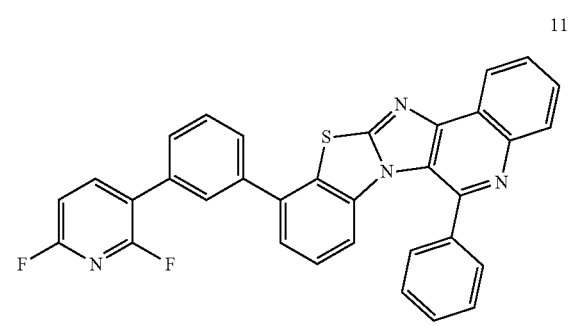
117
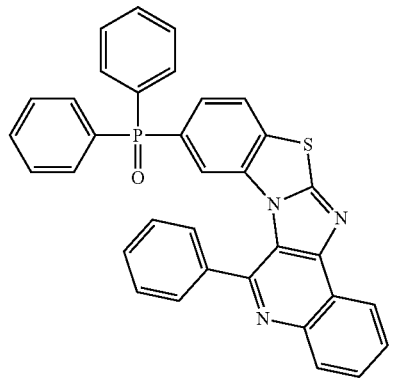
118
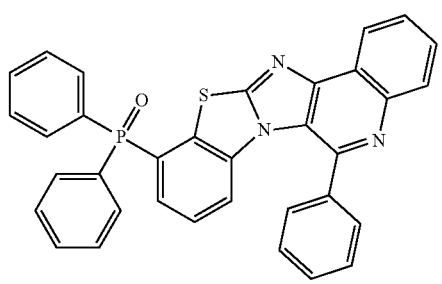
119
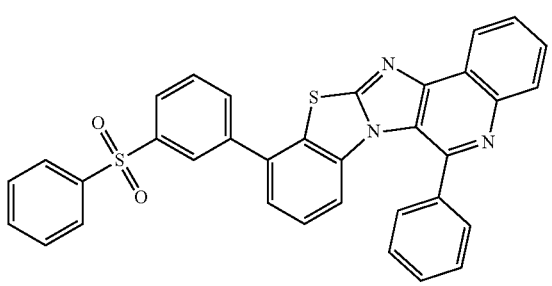
120
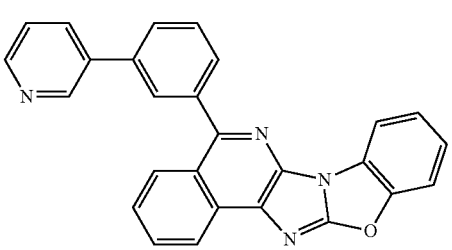
121
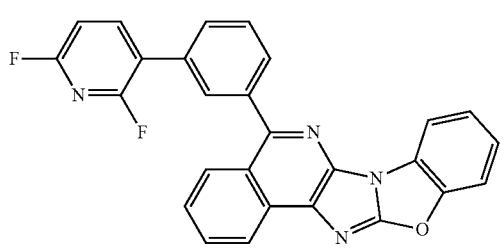
122

123
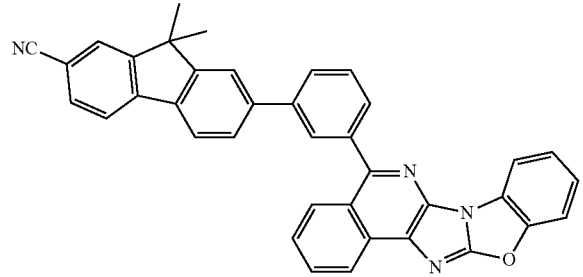
124
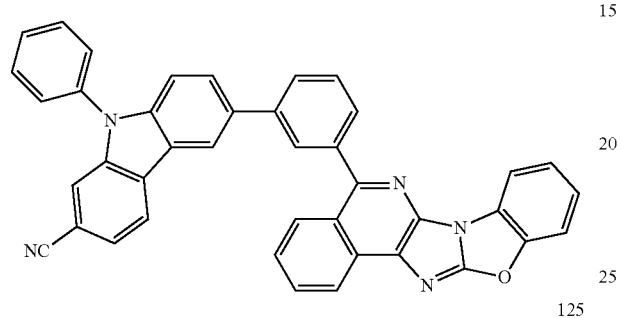
125
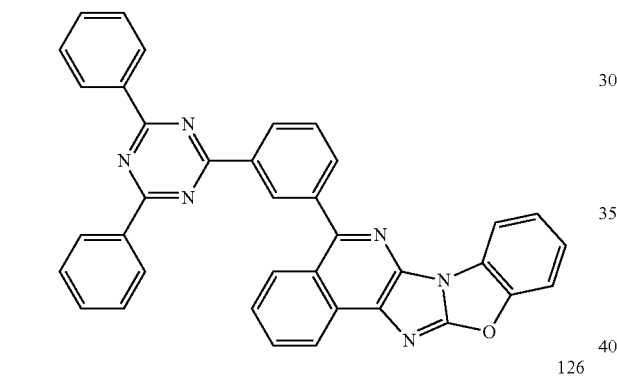
126
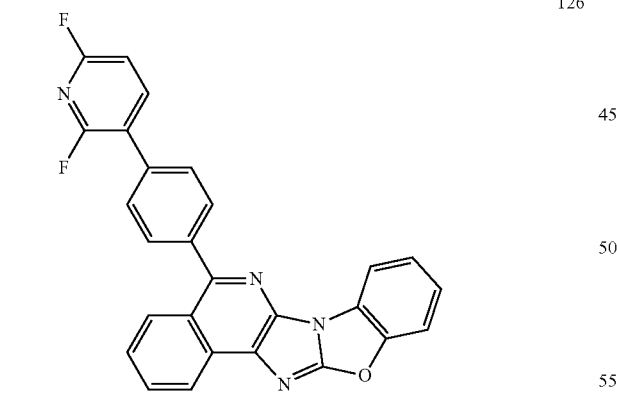
127
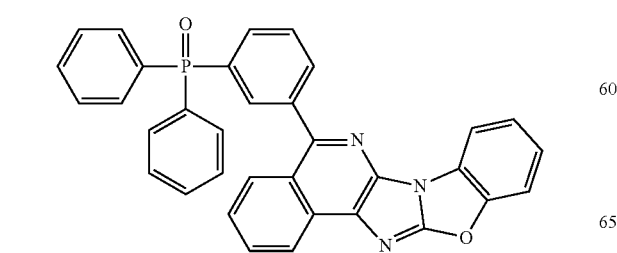
128
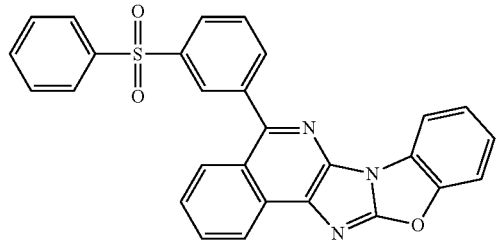
129
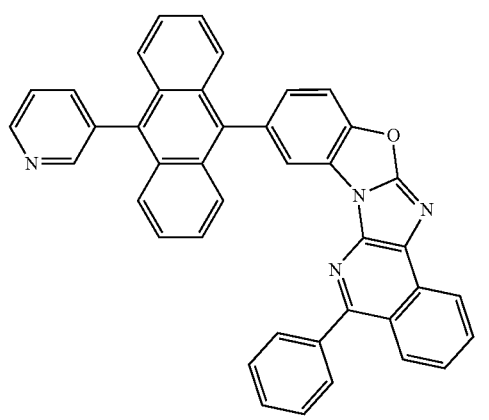
130
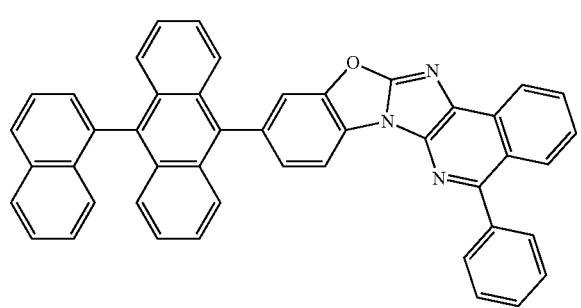
131
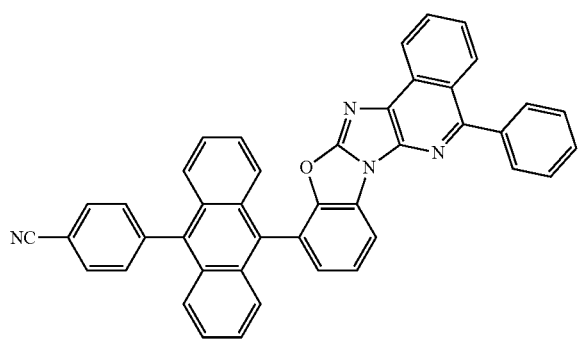
132
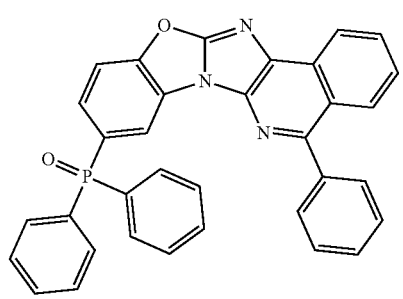

133
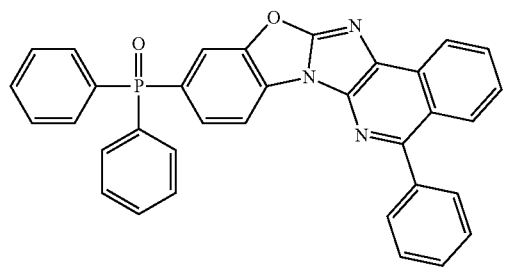
134
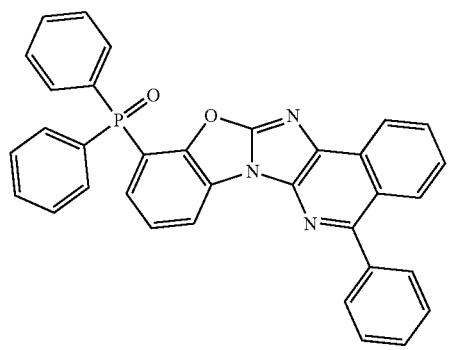
135
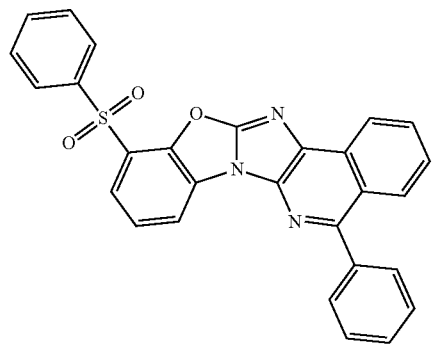
136
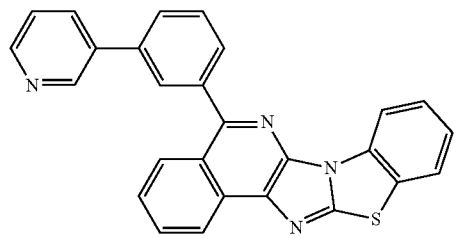
137
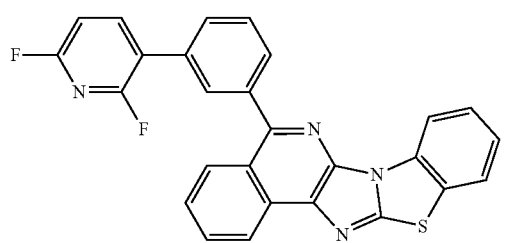
138
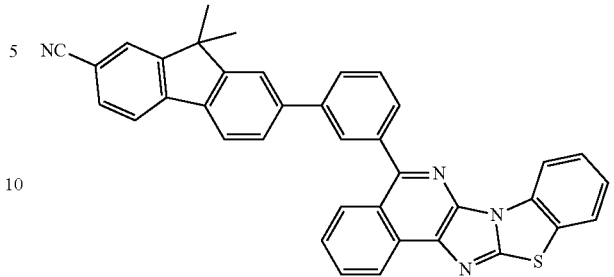
139
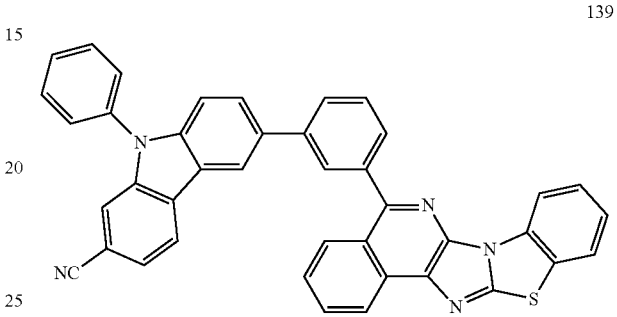
140
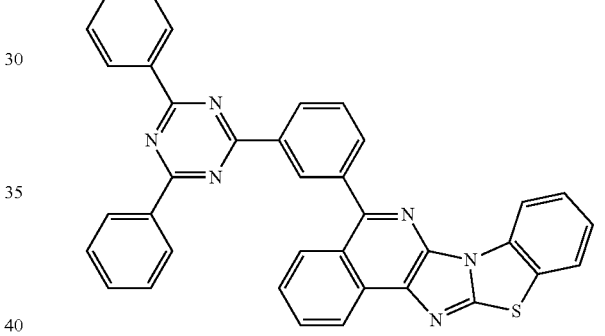
141
142
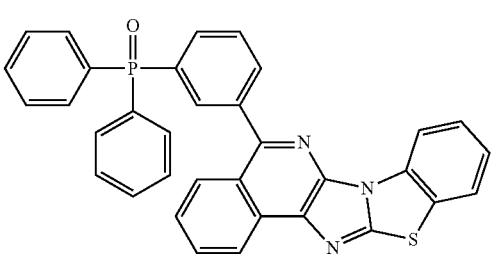

253
-continued
143
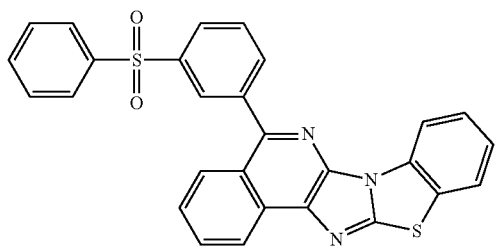
144
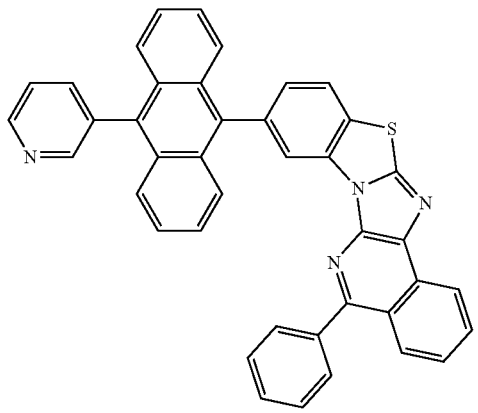
145
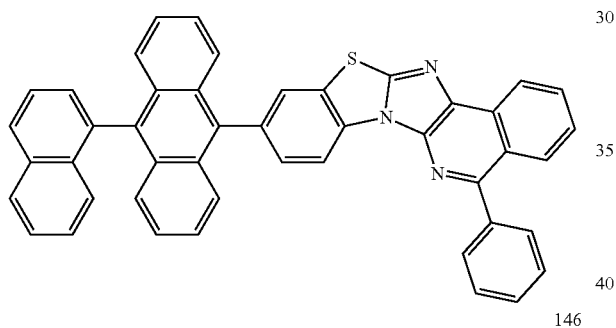
146
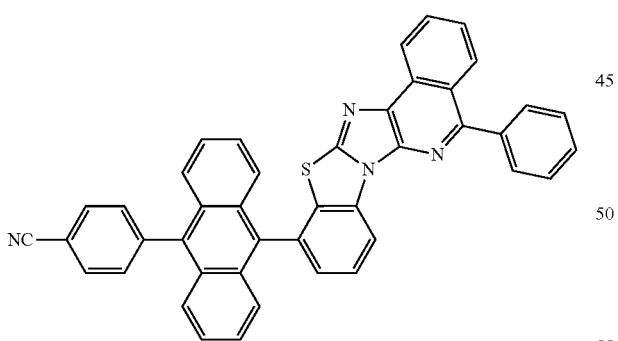
147
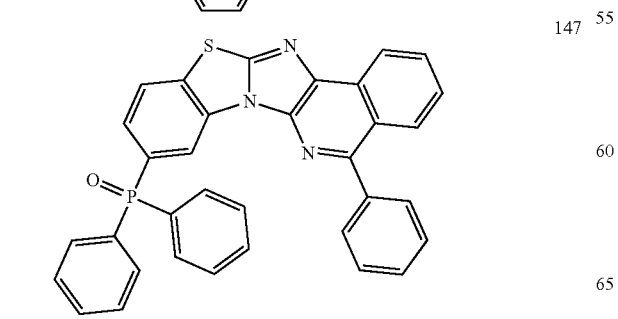
254
-continued
148
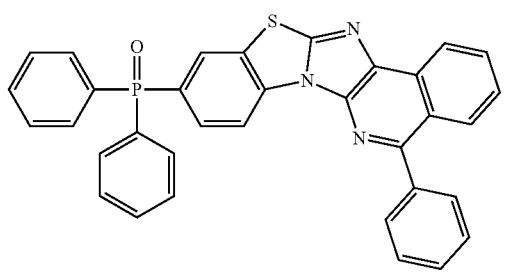
149
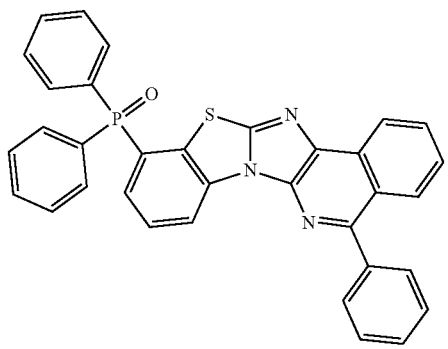
150
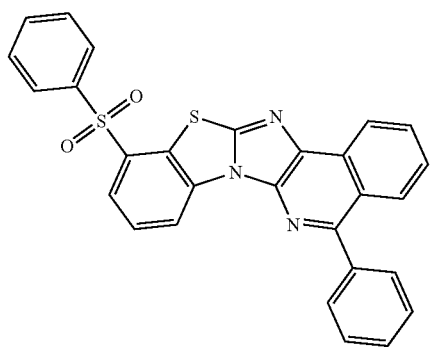
151
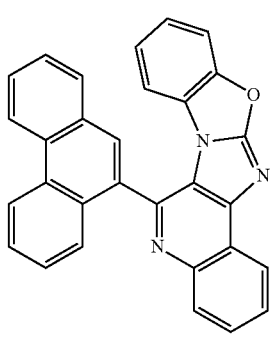

-continued

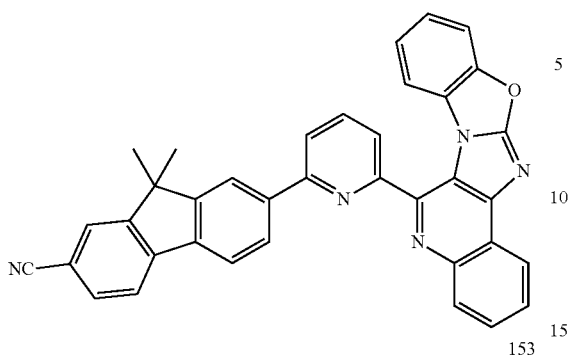
152

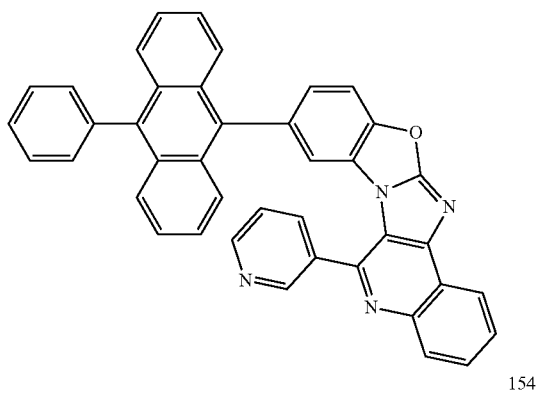
153

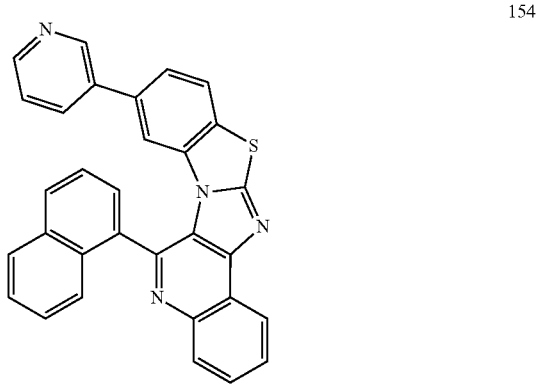
154

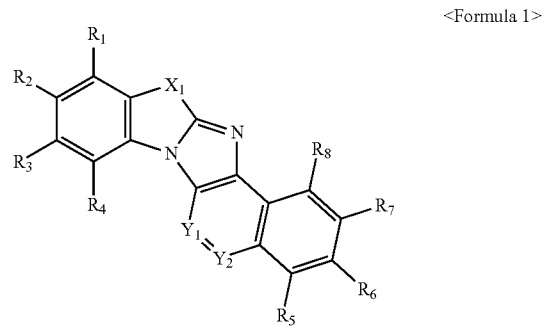
155

13. An organic light-emitting device comprising:
a first electrode;
a second electrode facing the first electrode; and
an organic layer disposed between the first electrode and the second electrode, the organic layer comprising an emission layer, wherein the organic layer comprises at least one condensed cyclic compound represented by Formula 1:

<Formula 1>

$$R_2 \begin{array}{c} R_1 \\ \diagup \\ \diagdown \end{array} X_1$$ ...structure with $R_1$–$R_8$, $X_1$, $Y_1$, $Y_2$...

$$*-(L_1)_{a1}-(Ar_1)_{b1},$$  <Formula 2> wherein, in Formulae 1 and 2,
$X_1$ is O or S,
$Y_1$ is $C(R_9)$ or N,
$Y_2$ is $C(R_{10})$ or N,
$L_1$ is selected from a substituted or unsubstituted $C_3$-$C_{60}$ carbocyclic group, a substituted or unsubstituted $C_1$-$C_{60}$ heterocyclic group, *—S(=O)($Q_1$)-*', *—S(=O)$_2$—*', *—P(=O)($Q_1$)-*', *—P(=O)$_2$—*', *—P(=S)($Q_1$)-*', or *—P(=S)$_2$—*',
a1 is an integer selected from 0 to 4, wherein when a1 is 2 or greater, at least two $L_1$(s) are the same or different from each other,
$Ar_1$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed hetero polycyclic group, —S(=O)($Q_1$)($Q_2$), —S(=O)$_2$($Q_1$), —P(=O)($Q_1$)($Q_2$), —P(=O)$_2$($Q_1$), —P(=S)($Q_1$)($Q_2$), or —P(=S)$_2$($Q_1$),
b1 is an integer selected from 1 to 4 wherein when b1 is 2 or greater, at least two $Ar_1$(s) are the same or different from each other,
$R_1$ to $R_{10}$ are each independently selected from a group represented by Formula 2, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), or —P(=O)($Q_1$)($Q_2$), at least one of $R_1$ to $R_{10}$ is the group represented by Formula 2, and at least one substituent selected from a substituent(s) of the substituted $C_3$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group is selected from:

deuterium, —F, —Cl, —Br, –I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazino, group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic, group, —Si($Q_{11}$)($Q_{12}$)($Q_{13}$), —N($Q_{11}$)($Q_{12}$), —B($Q_{11}$)($Q_{12}$), —C(=O)$_2$($Q_{11}$), or —P(=O)($Q_{11}$)($Q_{12}$);

a $C_3$-$C_{10}$ cycloalkyl, group a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, or a terphenyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group, each substituted with at least one selected from deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, —Si($Q_{21}$)($Q_{22}$)($Q_{23}$), —N($Q_{21}$)($Q_{22}$), —B($Q_{21}$)($Q_{22}$), —(=O)($Q_{21}$), —S(=O)$_2$($Q_{21}$), or —P(=O)($Q_{21}$)($Q_{22}$); or —Si($Q_{31}$)($Q_{32}$)($Q_{33}$), —N($Q_{31}$)($Q_{33}$), —B($Q_{31}$)($Q_{32}$), —C(=O)($Q_{31}$), —S(=O)$_2$($Q_{31}$), or —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ are each independently selected from hydrogen, deuterium, —F, —Cl, —Br, —I, a hydroxyl group, a cyano group, a nitro group, an amino group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group a biphenyl group, or a terphenyl group, and

* and *' each indicate a binding site to a neighboring atom.

14. The organic light-emitting device of claim 13, wherein
the first electrode is an anode,
the second electrode is a cathode,
the organic layer further comprises a hole transport region disposed between the first electrode and the emission layer and an electron transport region between the emission layer and the second electrode,
the hole transport region comprises a hole injection layer, a hole transport layer, a buffer layer, an emission auxiliary layer, an electron blocking layer, or any combination thereof, and
the electron transport region comprises an emission auxiliary layer, a hole blocking layer, an electron transport layer, an electron injection layer, or any combination thereof.

15. The organic light-emitting device of claim 14, wherein the electron transport region comprises the condensed cyclic compound of claim 1.

16. The organic light-emitting device of claim 14, wherein the electron transport region comprises an electron transport layer, and
the electron transport layer comprises the condensed cyclic compound of claim 1.

17. The organic light-emitting device of claim 14, wherein the emission layer comprises the condensed cyclic compound of claim 1.

18. The organic light-emitting device of claim 17, wherein the emission layer further comprises a dopant,
an amount of the condensed cyclic compound in the emission layer is larger than an amount of the dopant,
the condensed cyclic compound in the emission layer is configured to serve as a host, and
the dopant is a phosphorescent dopant or a fluorescent dopant.

19. The organic light-emitting device of claim 16, wherein the electron transport region comprises an emission auxiliary layer, and
the emission auxiliary layer comprises the condensed cyclic compound of claim 1.

20. The organic light-emitting device of claim 19, wherein the electron transport region further comprises an electron transport layer, and
the emission auxiliary layer is disposed between the electron transport layer and the emission layer.

* * * * *